(12) United States Patent
Nishino et al.

(10) Patent No.: US 9,212,348 B2
(45) Date of Patent: Dec. 15, 2015

(54) METHOD FOR PRODUCING HEMATOPOIETIC STEM CELLS USING PYRAZOLE COMPOUNDS

(75) Inventors: Taito Nishino, Tokyo (JP); Makiko Yui, Yokohama (JP); Yasuyuki Asai, Yokohama (JP); Ayako Asai, legal representative, Tokyo (JP)

(73) Assignees: NISSAN CHEMICAL INDUSTRIES, LTD., Tokyo (JP); REPROCELL INCORPORATED, Yokohama-shi (JP)

( * ) Notice: Subject to any disclaimer, the term of this patent is extended or adjusted under 35 U.S.C. 154(b) by 0 days.

(21) Appl. No.: 13/990,959

(22) PCT Filed: Dec. 1, 2011

(86) PCT No.: PCT/JP2011/077832
§ 371 (c)(1),
(2), (4) Date: Nov. 4, 2013

(87) PCT Pub. No.: WO2012/074068
PCT Pub. Date: Jun. 7, 2012

(65) Prior Publication Data
US 2014/0057353 A1    Feb. 27, 2014

(30) Foreign Application Priority Data

Dec. 1, 2010 (JP) .................... 2010-268775
Sep. 30, 2011 (JP) .................... 2011-217827

(51) Int. Cl.
| | | |
|---|---|---|
| C12N 15/00 | (2006.01) | |
| C12N 5/0789 | (2010.01) | |
| C07D 231/22 | (2006.01) | |
| A61K 35/28 | (2015.01) | |

(52) U.S. Cl.
CPC ............ *C12N 5/0647* (2013.01); *C07D 231/22* (2013.01); *A61K 35/28* (2013.01); *C12N 2501/125* (2013.01); *C12N 2501/145* (2013.01); *C12N 2501/26* (2013.01); *C12N 2501/999* (2013.01)

(58) Field of Classification Search
None
See application file for complete search history.

(56) References Cited

U.S. PATENT DOCUMENTS

| | | |
|---|---|---|
| 2003/0082158 A1 | 5/2003 | Symonds et al. |
| 2004/0072771 A1 | 4/2004 | Symonds et al. |
| 2005/0063958 A1 | 3/2005 | Symonds et al. |
| 2006/0069140 A1 | 3/2006 | Miyaji et al. |
| 2008/0044394 A1 | 2/2008 | Symonds et al. |
| 2009/0131676 A1 | 5/2009 | Miyaji et al. |
| 2009/0198060 A1 | 8/2009 | Miyaji et al. |
| 2009/0253751 A1 | 10/2009 | Miyaji et al. |
| 2010/0266556 A1 | 10/2010 | Nishino et al. |
| 2010/0310536 A1 | 12/2010 | Nakamura et al. |

FOREIGN PATENT DOCUMENTS

| | | |
|---|---|---|
| JP | 2000 23674 | 1/2000 |
| JP | 2001 161350 | 6/2001 |
| JP | 2002 502617 | 1/2002 |
| JP | 2005 528319 | 9/2005 |
| JP | 2006 506452 | 2/2006 |
| JP | 2009 501695 | 1/2009 |
| JP | 2009 40692 | 2/2009 |
| WO | WO 03/103686 A1 | 12/2003 |
| WO | 2007 052808 | 5/2007 |
| WO | 2007 142308 | 12/2007 |
| WO | 2009 072624 | 6/2009 |
| WO | 2009 072635 | 6/2009 |
| WO | WO 2010/059401 A2 | 5/2010 |
| WO | WO 2010/059401 A3 | 5/2010 |

OTHER PUBLICATIONS

Aggarwal et al. (2012, Current Molecular Medicine 12: 34-49; author manuscript available online at http://www.ncbi.nlm.nih.gov/pmc/articles/PMC3286491/pdf/nihms356893.pdf.*
Kanji et al. (2011, Recent Patents in Biotechnology 5: 40-43 author manuscript available online at http://www.ncbi.nlm.nih.gov/pmc/articles/PMC3294454/pdf/nihms-356918.pdf.*
Nishino et al., 2009, Experimental Hematology 37: 1364-1377.*
Nishino et al., 2012, Expert Opinion on Biological Therapy 12: 743-756.*
Extended European Search Report issued Mar. 28, 2014, in European Patent Application No. 11845184.8.
U.S. Appl. No. 13/991,024, filed May 31, 2013, Nishino, et al.

(Continued)

*Primary Examiner* — Christopher M Babic
*Assistant Examiner* — Kimberly A Aron
(74) *Attorney, Agent, or Firm* — Oblon, McClelland, Maier & Neustadt, L.L.P.

(57) ABSTRACT

An expanding agent for hematopoietic stem cells and/or hematopoietic progenitor cells useful as a therapy for various hematopoietic diseases and useful for improvement in the efficiency of gene transfer into hematopoietic stem cells for gene therapy is provided.
A method of producing hematopoietic stem cells and/or hematopoietic progenitor cells, which comprises expanding hematopoietic stem cells by culturing hematopoietic stem cells ex vivo in the presence of a compound represented by the formula following (I), a tautomer or pharmaceutically acceptable salt of the compound or a solvate thereof (wherein $R^1$ to $R^8$ are as defined in the description).

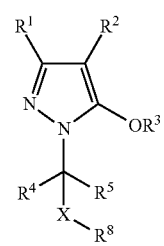

(1)

18 Claims, 3 Drawing Sheets

(56) References Cited

OTHER PUBLICATIONS

Figure 1:
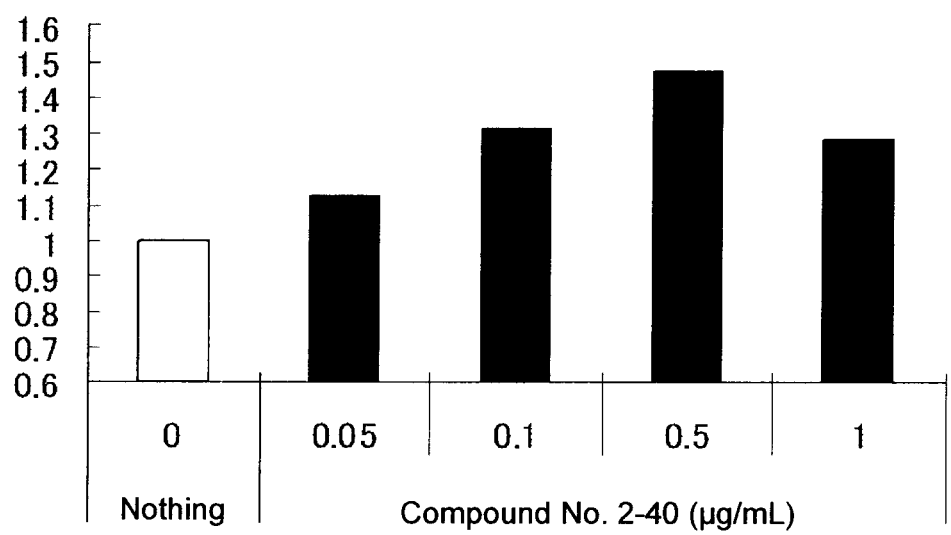

Nishino, T. et al., "Ex vivo expansion of human hematopoietic stem cells by a small-molecule agonist of c-MPL", Experimental Hematology, vol. 37, pp. 1364 to 1377.e4, (2009).
Lu, L. et al., "The Selective Enhancing Influence of Hemin and Products of Human Erythrocytes on Colony Formation by Human Multipotential ($CFU_{GEMM}$) and Erythroid ($BFU_E$) Progenitor Cells In Vitro", Exp. Hematol., International Society for Experimental Hematology, vol. 11, No. 8, pp. 721 to 729, (Sep. 1983).
Taguchi, A. et al., "Administration of $CD34^+$ cells after stroke enhances neurogenesis via angiogenesis in a mouse model", Research article, Related Commentary, The Journal of Clinical Investigation, vol. 114, No. 3, p. 330 to 338, (Aug. 2004).
Orlic, D., Bone marrow cells regenerate infracted myocardium, letters to nature, Nature, vol. 410, pp. 701 to 705, (Apr. 5, 2001).
Tateishi-Yuyama, E. et al., "Therapeutic angiogenesis for patients with limb ischaemia by autologous transplantation of bone-marrow cells: a pilot study and a randomized controlled trial", The Lancet, vol. 360, pp. 427 to 435, (Aug. 10, 2002).
Iwasaki, H. et al., "Dose-Dependent Contribution of CD34-Positive Cell Transplantation to Concurrent Vasculogenesis and Cardiomyogenesis for Functional Regenerative Recovery After Myocardial Infarction", Molecular Cardiology, Circulation, vol. 113, pp. 1311 to 1325, (Mar. 14, 2006).
Kurtzberg, J. et al., Placental Blood as a Source of Hematopoietic Stem Cells for Transplantation Into Unrelated Recipients, The New England Journal of Medicine, vol. 335, No. 3, pp. 157 to 169, (Jul. 18, 1996).
Nathwani, A. et al., "A review of gene therapy for haematological disorders", British Journal of Haematology, vol. 128, pp. 3 to 17, (2004).
Delaney, C. et al., "Notch-mediated Expansion of Human Cord Blood Progenitor Cells Capable of Rapid Myeloid.Reconstitution", National Institute of Health, Nat. Med., vol. 16, No. 2, pp. 1-16, (Feb. 2010).
Ema, H. et al., "Colony Formation of Clone-Sorted Human Hematopoietic Progenitors", Blood, vol. 75, No. 10, pp. 1941-1946, (May 15, 1990).
Ishizawa, L. et al., "Immunomagnetic Separation of $CD34^+$ Cells from Human Bone Marrow, Cord Blood, and Mobilized Peripheral Blood", Journal of Hematotherapy, vol. 2, pp. 333 to 338, (1993).
Cassel, A. et al., "Retroviral-mediated gene transfer into CD34-enriched human peripheral blood stem cells", Experimental Hematology, International Society for Experimental Hematology, vol. 21, pp. 585 to 591, (1993).
Bhatia, M. et al., "Purification of primitive human hematopoietic cells capable of repopulating immune-deficient mice", Proc. Natl. Acad. Sci., Medical Sciences, vol. 94, pp. 5320 to 5325, (May 1997).
Larochelle, A. et al., "Identification of primitive human hematopoietic cells capable of repopulating NOD/SCID mouse bone marrow: Implications for gene therapy", Nature Medicine, vol. 2, No. 12, pp. 1329 to 1337, (Dec. 1996).
Shah, A., "Flt3 Ligand Induces Proliferation of Quiescent Human Bone Marrow $CD34^+$ CD38– Cells and Maintains Progenitor Cells In Vitro", Blood, vol. 87, No. 9, pp. 3563 to 3570, (1996).
Dick, J. et al., "Assay of Human Stem Cells by Repopulation of NOD/SCID Mice", Hematopoietic Stem Cells, Stems Cells, vol. 15 (suppl 1), pp. 199 to 207, (1997).
Suzuki, T. et al., "Highly Efficient Ex Vivo Expansion of Human Hematopoietic Stem Cells Using Deltal-Fc Chimeric Protein", Stem Cells, vol. 24, pp. 2456 to 2465, (2006).
McNiece, I. et al., "Ex vivo expanded peripheral blood progenitor cells provide rapid neutrophil recovery after high-dose chemotherapy in patients with breast cancer", Clinical Observations, Interventions, and Therapeutic Trials, Blood, vol. 96, No. 9, pp. 3001 to 3007, (Nov. 1, 2000).
Kaushansky, K., "Thrombopoietin and the Hematopoietic Stem Cell", Ann. N.Y. Acad. Sci., New York Academy of Sciences, vol. 1044, pp. 139 to 141, (2005).
Kawano, Y. et al., "Ex vivo expansion of G-CSF-mobilized peripheral blood $CD133^+$ progenitor cells on coculture with human stromal cells", Experimental Hematology, vol. 34, pp. 150 to 158, (2006).
Kawada, H. et al., "Rapid ex vivo expansion of human umbilical cord hematopoietic progenitors using a novel culture system", Experimental Hematology, vol. 27, pp. 904 to 915, (1999).
Chute, J. et al., "Inhibition of aldehyde dehydrogenase and retinoid signaling induces the expansion of human hematopoietic stem cells", Proc Natl Acad Sci, PNAS, vol. 103, No. 31, pp. 11707 to 11712, (Aug. 1, 2006).
Milhem, M. et al., "Modification of hematopoietic stem cell fate by 5aza 2'deoxycytidine and trichostatin A", Hematopoiesis, Blood, vol. 103, No. 11, pp. 4102 to 4110, (Jun. 1, 2004).
Leung, A.Y.H., et al., "All-trans retinoic acid (ATRA) enhances maintenance of primitive human hematopoietic progenitors and skews them towards myeloid differentiation in a stroma-noncontact culture systems", Experimental Hematology, vol. 33, pp. 422 to 427, (2005).
Boitano, A. et al., "Aryl Hydrocarbon Receptor Antagonists Promote the Expansion of Human Hematopoietic Stem Cells", Science, vol. 329, pp. 1345 to 1348, (Sep. 10, 2010).
Appelbaum, F., "The Use of Colony Stimulating Factors in Marrow Transplantation", Cancer, vol. 72, pp. 3387 to 3392, (1993).
International Search Report Issued Feb. 28, 2012 in PCT/JP11/77832 Filed Dec. 1, 2011.

\* cited by examiner

METHOD FOR PRODUCING HEMATOPOIETIC STEM CELLS USING PYRAZOLE COMPOUNDS

TECHNICAL FIELD

The present invention relates to a method of expanding hematopoietic stem cells and/or hematopoietic progenitor cells using a compound having a blood cell expanding effect, in particular, to a method of expanding hematopoietic stem cells and/or hematopoietic progenitor cells by culturing hematopoietic stem cells in a culture medium containing at least one species selected from various cytokines and growth factors, a gene therapy method using the expanding method and a cell therapy material using hematopoietic stem cells and/or hematopoietic progenitor cells obtained by the expanding method.

BACKGROUND ART

Blood contains various lineages of blood cells having biological functions, such as the erythrocytic lineage associated with oxygen delivery, the megakaryocytic lineage generating thrombocytes, the granulocytic lineage associated with prevention of infections, the myeloid lineage such as monocytes and/or macrophages and the lymphocytic lineage responsible for immunity such as T cells and B cells. All these blood cells differentiate and mature from the common origin, hematopoietic stem cells, and are maintained and generated in an individual throughout its life. Hematopoietic stem cells are defined as cells having both pluripotency which allows them to differentiate into functional cells such as lymphocytes, erythrocytes and leukocytes and the ability to regenerate themselves while maintaining the pluripotency (self-renewal).

Previous studies have revealed that hematopoietic stem cells first diverge two ways into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-EO), while lymphoid stem cells differentiate into T cells via T lymphoid progenitor cells and into B cells via B lymphoid progenitor cells. Among them, cells forming multipotential colonies with diameters of at least 1 mm are called HPP-CFU colony forming cells and are known as the least differentiated hematopoietic progenitor cells, along with mixed colony forming cells (CFU-GEMM). These myeloid stem cells and various hematopoietic progenitor cells derived from them are identified by the properties of colonies they form on soft agar, semisolid methylcellulose media or the like in the presence of various cytokines (Non-Patent Document 1).

In recent years, as a curative therapy for a number of intractable diseases such as various blood diseases attributed to hematopoietic dysfunction and immune dysfunction, cancer, immunodeficiency, autoimmune diseases and inborn error of metabolism, autologous or allogeneic transplantation of hematopoietic stem cells have been performed. Quite recently, the effectiveness of transplantation of $CD34^+$ cells including hematopoietic stem cells in treating cerebral infarction, myocardial infarction and obstructive arteriosclerosis was reported (Non-Patent Documents 2, 3, 4 and 5). Attempts to regenerate nerves and muscles through hematopoietic stem cell transplantation are in progress. For example, nerve regeneration in cerebral infarction model mice through angiogenesis caused by transplantation of cord blood-derived $CD34^+$ cells (Non-Patent Document 2) and the possibility of repair of damaged muscles using $CD34^+$ cells were reported (Non-Patent Document 5 and Patent Document 1). Among them, bone marrow transplantation has been used in many cases of treatment and most established as a standard hematopoietic cell transplantation therapy. However, because for bone marrow transplantation, the human leukocyte antigens (HLA) of the bone marrow donor and the transplant recipient have to match closely, there is a problem that bone marrow from donors are in short supply. Besides, the need for at least 4 days of hospitalization and pain, fever and bleeding caused by collection of a large amount of bone marrow are a heavy burden to donors.

In addition to bone marrow, peripheral blood is also used as an alternative source of hematopoietic stem cells nowadays. Hematopoietic stem cells mobilized from the bone marrow to peripheral blood by administration of granulocyte colony stimulating factor (G-CSF) to a human are used for transplantation after enrichment using a blood cell separator. However, donors for peripheral blood hematopoietic stem cell transplantation have to bear a heavy burden of the need for administration of G-CSF for 4 to 6 consecutive days which may cause side effects (such as blood coagulation and spleen hypertrophy). Besides, because the efficiency of the mobilization of hematopoietic stem cells from the bone marrow to peripheral blood by G-CSF varies from donor to donor, hematopoietic stem cells are not obtained sufficiently in some cases.

Just recently, it has been found that cord blood contains the same degree of hematopoietic stem cells as bone marrow and is useful for hematopoietic stem cell transplantation (Non-Patent Document 6). Because cord blood transplantation does not require complete HLA matching and is less likely to cause severe acute graft-versus-host disease (GVHD) than bone marrow and peripheral blood transplantation, cord blood is established as useful and has been used more frequently. However, because cord blood is obtained in a small amount from one donor and does not contain many hematopoietic stem cells, its use is mainly limited to children.

Furthermore, hematopoietic stem cells are also considered as useful cells for gene therapy of fatal genetic diseases with no effective cure, HIV infection, chronic granulomatosis and germ cell tumor. However, in order to transfect hematopoietic stem cells with a retrovirus vector carrying a target gene efficiently, it is necessary to artificially promote the proliferation of hematopoietic stem cells, which are usually in the stationary phase, by recruiting them into the cell cycle. Besides, in order to be successfully transplanted and express a transgene for a long time, the transfected hematopoietic stem cells have to be kept undifferentiated in culture ex vivo. Therefore, gene transfer by an improved cell culture method has been desired for efficient gene transfer and successful transplantation therapy (Non-Patent Document 7).

Meanwhile, hematopoietic progenitor cells are important for initial hematopoietic recovery after bone marrow or cord blood transplantation and are considered as effective, especially, in preventing early posttransplant infections. Therefore, transplantation of an insufficient number of hematopoietic progenitor cells can delay initial hematopoietic recovery and lower the posttransplant survival rate (Non-Patent Document 8).

To solve the above-mentioned problems with hematopoietic stem cell transplantation and gene therapy, a technique for expanding hematopoietic stem cells and/or hematopoietic progenitor cells ex vivo is demanded, and various culture methods have been attempted so far.

Here, hematopoietic stem cells and hematopoietic progenitor cells, which are to be cultured, are explained. It was revealed that in human, hematopoietic stem cells and various hematopoietic progenitor cells derived from them are found in populations of $CD34^+$ cells expressing the CD34 molecule as a cell surface antigen, and hence hematopoietic stem cells can be enriched as a $CD34^+$ cell population (Non-Patent Document 9). Specifically speaking, they are often enriched by mixing a cell population to be separated with a CD34 antibody labeled with magnetic beads and magnetically collecting $CD34^+$ cells (Non-Patent Documents 10 and 11). $CD34^+$ cell populations contain less than 10% of $CD34^+CD38^-$ cell populations not expressing the CD38 molecule as a cell surface antigen. It has come to be considered that hematopoietic stem cells are more enriched in $CD34^+CD38^-$ cell populations than in $CD34^+$ cell populations (Non-Patent Documents 12 and 13). In order to determine the proportion of undifferentiated hematopoietic progenitor cells in a cell population, HPP-CFU colony forming cells are usually counted as mentioned above (Non-Patent Document 14). In recent years, it has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells (Non-Patent Document 15).

Conventional techniques for expanding hematopoietic stem cells and/or hematopoietic progenitor cells will also be explained. As mentioned above, since hematopoietic stem cells are more enriched in $CD34^+$ cells, $CD34^+$ cells are mainly used as the starting cells for expansion. Expansion of hematopoietic stem cells and hematopoietic progenitor cells from $CD34^+$ cells in culture in the presence of a cytokine or a growth factor such as stem cell factor (SCF), interleukin-3 (IL-3), interleukin-6 (IL-6), interleukin-6 (IL-6)/soluble IL-6 receptor complex, interleukin-11 (IL-11), granulocyte colony stimulating factor (G-CSF), granulocyte-macrophage colony stimulating factor (GM-CSF), flk2/flt3 ligand (FL), thrombopoietin (TPO) and erythropoietin or Notch ligand (such as Delta 1) has been reported (Patent Documents 2 and 3 and Non-Patent Documents 8, 14, 16 and 17). Among them, TPO has especially excellent effect on hematopoietic stem cell expansion and used for in most of cases of expansion (Non-Patent Document 18). Hematopoietic stem cells and hematopoietic progenitor cells expand in culture in the presence of such various cytokines and growth factors, but hematopoietic stem cells expand only by several times. Besides, these cytokines and growth factors are all produced as recombinant proteins, it may be difficult to obtain them for expansion stably, in a large amount, at low cost, or quickly.

For ex vivo expansion of hematopoietic stem cells, coculture systems using a different type of cells as feeder cells in the presence of various cytokines were reported. For example, expansion of hematopoietic stem cells in coculture with human bone marrow stromal cells was attempted (Non-Patent Document 19). An attempt to expand $CD34^+$ cells in the presence of TPO, FL and SCF using mouse bone marrow cell line HESS-5 was also reported (Non-Patent Document 20). However, because these coculture systems use foreign cells, there is a risk that cells infected with an unknown pathogen whose existence has not been confirmed may also be transplanted to patients. Furthermore, when stromal cells from a different kind of animal are used, the stromal cells have to be separated completely from $CD34^+$ cells because otherwise there is a risk of causing immune response in the recipient after transplantation.

In addition, ex vivo expansion of hematopoietic stem cells in culture in the presence of various cytokines such as TPO combined with low molecular weight compounds, not just various cytokines only, has been reported. Examples of such low molecular weight compounds include copper chelators, the combination of a histone deacetylase inhibitor and a DNA methylase inhibitor, all-trans retinoic acid, aldehyde dehydrogenase inhibitors, arylhydrocarbon receptor antagonists and the like (Non-Patent Documents 21, 22, 23 and 24 and Patent Document 4). However, addition of any of them is not effective enough since hematopoietic stem cells expand by only several times, or cells have to be cultured for about 3 weeks.

It is known that treatments which promote rapid hematopoietic and immune recovery after transplantation of hematopoietic stem cells are quite effective in eliminating the risk of infections and shortening hospitalization. As such a treatment, posttransplant administration of the hematopoietic cytokine, granulocyte colony stimulating factor (G-CSF), is conducted in clinical settings (Non-Patent Document 25). However, it is effective only for leukocytes, and effective treatments which promote recovery of blood cells of all lineages through expansion of hematopoietic stem cells and/or hematopoietic progenitor cells before transplantation are demanded.

PATENT DOCUMENTS

Patent Document 1: JP-A-2009-40692
Patent Document 2: JP-A-2001-161350
Patent Document 3: JP-A-2000-23674
Patent Document 4: JP-A-2002-502617

NON-PATENT DOCUMENTS

Non-Patent Document 1: Lu, L. et al.; Exp. Hematol., 1983 vol. 11, p. 721-9
Non-Patent Document 2: Taguchi, A et al.; J Clin Invest., 2004, vol. 114, 330-8
Non-Patent Document 3: Orlic, D et al.; Nature, 410, 701-5.2001
Non-Patent Document 4: Tateishi-Yuyama, E et al.; Lancet, 360, 427-35. 2002
Non-Patent Document 5: Iwasaki, H et al.; Circulation, 2006, vol. 113, 1311-25
Non-Patent Document 6: Kurtzberg, J. et al.; New Eng. J. Med., 1996, vol. 335, p. 157-66
Non-Patent Document 7: Nathwani, A C. et al.; Br J. Haematol., 2005, vol. 128, p. 3-17
Non-Patent Document 8: Delaney, C. et al.; Nat. Med., 2010, vol. 16, p. 232-6
Non-Patent Document 9: Ema, H. et al.; Blood, 1990, vol. 75, p. 1941-6
Non-Patent Document 10: Ishizawa, L. et al.; J. Hemathother., 1993, vol. 2, p. 333-8
Non-Patent Document 11: Cassel, A. et al.; Exp. Hematol., 1993, vol. 21, p. 585-91
Non-Patent Document 12: Bhatia, M. et al.; Proc. Natl. Acad. Sci. USA, 1997, vol. 94, p. 5320-25
Non-Patent Document 13: Larochelle, A. et al.; Nat. Med., 1996, vol. 2, p. 1329-37

Non-Patent Document 14: Shah, A J et al.; Blood., 1996, vol. 87, p. 3563-3570
Non-Patent Document 15: Dick, J E et al.; Stem Cells., 1997, vol. 15, p. 199-203
Non-Patent Document 16: Suzuki, T et al.; Stem Cells., 2006, vol. 24, p. 2456-2465
Non-Patent Document 17: McNiece et al.; Blood., 2000, vol. 96, p. 3001-3007
Non-Patent Document 18: Kaushansky, K et al.; Ann NY Acad. Sci., 2005, vol. 1044, p. 139-141
Non-Patent Document 19: Kawano, Y et al.; Exp Hematol., 2006, vol. 34, p. 150-8
Non-Patent Document 20: Kawada, H et al.; Exp Hematol., 1999, vol. 27, p. 904-15
Non-Patent Document 21: Chute, J P et al.; Proc Natl Acad Sci USA., 2006, vol. 103, p. 11707-12
Non-Patent Document 22: Milhem, M et al.; Blood., 2004, vol. 103, p. 4102-10
Non-Patent Document 23: Leung, A Y et al.; Exp Hematol., 2005, vol. 33, p. 422-7
Non-Patent Document 24: Boitano, A E et al.; Science., 2010, vol. 329, p. 1345-8
Non-Patent Document 25: Appelbaum, F R.; Cancer., 1993, vol. 72, p. 3387-92

DISCLOSURE OF THE INVENTION

Technical Problem

An object of the present invention is to expand hematopoietic stem cells and/or hematopoietic progenitor cells ex vivo efficiently in a short term using a biologically safe and inexpensively obtainable compound. Another object of the present invention is to use an index more effective than conventional ones in determining the expansion effect of such a compound on hematopoietic stem cells. A still another object of the present invention is to provide an expansion agent for hematopoietic stem cells and/or hematopoietic progenitor cells useful for improvement in the efficiency of gene transfer into hematopoietic stem cells for gene therapy and useful for treatment of various hematopoietic disorders caused by dysfunctional hematopoietic stem cells and/or hematopoietic progenitor cells and muscle and nerve diseases accompanying damaged tissues.

Solution to Problems

The present inventors conducted extensive research on compounds having expansion activity to find a method of expanding hematopoietic stem cells and/or hematopoietic progenitor cells from human hematopoietic stem cells. As a result, the present inventors found that the compounds represented by the following formula show excellent expansion activity on $CD34^+$ cells, $CD34^+CD38^-$ cells, HPP-CFU colony forming cells, and SRC and are highly useful as an expansion agent for human hematopoietic stem cells and/or hematopoietic progenitor cells and accomplished the present invention.

Namely, the present invention relates to the following [1] to [29]:

[1] A method of producing hematopoietic stem cells and/or hematopoietic progenitor cells, which comprises expanding hematopoietic stem cells and/or hematopoietic progenitor cells by culturing hematopoietic stem cells ex vivo in the presence of a pyrazole compound represented by the formula (1):

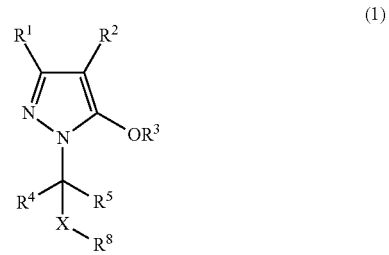

[wherein $R^1$ is a hydrogen atom, $C_1$-$C_{10}$ alkyl, $C_1$-$C_{10}$ alkyl substituted with $R^{17}$, $C_1$-$C_{10}$ haloalkyl, $C_3$-$C_{10}$ cycloalkyl, $C_3$-$C_{10}$ halocycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, —C($R^{12}$)=NO$R^{13}$, D1 to D23, cyano, phenyl, phenyl substituted with a $R^{11}$'s, benzyl or benzyl having a benzene ring which may be substituted with a $R^{11}$'s, when a is an integer of at least 2, each $R^{11}$ may be identical with or different from one another, and when there are two neighboring $R^{11}$'s, the two neighboring $R^{11}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^{3'}$)—, —CH$_2$N($R^{3'}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{3'}$)CH=CH—, —OCH=N—, —SCH=N—, —N($R^{3'}$)CH=N—, —N($R^{3'}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is a hydrogen atom, a halogen atom, cyano, $C_1$-$C_{10}$ alkyl, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)$R^{12}$, —C(O)O$R^{12}$, —C(O)N($R^{13}$)$R^{12}$, —C($R^{12}$)=N$R^{13}$, —C($R^{12}$)=NO$R^{13}$, D1 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—CH$_2$CH$_2$N($R^{3'}$)—, —CH$_2$N($R^{3'}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^{3'}$)CH=CH—, —OCH=N—, —SCH=N—, —N($R^{3'}$)CH=N—, —N($R^{3'}$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_6$ alkyl, $C_3$-$C_6$ cycloalkyl, $C_1$-$C_6$ alkoxy $C_1$-$C_6$ alkyl, $C_2$-$C_6$ alkenyl, $C_2$-$C_6$ alkenyl optionally substituted with $R^{31}$, $C_2$-$C_6$ alkynyl, $C_2$-$C_6$ alkynyl optionally substituted with $R^{31}$, —C(O)$R^{12}$, —C(O)O$R^{12}$, —C(O)N($R^{12}$)$R^{13}$, —Si($R^{32}$)($R^{33}$)$R^{34}$, benzyl or benzyl having a benzene ring which may be substituted with g $R^{15}$'s, and when g is an integer of at least 2, each $R^{15}$ may be identical with or different from one another, X is a single bond or —(C$R^6R^7$)$_n$— each of $R^4$ and $R^5$ is independently $C_1$-$C_6$ alkyl or $C_3$-$C_6$ cycloalkyl, and $R^4$ and $R^5$ may form —CH$_2$CH$_2$—, —CH$_2$CH$_2$CH$_2$—, —CH$_2$CH$_2$CH$_2$CH$_2$— or —CH$_2$CH$_2$CH$_2$CH$_2$CH$_2$— to form a 3-membered, 4-membered, 5-membered or 6-membered ring together with the carbon atoms attached to $R^4$ and $R^5$, each of $R^6$ and $R^7$ is independently a hydrogen atom or $C_1$-$C_6$ alkyl, $R^8$ is D1 to D23, E1 to E8, M1 to M9, $C_3$-$C_{10}$ cycloalkyl, F1, F2, $C_3$-$C_{10}$ cycloalkenyl, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^y$)—, —CH$_2$N($R^y$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N($R^y$)CH=CH—, —OCH=N—, —SCH=N—, —N($R^y$)CH=N—, —N($R^y$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, D1 to D23 are aromatic heterocyclic rings represented by the following structural formulae, respectively,

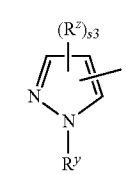
D1

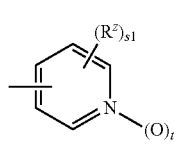
D2

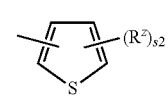
D3

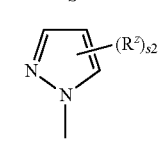
D4

D5

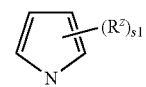
D6

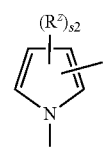
D7

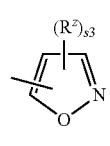
D8

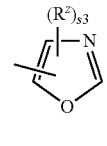
D9

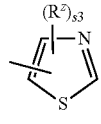
D10

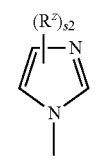
D11

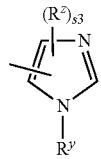
D12

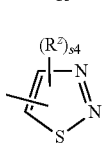
D13

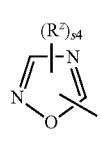
D14

D15

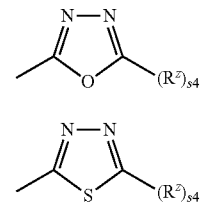
D16

D17 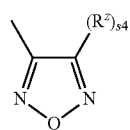
D18 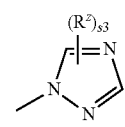
D19 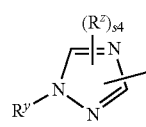
D20 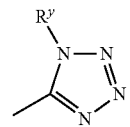
D21 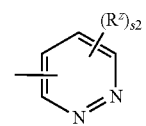
D22 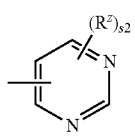
D23 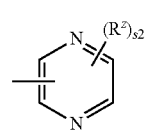
E1 to E8 are saturated heterocyclic rings represented by the following structural formulae, respectively,
E1 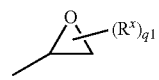
E2 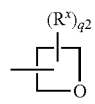
E3 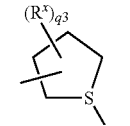
E4 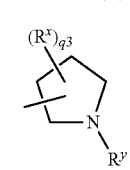
E5 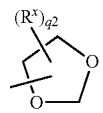
E6 
E7 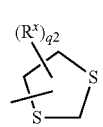
E8 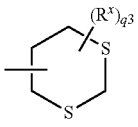
M1 to M9 are partially unsaturated aromatic heterocyclic rings represented by the following formulae, respectively,
M1 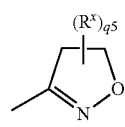
M2 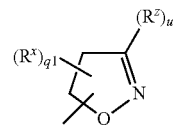
M3 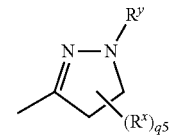
M4 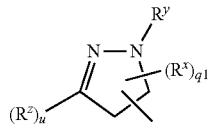
M5 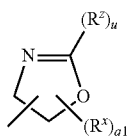
M6 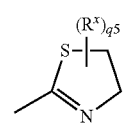

-continued

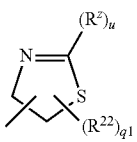
M7

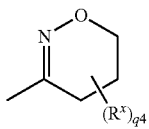
M8

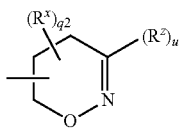
M9

F1 to F2 are rings represented by the following formulae, respectively,

F1

F2

$R^x$ is a hydrogen atom, $C_1$-$C_6$ alkyl, $C_1$-$C_6$ haloalkyl, $C_3$-$C_6$ cycloalkyl, $C_3$-$C_6$ halocycloalkyl, —$OR^{82}$, —$C(O)R^{12}$, —$C(O)OR^{12}$, phenyl, phenyl which may be substituted with d $R^{15}$'s, benzyl or benzyl having a benzene ring which may be substituted with d $R^{15}$'s, and when d is an integer of at least 2, each $R^{15}$ may be identical with or different from one another,
$R^y$ is $C_1$-$C_{10}$ alkyl, $C_1$-$C_{10}$ haloalkyl, $C_3$-$C_{10}$ cycloalkyl, $C_3$-$C_{10}$ halocycloalkyl, phenyl, phenyl which may be substituted with d $R^{15}$'s, benzyl or benzyl having a benzene ring which may be substituted with d $R^{15}$'s, and when d is an integer of at least 2, each $R^{15}$ may be identical with or different from one another,
$R^z$ is a halogen atom, cyano, nitro, $C_1$-$C_{10}$ alkyl, $C_1$-$C_{10}$ haloalkyl, $C_1$-$C_{10}$ alkoxy, $C_1$-$C_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —$C(O)NH_2$, —$C(S)NH_2$, —$S(O)_2NH_2$, phenoxy, phenyl or phenyl which may be substituted with m $R^{16}$'s, and when m is an integer of at least 2, each $R^{16}$ may be identical with or different from one another, and
when s1, s2 or s3 is an integer of at least 2, each $R^z$ may be identical with or different from one another, and
when there are two neighboring $R^z$'s, the two neighboring $R^z$'s, may form —$CH_2CH_2CH_2$—, —$CH_2CH_2CH_2OCH_2$—, —$OCH_2O$—, $CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$OCH_2CH_2O$—, —$OCH_2CH_2S$—, —$CH_2CH$═$CH$—, —$OCH$═$CH$—, —$SCH$═$CH$—, —$N(R^y)CH$═$CH$—, —$OCH$═$N$—, —$SCH$═$N$—, —$N(R^y)CH$═$N$—, —$N(R^y)N$═$CH$—, —$CH$═$CHCH$═$CH$—, —$OCH_2CH$═$CH$—, —$N$═$CHCH$═$CH$—, —$N$═$CHCH$═$N$— or —$N$═$CHN$═$CH$— to form, together with the carbon atoms attached to the two neighboring $R^z$'s, a 5-membered or 6-membered ring which may have one or more hydrogen atoms on the ring-constituting carbon atoms replaced by one or more Z's which may be identical with or different from one another, if two or more Z's are present,
$R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, $C_1$-$C_6$ alkoxy($C_1$-$C_6$) alkyl, $C_1$-$C_6$ alkoxy($C_1$-$C_6$) alkoxy, nitro, cyano or phenyl,
each of $R^{12}$ and $R^{13}$ is independently a hydrogen atom, $C_1$-$C_{10}$ alkyl, $C_3$-$C_{10}$ cycloalkyl, $C_1$-$C_{10}$ haloalkyl, $C_3$-$C_{10}$ halocycloalkyl, D1 to D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, and
when there are two neighboring $R^{14}$'s, the two neighboring $R^{14}$'s may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$CH_2OCH_2$—, —$OCH_2CH_2O$—, —$OCH_2CH_2S$—, —$CH_2CH$═$CH$—, —$OCH$═$CH$—, —$SCH$═$CH$—, —$N(R^y)CH$═$CH$—, —$OCH$═$N$—, —$SCH$═$N$—, —$N(R^y)CH$═$N$—, —$N(R^y)N$═$CH$—, —$CH$═$CHCH$═$CH$—, —$OCH_2CH$═$CH$—, —$N$═$CHCH$═$CH$—, —$N$═$CHCH$═$N$— or —$N$═$CHN$═$CH$— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present,
$R^{14}$ is a halogen atom, nitro, cyano, $C_1$-$C_{10}$ alkyl, $C_1$-$C_{10}$ haloalkyl, $C_1$-$C_{10}$ alkoxy, $C_1$-$C_{10}$ haloalkoxy, phenoxy or phenyl,
$R^{15}$ is a halogen atom, $C_1$-$C_6$ alkyl, $C_1$-$C_6$ alkoxy, $C_1$-$C_6$ haloalkyl, $C_1$-$C_6$ haloalkoxy, $C_3$-$C_6$ cycloalkyl, $C_3$-$C_6$ cycloalkoxy, $C_3$-$C_6$ halocycloalkyl, $C_3$-$C_6$ halocycloalkoxy, nitro, cyano or phenyl,
$R^{16}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_3$-$C_{10}$ cycloalkyl, $C_3$-$C_{10}$ cycloalkoxy, $C_3$-$C_{10}$ halocycloalkyl, $C_3$-$C_{10}$ halocycloalkoxy, nitro, cyano or phenyl, and when there are two neighboring $R^{16}$'s, the two neighboring $R^{16}$'s may form —$OCH_2O$— to form a 5-membered ring together with the carbon atoms to the two $R^{16}$'s,
$R^{17}$ is —$C(O)OR^{12}$, phenyl or phenyl substituted with a $R^{11}$'s, and when a is an integer of at least 2, each $R^{11}$ may be identical with or different from one another,
$R^{21}$ is a halogen atom, nitro, cyano, $C_1$-$C_{10}$ alkyl, $C_1$-$C_{10}$ haloalkyl, $C_3$-$C_{10}$ cycloalkyl, $C_3$-$C_{10}$ halocycloalkyl, $C_1$-$C_6$ alkoxy($C_1$-$C_6$) alkyl, —$OR^{23}$, —$C(O)R^{24}$, —$C(O)OR^{24}$, —$NR^{24}R^{25}$, —$C(O)NR^{24}R^{25}$, —$S(O)_2NR^{24}R^{25}$, phenyl or phenyl which may be substituted with f $R^{22}$'s, and when f is an integer of at least 2, each $R^{22}$ may be identical with or different from one other, and
when there are two neighboring $R^{22}$'s, the two neighboring $R^{22}$'s may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2N(R^y)$—, —$CH_2N(R^y)CH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —OCH$_2$CH$_2$S—, —CH$_2$CH=CH—, —OCH=CH—, —SCH=CH—, —N(R$^{3'}$)CH=CH—, —OCH=N—, —SCH=N—, —N(R$^{3'}$)CH=N—, —N(R$^{3'}$)N=CH—, —CH=CHCH=CH—, —OCH$_2$CH=CH—, —N=CHCH=CH—, —N=CHCH=N— or —N=CHN=CH— to form, together with the carbon atoms attached to the two R$^{22}$'s, a 5-membered or 6-membered ring which may have one or more hydrogen atoms on the ring-constituting carbon atoms replaced by one or more Z's which may be identical with or different from one another, if two or more Z's are present, R$^{22}$ is a halogen atom, C$_1$-C$_{10}$ alkyl, C$_1$-C$_{10}$ alkoxy, C$_1$-C$_{10}$ haloalkyl, C$_1$-C$_{10}$ haloalkoxy, C$_3$-C$_{10}$ cycloalkyl, C$_3$-C$_{10}$ cycloalkoxy, C$_3$-C$_{10}$ halocycloalkyl, C$_3$-C$_{10}$ halocycloalkoxy, nitro, cyano or phenyl, R$^{23}$ is a hydrogen atom, C$_1$-C$_{10}$ alkyl, C$_1$-C$_{10}$ haloalkyl, C$_3$-C$_{10}$ cycloalkyl, C$_3$-C$_{10}$ halocycloalkyl, C$_1$-C$_6$ alkoxy(C$_1$-C$_6$) alkyl, phenyl, phenyl which may be substituted with f R$^{22}$'s, benzyl or benzyl having a benzene ring which may be substituted with f R$^{22}$'s, when f is an integer of at least 2, each R$^{22}$ may be identical with different from one another, each of R$^{24}$ and R$^{25}$ is independently a hydrogen atom, C$_1$-C$_{10}$ alkyl, C$_3$-C$_{10}$ cycloalkyl, C$_1$-C$_{10}$ haloalkyl, C$_3$-C$_{10}$ halocycloalkyl, benzyl, benzyl having a benzene ring which may optionally be substituted with b R$^{14}$'s, 1-phenethyl, 1-phenethyl having a benzene ring which may optionally be substituted with b R$^{14}$'s, 2-phenethyl, 2-phenethyl having a benzene ring which may optionally be substituted with b R$^{14}$'s, phenyl or phenyl which may optionally be substituted with b R$^{14}$'s, and when b is an integer of at least 2, each R$^{14}$ may be identical with or different from one another, R$^{31}$ is a halogen atom or phenyl, each of R$^{32}$, R$^{33}$ and R$^{34}$ is independently C$_1$-C$_{10}$ alkyl, C$_3$-C$_{10}$ cycloalkyl, benzyl, benzyl having a benzene ring which may optionally be substituted with b R$^{14}$'s, phenyl or phenyl which may optionally be substituted with b R$^{14}$'s, and when b is an integer of at least 2, each R$^{14}$ may be identical with or different from one another, R$^{81}$ is a halogen atom, nitro, cyano, C$_1$-C$_{10}$ alkyl, C$_1$-C$_{10}$ haloalkyl, C$_3$-C$_{10}$ cycloalkyl, C$_3$-C$_{10}$ halocycloalkyl, C$_1$-C$_6$ alkoxy(C$_1$-C$_6$) alkyl, —OR$^{23}$, —C(R$^{83}$)=NR$^{84}$, —C(R$^{83}$)=NOR$^{84}$, —C(O)R$^{24}$, —C(O)OR$^{24}$, —S(O)CR$^{24}$, —OS(O)$_2$R$^{24}$, —NR$^{24}$R$^{25}$, —C(O)NR$^{24}$R$^{25}$, —C(S)NH$_2$, —S(O)$_2$NR$^{24}$R$^{25}$, phenyl or phenyl which may be substituted with m R$^{22}$'s, and when m is an integer of at least 2, each R$^{22'}$ may be identical with or different from one another, R$^{82}$ is a hydrogen atom, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy(C$_1$-C$_6$) alkyl, phenyl, phenyl which may be substituted with d R$^{15}$'s, benzyl or benzyl having a benzene ring which may be substituted with d R$^{15}$'s, and when d is an integer of at least 2, each R$^{15'}$ may be identical with or different from one another, each of R$^{83}$ and R$^{84}$ is independently a hydrogen atom, C$_1$-C$_6$ alkyl, C$_1$-C$_6$ haloalkyl, C$_3$-C$_6$ cycloalkyl, C$_3$-C$_6$ halocycloalkyl, phenyl, phenyl which may be substituted with d R$^{15}$'s, benzyl or benzyl having a benzene ring which may be substituted with d R$^{15}$'s, and when d is an integer of at least 2, each R$^{15'}$ may be identical with or different from one another, Z is a halogen atom, cyano, nitro, C$_1$-C$_{10}$ alkyl, C$_1$-C$_{10}$ haloalkyl, C$_1$-C$_{10}$ alkoxy, C$_1$-C$_{10}$ haloalkoxy, alkylsulfonyloxy, haloalkylsulfonyloxy, alkylthio, haloalkylthio, alkylsulfinyl, haloalkylsulfinyl, alkylsulfonyl, haloalkylsulfonyl, —C(O)NH$_2$, —C(S)NH$_2$ or —S(O)$_2$NH$_2$, a, b, d, e, f, g, k and m are integers of from 0 to 5, c is an integer of from 0 to 2, q1 is an integer of from 0 to 3, q2 is an integer of from 0 to 5, q3 is an integer of from 0 to 7, q4 is an integer of from 0 to 6, q5 is an integer of from 0 to 4, r is an integer of from 0 to 2, s1 is an integer of from 0 to 4, s2 is an integer of from 0 to 3, s3 is an integer of from 0 to 2, s4 is an integer of 0 or 1, n is an integer of 1, t is an integer of from 0 or 1, u is an integer of 0 or 1], a tautomer of the compound or a pharmaceutically acceptable salt or solvate thereof.

[2] The method of producing hematopoietic stem cells and/or hematopoietic progenitor cells according to claim 1, wherein X is —(CR$^6$R$^7$)$_n$—.

[3] The method of producing hematopoietic stem cells and/or hematopoietic progenitor cells according to claim 2, wherein R$^1$ is C$_1$-C$_{10}$ alkyl, C$_1$-C$_{10}$ alkyl substituted with R$^{17}$, C$_1$-C$_6$ haloalkyl, C$_3$-C$_6$ cycloalkyl, —C(O)R$^{12}$, —C(O)OR$^{12}$, —C(O)N(R$^{13}$)R$^{12}$, —C(R$^{12}$)=NR$^{13}$, —C(R$^{12}$)=NOR$^{13}$, D1 to D12, D18, D19, D21 to D23, phenyl or phenyl substituted with a R$^{11}$'s, and when a is an integer of at least 2, each R$^{11}$ may be identical with or different from one another, when there are two neighboring R$^{11}$'s, the two neighboring R$^{11}$'s may form —OCH$_2$O—, —OCH$_2$CH$_2$O—, —OCH=CH—, —CH=CHCH=CH— or —N=CHCH=CH— to form, together with the carbon atoms attached to the two R$^{11}$'s, a 5-membered or 6-membered ring which may have one or more hydrogen atoms on the ring-constituting carbon atoms optionally replaced by one or more Z's which may be identical with or different from one another, if two or more Z's are present, R$^2$ is a hydrogen atom, a halogen atom, C$_1$-C$_6$ alkyl, C$_3$-C$_6$ cycloalkyl, D1, D2, D4 to D12, D18, D19, D21 to D23, —C(O)R$^{12}$, —C(O)OR$^{12}$, benzyl, benzyl having a benzene ring optionally substituted with e R$^{21}$'s, phenyl or phenyl optionally substituted with e R$^{21}$'s, when e is an integer of at least 2, each R$^{21}$ may be identical with or different from one another, when there are two neighboring R$^{21}$'s, the two neighboring R$^{21}$'s may form —OCH$_2$O—, —OCH$_2$CH$_2$O—, —OCH=CH— or —CH=CHCH=CH— to form, together with the carbon atoms attached to the two R$^{21}$'s, a 5-membered or 6-membered ring which may have one or more hydrogen atoms on the ring-constituting carbon atoms replaced by one or more Z's which may be identical with or different from one another, if two or more Z's are present, R$^3$ is a hydrogen atom, C$_1$-C$_4$ alkyl, C$_3$-C$_4$ cycloalkyl, C$_1$-C$_4$ alkoxy(C$_1$-C$_4$) alkyl, —C(O)R$^{12}$, —C(O)OR$^{12}$, —C(O)N(R$^{12}$)R$^{13}$, —Si(R$^{32}$)(R$^{33}$)R$^{34}$, benzyl or benzyl having a benzene ring which may be substituted with g R$^{15}$'s, and when g is an integer of at least 2, each R$^{15}$ may be identical with or different from one another, each of R$^4$ and R$^5$ is independently C$_1$-C$_4$ alkyl, each of R$^6$ and R$^7$ is a hydrogen atom, R$^8$ is D1, D2, D4, D5, D7 to D12, D19, D22, D23, E1 to E8, F1, F2, C$_3$-C$_{10}$ cycloalkyl, phenyl or phenyl optionally substituted with k R$^{81}$'s, and when k is an integer of at least 2, each R$^{81}$ may be identical with or different from one another, when there are two neighboring R$^{81}$'s, the two neighboring R$^{81}$'s may form —OCH$_2$O—, —CH$_2$CH$_2$CH$_2$—, —OCH$_2$CH$_2$O—, —OCH=CH—, —CH=CHCH=CH— or —N=CHCH=CH— to form, together with the carbon atoms attached to the two R$^{81}$'s, a 5-membered or 6-membered ring which may have one or more hydrogen atoms on the ring-constituting carbon atoms replaced by one or more Z's which may be identical with or different from one another, if two or more Z's are present, $R^x$ is a hydrogen atom, $C_1$-$C_6$ alkyl, $C_1$-$C_6$ haloalkyl or phenyl, $R^y$ is $C_1$-$C_6$ alkyl, $C_3$-$C_6$ cycloalkyl, phenyl or phenyl which may be substituted with d $R^{15}$'s, and when d is an integer of at least 2, each $R^{15}$ may be identical with or different from one another, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, $R^{11}$ is a halogen atom, $C_1$-$C_{10}$ alkyl, $C_1$-$C_{10}$ alkoxy, $C_1$-$C_{10}$ haloalkyl, —$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl, each of $R^{12}$ and $R^{13}$ is independently a hydrogen atom, $C_1$-$C_6$ alkyl, $C_3$-$C_6$ cycloalkyl, $C_1$-$C_6$ haloalkyl, $C_1$-$C_6$ halocycloalkyl, D2, D4, D5, D7, D21, D22, D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, when there are two neighboring $R^{14}$'s, the two neighboring $R^{14}$'s may form —$OCH_2O$—, —$OCH_2CH_2O$—, —$OCH=CH$—, —$CH=CHCH=CH$— or —$N=CHCH=CH$— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present, $R^{14}$ is a halogen atom, nitro, cyano, $C_1$-$C_6$ alkyl, $C_1$-$C_6$ haloalkyl, —$C_6$ alkoxy, —$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy, and when there are two neighboring $R^{16}$'s, the two neighboring $R^{16}$'s may form —$OCH_2O$— to form a 5-membered ring together with the carbon atoms to the two $R^{16}$'s, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, —$C_{10}$ haloalkoxy, nitro, cyano, phenoxy, phenyl or phenyl which may be substituted with f $R^{22}$'s, and when f is an integer of at least 2, each $R^{22}$ may be identical with or different from one other, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$'s, the two neighboring $R^{22}$'s may form —$OCH_2O$— to form, together with the carbon atoms attached to the two $R^{22}$'s, a 5-membered ring each of $R^{32}$, $R^{33}$ and $R^{34}$ is independently $C_1$-$C_6$ alkyl, $C_3$-$C_6$ cycloalkyl, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl.

[4] The method of producing hematopoietic stem cells and/or hematopoietic progenitor cells according to claim 3, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —$C(O)OR^{12}$, D2, D4, D5, D7, D21 to D23, phenyl or phenyl substituted with a $R^{11}$'s, and when a is an integer of at least 2, each $R^{11}$ may be identical with or different from one another, when there are two neigh $R^{11}$'s, the two neighboring $R^{11}$'s may form —$CH=CHCH=CH$— to form, together with the carbon atoms attached to the two $R^{11}$'s, a 6-membered ring which may have one or more hydrogen atoms on the ring-constituting carbon atoms replaced by one or more Z's which may be identical with or different from one another, if two or more Z's are present, $R^2$ is a hydrogen atom, a halogen atom, $C_1$-$C_6$ alkyl, $C_3$-$C_6$ cycloalkyl, D2, D7, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —$OCH_2O$—, —$OCH_2CH_2O$—, —$OCH=CH$— or —$CH=CHCH=CH$— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —$C(O)R^{12}$, —$C(O)OR^{12}$, —$C(O)N(R^{12})R^{13}$, —$Si(R^{32})(R^{33})R^{34}$ or benzyl, $R^8$ is D2, D7, D23, F1, F2, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —$OCH_2O$—, —$CH_2CH_2CH_2$— or —$CH=CHCH=CH$— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, each of $R^{12}$ and $R^{13}$ is independently a hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, $R^{17}$ is —$C(O)OR^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, each of $R^{32}$, $R^{33}$ and $R^{34}$ is independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy.

[5] The method of producing hematopoietic stem cells and/or hematopoietic progenitor cells according to claim 4, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, and when a is an integer of at least 2, each $R^{11}$ may be identical with or different from one another, $R^2$ is a hydrogen atom, a halogen atom, $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $R^8$ is D2, F1, F2, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, $R^{12}$ is $C_1$-$C_6$ alkyl, $R^{17}$ is —C(O)OR$^{12}$ or phenyl, $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and $R^{81}$ is a halogen atom, $C_1$-$C_6$ alkyl, $C_1$-$C_6$ haloalkyl, $C_1$-$C_6$ alkoxy, phenyl or phenoxy.

[6] The method of producing hematopoietic stem cells and/or hematopoietic progenitor cells according to claim 1, wherein $R^2$ is a hydrogen atom, a halogen atom, cyano, $C_1$-$C_{10}$ alkyl, $C_1$-$C_{10}$ alkyl substituted with $R^{17}$, $C_3$-$C_{10}$ cycloalkyl, $C_2$-$C_{10}$ alkenyl, $C_2$-$C_{10}$ alkenyl substituted with a halogen atom, $C_2$-$C_{10}$ alkynyl, $C_2$-$C_{10}$ alkynyl substituted with a halogen atom, —C(O)R$^{12}$, —C(O)OR$^{12}$, —C(R$^{12}$)=NR$^{13}$, —C(R$^{12}$)=NOR$^{13}$, D1 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^y$)—, —CH$_2$N(R$^y$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^y$)CH=CH—, —OCH=N—, —SCH=N—, —N(R$^y$)CH=N—, —N(R$^y$)N=CH—, —CH=CHCH=CH—, —OCH$_2$CH=CH—, —N=CHCH=CH—, —N=CHCH=N— or —N=CHN=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, and X is a single bond.

[7] The method of producing hematopoietic stem cells and/or hematopoietic progenitor cells according to claim 6, wherein $R^1$ is $C_1$-$C_{10}$ alkyl, $C_1$-$C_{10}$ alkyl substituted with $R^{17}$, $C_1$-$C_6$ haloalkyl, $C_3$-$C_6$ cycloalkyl, —C(O)R$^{12}$, —C(O)OR$^{12}$, —C(O)N(R$^{13}$)R$^{12}$, —C(R$^{12}$)=NOR$^{13}$, D1 to D12, D18, D19, D21 to D23, phenyl or phenyl substituted with a $R^{11}$'s, when a is an integer of at least 2, each $R^{11}$ may be identical with or different from one another, and when there are two neighboring $R^{11}$'s, the two neighboring $R^{11}$'s may form —OCH$_2$O—, —OCH$_2$CH$_2$O—, —OCH=CH—, —CH=CHCH=CH— or —N=CHCH=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is $C_1$-$C_6$ alkyl, $C_3$-$C_6$ cycloalkyl, D1, D2, D4 to D12, D18, D19, D21 to D23, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, and when there are two neighboring $R^{21}$'s, the two neighboring $R^{21}$'s may form —OCH$_2$O—, —OCH$_2$CH$_2$O—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)R$^{12}$, —C(O)OR$^{12}$, —C(O)N(R$^{12}$)R$^{13}$, —Si(R$^{32}$)(R$^{33}$)R$^{34}$, benzyl or benzyl having a benzene ring which may be substituted with g $R^{15}$'s, and when g is an integer of at least 2, each $R^{15}$ may be identical with or different from one another, each of $R^4$ and $R^5$ is independently $C_1$-$C_4$ alkyl, $R^8$ is D1, D2, D4, D5, D7 to D12, D19, D22, D23, E1 to E9, F1, F2, $C_3$-$C_{10}$ cycloalkyl, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —OCH$_2$O—, —CH$_2$CH$_2$CH$_2$—, —OCH$_2$CH$_2$O—, —OCH=CH—, —CH=CHCH=CH— or —N=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^x$ is a hydrogen atom, $C_1$-$C_6$ alkyl, $C_1$-$C_6$ haloalkyl or phenyl, $R^y$ is $C_1$-$C_6$ alkyl, $C_3$-$C_6$ cycloalkyl, phenyl or phenyl which may be substituted with d $R^{15}$'s, benzyl or benzyl having a benzene ring which may be substituted with d $R^{15}$'s, and when d is an integer of at least 2, each $R^{15}$ may be identical with or different from one another, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s1, s2 or s3 is an integer of at least 2, each $R^z$ may be identical with or different from one another, $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, $C_1$-$C_6$ alkoxy($C_1$-$C_6$) alkyl, $C_1$-$C_6$ alkoxy($C_1$-$C_6$) alkoxy, nitro or phenyl, each of $R^{12}$ and $R^{13}$ is independently a hydrogen atom, $C_1$-$C_6$ alkyl, $C_3$-$C_6$ cycloalkyl, $C_1$-$C_6$ haloalkyl, $C_3$-$C_6$ halocycloalkyl, D2, D4, D5, D7, D21, D22, D23, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, and when there are two neighboring $R^{14}$'s, the two neighboring $R^{14}$'s may form —OCH$_2$O—, —OCH$_2$CH$_2$O—, —OCH=CH—, —CH=CHCH=CH— or —N=CHCH=CH— to form, together with the carbon atoms attached to the two $R^{14}$'s, a 5-membered or 6-membered ring which may have one or more hydrogen atoms on the ring-constituting carbon atoms replaced by one or more Z's which may be identical with or different from one another, if two or more Z's are present, $R^{14}$ is a halogen atom, nitro, cyano, $C_1$-$C_6$ alkyl, $C_1$-$C_6$ haloalkyl, $C_1$-$C_6$ alkoxy, $C_1$-$C_6$ haloalkoxy, phenoxy or phenyl, $R^{15}$ is a halogen atom, $C_1$-$C_6$ alkyl, $C_1$-$C_6$ alkoxy or $C_1$-$C_6$ haloalkyl, $R^{16}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{16}$'s, the two neighboring $R^{16}$'s may form —OCH$_2$O— to form a 5-membered ring together with the carbon atoms to the two $R^{16}$'s, $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one other, $R^{22}$ is a halogen atom, $C_1$-$C_{10}$ alkyl, $C_1$-$C_{10}$ alkoxy, $C_1$-$C_{10}$ haloalkyl or $C_1$-$C_{10}$ haloalkoxy and when there are two neighboring $R^{22}$'s, the two neighboring $R^{22}$'s may form —OCH$_2$O— to form, together with the carbon atoms attached to the two $R^{22}$'s, a 5-membered ring, each of $R^{32}$, $R^{33}$ and $R^{34}$ is independently $C_1$-$C_6$ alkyl, $C_3$-$C_6$ cycloalkyl, benzyl, benzyl having a benzene ring which may optionally be substituted with b $R^{14}$'s, phenyl or phenyl which may optionally be substituted with b $R^{14}$'s, and when b is an integer of at least 2, each $R^{14}$ may be identical with or different from one another, $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_6$ alkoxy($C_1$-$C_6$) alkyl, $C_1$-$C_6$ alkoxy($C_1$-$C_6$) alkoxy, $C_3$-$C_6$ cycloalkyl, $C_3$-$C_6$ halocycloalkyl, phenyl, phenoxy, nitro or cyano, and Z is a halogen atom or $C_1$-$C_6$ alkyl.

[8] The method of producing hematopoietic stem cells and/or hematopoietic progenitor cells according to claim 7, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, —C(O)OR$^{12}$, D2, D4, D5, D7, D21, D23, phenyl or substituted with a $R^{11}$'s, when a is an integer of at least 2, each $R^{11}$ may be identical with or different from one another, and when there are two neighboring $R^{11}$'s, the two neighboring $R^{11}$'s may form —CH=CHCH=CH— to form, together with the carbon atoms attached to the two $R^{11}$'s, a 5-membered or 6-membered ring which may have one or more hydrogen atoms on the ring-constituting carbon atoms replaced by one or more Z's which may be identical with or different from one another, if two or more Z's are present, $R^2$ is $C_1$-$C_6$ alkyl, $C_3$-$C_6$ cycloalkyl, D2, D7, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $C_1$-$C_4$ alkyl, $C_3$-$C_4$ cycloalkyl, $C_1$-$C_4$ alkoxy($C_1$-$C_4$) alkyl, —C(O)R$^{12}$, —C(O)OR$^{12}$, —C(O)N(R$^{12}$)R$^{13}$, —Si(R$^{32}$)(R$^{33}$)R$^{34}$ or benzyl, $R^8$ is D2, D7, D23, F1, F2, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 or s3 is an integer of at least 2, each $R^z$ may be identical with or different from one another, each of $R^{12}$ and $R^{13}$ is independently a hydrogen atom, $C_1$-$C_6$ alkyl or $C_3$-$C_6$ cycloalkyl, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, $R^{17}$ is —C(O)OR$^{12}$ or phenyl, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, each of $R^{32}$, $R^{33}$ and $R^{34}$ is independently $C_1$-$C_6$ alkyl or $C_3$-$C_6$ cycloalkyl, and $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl or phenoxy.

[9] The method of producing hematopoietic stem cells and/or hematopoietic progenitor cells according to claim 8, wherein $R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, when a is an integer of at least 2, each $R^{11}$ may be identical with or different from one another, $R^2$ is $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^3$ is a hydrogen atom, $R^8$ is D2, F1, F2, phenyl or phenyl optionally substituted with k $R^{81}$'s, and when k is an integer of at least 2, each $R^{81}$ may be identical with or different from one another, and when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, $R^{12}$ is $C_1$-$C_6$ alkyl, $R^{17}$ is —$C(O)OR^{12}$ or phenyl, $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, and $R^{81}$ is a halogen atom, $C_1$-$C_6$ alkyl, $C_1$-$C_6$ haloalkyl, $C_1$-$C_6$ alkoxy or phenoxy.

[10] The method of producing hematopoietic stem cells and/or hematopoietic progenitor cells according to any one of the above [1] to [9], wherein the hematopoietic stem cells and/or hematopoietic progenitor cells to be expanded ex vivo are CD34$^+$ cells.

[11] The method of producing hematopoietic stem cells and/or hematopoietic progenitor cells according to any one of the above [1] to [9], wherein the hematopoietic stem cells and/or hematopoietic progenitor cells to be expanded ex vivo are CD34$^+$CD38$^-$ cells.

[12] The method of producing hematopoietic stem cells and/or hematopoietic progenitor cells according to any one of the above [1] to [9], wherein the cells to be expanded are HPP-CFU colony forming cells.

[13] The method of producing hematopoietic stem cells and/or hematopoietic progenitor cells according to any one of the above [1] to [9] wherein the cells to be expanded are SCID-repopulating cells (SRC).

[14] The method of producing hematopoietic stem cells and/or hematopoietic progenitor cells according to any one of the above [1] to [13], which uses a culture medium containing at least one blood cell stimulating factor.

[15] The method of producing hematopoietic stem cells and/or hematopoietic progenitor cells according to the above [14], wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

[16] The method of producing hematopoietic stem cells and/or hematopoietic progenitor cells according to the above [15], wherein the blood cell stimulating factor is at least one species selected from the group consisting of stem cell factor (SCF), thrombopoietin (TPO) and flk2/flt3 ligand (FL).

[17] The method of producing hematopoietic stem cells and/or hematopoietic progenitor cells according to any one of the above [1] to [16], wherein the hematopoietic stem cells are obtained from the bone marrow, the liver, the spleen, peripheral blood or cord blood.

[18] The method of producing hematopoietic stem cells and/or hematopoietic progenitor cells according to the above [17], wherein the hematopoietic stem cells are obtained from cord blood.

[19] The method of producing hematopoietic stem cells and/or hematopoietic progenitor cells according to the above [18], which comprises culturing hematopoietic stem cells and/or hematopoietic progenitor cells in the presence of at least one species selected from the group consisting of stem cell factor (SCF), thrombopoietin (TPO) and flk2/flt3 ligand (FL).

[20] Hematopoietic stem cells and/or hematopoietic progenitor cells obtained by the method as defined in any one of the above [1] to [19].

[21] A cell therapy material to be transplanted into a human for treatment of a disease, which comprises hematopoietic stem cells and/or hematopoietic progenitor cells produced by the method as defined in any one of the above [1] to [19].

[22] A reagent kit for expanding hematopoietic stem cells and/or hematopoietic progenitor cells, which comprises a compound represented by the following formula (I), a tautomer or pharmaceutically acceptable salt of the compound or a solvate thereof as an active ingredient.

[23] A method of producing transformed hematopoietic stem cells, which comprises transferring a gene into hematopoietic stem cells and/or hematopoietic progenitor cells while culturing the hematopoietic stem cells and/or hematopoietic progenitor cells ex vivo in the presence of a compound represented by the following formula (I), a tautomer or pharmaceutically acceptable salt of the compound or a solvate thereof, or expanding hematopoietic stem cells carrying a gene transferred into them by culturing the hematopoietic stem cells ex vivo in the presence of a compound represented by the formula (I), a tautomer or pharmaceutically acceptable salt of the compound or a solvate thereof.

[24] The method of producing transformed hematopoietic stem cells according to the above [23], which uses a culture medium containing at least one blood cell stimulating factor.

[25] The method of producing transformed hematopoietic stem cells according to the above [24], wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

[26] The method of producing transformed hematopoietic stem cells according to any one of the above [23] to [25], wherein the hematopoietic stem cells and/or hematopoietic progenitor cells are obtained from the bone marrow, the liver, the spleen, peripheral blood or cord blood.

[27] Transformed hematopoietic stem cells obtained by the method as defined in any one of the above [23] to [26].

[28] A cell therapy material to be transplanted into a human for treatment of a disease, which comprises transformed hematopoietic stem cells produced by the method as defined in any one of the above [23] to [26].

[29] The cell therapy material according to the above [21] or [28], wherein the disease to be treated is leukemia, aplastic anemia, granulocytopenia, lymphopenia, thrombocytopenia, myelodysplastic syndrome, malignant lymphoma, myeloproliferative disease, a genetic blood disease, a solid tumor, an autoimmune disease, immunodeficiency, diabetes mellitus, nerve injury, muscle injury, cerebral infarction, myocardial infarction or obstructive arteriosclerosis.

Advantageous Effect(s) of Invention

According to the present invention, it is possible to expand hematopoietic stem cells and/or hematopoietic progenitor cells by culturing hematopoietic stem cells ex vivo by using pyrazole compounds represented by the above-mentioned chemical formula (hereinafter referred to also as specific compounds). Hematopoietic stem cells and/or hematopoietic progenitor cells produced by using the specific compounds can be used as a cell transplant for treatment of diseases. The specific compounds of the present invention also make it possible to provide a cell transplant (graft) soon as required even from a transplant source which can be obtained in a limited amount, by expanding hematopoietic stem cells and/or hematopoietic progenitor cells easily. Because the specific compounds of the present invention have an effect of expanding hematopoietic stem cells and/or hematopoietic progenitor cells, they are useful as pharmaceutical agents for use in vivo and can be used as preventing, therapeutic or alleviating agent for diseases against which in vivo expansion of hematopoietic stem cells and/or hematopoietic progenitor cells is effective.

The specific compounds of the present invention are low-molecular-weight compounds which can be produced by ordinary processes for organic synthesis. Therefore, they can be easily produced under conditions under which cells of microorganisms and the like are inviable and can be obtained nearly free of impurities by stricter purification. Therefore, the method using the specific compounds makes it possible to prevent contamination with an unknown pathogen or a biomaterial from an animal other than human, as compared with conventional methods using a protein such as cytokines and growth factors obtained by gene recombination technology. Namely, hematopoietic stem cells produced by the method of the present invention can avoid infection, contamination with foreign genes or immune response to foreign proteins. While being proteins, cytokines and growth factors can be stored or used within very narrow optimal ranges in terms of pH, heat and ion strength, the specific compounds can be used and stored under relatively broad ranges of conditions. In addition, because the specific compounds can be produced inexpensively and continuously unlike proteins, it is possible to eventually reduce treatment cost.

DESCRIPTION OF DRAWING(S)

FIG. 1 A graph showing that $CD34^+$ cells were expanded more remarkably in a culture of $CD34^+$ cells in the presence of a specific compound than in the absence of the specific compound. The ordinate of the graph is the number of $CD34^+$ cells cultured in the presence of the specific compound relative to that in the absence of the compound.

Figure 2:
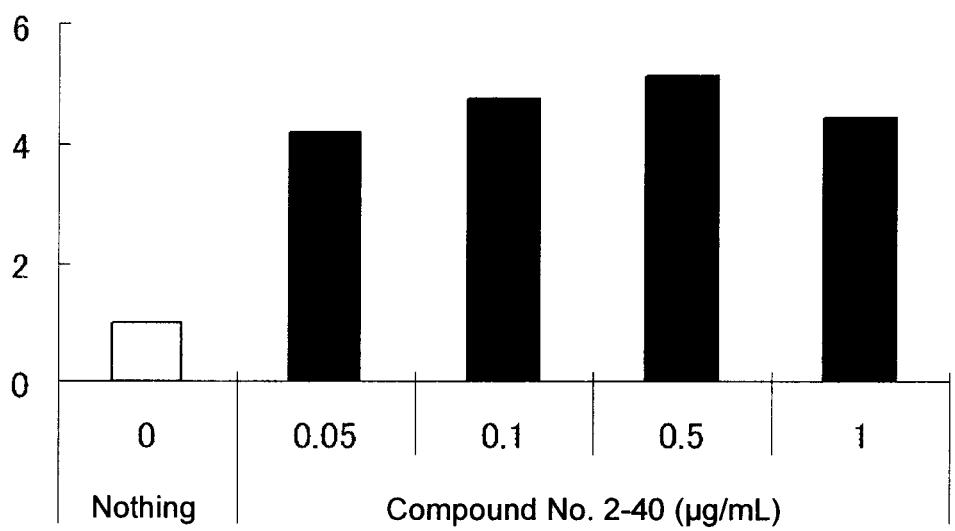

FIG. 2 A graph showing that $CD34^+CD38^-$ cells were expanded more remarkably in a culture of $CD34^+$ cells in the presence of a specific compound than in the absence of the specific compound. The ordinate of the graph is the number of $CD34^+CD38^-$ cells cultured in the presence of the specific compound relative to that in the absence of the compound.

Figure 3:
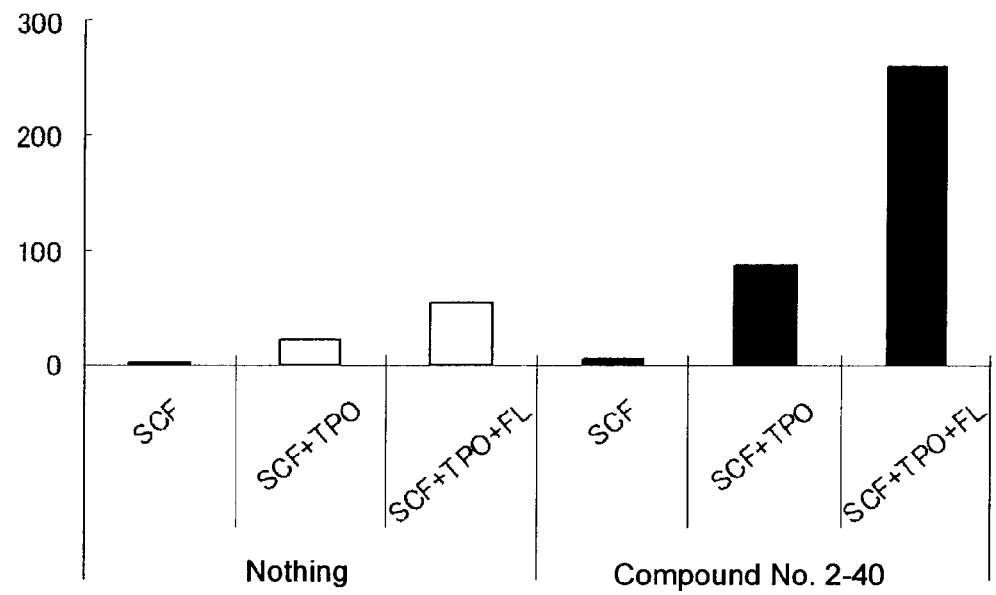

FIG. 3 A graph showing that $CD34^+CD38^-$ cells were expanded more remarkably in a culture of $CD34^+$ cells in the presence of a specific compound than in the absence of the specific compound. The ordinate of the graph is the number of $CD34^+CD38^-$ cells cultured in the presence of the specific compound relative to that in the absence of the compound.

Figure 4:
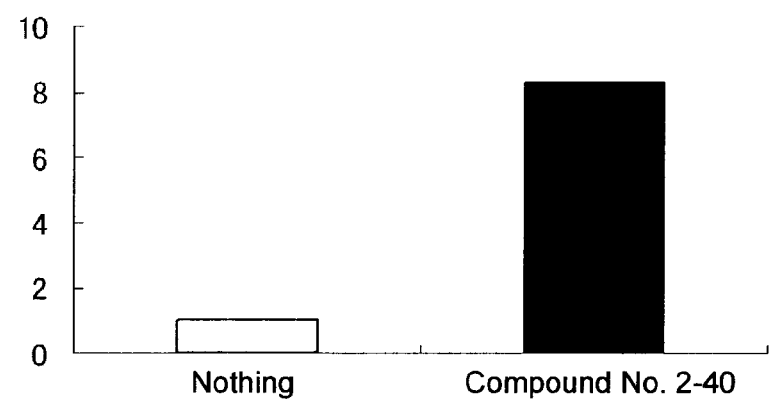

FIG. 4 A graph showing that $CD34^+CD38^-$ cells were expanded more remarkably in a culture of $CD34^+CD38^-$ cells in the presence of a specific compound than in the absence of the specific compound. The ordinate of the graph is the number of $CD34^+CD38^-$ cells cultured in the presence of the specific compound relative to that in the absence of the compound.

Figure 5:
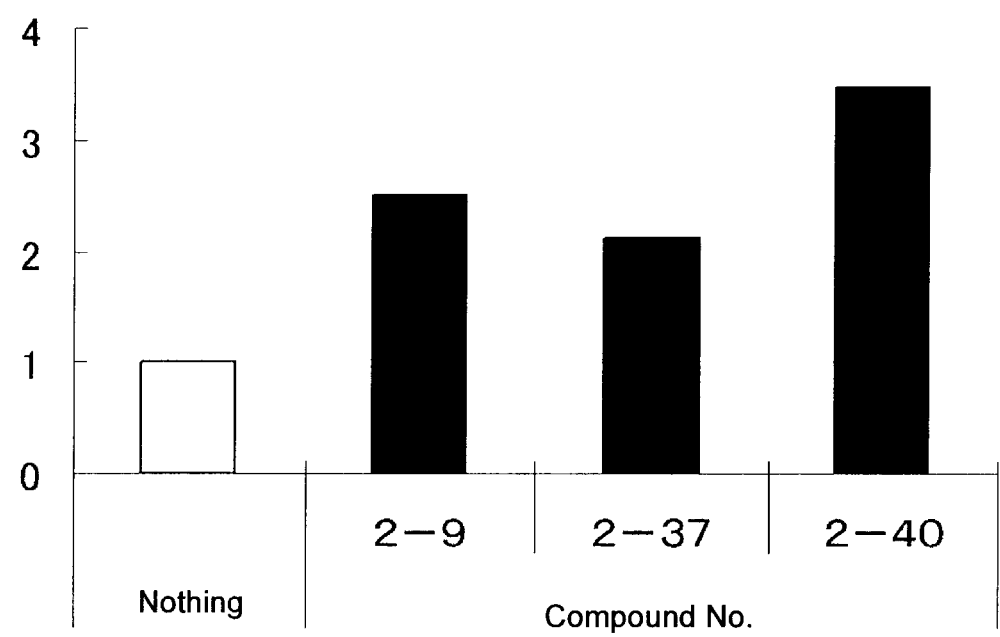

FIG. 5 A graph showing that SRC were expanded more remarkably from $CD34^+$ cells cultured in the presence of a specific compound than from $CD34^+$ cells cultured in the absence of the compound, when assayed after transplantation of the cultured $CD34^+$ cells into immunodeficient mice. The ordinate of the graph is the engrafted proportion of human $CD45^+$ cells in the mice transplanted with the $CD34^+$ cells cultured in the presence of the specific compound based on the proportion of human $CD45^+$ cells in the mice transplanted with those in the absence of the compound.

DESCRIPTION OF EMBODIMENT(S)

Now, the present invention will be described in further detail.

The terms used herein are defined as follows.

Hematopoietic stem cells are defined as cells having both pluripotency which allows them to differentiate into blood cells of all lineages and the ability to regenerate themselves while maintaining the pluripotency.

Multipotent hematopoietic progenitor cells are cells which can differentiate into a plurality of blood cell lineages, though not into all blood cell lineages.

Unipotent hematopoietic progenitor cells are cells which can differentiate into only one blood cell lineage.

Hematopoietic progenitor cells are a group of cells which covers both multipotent and unipotent hematopoietic progenitor cells. For example, the hematopoietic progenitor cells in the present invention may be granulocyte-macrophage colony forming cells (CFU-GM), eosinophil colony forming cells (EO-CFC), erythroid burst forming cells (BFU-E) as erythroid progenitor cells, megakaryocyte colony forming cells (CFU-MEG) or myeloid stem cells (mixed colony forming cells, CFU-GEMM). Among them, cells forming multipotent colonies with diameters of at least 1 mm are called HPP-CFU colony forming cells and are defined as the least differentiated hematopoietic progenitor cells, along with mixed colony forming cells (CFU-GEMM) (McNiece, I. K., et al. 1989. Detection of a human CFC with a high proliferative potential. Blood. 74: 609-612.).

$CD34^+$ means expressing CD (cluster of differentiation) 34 antigen on the cell surface. This antigen is a marker for hematopoietic stem cells and/or hematopoietic progenitor cells and disappears as the cell differentiates. Populations of $CD34^+$ cells are enriched with hematopoietic stem cells and/or hematopoietic progenitor cells. In the present invention, $CD34^+$ cells mean a cell population containing $CD34^+$ cells unless otherwise noted. The same applies to the after-mentioned $CD34^+CD38^-$ cells.

$CD38^-$ means not expressing CD38 antigen on the cell surface. The expression of this antigen increases as blood cells differentiate.

$CD34^+CD38^-$ cells mean cells expressing CD34 antigen but not expressing CD38 antigen. $CD34^+CD38^-$ cells are characterized as a group of cells containing more hematopoietic stem cells than $CD34^+$ cells.

It has become possible to experimentally test for the presence of human hematopoietic stem cells which have bone marrow repopulating ability by using NOD/SCID mice obtained by crossing diabetic mice and immunodeficient mice. The cells detected by this assay are called SCID-repopulating cells (SRC) and considered the closest to human hematopoietic stem cells.

In the present invention, differentiation of hematopoietic stem cells and/or hematopoietic progenitor cells covers conversion of hematopoietic stem cells to hematopoietic progenitor cells, conversion of multipotent hematopoietic progenitor cells to unipotent hematopoietic progenitor cells and conversion of hematopoietic progenitor cells to cells having specific functions, i.e., mature blood cells such as erythrocytes, leukocytes and megakaryocytes.

In the present invention, expansion of hematopoietic stem cells means that the number of hematopoietic stem cells after culturing is greater than that before culturing. Expansion of hematopoietic progenitor cells means that the number of hematopoietic stem progenitor cells after culturing is greater than that before culturing (which may be 0). Not only the number of hematopoietic stem cells but also the number of hematopoietic progenitor cells in a hematopoietic stem cell culture can be greater after culturing than before culturing as a result of differentiation of some hematopoietic cells into hematopoietic progenitor cells, even with no eventual increase in the number of hematopoietic stem cells in some cases.

In the present invention, the hematopoietic stem cells before culturing may be a cell population containing cells other than hematopoietic stem cells (such as hematopoietic progenitor cells) like the above-mentioned $CD34^+$ cells.

In the present invention, the cell population after culturing may be a cell population containing only hematopoietic stem cells resulting from self-renewal of hematopoietic stem cells in the culture, a cell population containing of hematopoietic progenitor cells differentiated from hematopoietic stem cells or a cell population containing both hematopoietic stem cells and hematopoietic progenitor cells. Usually, cultured cells are a population containing both hematopoietic stem cells and hematopoietic progenitor cells resulting from self-renewal and differentiation of hematopoietic stem cells. When the main purpose is expansion of hematopoietic stem cells, the number of hematopoietic progenitor cells may be greater or smaller after culturing than before culturing.

In the present invention, hematopoietic stem cell expansion activity means the ability to proliferate hematopoietic stem cells having the above-mentioned functions and increase the number of hematopoietic stem cells having the same functions. In the present invention, hematopoietic stem cell differentiating activity means the ability to induce differentiation of hematopoietic stem cells and convert them into hematopoietic progenitor cells having the above-mentioned functions and further into mature blood cells (such as erythrocytes, leukocytes and megakaryocytes).

The specific compounds used in the present invention act on hematopoietic stem cells and/or hematopoietic progenitor cells and shows such an activity that they help hematopoietic stem cells and/or hematopoietic progenitor cells proliferate and survive when they are cultured ex vivo. The compounds are capable of proliferating hematopoietic stem cells and/or hematopoietic progenitor cells with minimal differentiation. In some cases of treatment by transplantation of hematopoietic stem cells such as peripheral stem cells and cord blood stem cells, hematopoietic stem cells and/or hematopoietic progenitor cells as the transplant cannot be obtained in sufficient numbers to carry out the transplantation or cannot be transplanted with a high success rate. By using the compounds, it is possible to expand collected hematopoietic stem cells ex vivo and obtain hematopoietic stem cells and/or hematopoietic progenitor cells in the amount required to carry out the transplantation even in such cases. Specifically, it is possible to expand hematopoietic stem cells and/or hematopoietic progenitor cells with minimal differentiation by culturing them in a medium containing the compounds and use them for transplantation. It is also possible to expand hematopoietic stem cells and/or hematopoietic progenitor cells more efficiently by further adding various cytokines or growth factors, by coculturing them with stromal cells, or by further adding other low-molecular-weight compounds which act on hematopoietic stem cells and/or hematopoietic progenitor cells.

In the method of the present invention, the collected cells to be cultured for transplantation may be a cell population containing other cells than hematopoietic stem cells such as hematopoietic progenitor cells or may be an isolated population substantially containing hematopoietic stem cells only, such as $CD34^+$ cells, $CD34^+CD38^-$ cells, $CD90^+$ cells, $CD133^+$ cells and the like. The cells may contain either or both of hematopoietic stem cells and hematopoietic progenitor cells and further contain other mature blood cells.

The source of the hematopoietic stem cells and/or hematopoietic progenitor cells in the method of the present invention may be any tissue as long as it contains hematopoietic stem cells, and it may preferably be human bone marrow, peripheral blood, peripheral blood containing hematopoietic stem cells mobilized by a cytokine or the like, spleen, liver or cord blood.

The hematopoietic stem cells can be cultured in a culture vessel generally used for animal cell culture such as a Petri dish, a flask, a plastic bag, a Teflon (registered trademark) bag, optionally after preliminary coating with an extracellular matrix or a cell adhesion molecule. The materials for such a coating may be collagens I to XIX, fibronectin, vitronectin, laminins 1 to 12, nitrogen, tenascin, thrombospondin, von Willebrand factor, osteoponin, fibrinogen, various types of elastin, various types of proteoglycan, various types of cadherin, desmocolin, desmoglein, various types of integrin, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The nutrient medium to be used for culturing hematopoietic stem cells by using the compounds of the present invention may be a natural medium, a semi-synthetic medium or a synthetic medium in terms of composition, and may be a solid medium, a semisolid medium or a liquid medium in terms of shape, and any nutrient medium used for animal cell culture, especially for hematopoietic stem cell and/or hematopoietic progenitor cell culture, may be used. As such a nutrient medium, Dulbecco's Modified Eagles's Medium (DMEM), Ham's Nutrient Mixture F12, McCoy's 5A medium, Eagles's Minimum Essential Medium (EMEM), αMEM medium (alpha Modified Eagles's Minimum Essential Medium), RPMI1640 medium, Iscove's Modified Dulbecco's Medium (IMDM), StemPro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich) or QBSF-60 (Quality Biological) may be mentioned.

Such a medium may contain sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be added in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The cytokines to be added to the medium may be interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon- 13 (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO) and thrombopoietin (TPO), but are not limited to those mentioned above.

The growth factors to be added to the medium may be transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 2, 3, 5 or 7 (Angpt 2, 3, 5 or 7), insulin-like growth factor (IGF), insulin-like growth factor binding protein (IGFBP) and Pleiotrophin, but are not limited to those mentioned above.

Besides, recombinant cytokines or growth factors having an artificially modified amino acid sequence such as IL-6/soluble IL-6 receptor complex, and Hyper IL-6 (IL-6/soluble IL-6 receptor fusion protein) may also be added.

Among the above-mentioned cytokines and growth factors, preferred are stem cell factor (SCF), interleukin-3 (IL-3), interleukin-6 (IL-6), interleukin-11 (IL-11), flk2/flt3 ligand (FL), granulocyte colony stimulating factor (G-CSF), granulocyte-macrophage colony stimulating factor (GM-CSF), thrombopoietin (TPO), erythropoietin (EPO), Notch ligand (Delta 1), Pleiotrophin and the like, and more preferred are stem cell factor (SCF), flk2/flt3 ligand (FL), thrombopoietin (TPO) and the like. Cytokines and growth factors are usually added to culture at a concentration of 0.1 ng/mL to 1000 ng/mL, preferably from 1 ng/mL to 100 ng/mL.

In addition, at least one chemical substance known to be effective for expansion of hematopoietic stem cells and/or hematopoietic progenitor cells may be added to the medium singly or in combination. Examples of such substances include copper chelators represented by tetraethylenepentamine, histone deacetylase inhibitors represented by trichostatin A, DNA methylase inhibitors represented by 5-aza-2'-deoxycytidine, retinoic acid receptor ligands represented by all-trans retinoic acid, aldehyde dehydrogenase inhibitors represented by dimethylaminobenzaldehyde, glycogen synthase kinase-3 inhibitors represented by 6-bromoindirubin-3'-oxime (6BIO), arylhydrocarbon receptor antagonists represented by 1-methyl-N-[2-methyl-4-[2-(2-methylphenyl) diazenyl]phenyl-1H-pyrazole-5-carboxamide (CH223191) and prostaglandin E2, but they are not limited to those mentioned above.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

When a specific compound of the present invention is added to such a medium as mentioned above, it is first dissolved in an appropriate solvent and added to the medium so that the concentration of the compound will be from 100 nM to 10 mM, preferably from 300 nM to 300 μM, more preferably from 1 μM to 100 μM, particularly preferably from 3 μM to 30 μM. Examples of the appropriate solvent include dimethyl sulfoxide (DMSO) and various alcohols, but it is not restricted thereto. The specific compounds may be immobilized on the surface of the substrate or support used for the culture. The specific compounds may be provided or stored in a certain form, for example, in a solid form as a tablet, a pill, a capsule or a granule, in a liquid form as a solution or suspension in an appropriate solvent or solubilizer, or in the form bound to the substrate or support. When they are formulated into such a form, additives such as a preservative like p-hydroxybenzoates, an excipient like lactose, glucose, sucrose and mannitol; a lubricant like magnesium stearate and talc; a binder like polyvinyl alcohol, hydroxypropylcellulose and gelatin, a surfactant like fatty acid esters, a plasticizer like glycerin may be added. The additives are not restricted to those mentioned above and a person skilled in the art can use any additives of choice.

The hematopoietic stem cells are cultured usually at a temperature of from 25 to 39° C., preferably from 33 to 39° C., in the atmosphere having a $CO_2$ concentration of from 4 to 10 vol %, preferably from 4 to 6 vol %, usually for a period of from 3 to 35 days, preferably from 5 to 21 days, more preferably from 7 to 14 days.

When the hematopoietic stem cells are cocultured with stromal cells by the method of the present invention, collected bone marrow cells may be grown directly in culture. Alternatively, it is possible to separate collected bone marrow into stromal cells, hematopoietic stem cells, hematopoietic progenitor cells and other cells, and coculture the hematopoietic stem cells with stromal cells from an individual other than the bone marrow donor. It is also possible to first grow stromal cells only and add and grow hematopoietic stem cells in coculture. When these cells are cocultured, it is possible to use such media and culture conditions as mentioned above.

Hematopoietic stem cells and/or hematopoietic progenitor cells expanded by the method of the present invention can be used as a cell transplant. Because hematopoietic stem cells can differentiate into blood cells of all lineages, they may be transplanted after differentiated into a certain type of blood cells ex vivo. Hematopoietic stem cells and/or hematopoietic progenitor cells expanded by the method of the present invention may be transplanted as they are, or after enrichment using a cell surface antigen as an index, for example, by a magnetic bead method or by a cell sorting method. Such a cell surface antigen molecule may be CD2, CD3, CD4, CD8, CD13, CD14, CD15, CD16, CD19, CD24, CD33, CD34, CD38, CD41, CD45, CD56, CD66, CD90, CD133 or glycophorin A, but is not restricted thereto. The expanded hematopoietic stem cells and/or hematopoietic progenitor cells may be transplanted to its donor or another individual.

Namely, hematopoietic stem cells and/or hematopoietic progenitor cells expanded by the method of the present invention can be used as a graft for hematopoietic stem cell therapy as a substitute for conventional bone marrow or cord blood transplantation. The transplantation of hematopoietic stem cells and hematopoietic progenitor cells expanded by the method of the present invention is carried out in the same manner as conventional bone marrow or cord blood transplantation, except for the cells to be used. Hematopoietic stem cells and/or hematopoietic progenitor cells expanded by the method of the present invention can also be used as a graft to promote regeneration of nerves and muscles damaged by a traumatic injury or a vascular disorder. The graft may be a composition containing a buffer solution, an antibiotic, a pharmaceutical in addition to hematopoietic stem cells and/or hematopoietic progenitor cells expanded by the method of the present invention.

The hematopoietic stem cell and/or hematopoietic progenitor cell transplant obtained by expansion by the method of the present invention is useful for treatment of not only various types of leukemia but also various diseases. For example, in a case of treatment of a solid cancer patient by chemotherapy or radiotherapy which may cause myelosuppression as a side effect, the patient can recover from hematopoietic damage quickly if the hematopoietic stem cells and/or hematopoietic progenitor cells collected from the bone marrow or peripheral blood of the patient preliminarily to the treatment are expanded ex vivo and returned to the patient after the treatment. Thus, a more intense chemotherapy becomes available with an improved therapeutic effect. It is also possible to alleviate a deficiency in a certain type of blood cells in a patient by differentiating hematopoietic stem cells and/or hematopoietic progenitor cells obtained by the method of the present invention into such a type of blood cells and returning them into the patient. A transplant obtained by the method of the present invention is effective against diseases accompanying decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity, immune dysfunction, diseases accompanying nerve damage, diseases accompanying muscle damage and ischemic diseases.

As specific examples, chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, gramulocytopenia, lymphopenia, thrombocytopenia, idiopathic thrombocytopenic purpura, thrombotic thrombocytopenic purpura, Kasabach-Merritt syndrome, malignant lymphoma, Hodgkin's disease, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, traumatic spinal cord injury, nerve injury, neurotmesis, skeletal muscle injury, scarring, diabetes mellitus, cerebral infarction, myocardial infarction, obstructive arteriosclerosis and the like may be mentioned.

Hematopoietic stem cells expanded according to the present invention can be used for gene therapy. Gene therapy using hematopoietic stem cells has been difficult because the transfer of a target gene into hematopoietic stem cells at the stationary phase is inefficient, and hematopoietic stem cells differentiate in culture during a gene transfer procedure. However, use of the low-molecular-weight compounds of the present invention in culture makes it possible to expand hematopoietic stem cells while suppressing differentiation of hematopoietic stem cells and improve the gene transfer efficiency considerably. In the gene therapy, a therapeutic gene is transfected into hematopoietic stem cells using the low-molecular-weight compounds of the present invention, and the resulting transfected cells (i.e., transformed hematopoietic stem cells) are transplanted into patients. The therapeutic gene to be transfected is appropriately selected among genes for hormones, cytokines, receptors, enzymes, polypeptides and the like according to the disease (Advance in Pharmacology 40, Academic Press, 1997). Specific examples of the gene include genes for insulin, amylase, proteases, lipases, trypsinogen, chymotrypsinogen, carboxypeptidases, ribonucleases, deoxyribonucleases, phospholipase A2, esterases, $\alpha$1-antitrypsin, blood coagulation factors (VII, VIII, IX and the like), protein C, protein S, antithrombin, UDP glucuronyl transferase, ornithine transcarbanoylase, hemoglobin, NADPH oxidase, glucocerebrosidase, $\alpha$-galactosidase, $\alpha$-glucosidase, $\alpha$-iduronidase, chytochrome P450 enzymes, adenosine deaminase, Bruton kinase, complements C1 to C4, JAK3, common cytokine receptor $\gamma$ chain, Ataxia Telangiectasia Mutated (ATM), Cystic Fibrosis (CF), myocilin, thymic humoral factor, thymopoietin, gastrin, selectins, cholecystokinin, serotinin, substance P, Major Histocompatibility Complex (MHC), multiple drug resistance factor (MDR-1) and the like.

In addition, RNA genes suppressing expression of disease genes are effective as therapeutic genes and can be used in the method of the present invention. For example, antisense RNA, siRNA, shRNA decoy RNA, ribozymes and the like may be mentioned.

For transfer of a therapeutic gene into hematopoietic stem cells, ordinary gene transfer methods for animal cells, such as those using vectors for animal cells such as retrovirus vectors like murine stem cell vector (MSCV) and Moloney murine leukemia virus (MmoLV), adenovirus vectors, adeno-associated virus (AAV) vectors, herpes simplex virus vectors and lentivirus vectors (for vectors for gene therapy, see Verma, I. M., Nature, 389:239, 1997), calcium phosphate coprecipitation, DEAE-dextran transfection, electroporation, a liposome method, lipofection, microinjection or the like may be used. Among them, retrovirus vectors, adeno-associated virus vectors or lentivirus vectors are preferred because their integration into the chromosomal DNA is expected to allow eternal expression of the gene.

For example, an adeno-associated virus (AAV) vector is prepared as follows. First, 293 cells are transfected with a vector plasmid obtained by inserting a therapeutic gene between the ITRs (inverted terminal repeats) at both ends of wild-type adeno-associated virus DNA and a helper plasmid for supplementing virus proteins and subsequently infected with an adenovirus as a helper virus to induce production of virus particles containing AAV vectors. Instead of the adenovirus, a plasmid for expression of an adenovirus gene which functions as a helper may be transfected. Next, hematopoietic stem cells are infected with the virus particles. It is preferred to insert an appropriate promoter, enhancer, insulator or the like upstream of the target gene in the vector DNA to regulate expression of the gene. Introduction of a marker gene such as a drug resistance gene in addition to the therapeutic gene makes it easy to select cells carrying the therapeutic gene. The therapeutic gene may be a sense gene or an antisense gene.

When hematopoietic stem cells are transfected with a therapeutic gene, the cells are cultured by an appropriate method selected from the culture methods mentioned above for expansion of hematopoietic stem cells by the person in charge. The gene transfer efficiency can be evaluated by a standard method in the art. It is possible to transfect a gene into hematopoietic stem cells otherwise, expand the resulting cells (transformed hematopoietic stem cells) by the above-mentioned method of expanding hematopoietic stem cells and use the resulting transformed hematopoietic stem cells for gene therapy.

The transplant for gene therapy may be a composition containing a buffer solution, an antibiotic, a pharmaceutical and the like in addition to transformed hematopoietic stem cells.

The diseases to be treated by gene therapy targeting blood cells include chronic granulomatosis, severe combined immunodeficiency syndrome, adenosine deaminase (ADA) deficiency, agammaglobulinemia, Wiskott-Aldrich syndrome, Chediak-Higashi syndrome, immunodeficiency syndrome such as acquired immunodeficiency syndrome (AIDS), hepatitis B, hepatitis C, congenital anemia such as thalassemia, hemolytic anemia due to enzyme deficiency, Fanconi's anemia and sicklemia, lysosomal storage disease such as Gaucher's disease and mucopolysaccharidosis, adrenoleukodystrophy, various kinds of cancers and tumors.

Preferred embodiments of the method of expansion and transfection of hematopoietic stem cells and/or hematopoietic progenitor cells and the method of transplantation of the expanded or transfected hematopoietic stem cells and/or hematopoietic progenitor cells by using the compounds of the present invention will be described below.

First, for expansion of hematopoietic stem cells and/or hematopoietic progenitor cells, cord blood, bone marrow, peripheral blood or the like is collected, and a cell population enriched with hematopoietic stem cells and/or hematopoietic progenitor cells is separated from it. As such a cell population, $CD34^+$ cells, $CD34^+CD38^-$ cells, $CD90^+$ cells, $CD133^+$ cells may be mentioned. For example, $CD34^+$ cells can be separated by density centrifugation combined with magnetic cell sorting (MACS) or flow cytometry (Flow Cytometry). For example, CPD (citrate-phosphate-dextran)-treated blood is fractioned by density centrifugation to separate and collect a mononuclear cell enriched fraction (hereinafter referred to as nucleated cell fraction). As density centrifugation, dextran or Ficoll density centrifugation, Ficoll-paque density gradient centrifugation, Percoll discontinuous density gradient centrifugation or Lymphoprep density gradient centrifugation may be mentioned. Then, magnetic beads coated with an anti-human CD34 monoclonal antibody (Miltenyi Biotec; hereinafter referred to CD34 antibody magnetic beads) and the collected nucleated cell fraction are mixed and incubated at from 2 to 8° C. (for about 30 minutes) to bind $CD34^+$ cells in the nucleated cell fraction to the antibody magnetic beads. The antibody magnetic bead/$CD34^+$ cell complexes are separated and collected by a specialized magnetic cell separator such as autoMACS system (Miltenyi Biotec). The $CD34^+$ cells thus obtained are cultured using a compound of the present invention. The conditions, incubator and medium for culturing $CD34^+$ cells, the species and amount of the compound, the kinds and amounts of additives and the incubation time and temperature may be selected appropriately from those disclosed herein by the person in charge, but are not restricted thereto. $CD34^+$ cells are transfected with a gene which is obtained by cloning a target gene into a vector by a standard method in the art, and incubating the vector and $CD34^+$ cells in the presence of the compound of the present invention. The kinds of the target gene and the vector, the transfection method and the culture method may be selected appropriately from those disclosed herein by the person in charge, but are not restricted thereto.

After culturing, the total cell count is measured by trypan blue assay or the like, while the cell culture is stained with an anti CD34 antibody and an anti CD38 antibody labeled with a fluorescent dye such as FITC (fluorescein isothiocyanate), PE (phycoerythrin) or APC (allophycocyanin), and the proportion of $CD34^+CD38^-$ cells is analyzed by flow cytometry. Thus, it is possible to determine how much hematopoietic stem cells and hematopoietic progenitor cells are expanded in the cell culture. The proportion of the least differentiated cells can be determined by subjecting part of the cell culture to colony assay and counting the resulting HPP-CFC colonies. The transgene can be detected by analyzing DNA or RNA extracted from the cells by southern blotting, northern blotting, RT-PCR (Reverse Transcriptase Polymerase Chain Reaction) or the like. The efficiency of transfer of the target gene is determined by detecting the protein expressed by the transgene by ELISA (Enzyme Linked ImmunoSorvent Assay) or flow cytometry using a specific antibody or by measuring the functional activity of the protein by an enzyme assay.

Expanded or transfected hematopoietic stem cells and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. In such cases, the disease to be treated, the pretreatment and the cell transplantation method are selected appropriately by the person in charge. The engraftment of transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carry out transplantation therapy and gene therapy safely and easily in a short term by using the expanded cells.

Because hematopoietic stem cells and/or hematopoietic progenitor cells can be expanded efficiently by the method of the present invention, the specific compounds of the present invention can be used as a reagent for research on hematopoietic stem cells and/or hematopoietic progenitor cells. For example, in a study to elucidate the factor regulating differentiation and growth of hematopoietic stem cells by identifying the colony forming cells in a culture of hematopoietic stem cells and analyzing the change in cell surface differentiation markers and gene expression, when hematopoietic stem cells are cultured in the presence of a putative factor, addition of a compound of the present invention makes it possible to expand the hematopoietic stem cells and/or hematopoietic progenitor cells to be analyzed efficiently. The incubation conditions, the incubator and the culture medium, the species and amount of the compound of the present invention, the kinds and amounts of additives and the incubation time and temperature used to elucidate such a factor may be selected appropriately from those disclosed herein by the person in charge. The colony forming cells emerging in the culture can be observed under a microscope normally used in the art, optionally after staining them using an antibody specific for the colony forming cells. The change in gene expression caused by such a putative factor can be detected by analyzing DNA or RNA extracted from the cells by southern blotting, northern blotting, RT-PCR or the like. The cell surface differentiation markers can be detected by ELISA or flow cytometry using a specific antibody to examine the effect of the putative factor on differentiation and growth of the cells.

When $R^3$ is a hydrogen atom, the compounds of the present invention represented by the formula (1) can have tautomers (2) to (4) which undergo endocyclic or exocyclic isomerization, and the present invention covers these tautomers (2) to (4) and mixtures containing them in any ratios.

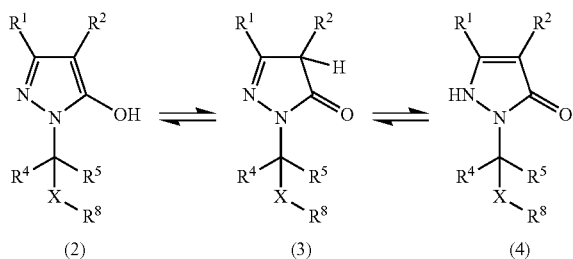

When the compounds of the present invention have an asymmetric center, whether or not resulting from an isomerization, the present invention covers both resolved optical isomers and mixtures containing them in any ratios.

The compounds of the present invention can have geometrical isomers such as E-isomers and Z-isomers, whether or not resulting from an isomerization, depending on the substituents, and the present invention covers both these geometrical isomers and mixtures containing them in any ratios.

The specific compounds of the present invention represented by the formula (1) may be converted to pharmaceutically acceptable salts or may be liberated from the resulting salts, if necessary. Some of the compounds of the present invention can be converted, by ordinary methods, to acid addition salts with hydrogen halides such as hydrofluoric acid, hydrochloric acid, hydrobromic acid and hydriodic acid, with inorganic acids such as nitric acid, sulfuric acid, phosphoric acid, chloric acid and perchloric acid, with sulfonic acids such as methanesulfonic acid, ethanesulfonic acid, trifluoromethanesuflonic acid, benzenesulfonic acid and p-toluenesulfonic acid, with carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, with amino acids such as glutamic acid asparatic acid.

Some of the compounds of the present invention can be converted, by ordinary methods, to metal salts with alkali metals such as lithium sodium and potassium, with alkaline earth metals such as calcium, barium and magnesium, with metals such as aluminum, zinc and copper.

The specific compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds which serve as prodrugs are derivatives of the specific compounds the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985). In the present invention, when the compound has a hydroxy group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO(m-CO$_2$Na—Ph), —OCOCH$_2$CH$_2$CO$_2$Na, —OCOCH(NH$_2$)CH$_3$, —OCOCH$_2$N(CH$_3$)$_2$ and the like. When the specific compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

Next, specific examples of each substituent used herein will be given below. "n" denotes normal, "i" denotes iso, "s" denotes secondary, "t" or "tert" denotes tertiary, and "Ph" denotes phenyl.

As a halogen atom in the compounds of the present invention, a fluorine atom, a chlorine atom, a bromine atom or an iodine atom may be mentioned. Herein, the expression "halo" also means such a halogen atom.

The expression $C_\alpha$-$C_\beta$ alkyl herein means a linear or branched hydrocarbon group containing from $\alpha$ to $\beta$ carbon atoms such as a methyl group, an ethyl group, a n-propyl group, an i-propyl group, a n-butyl group, an i-butyl group, a s-butyl group, a t-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 1,1-dimethylbutyl group, a 1,3-dimethylbutyl group, a heptyl group, an octyl group, a nonyl group, a decyl group, an undecyl group or a dodecyl group, and those within the designated carbon number range are selected.

The expression $C_\alpha$-$C_\beta$ haloalkyl herein means a linear or branched hydrocarbon group containing from $\alpha$ to $\beta$ carbon atoms in which hydrogen atom(s) on carbon atom(s) are optionally substituted with halogen atom(s) which may be identical with or different from one another if two or more halogen atoms are present, such as a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a difluoroiodomethyl group, a 2-fluoroethyl group, a 2-chloroethyl group, a 2-bromoethyl group, a 2,2-difluoroethyl group, a 2-chloro2-fluoroethyl group, a 2,2-dichloroethyl group, a 2-bromo2-fluoroethyl group, a 2,2,2-trifluoroethyl group, a 2-chloro-2,2-difluoroethyl group, a 2,2-dichloro2-fluoroethyl group, a 2,2,2-trichloroethyl group, a 2-bromo-2,2-difluoroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 1-bromo-1,2,2,2-tetrafluoroethyl group, a 2-bromo-1,1,2,2-tetrafluoroethyl group, a 2-fluoropropyl group, a 2-chloropropyl group, a 2,3-dichloropropyl group, a 3,3,3-trifluoropropyl group, a 3-bromo-3,3-difluoropropyl group, 2,2,3,3-tetrafluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro1-methylethyl group, a 2-chloro1-methylethyl group, a 2-bromo-1-methylethyl group, a 2,2,2-trifluoro-1-(trifluoromethyl)ethyl group, a 1,2,2,2-tetrafluoro-1-(trifluoromethyl)ethyl group or a nonafluorobutyl group, and those within the designated carbon number range are selected.

The expression $C_\alpha$-$C_\beta$ cycloalkyl herein means a cyclic hydrocarbon group containing from α to β carbon atoms in the form of a 3- to 6-membered monocyclic or polycyclic ring which may optionally be substituted with an alkyl group as long as the number of carbon atoms does not exceed the designated carbon number range, such as a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a cyclohexyl group, a cycloheptyl group, a cyclooctyl group, a bicyclo [2.2.1]heptan-2-yl group, a 1-adamantyl group or a 2-adamantyl group, and those within the designated carbon number range are selected.

The expression $C_\alpha$-$C_\beta$ halocycloalkyl means a cyclic hydrocarbon group containing from α to β carbon atoms in the form of a 3- to 6-membered monocyclic or complex ring which may optionally be substituted with an alkyl group as long as the number of carbon atoms does not exceed the designated carbon number range, in which hydrogen atom(s) on carbon atom(s) in a ring moiety and/or in a side chain are optionally substituted with halogen atom(s) which may be identical with or different from one another if two or more halogen atoms are present, such as a 2-fluorocyclopropyl group, a 2-chlorocyclopropyl group, a 2,2-difluorocyclopropyl group, a 2,2-dichlorocyclopropyl group, a 2,2-dibromocyclopropyl group, a 2,2-difluoro1-methylcyclopropyl group, a 2,2-dichloro1-methylcyclopropyl group, a 2,2,3,3-tetrafluorocyclobutyl group or a 2-chloro-2,3,3-trifluorocyclobutyl group, and those within the designated carbon atom range are selected.

The expression $C_\alpha$-$C_\beta$ alkenyl herein means a linear or branched unsaturated hydrocarbon group containing from α to β carbon atoms and having one or more double bonds in the molecule such as a vinyl group, a 1-propenyl group, a 2-propenyl group, a 1-methylethenyl group, a butenyl group, a 1-methyl-2-propenyl group, a 2-methyl2-propenyl group, a 2-pentenyl group, a 2-methyl-2-butenyl group, a 3-methyl-2-butenyl group, a 2-ethyl2-propenyl group, a 1,1-dimethyl-2-propenyl group, a 2-hexenyl group, a 2-methyl-2-pentenyl group, a 2,4-dimethyl-2,6-heptadienyl group or a 3,7-dimethyl-2,6-octadienyl group, and those within the designated carbon atom range are selected.

The expression $C_\alpha$-$C_\beta$ alkynyl herein means a linear or branched unsaturated hydrocarbon group containing from α to β carbon atoms and having one or more triple bonds in the molecule such as an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group or a 2-hexynyl group, and those within the designated carbon atom range are selected.

The expression $C_\alpha$-$C_\beta$ alkoxy herein means an alkyl-O— group in which the alkyl is a previously mentioned alkyl group containing from α to β carbon atoms, such as a methoxy group, an ethoxy group, a n-propyloxy group, an i-propyloxy group, a n-butyloxy group, an i-butyloxy group, a s-butyloxy group, a t-butyloxy group, a n-pentyloxy group, a n-hexyloxy group, and those within the designated carbon atom range are selected.

The expression $C_\alpha$-$C_\beta$ haloalkoxy herein means a haloalkyl-O— group in which the haloalkyl is a previously mentioned haloalkyl group containing from α to β carbon atoms, such as a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2,-tetrafluoroethoxy group, a 2-chloro-1,1,2-trifluoroethoxy group, a 2-bromo-1,1,2-trifluoroethoxy group, a pentafluoroethoxy group, a 2,2-dichloro-1,1,2-trifluoroethoxy group, a 2,2,2-trichloro1,1-difluoroethoxy group, a 2-broMo-1,1,2,2-tetrafluoroethoxy group, a 2,2,3,3-tetrafluoropropyloxy group, a 1,1,2,3,3,3-hexafluoropropyloxy group, a 2,2,2-trifluoro1-(trifluoromethyl)ethoxy group, a heptafluoropropyloxy group or a 2-bromo-1,1,2,3,3,3-hexafluoropropyloxy group, and those within the designated carbon atom range are selected.

The expression $C_\alpha$-$C_\beta$ alkylthio herein means an alkyl-S— group in which the alkyl is a previously mentioned alkyl group containing from α to β carbon atoms, such as a methylthio group, an ethylthio group, a n-propylthio group, an i-propylthio group, a n-butylthio group, an i-butylthio group, a s-butylthio group, a t-butylthio group, a n-pentylthio group or a n-hexylthio group, and those within the designated carbon atom range are selected.

The expression $C_\alpha$-$C_\beta$ haloalkylthio herein means a haloalkyl-S— group in which the haloalkyl is a previously mentioned haloalkyl group containing from α to β carbon atoms, such as a difluoromethylthio group, a trifluoromethylthio group, a chlorodifluoroethylthio group, a bromodifluoroethylthio group, a 2,2,2-trifluoroethylthio group, a 1,1,2,2-tetrafluoroethylthio group, a 2-chloro-1,1,2-trifluoroethylthio group, a pentafluoroethylthio group, a 2-bromo-1,1,2,2-tetrafluoroethylthio group, a 1,1,2,3,3,3-hexafluoropropylthio group, a heptafluoropropylthio group, a 1,2,2,2-tetrafluoro1-(trifluoromethyl)ethylthio group or a nonafluorobutylthio group, and those within the designated carbon atom range are selected.

The expression $C_\alpha$-$C_\beta$ alkylsulfinyl herein means an alkyl-S(O)— group in which the alkyl is a previously mentioned alkyl group containing from α to β carbon atoms, such as a methylsulfinyl group, an ethylsulfinyl group, a n-propylsulfinyl group, an i-propylsulfinyl group, a n-butylsulfinyl group, an i-butylsulfinyl group, a s-butylsulfinyl group or a t-butylsulfinyl group, and those within the designated carbon atom range are selected.

The expression $C_\alpha$-$C_\beta$ haloalkylsulfinyl herein means a haloalkyl-S(O)— group in which the haloalkyl is a previously mentioned haloalkyl group containing from α to β carbon atoms, such as a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 2-bromo-1,1,2,2-tetrafluoroethylsulfinyl group, a 1,2,2,2-tetrafluoro-1-(trifluoromethyl)ethylsulfinyl group or a nonafluorobutylsulfinyl group, and those within the designated carbon atom range are selected.

The expression $C_\alpha$-$C_\beta$ alkylsulfonyl herein means an alkyl-$SO_2$— group in which the haloalkyl is a previously mentioned haloalkyl group containing from α to β carbon atoms, such as a methylsulfonyl group, an ethylsulfonyl group, a n-propylsulfonyl group, an i-propylsulfonyl group, a n-butylsulfonyl group, an i-butylsulfonyl group, a s-butylsulfonyl group, a t-butylsulfonyl group, a n-pentylsulfonyl group or a n-hexylsulfonyl group, and those within the designated carbon atom range are selected.

The expression $C_\alpha$-$C_\beta$ haloalkylsulfonyl herein means a haloalkyl-$SO_2$— group in which the haloalkyl is a previously mentioned haloalkyl group containing from α to β carbon atoms, such as adifluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group, a 2-chloro-1,1,2-trifluoroethylsulfonyl group or a 2-bromo-1,1,2,2-tetrafluoroethylsulfonyl group, and those within the designated carbon atom range are selected.

The expression $C_\alpha$-$C_\beta$ alkylamino herein means an amino group in which either hydrogen atom is replaced by a previously mentioned alkyl group containing from α to β carbon atoms, such as a methylamino group, an ethylamino group, a n-propylamino group, an i-propylamino group, a n-butylamino group, an i-butylamino group or a t-butylamino group, and those within the designated carbon atom range are selected.

The expression di($C_\alpha$-$C_\beta$ alkyl)amino herein means an amino group in which both hydrogen atoms are replaced by previously mentioned alkyl groups containing from a to carbon atoms which may be identical with or different from each other, such as a dimethylamino group, an ethyl(methyl)amino group, a diethylamino group, a n-propyl(methyl)amino group, an i-propyl(methyl)amino group, a di(n-propyl)amino group, a n-butyl(methyl)amino group, an i-butyl(methyl) amino group or a t-butyl(methyl)amino group, and those within the designated carbon atom range are selected.

The expression $C_\alpha$-$C_\beta$ alkylimino herein means an alkyl-N= group in which the alkyl means a previously mentioned alkyl group containing from α to β carbon atoms, such as a methylimino group, an ethylimino group, a n-propylimino group, an i-propylimino group, a n-butylimino group, an i-butylimino group, a s-butylimino group, a n-pentylimino group or a n-hexylimino group, and those within the designated carbon atom range are selected.

The expression $C_\alpha$-$C_\beta$ alkoxyimino herein means an alkoxy-N=group in which the alkoxy means a previously mentioned alkoxy group containing from α to β carbon atoms, such as a methoxyimino group, an ethoxyimino group, a n-propyloxyimino group, an i-propyloxyimino group, a n-butyloxyimino group, a n-pentyloxyimino group or a n-hexyloxyimino group, and those within the designated carbon atom range are selected.

The expression $C_\alpha$-$C_\beta$ alkylcarbonyl herein means an alkyl-C(O)— group in which the alkyl means a previously mentioned alkyl group containing from α to β carbon atoms, such as an acetyl group, a propionyl group, a butyryl group, an isobutyryl group, a valeryl group, an isovaleryl group, a 2-methylbutanoyl group, a pivaloyl group, a hexanoyl group or a heptanoyl group, and those within the designated carbon atom range are selected.

The expression $C_\alpha$-$C_\beta$ haloalkylcarbonyl herein means a haloalkyl-C(O)— group in which the haloalkyl means a previously mentioned haloalkyl group containing from α to β carbon atoms, such as a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group or a 3-chloro-2,2-dimethylpropanoyl group, and those within the designated carbon atom range are selected.

The expression $C_\alpha$-$C_\beta$ alkoxycarbonyl herein means an alkyl-O—C(O)— group in which the alkyl means a previously mentioned alkoxy group containing from α to β carbon atoms, such as a methoxycarbonyl group, an ethoxycarbonyl group, a n-propyloxycarbonyl group, an i-propyloxycarbonyl group, a n-butoxycarbonyl group, an i-butoxycarbonyl group or a t-butoxycarbonyl group, and those within the designated carbon atom range are selected.

The expression $C_\alpha$-$C_\beta$ haloalkoxycarbonyl herein means a haloalkyl-O—C(O)— group in which the haloalkyl means a previously mentioned haloalkyl group containing from α to β carbon atoms, such as a 2-chloroethoxycarbonyl group, a 2,2-difluoroethoxycarbonyl group, a 2,2,2-trifluoroethoxycarbonyl group or a 2,2,2-trichloroethoxycarbonyl group, and those within the designated carbon atom range are selected.

The expression $C_\alpha$-$C_\beta$ alkylaminocarbonyl herein means a carbamoyl group in which either hydrogen atom is replaced by a previously mentioned alkyl group containing from α to β carbon atoms, such as a methylcarbamoyl group, an ethylcarbamoyl group, a n-propylcarbamoyl group, an i-propylcarbamoyl group, a n-butylcarbamoyl group, an i-butylcarbamoyl group, a s-butylcarbamoyl group or a t-butylcarbamoyl group, and those within the designated carbon atom range are selected.

The expression $C_\alpha$-$C_\beta$ haloalkylaminocarbonyl herein means a carbamoyl group in which either hydrogen atom is replaced by a previously mentioned haloalkyl group containing from α to β carbon atoms, such as a 2-fluoroethylcarbamoyl group, a 2-chloroethylcarbamoyl group, a 2,2-difluoroethylcarbamoyl group or a 2,2,2-trifluoroethylcarbamoyl group, and those within the designated carbon atom range are selected.

The expression di($C_\alpha$-$C_\beta$ alkyl)aminocarbonyl herein means a carbamoyl group in which both hydrogen atoms are replaced by previously mentioned alkyl groups containing from α to β carbon atoms which may be identical with or different from each other, such as an N,N-dimethylcarbamoyl group, an N-ethyl-N-methylcarbamoyl group, an N,N-diethylcarbamoyl group, an N,N-di-n-propylcarbamoyl group or an N,N-di-n-butylcarbamoyl group, and those within the designated carbon atom range are selected.

The expression $C_\alpha$-$C_\beta$ alkylaminosulfonyl herein means a sulfamoyl group in which either hydrogen atom is replaced by a previously mentioned alkyl group containing from α to β carbon atoms, such as a methylsulfamoyl group, an ethylsulfamoyl group, a n-propylsulfamoyl group, an i-propylsulfamoyl group, a n-butylsulfamoyl group, an i-butylsulfamoyl group, a s-butylsulfamoyl group or a t-butylsulfamoyl group, and those within the designated carbon atom range are selected.

The expression di($C_\alpha$-$C_\beta$ alkyl)aminosulfonyl herein means a sulfamoyl group in which both hydrogen atoms are replaced by previously mentioned alkyl groups containing from α to β carbon atoms which may be identical with or different from each other, such as an N,N-dimethylsulfamoyl group, an N-ethyl-N-methylsulfamoyl group, an N,N-diethylsulfamoyl group, an N,N-di-n-propylsulfamoyl group or an N,N-di-n-butylsulfamoyl group, and those within the designated carbon atom range are selected.

The expression tri($C_\alpha$-$C_\beta$ alkyl)silyl herein means a silyl group substituted with previously mentioned alkyl groups containing from α to β carbon atoms which may be identical with or different from one another, such as a trimethylsilyl group, a triethylsilyl group, a tri(n-propyl)silyl group, an ethyldimethylsilyl group, a n-propyldimethylsilyl group, a n-butyldimethylsilyl group, an i-butyldimethylsilyl group or a t-butyldimethylsilyl group, and those within the designated carbon atom range are selected.

The expression $C_\alpha$-$C_\beta$ alkylsulfonyloxy herein means an alkylsulfonyl-O— group in which the alkylsulfonyl means a previously mentioned alkylsulfonyl group containing from α to β carbon atoms, such as a methylsulfonyloxy group, an ethylsulfonyloxy group, a n-propylsulfonyloxy group or an i-propylsulfonyloxy group, and those within the designated carbon atom range are selected.

The expression $C_\alpha$-$C_\beta$ haloalkylsulfonyloxy herein means a haloalkylsulfonyl-O— group in which the haloalkylsulfonyl means a previously mentioned haloalkylsulfonyl group containing from α to β carbon atoms, such as a difluoromethylsulfonyloxy group, a trifluoromethylsulfonyloxy group, a chlorodifluoromethylsulfonyloxy group or a bromodifluoromethylsulfonyloxy group, and those within the designated carbon atom range are selected.

The expression $C_\alpha$-$C_\beta$ alkoxy ($C_\delta$-$C_\epsilon$) alkyl herein means a previously mentioned alkyl group containing from δ to ε carbon atoms in which hydrogen atom(s) on carbon atom(s) are optionally substituted with previously mentioned alkoxy group(s) containing from α to β carbon atoms, and those within the designated carbon atom range are selected.

The expression $C_\alpha$-$C_\beta$ alkoxy($C_\delta$-$C_\epsilon$) alkoxy herein means a previously mentioned alkoxy group containing from δ to ε carbon atoms in which hydrogen atom(s) on carbon atom(s) are optionally substituted with previously mentioned alkoxy group(s) containing from α to β carbon atoms, and those within the designated carbon atom range are selected.

The expression ($C_\alpha$-$C_\beta$) alkenyl optionally substituted with a halogen atom or ($C_\alpha$-$C_\beta$) alkenyl optionally substituted with $R^{31}$ herein means a previously mentioned alkynyl group containing from a to b carbon atoms in which hydrogen atom(s) on carbon atom(s) are substituted with optional halogen atom(s) or $R^{31}$, and those within the designated carbon atom range are selected. When there are two or more halogen atoms or the substituent $R^{31}$'s on an ($C_\alpha$-$C_\beta$) alkenyl group, the $R^{31}$'s or the halogen atoms may be identical with or different from one another.

The expression ($C_\alpha$-$C_\beta$) alkynyl optionally substituted with a halogen atom or ($C_\alpha$-$C_\beta$) alkynyl optionally substituted with $R^{31}$ herein means a previously mentioned alkynyl group containing from a to b carbon atoms in which hydrogen atom(s) on carbon atom(s) are substituted with optional halogen atom(s) or $R^{31}$, and those within the designated carbon atom range are selected. When there are two or more halogen atoms or the substituent $R^{31}$'s on an ($C_\alpha$-$C_\beta$) alkynyl group, the $R^{31}$'s or the halogen atoms may be identical with or different from one another.

The expression benzyl having a benzene ring optionally substituted with e $R^{21}$'s, benzyl having a benzene ring which may be substituted with f $R^{22}$'s or benzyl having a benzene ring which may be substituted with g $R^{15}$'s herein means a previously mentioned benzyl group in which the hydrogen atoms on e, f or g carbon atom(s) in the benzene ring are optionally substituted with optional $R^{21}$'s, $R^{22}$'s or $R^{15}$'s. When there are two or more $R^{21}$'s, $R^{22}$'s or $R^{15}$'s in the benzene ring, they may be identical with or different from one another.

The expression phenyl optionally substituted with e $R^{21}$'s, phenyl which may be substituted with f $R^{22}$'s or phenyl optionally substituted with k $R^{81}$'s herein means a previously mentioned phenyl group in which the hydrogen atoms on e, f, or k carbon atoms in the benzene ring are optionally substituted with optional $R^{21}$'s, $R^{22}$'s or $R^{81}$'s. When there are two or more $R^{21}$'s $R^{22}$'s or $R^{81}$'s in the benzene ring, they may be identical with or different from one another.

The expression 1-phenethyl having a benzene ring which may optionally be substituted with b $R^{14}$'s herein means a 1-phenethyl group having a benzene ring in which the hydrogen atoms on b carbon atoms are optionally substituted with optional $R^{14}$'s. When there are two or more $R^{14}$'s in the benzene ring, they may be identical with or different from one another.

The expression 2-phenethyl having a benzene ring which may optionally be substituted with b $R^{14}$'s herein means a 2-phenethyl group having a benzene ring in which the hydrogen atoms on b carbon atoms are optionally substituted with optional $R^{14}$'s. When there are two or more $R^{14}$'s in the benzene ring, they may be identical with or different from one another.

The expression ($C_\alpha$-$C_\beta$) alkyl substituted with $R^{17}$ herein means a previously mentioned alkyl group containing from α to β carbon atoms in which hydrogen atom(s) on carbon atom(s) are optionally substituted with $R^{17}$, and those within the designated carbon atom range are selected. When there are two or more $R^{17}$'s on an alkyl group on the ($C_\alpha$-$C_\beta$) alkyl group, the $R^{17}$'s may be identical with or different from one another.

As the scope of the substituent represented by $R^1$ in the compounds which fall within the present invention, the following sets may, for example, be mentioned.

$R^1$-I: $C_1$-$C_6$ alkyl.

$R^1$-II: $C_1$-$C_6$ alkyl, $C_1$-$C_6$ alkyl substituted with $R^{17}$, $C_1$-$C_6$ haloalkyl, $C_3$-$C_6$ cycloalkyl, phenyl and phenyl substituted with a $R^{11}$'s [wherein $R^{11}$ is a halogen atom, $C_1$-$C_6$ alkyl or $C_1$-$C_6$ alkoxy, and when a is an integer of at least two, each $R^{11}$ may be identical with or different from one another, $R^{12}$ is $C_1$-$C_6$ alkyl, $R^{17}$ is —C(O)O$R^{12}$ or phenyl, and a is an integer of from 1 to 5].

$R^1$-III: $C_1$-$C_6$ alkyl, $C_1$-$C_6$ haloalkyl, $C_3$-$C_6$ cycloalkyl, $C_1$-$C_6$ alkyl substituted with $R^{17}$, D5, phenyl and phenyl substituted with a $R^{11}$'s [wherein $R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro, and when a is an integer of at least two, each $R^{11}$ may be identical with or different from one another, and when there are two neighboring $R^{11}$'s, the two neighboring $R^{11}$'s may form —CH=CHCH=CH— to form a 6-membered ring together with the carbon atoms attached to the two $R^{11}$'s, $R^z$ is a halogen atom or $C_1$-$C_6$ alkyl, $R^{12}$ is $C_1$-$C_6$ alkyl, $R^{17}$ is —C(O)O $R^{12}$ or phenyl, a is an integer of from 1 to 5, and s2 is an integer of from 0 to 3].

$R^1$-IV: $C_1$-$C_6$ alkyl, $C_1$-$C_6$ alkyl substituted with $R^{17}$, $C_1$-$C_6$ haloalkyl, $C_3$-$C_6$ cycloalkyl, —C(O)O $R^{12}$, D2, D4, D5, D7, D21, D22, D23, phenyl and phenyl substituted with a $R^{11}$'s [wherein $R^{11}$ is a halogen atom, $C_1$-$C_{10}$ alkyl, $C_1$-$C_{10}$ alkoxy, $C_1$-$C_{10}$ haloalkyl, $C_1$-$C_{10}$ haloalkoxy, nitro or phenyl, $R^{12}$ is a hydrogen atom, $C_1$-$C_6$ alkyl or $C_3$-$C_6$ cycloalkyl, and when a is an integer of at least 2, each $R^{11}$ may be identical with or different from one another, and when there are two neighboring $R^{11}$'s, the two neighboring $R^{11}$'s may form, together with the carbon atoms attached to the two $R^{11}$'s, —CH=CHCH=CH— to form a 6-membered ring which may have one or more hydrogen atoms on the ring-constituting carbon atoms replaced by one or more Z's which may be identical with or different from one another, if two or more Z's are present, $R^{12}$ is a hydrogen atom, $C_1$-$C_6$ alkyl or $C_3$-$C_6$ cycloalkyl, $R^{17}$ is —C(O)O $R^{12}$ or phenyl, Z is a halogen atom or $C_1$-$C_6$ alkyl, $R^y$ is $C_1$-$C_6$ alkyl or phenyl, $R^z$ is a halogen atom, $C_1$-$C_6$ alkyl, phenoxy, phenyl or phenyl which may be substituted with m $R^{16}$'s, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, and when m is an integer of at least 2, each $R^{16}$ may be identical with or different from one another, when s2 or s3 is an integer of at least 2, each $R^z$ may be identical with or different from one another, a is an integer of from 1 to 5, m is an integer of from 1 to 5, s2 is an integer of from 0 to 3, and s3 is an integer of from 0 to 2].

As the scope of the substituent represented by $R^2$ in the compounds which fall within the present invention, the following sets may, for example, be mentioned.

$R^2$-I: a hydrogen atom, $C_1$-$C_6$ alkyl, phenyl and phenyl optionally substituted with e $R^{21}$'s [wherein $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl or phenyl, and when e is an integer of at least 2, each $R^{21}$ may be identical with or different from one another, and e is an integer of from 1 to 5].

$R^2$-II: a hydrogen atom, $C_1$-$C_6$ alkyl, D2, benzyl, benzyl having a benzene ring optionally substituted with e $R^{21}$'s, phenyl and phenyl optionally substituted with e $R^{21}$'s [wherein $R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl, when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, Z is a halogen atom or $C_1$-$C_6$ alkyl, $R^z$ is a halogen atom, $C_1$-$C_6$ alkyl, phenoxy or phenyl, and when s2 is an integer of at least 2, each $R^z$ may be identical with or different from one another, e is an integer of from 1 to 5, and s2 is an integer of from 0 to 3].

$R^2$-III: a hydrogen atom, $C_1$-$C_6$ alkyl, D2, D7, benzyl, benzyl having a benzene ring optionally substituted with e $R^{21}$'s, phenyl and phenyl optionally substituted with e $R^{21}$'s [wherein $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one another, and when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, Z is a halogen atom or $C_1$-$C_6$ alkyl, and when f is an integer of at least 2, each $R^{22}$ may be identical with or different from one another, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, e is an integer of from 1 to 5, f is an integer of from 1 to 5, m is an integer of from 1 to 5, and s2 is an integer of from 0 to 3].

$R^2$-IV: a hydrogen atom, $C_1$-$C_6$ alkyl, $C_3$-$C_6$ cycloalkyl, D2, D7, benzyl, benzyl having a benzene ring optionally substituted with e $R^{21}$'s, phenyl and phenyl optionally substituted with e $R^{21}$'s [wherein $R^{21}$ is a halogen atom, $C_1$-$C_{10}$ alkyl, $C_3$-$C_{10}$ cycloalkyl, $C_1$-$C_{10}$ alkoxy, $C_1$-$C_6$ alkoxy($C_1$-$C_6$) alkoxy, $C_1$-$C_{10}$ haloalkyl, $C_1$-$C_{10}$ haloalkoxy, nitro, cyano, phenoxy, phenyl or phenyl which may be substituted with f $R^{22}$'s, and when f is an integer of at least 2, each $R^{22}$ may be identical with or different from one another, and when e is an integer of at least 2, each $R^{21}$ may be identical with or different from one another, and when there are two neighboring $R^{21}$'s, the two neighboring $R^{21}$'s may form —$OCH_2O$—, —$OCH_2CH_2O$—, —OCH=CH— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present, $R^{22}$ is a halogen atom, $C_1$-$C_6$ alkyl, $C_1$-$C_6$ alkoxy, $C_1$-$C_6$ haloalkyl or $C_1$-$C_6$ haloalkoxy, Z is a halogen atom or $C_1$-$C_6$ alkyl, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, e is an integer of from 1 to 5, f is an integer of from 1 to 5, m is an integer of from 1 to 5, and s2 is an integer of from 0 to 3].

As the scope of the substituent represented by $R^3$ in the compounds which fall within the present invention, the following sets may, for example, be mentioned.

$R^3$-I: a hydrogen atom.

$R^3$-II: a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$ and —C(O)N($R^{12}$)$R^{13}$ [wherein each of $R^{12}$ and $R^{13}$ is independently a hydrogen atom, $C_1$-$C_6$ alkyl or $C_3$-$C_6$ cycloalkyl], —Si($R^{32}$)($R^{33}$)$R^{34}$ [wherein each of $R^{32}$, $R^{33}$ and $R^{34}$ is independently $C_1$-$C_6$ alkyl or $C_3$-$C_6$ cycloalkyl].

$R^3$-III: a hydrogen atom, $C_1$-$C_4$ alkyl, $C_3$-$C_4$ cycloalkyl, $C_1$-$C_4$ alkoxy($C_1$-$C_4$) alkyl, —C(O)$R^{12}$, —C(O)O$R^{12}$ and —C(O)N($R^{12}$)$R^{13}$ [wherein each of $R^{12}$ and $R^{13}$ is independently a hydrogen atom, $C_1$-$C_6$ alkyl or $C_3$-$C_6$ cycloalkyl], —Si($R^{32}$)($R^{33}$)$R^{34}$ [wherein each of $R^{32}$, $R^{33}$ and $R^{34}$ is independently $C_1$-$C_6$ alkyl or $C_3$-$C_6$ cycloalkyl], benzyl or benzyl having a benzene ring which may be substituted with g $R^{15}$'s [wherein $R^{15}$ is a halogen atom, $C_1$-$C_6$ alkyl, $C_1$-$C_6$ alkoxy or $C_1$-$C_6$ haloalkyl, and when g is an integer of at least 2, each $R^{15}$ may be identical with or different from one another, and g is an integer of from 1 to 5].

As the scope of the substituent represented by $R^4$ in the compounds which fall within the present invention, the following sets may, for example, be mentioned.

$R^4$-I: $C_1$-$C_4$ alkyl.

As the scope of the substituent represented by $R^5$ in the compounds which fall within the present invention, the following sets may, for example, be mentioned.

$R^5$-I: $C_1$-$C_4$ alkyl.

As the scope of the substituent represented by $R^4$ and $R^5$ in the compounds which fall within the present invention, the following sets may, for example, be mentioned.

$R^4$+$R^5$: —$CH_2CH_2$—, —$CH_2CH_2CH_2$—, —$CH_2CH_2CH_2CH_2$— or —$CH_2CH_2CH_2CH_2CH_2$—, which forms a 3-membered, 4-membered, 5-membered or 6-membered ring together with the carbon atoms attached to $R^4$ and $R^5$.

As the scope of the substituent represented by $R^8$ in the compounds which fall within the present invention, the following sets may, for example, be mentioned.

$R^8$-I: F1 phenyl, 1-naphthyl or 2-naphthyl.

$R^8$-II: D2, F1, phenyl and phenyl optionally substituted with k $R^{81}$'s [wherein $R^{81}$ is a halogen atom, $C_1$-$C_6$ alkyl, $C_1$-$C_6$ haloalkyl, $C_1$-$C_6$ alkoxy, phenyl or phenoxy, and when k is an integer of at least 2, each $R^{81}$ may be identical with or different from one another, and when there are two neighboring $R^{81}$'s, the two neighboring $R^{81}$'s may form —$OCH_2O$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy or phenyl, and when s2 is an integer of at least 2, each $R^z$ may be identical with or different from one another, k is an integer of from 1 to 5, and s2 is an integer of from 0 to 3].

$R^8$-III: D2, F1, phenyl and phenyl optionally substituted with k $R^{81}$'s [wherein $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy, and when k is an integer of at least 2, each $R^{81}$ may be identical with or different from one another, and when there are two neighboring $R^{81}$'s, the two neighboring $R^{81}$'s may form —OCH$_2$O— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom or $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, k is an integer of from 1 to 5, m is an integer of from 1 to 5, and s2 is an integer of from 0 to 3].

$R^8$-IV: D2, D7, D23, F1, F2, phenyl and phenyl optionally substituted with k $R^{81}$s [wherein $R^{81}$ is a halogen atom, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_3$-$C_6$ halocycloalkoxy, $C_1$-$C_2$ alkoxy($C_1$-$C_2$) alkoxy, $C_3$-$C_6$ cycloalkyl, $C_3$-$C_6$ halocycloalkyl, phenyl or phenoxy, and when k is an integer of at least 2, each $R^{81}$ may be identical with or different from one another, and when there are two neighboring $R^{81}$'s, the two neighboring $R^{81}$'s may form —OCH$_2$O— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present, $R^z$ is a halogen atom, $C_1$-$C_6$ alkyl, phenoxy, phenyl or phenyl which may be substituted with m $R^{16}$'s, and when m is an integer of at least 2, each $R^{16}$ may be identical with or different from one another, and when s2 is an integer of at least 2, each $R^z$ may be identical with or different from one another, $R^{16}$ is a halogen atom, $C_1$-$C_6$ alkyl, $C_1$-$C_6$ alkoxy, $C_1$-$C_6$ haloalkyl or $C_1$-$C_6$ haloalkoxy, k is an integer of from 1 to 5, m is an integer of from 1 to 5, and s2 is an integer of from 0 to 3].

As the scope of the substituent represented by X in the compounds which fall within the present invention, the following sets may, for example, be mentioned.

X-1: a single bond.

X-2: —CH$_2$—.

The sets indicating the scope of each substituent in the compounds which fall within the present invention may be combined arbitrarily to indicate the scope of the compounds of the present invention. The scope of $R^1$, $R^2$, $R^3$, $R^8$ or X may be combined, for example, as shown in Table 1. The combinations shown in Table 1 merely exemplify the present invention, and the present invention is by no means restricted thereto.

TABLE 1

| $R^1$ | $R^2$ | $R^3$ | $R^8$ | X |
|---|---|---|---|---|
| $R^1$-I | $R^2$-I | $R^3$-I | $R^8$-I | X-1 |
| $R^1$-I | $R^2$-I | $R^3$-I | $R^8$-II | X-1 |
| $R^1$-I | $R^2$-I | $R^3$-I | $R^8$-III | X-1 |
| $R^1$-I | $R^2$-I | $R^3$-I | $R^8$-IV | X-1 |
| $R^1$-I | $R^2$-I | $R^3$-II | $R^8$-I | X-1 |
| $R^1$-I | $R^2$-I | $R^3$-II | $R^8$-II | X-1 |
| $R^1$-I | $R^2$-I | $R^3$-II | $R^8$-III | X-1 |
| $R^1$-I | $R^2$-I | $R^3$-II | $R^8$-IV | X-1 |
| $R^1$-I | $R^2$-I | $R^3$-III | $R^8$-I | X-1 |
| $R^1$-I | $R^2$-I | $R^3$-III | $R^8$-II | X-1 |
| $R^1$-I | $R^2$-I | $R^3$-III | $R^8$-III | X-1 |
| $R^1$-I | $R^2$-I | $R^3$-III | $R^8$-IV | X-1 |
| $R^1$-I | $R^2$-II | $R^3$-I | $R^8$-I | X-1 |
| $R^1$-I | $R^2$-II | $R^3$-I | $R^8$-II | X-1 |
| $R^1$-I | $R^2$-II | $R^3$-I | $R^8$-III | X-1 |
| $R^1$-I | $R^2$-II | $R^3$-I | $R^8$-IV | X-1 |
| $R^1$-I | $R^2$-II | $R^3$-II | $R^8$-I | X-1 |
| $R^1$-I | $R^2$-II | $R^3$-II | $R^8$-II | X-1 |
| $R^1$-I | $R^2$-II | $R^3$-II | $R^8$-III | X-1 |
| $R^1$-I | $R^2$-II | $R^3$-II | $R^8$-IV | X-1 |
| $R^1$-I | $R^2$-II | $R^3$-III | $R^8$-I | X-1 |
| $R^1$-I | $R^2$-II | $R^3$-III | $R^8$-II | X-1 |
| $R^1$-I | $R^2$-II | $R^3$-III | $R^8$-III | X-1 |
| $R^1$-I | $R^2$-II | $R^3$-III | $R^8$-IV | X-1 |
| $R^1$-I | $R^2$-III | $R^3$-I | $R^8$-I | X-1 |
| $R^1$-I | $R^2$-III | $R^3$-I | $R^8$-II | X-1 |
| $R^1$-I | $R^2$-III | $R^3$-I | $R^8$-III | X-1 |
| $R^1$-I | $R^2$-III | $R^3$-I | $R^8$-IV | X-1 |
| $R^1$-I | $R^2$-III | $R^3$-II | $R^8$-I | X-1 |
| $R^1$-I | $R^2$-III | $R^3$-II | $R^8$-II | X-1 |
| $R^1$-I | $R^2$-III | $R^3$-II | $R^8$-III | X-1 |
| $R^1$-I | $R^2$-III | $R^3$-II | $R^8$-IV | X-1 |
| $R^1$-I | $R^2$-III | $R^3$-III | $R^8$-I | X-1 |
| $R^1$-I | $R^2$-III | $R^3$-III | $R^8$-II | X-1 |
| $R^1$-I | $R^2$-III | $R^3$-III | $R^8$-III | X-1 |
| $R^1$-I | $R^2$-III | $R^3$-III | $R^8$-IV | X-1 |
| $R^1$-I | $R^2$-IV | $R^3$-I | $R^8$-I | X-1 |
| $R^1$-I | $R^2$-IV | $R^3$-I | $R^8$-II | X-1 |
| $R^1$-I | $R^2$-IV | $R^3$-I | $R^8$-III | X-1 |
| $R^1$-I | $R^2$-IV | $R^3$-I | $R^8$-IV | X-1 |
| $R^1$-I | $R^2$-IV | $R^3$-II | $R^8$-I | X-1 |
| $R^1$-I | $R^2$-IV | $R^3$-II | $R^8$-II | X-1 |
| $R^1$-I | $R^2$-IV | $R^3$-II | $R^8$-III | X-1 |
| $R^1$-I | $R^2$-IV | $R^3$-II | $R^8$-IV | X-1 |
| $R^1$-I | $R^2$-IV | $R^3$-III | $R^8$-I | X-1 |
| $R^1$-I | $R^2$-IV | $R^3$-III | $R^8$-II | X-1 |
| $R^1$-I | $R^2$-IV | $R^3$-III | $R^8$-III | X-1 |
| $R^1$-I | $R^2$-IV | $R^3$-III | $R^8$-IV | X-1 |
| $R^1$-II | $R^2$-I | $R^3$-I | $R^8$-I | X-1 |
| $R^1$-II | $R^2$-I | $R^3$-I | $R^8$-II | X-1 |
| $R^1$-II | $R^2$-I | $R^3$-I | $R^8$-III | X-1 |
| $R^1$-II | $R^2$-I | $R^3$-I | $R^8$-IV | X-1 |
| $R^1$-II | $R^2$-I | $R^3$-II | $R^8$-I | X-1 |
| $R^1$-II | $R^2$-I | $R^3$-II | $R^8$-II | X-1 |
| $R^1$-II | $R^2$-I | $R^3$-II | $R^8$-III | X-1 |
| $R^1$-II | $R^2$-I | $R^3$-II | $R^8$-IV | X-1 |
| $R^1$-II | $R^2$-I | $R^3$-III | $R^8$-I | X-1 |
| $R^1$-II | $R^2$-I | $R^3$-III | $R^8$-II | X-1 |
| $R^1$-II | $R^2$-I | $R^3$-III | $R^8$-III | X-1 |
| $R^1$-II | $R^2$-I | $R^3$-III | $R^8$-IV | X-1 |
| $R^1$-II | $R^2$-II | $R^3$-I | $R^8$-I | X-1 |
| $R^1$-II | $R^2$-II | $R^3$-I | $R^8$-II | X-1 |
| $R^1$-II | $R^2$-II | $R^3$-I | $R^8$-III | X-1 |
| $R^1$-II | $R^2$-II | $R^3$-I | $R^8$-IV | X-1 |
| $R^1$-II | $R^2$-II | $R^3$-II | $R^8$-I | X-1 |
| $R^1$-II | $R^2$-II | $R^3$-II | $R^8$-II | X-1 |
| $R^1$-II | $R^2$-II | $R^3$-II | $R^8$-III | X-1 |
| $R^1$-II | $R^2$-II | $R^3$-II | $R^8$-IV | X-1 |
| $R^1$-II | $R^2$-II | $R^3$-III | $R^8$-I | X-1 |
| $R^1$-II | $R^2$-II | $R^3$-III | $R^8$-II | X-1 |
| $R^1$-II | $R^2$-II | $R^3$-III | $R^8$-III | X-1 |
| $R^1$-II | $R^2$-II | $R^3$-III | $R^8$-IV | X-1 |
| $R^1$-II | $R^2$-III | $R^3$-I | $R^8$-I | X-1 |
| $R^1$-II | $R^2$-III | $R^3$-I | $R^8$-II | X-1 |
| $R^1$-II | $R^2$-III | $R^3$-I | $R^8$-III | X-1 |
| $R^1$-II | $R^2$-III | $R^3$-I | $R^8$-IV | X-1 |
| $R^1$-II | $R^2$-III | $R^3$-II | $R^8$-I | X-1 |
| $R^1$-II | $R^2$-III | $R^3$-II | $R^8$-II | X-1 |

TABLE 1-continued

| R¹ | R² | R³ | R⁸ | X |
|---|---|---|---|---|
| R¹-II | R²-III | R³-II | R⁸-III | X-1 |
| R¹-II | R²-III | R³-III | R⁸-I | X-1 |
| R¹-II | R²-III | R³-III | R⁸-II | X-1 |
| R¹-II | R²-III | R³-III | R⁸-III | X-1 |
| R¹-II | R²-III | R³-III | R⁸-IV | X-1 |
| R¹-II | R²-IV | R³-I | R⁸-I | X-1 |
| R¹-II | R²-IV | R³-I | R⁸-II | X-1 |
| R¹-II | R²-IV | R³-I | R⁸-III | X-1 |
| R¹-II | R²-IV | R³-I | R⁸-IV | X-1 |
| R¹-II | R²-IV | R³-II | R⁸-I | X-1 |
| R¹-II | R²-IV | R³-II | R⁸-II | X-1 |
| R¹-II | R²-IV | R³-II | R⁸-III | X-1 |
| R¹-II | R²-IV | R³-II | R⁸-IV | X-1 |
| R¹-II | R²-IV | R³-III | R⁸-I | X-1 |
| R¹-II | R²-IV | R³-III | R⁸-II | X-1 |
| R¹-II | R²-IV | R³-III | R⁸-III | X-1 |
| R¹-II | R²-IV | R³-III | R⁸-IV | X-1 |
| R¹-III | R²-I | R³-I | R⁸-I | X-1 |
| R¹-III | R²-I | R³-I | R⁸-II | X-1 |
| R¹-III | R²-I | R³-I | R⁸-III | X-1 |
| R¹-III | R²-I | R³-I | R⁸-IV | X-1 |
| R¹-III | R²-I | R³-II | R⁸-I | X-1 |
| R¹-III | R²-I | R³-II | R⁸-II | X-1 |
| R¹-III | R²-I | R³-II | R⁸-III | X-1 |
| R¹-III | R²-I | R³-II | R⁸-IV | X-1 |
| R¹-III | R²-I | R³-III | R⁸-I | X-1 |
| R¹-III | R²-I | R³-III | R⁸-II | X-1 |
| R¹-III | R²-I | R³-III | R⁸-III | X-1 |
| R¹-III | R²-I | R³-III | R⁸-IV | X-1 |
| R¹-III | R²-II | R³-I | R⁸-I | X-1 |
| R¹-III | R²-II | R³-I | R⁸-II | X-1 |
| R¹-III | R²-II | R³-I | R⁸-III | X-1 |
| R¹-III | R²-II | R³-I | R⁸-IV | X-1 |
| R¹-III | R²-II | R³-II | R⁸-I | X-1 |
| R¹-III | R²-II | R³-II | R⁸-II | X-1 |
| R¹-III | R²-II | R³-II | R⁸-III | X-1 |
| R¹-III | R²-II | R³-II | R⁸-IV | X-1 |
| R¹-III | R²-II | R³-III | R⁸-I | X-1 |
| R¹-III | R²-II | R³-III | R⁸-II | X-1 |
| R¹-III | R²-II | R³-III | R⁸-III | X-1 |
| R¹-III | R²-II | R³-III | R⁸-IV | X-1 |
| R¹-III | R²-III | R³-I | R⁸-I | X-1 |
| R¹-III | R²-III | R³-I | R⁸-II | X-1 |
| R¹-III | R²-III | R³-I | R⁸-III | X-1 |
| R¹-III | R²-III | R³-I | R⁸-IV | X-1 |
| R¹-III | R²-III | R³-II | R⁸-I | X-1 |
| R¹-III | R²-III | R³-II | R⁸-II | X-1 |
| R¹-III | R²-III | R³-II | R⁸-III | X-1 |
| R¹-III | R²-III | R³-II | R⁸-IV | X-1 |
| R¹-III | R²-III | R³-III | R⁸-I | X-1 |
| R¹-III | R²-III | R³-III | R⁸-II | X-1 |
| R¹-III | R²-III | R³-III | R⁸-III | X-1 |
| R¹-III | R²-III | R³-III | R⁸-IV | X-1 |
| R¹-III | R²-IV | R³-I | R⁸-I | X-1 |
| R¹-III | R²-IV | R³-I | R⁸-II | X-1 |
| R¹-III | R²-IV | R³-I | R⁸-III | X-1 |
| R¹-III | R²-IV | R³-I | R⁸-IV | X-1 |
| R¹-III | R²-IV | R³-II | R⁸-I | X-1 |
| R¹-III | R²-IV | R³-II | R⁸-II | X-1 |
| R¹-III | R²-IV | R³-II | R⁸-III | X-1 |
| R¹-III | R²-IV | R³-II | R⁸-IV | X-1 |
| R¹-III | R²-IV | R³-III | R⁸-I | X-1 |
| R¹-III | R²-IV | R³-III | R⁸-II | X-1 |
| R¹-III | R²-IV | R³-III | R⁸-III | X-1 |
| R¹-III | R²-IV | R³-III | R⁸-IV | X-1 |
| R¹-IV | R²-I | R³-I | R⁸-I | X-1 |
| R¹-IV | R²-I | R³-I | R⁸-II | X-1 |
| R¹-IV | R²-I | R³-I | R⁸-III | X-1 |
| R¹-IV | R²-I | R³-I | R⁸-IV | X-1 |
| R¹-IV | R²-I | R³-II | R⁸-I | X-1 |
| R¹-IV | R²-I | R³-II | R⁸-II | X-1 |
| R¹-IV | R²-I | R³-II | R⁸-III | X-1 |
| R¹-IV | R²-I | R³-II | R⁸-IV | X-1 |
| R¹-IV | R²-I | R³-III | R⁸-I | X-1 |
| R¹-IV | R²-I | R³-III | R⁸-II | X-1 |
| R¹-IV | R²-I | R³-III | R⁸-III | X-1 |
| R¹-IV | R²-I | R³-III | R⁸-IV | X-1 |
| R¹-IV | R²-II | R³-I | R⁸-I | X-1 |
| R¹-IV | R²-II | R³-I | R⁸-II | X-1 |
| R¹-IV | R²-II | R³-I | R⁸-III | X-1 |
| R¹-IV | R²-II | R³-I | R⁸-IV | X-1 |
| R¹-IV | R²-II | R³-II | R⁸-I | X-1 |
| R¹-IV | R²-II | R³-II | R⁸-II | X-1 |
| R¹-IV | R²-II | R³-II | R⁸-III | X-1 |
| R¹-IV | R²-II | R³-II | R⁸-IV | X-1 |
| R¹-IV | R²-II | R³-III | R⁸-I | X-1 |
| R¹-IV | R²-II | R³-III | R⁸-II | X-1 |
| R¹-IV | R²-II | R³-III | R⁸-III | X-1 |
| R¹-IV | R²-II | R³-III | R⁸-IV | X-1 |
| R¹-IV | R²-III | R³-I | R⁸-I | X-1 |
| R¹-IV | R²-III | R³-I | R⁸-II | X-1 |
| R¹-IV | R²-III | R³-I | R⁸-III | X-1 |
| R¹-IV | R²-III | R³-I | R⁸-IV | X-1 |
| R¹-IV | R²-III | R³-II | R⁸-I | X-1 |
| R¹-IV | R²-III | R³-II | R⁸-II | X-1 |
| R¹-IV | R²-III | R³-II | R⁸-III | X-1 |
| R¹-IV | R²-III | R³-II | R⁸-IV | X-1 |
| R¹-IV | R²-III | R³-III | R⁸-I | X-1 |
| R¹-IV | R²-III | R³-III | R⁸-II | X-1 |
| R¹-IV | R²-III | R³-III | R⁸-III | X-1 |
| R¹-IV | R²-III | R³-III | R⁸-IV | X-1 |
| R¹-IV | R²-IV | R³-I | R⁸-I | X-1 |
| R¹-IV | R²-IV | R³-I | R⁸-II | X-1 |
| R¹-IV | R²-IV | R³-I | R⁸-III | X-1 |
| R¹-IV | R²-IV | R³-I | R⁸-IV | X-1 |
| R¹-IV | R²-IV | R³-II | R⁸-I | X-1 |
| R¹-IV | R²-IV | R³-II | R⁸-II | X-1 |
| R¹-IV | R²-IV | R³-II | R⁸-III | X-1 |
| R¹-IV | R²-IV | R³-II | R⁸-IV | X-1 |
| R¹-IV | R²-IV | R³-III | R⁸-I | X-1 |
| R¹-IV | R²-IV | R³-III | R⁸-II | X-1 |
| R¹-IV | R²-IV | R³-III | R⁸-III | X-1 |
| R¹-IV | R²-IV | R³-III | R⁸-IV | X-1 |
| R¹-I | R²-I | R³-I | R⁸-I | X-2 |
| R¹-I | R²-I | R³-I | R⁸-II | X-2 |
| R¹-I | R²-I | R³-I | R⁸-III | X-2 |
| R¹-I | R²-I | R³-I | R⁸-IV | X-2 |
| R¹-I | R²-I | R³-II | R⁸-I | X-2 |
| R¹-I | R²-I | R³-II | R⁸-II | X-2 |
| R¹-I | R²-I | R³-II | R⁸-III | X-2 |
| R¹-I | R²-I | R³-II | R⁸-IV | X-2 |
| R¹-I | R²-I | R³-III | R⁸-I | X-2 |
| R¹-I | R²-I | R³-III | R⁸-II | X-2 |
| R¹-I | R²-I | R³-III | R⁸-III | X-2 |
| R¹-I | R²-I | R³-III | R⁸-IV | X-2 |
| R¹-I | R²-II | R³-I | R⁸-I | X-2 |
| R¹-I | R²-II | R³-I | R⁸-II | X-2 |
| R¹-I | R²-II | R³-I | R⁸-III | X-2 |
| R¹-I | R²-II | R³-I | R⁸-IV | X-2 |
| R¹-I | R²-II | R³-II | R⁸-I | X-2 |
| R¹-I | R²-II | R³-II | R⁸-II | X-2 |
| R¹-I | R²-II | R³-II | R⁸-III | X-2 |
| R¹-I | R²-II | R³-II | R⁸-IV | X-2 |
| R¹-I | R²-II | R³-III | R⁸-I | X-2 |
| R¹-I | R²-II | R³-III | R⁸-II | X-2 |
| R¹-I | R²-II | R³-III | R⁸-III | X-2 |
| R¹-I | R²-II | R³-III | R⁸-IV | X-2 |
| R¹-I | R²-III | R³-I | R⁸-I | X-2 |
| R¹-I | R²-III | R³-I | R⁸-II | X-2 |
| R¹-I | R²-III | R³-I | R⁸-III | X-2 |
| R¹-I | R²-III | R³-I | R⁸-IV | X-2 |
| R¹-I | R²-III | R³-II | R⁸-I | X-2 |
| R¹-I | R²-III | R³-II | R⁸-II | X-2 |
| R¹-I | R²-III | R³-II | R⁸-III | X-2 |
| R¹-I | R²-III | R³-II | R⁸-IV | X-2 |
| R¹-I | R²-III | R³-III | R⁸-I | X-2 |
| R¹-I | R²-III | R³-III | R⁸-II | X-2 |
| R¹-I | R²-III | R³-III | R⁸-III | X-2 |
| R¹-I | R²-III | R³-III | R⁸-IV | X-2 |
| R¹-I | R²-IV | R³-I | R⁸-I | X-2 |
| R¹-I | R²-IV | R³-I | R⁸-II | X-2 |
| R¹-I | R²-IV | R³-I | R⁸-III | X-2 |
| R¹-I | R²-IV | R³-I | R⁸-IV | X-2 |
| R¹-I | R²-IV | R³-II | R⁸-I | X-2 |
| R¹-I | R²-IV | R³-II | R⁸-II | X-2 |

TABLE 1-continued

| R¹ | R² | R³ | R⁸ | X |
|---|---|---|---|---|
| R¹-I | R²-IV | R³-II | R⁸-III | X-2 |
| R¹-I | R²-IV | R³-II | R⁸-IV | X-2 |
| R¹-I | R²-IV | R³-III | R⁸-I | X-2 |
| R¹-I | R²-IV | R³-III | R⁸-II | X-2 |
| R¹-I | R²-IV | R³-III | R⁸-III | X-2 |
| R¹-I | R²-IV | R³-III | R⁸-IV | X-2 |
| R¹-II | R²-I | R³-I | R⁸-I | X-2 |
| R¹-II | R²-I | R³-I | R⁸-II | X-2 |
| R¹-II | R²-I | R³-I | R⁸-III | X-2 |
| R¹-II | R²-I | R³-I | R⁸-IV | X-2 |
| R¹-II | R²-I | R³-II | R⁸-I | X-2 |
| R¹-II | R²-I | R³-II | R⁸-II | X-2 |
| R¹-II | R²-I | R³-II | R⁸-III | X-2 |
| R¹-II | R²-I | R³-II | R⁸-IV | X-2 |
| R¹-II | R²-I | R³-III | R⁸-I | X-2 |
| R¹-II | R²-I | R³-III | R⁸-II | X-2 |
| R¹-II | R²-I | R³-III | R⁸-III | X-2 |
| R¹-II | R²-I | R³-III | R⁸-IV | X-2 |
| R¹-II | R²-II | R³-I | R⁸-I | X-2 |
| R¹-II | R²-II | R³-I | R⁸-II | X-2 |
| R¹-II | R²-II | R³-I | R⁸-III | X-2 |
| R¹-II | R²-II | R³-I | R⁸-IV | X-2 |
| R¹-II | R²-II | R³-II | R⁸-I | X-2 |
| R¹-II | R²-II | R³-II | R⁸-II | X-2 |
| R¹-II | R²-II | R³-II | R⁸-III | X-2 |
| R¹-II | R²-II | R³-II | R⁸-IV | X-2 |
| R¹-II | R²-II | R³-III | R⁸-I | X-2 |
| R¹-II | R²-II | R³-III | R⁸-II | X-2 |
| R¹-II | R²-II | R³-III | R⁸-III | X-2 |
| R¹-II | R²-II | R³-III | R⁸-IV | X-2 |
| R¹-II | R²-III | R³-I | R⁸-I | X-2 |
| R¹-II | R²-III | R³-I | R⁸-II | X-2 |
| R¹-II | R²-III | R³-I | R⁸-III | X-2 |
| R¹-II | R²-III | R³-I | R⁸-IV | X-2 |
| R¹-II | R²-III | R³-II | R⁸-I | X-2 |
| R¹-II | R²-III | R³-II | R⁸-II | X-2 |
| R¹-II | R²-III | R³-II | R⁸-III | X-2 |
| R¹-II | R²-III | R³-II | R⁸-IV | X-2 |
| R¹-II | R²-III | R³-III | R⁸-I | X-2 |
| R¹-II | R²-III | R³-III | R⁸-II | X-2 |
| R¹-II | R²-III | R³-III | R⁸-III | X-2 |
| R¹-II | R²-III | R³-III | R⁸-IV | X-2 |
| R¹-II | R²-IV | R³-I | R⁸-I | X-2 |
| R¹-II | R²-IV | R³-I | R⁸-II | X-2 |
| R¹-II | R²-IV | R³-I | R⁸-III | X-2 |
| R¹-II | R²-IV | R³-I | R⁸-IV | X-2 |
| R¹-II | R²-IV | R³-II | R⁸-I | X-2 |
| R¹-II | R²-IV | R³-II | R⁸-II | X-2 |
| R¹-II | R²-IV | R³-II | R⁸-III | X-2 |
| R¹-II | R²-IV | R³-II | R⁸-IV | X-2 |
| R¹-II | R²-IV | R³-III | R⁸-I | X-2 |
| R¹-II | R²-IV | R³-III | R⁸-II | X-2 |
| R¹-II | R²-IV | R³-III | R⁸-III | X-2 |
| R¹-II | R²-IV | R³-III | R⁸-IV | X-2 |
| R¹-III | R²-I | R³-I | R⁸-I | X-2 |
| R¹-III | R²-I | R³-I | R⁸-II | X-2 |
| R¹-III | R²-I | R³-I | R⁸-III | X-2 |
| R¹-III | R²-I | R³-I | R⁸-IV | X-2 |
| R¹-III | R²-I | R³-II | R⁸-I | X-2 |
| R¹-III | R²-I | R³-II | R⁸-II | X-2 |
| R¹-III | R²-I | R³-II | R⁸-III | X-2 |
| R¹-III | R²-I | R³-II | R⁸-IV | X-2 |
| R¹-III | R²-I | R³-III | R⁸-I | X-2 |
| R¹-III | R²-I | R³-III | R⁸-II | X-2 |
| R¹-III | R²-I | R³-III | R⁸-III | X-2 |
| R¹-III | R²-I | R³-III | R⁸-IV | X-2 |
| R¹-III | R²-II | R³-I | R⁸-I | X-2 |
| R¹-III | R²-II | R³-I | R⁸-II | X-2 |
| R¹-III | R²-II | R³-I | R⁸-III | X-2 |
| R¹-III | R²-II | R³-I | R⁸-IV | X-2 |
| R¹-III | R²-II | R³-II | R⁸-I | X-2 |
| R¹-III | R²-II | R³-II | R⁸-II | X-2 |
| R¹-III | R²-II | R³-II | R⁸-III | X-2 |
| R¹-III | R²-II | R³-II | R⁸-IV | X-2 |
| R¹-III | R²-II | R³-III | R⁸-I | X-2 |
| R¹-III | R²-II | R³-III | R⁸-II | X-2 |
| R¹-III | R²-II | R³-III | R⁸-III | X-2 |
| R¹-III | R²-II | R³-III | R⁸-IV | X-2 |
| R¹-III | R²-III | R³-I | R⁸-I | X-2 |
| R¹-III | R²-III | R³-I | R⁸-II | X-2 |
| R¹-III | R²-III | R³-I | R⁸-III | X-2 |
| R¹-III | R²-III | R³-I | R⁸-IV | X-2 |
| R¹-III | R²-III | R³-II | R⁸-I | X-2 |
| R¹-III | R²-III | R³-II | R⁸-II | X-2 |
| R¹-III | R²-III | R³-II | R⁸-III | X-2 |
| R¹-III | R²-III | R³-II | R⁸-IV | X-2 |
| R¹-III | R²-III | R³-III | R⁸-I | X-2 |
| R¹-III | R²-III | R³-III | R⁸-II | X-2 |
| R¹-III | R²-III | R³-III | R⁸-III | X-2 |
| R¹-III | R²-III | R³-III | R⁸-IV | X-2 |
| R¹-III | R²-IV | R³-I | R⁸-I | X-2 |
| R¹-III | R²-IV | R³-I | R⁸-II | X-2 |
| R¹-III | R²-IV | R³-I | R⁸-III | X-2 |
| R¹-III | R²-IV | R³-I | R⁸-IV | X-2 |
| R¹-III | R²-IV | R³-II | R⁸-I | X-2 |
| R¹-III | R²-IV | R³-II | R⁸-II | X-2 |
| R¹-III | R²-IV | R³-II | R⁸-III | X-2 |
| R¹-III | R²-IV | R³-II | R⁸-IV | X-2 |
| R¹-III | R²-IV | R³-III | R⁸-I | X-2 |
| R¹-III | R²-IV | R³-III | R⁸-II | X-2 |
| R¹-III | R²-IV | R³-III | R⁸-III | X-2 |
| R¹-III | R²-IV | R³-III | R⁸-IV | X-2 |
| R¹-IV | R²-I | R³-I | R⁸-I | X-2 |
| R¹-IV | R²-I | R³-I | R⁸-II | X-2 |
| R¹-IV | R²-I | R³-I | R⁸-III | X-2 |
| R¹-IV | R²-I | R³-I | R⁸-IV | X-2 |
| R¹-IV | R²-I | R³-II | R⁸-I | X-2 |
| R¹-IV | R²-I | R³-II | R⁸-II | X-2 |
| R¹-IV | R²-I | R³-II | R⁸-III | X-2 |
| R¹-IV | R²-I | R³-II | R⁸-IV | X-2 |
| R¹-IV | R²-I | R³-III | R⁸-I | X-2 |
| R¹-IV | R²-I | R³-III | R⁸-II | X-2 |
| R¹-IV | R²-I | R³-III | R⁸-III | X-2 |
| R¹-IV | R²-I | R³-III | R⁸-IV | X-2 |
| R¹-IV | R²-II | R³-I | R⁸-I | X-2 |
| R¹-IV | R²-II | R³-I | R⁸-II | X-2 |
| R¹-IV | R²-II | R³-I | R⁸-III | X-2 |
| R¹-IV | R²-II | R³-I | R⁸-IV | X-2 |
| R¹-IV | R²-II | R³-II | R⁸-I | X-2 |
| R¹-IV | R²-II | R³-II | R⁸-II | X-2 |
| R¹-IV | R²-II | R³-II | R⁸-III | X-2 |
| R¹-IV | R²-II | R³-II | R⁸-IV | X-2 |
| R¹-IV | R²-II | R³-III | R⁸-I | X-2 |
| R¹-IV | R²-II | R³-III | R⁸-II | X-2 |
| R¹-IV | R²-II | R³-III | R⁸-III | X-2 |
| R¹-IV | R²-II | R³-III | R⁸-IV | X-2 |
| R¹-IV | R²-III | R³-I | R⁸-I | X-2 |
| R¹-IV | R²-III | R³-I | R⁸-II | X-2 |
| R¹-IV | R²-III | R³-I | R⁸-III | X-2 |
| R¹-IV | R²-III | R³-I | R⁸-IV | X-2 |
| R¹-IV | R²-III | R³-II | R⁸-I | X-2 |
| R¹-IV | R²-III | R³-II | R⁸-II | X-2 |
| R¹-IV | R²-III | R³-II | R⁸-III | X-2 |
| R¹-IV | R²-III | R³-II | R⁸-IV | X-2 |
| R¹-IV | R²-III | R³-III | R⁸-I | X-2 |
| R¹-IV | R²-III | R³-III | R⁸-II | X-2 |
| R¹-IV | R²-III | R³-III | R⁸-III | X-2 |
| R¹-IV | R²-III | R³-III | R⁸-IV | X-2 |
| R¹-IV | R²-IV | R³-I | R⁸-I | X-2 |
| R¹-IV | R²-IV | R³-I | R⁸-II | X-2 |
| R¹-IV | R²-IV | R³-I | R⁸-III | X-2 |
| R¹-IV | R²-IV | R³-I | R⁸-IV | X-2 |
| R¹-IV | R²-IV | R³-II | R⁸-I | X-2 |
| R¹-IV | R²-IV | R³-II | R⁸-II | X-2 |
| R¹-IV | R²-IV | R³-II | R⁸-III | X-2 |
| R¹-IV | R²-IV | R³-II | R⁸-IV | X-2 |
| R¹-IV | R²-IV | R³-III | R⁸-I | X-2 |
| R¹-IV | R²-IV | R³-III | R⁸-II | X-2 |
| R¹-IV | R²-IV | R³-III | R⁸-III | X-2 |
| R¹-IV | R²-IV | R³-III | R⁸-IV | X-2 |

The compounds of the present invention can be produced, for example, by the following processes.

Process A

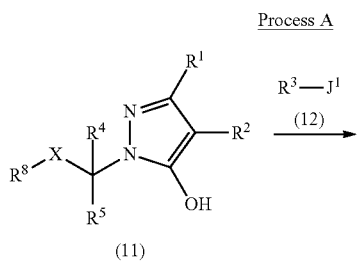

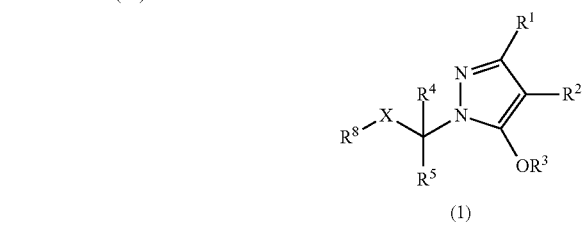

A compound presented by the formula (11) [wherein $R^1$, $R^2$, $R^4$, $R^5$, $R^8$ and X are the same as defined above] and a compound represented by the formula (12) [wherein $R^3$ is the same as defined above, and $J^1$ is a chlorine atom, a bromine atom, an iodine atom, a halosulfonyloxy group (such as a fluorosulfonyloxy group), a $C_1$-$C_4$ haloalkylsulfonyloxy group (such as a trifluoromethanesulfonyloxy group) or an arylsulfonyloxy group (such as a benzenesulfonyloxy group)] may be reacted, if necessary in the presence of a base, if necessary by using a solvent inert to the reaction, to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (12) may be used per 1 equivalent of the compound represented by the formula (11).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (11).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using from 1 to 10 equivalents of a compound represented by the formula (12) per 1 equivalent of a compound represented by the formula (11) in a solvent such as tetrahydrofuran, 1,4-dioxane, acetonitrile, N,N-dimethylformamide, chloroform, methylene chloride or toluene, if necessary by using from 1 to 3 equivalents of a base such as sodium hydride, potassium t-butoxide, potassium hydroxide, potassium carbonate, triethylamine or pyridine per 1 equivalent of the compound represented by the formula (11) at 0~100° C. for 10 minutes to 24 hours.

Process B

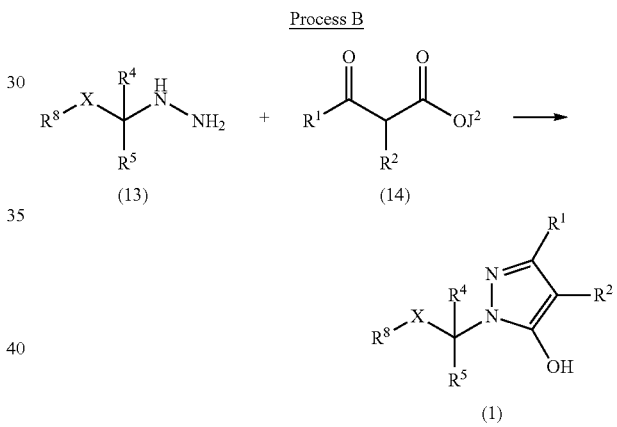

A compound represented by the formula (13) [wherein $R^4$, $R^5$, $R^8$ and X are the same as defined above] and a compound represented by the formula (14) [wherein $R^1$ and $R^2$ are the same as defined above, and $J^2$ is an alkyl group such as a methyl group or an ethyl group] are reacted, if necessary in the presence of an acid, if necessary by using a solvent inert to the reaction, by a known method disclosed in the literature such as WO 2005/061462 to obtain a compound of the present invention represented by the formula (1) [wherein $R^1$, $R^2$, $R^4$, $R^5$, $R^8$ and X are the same as defined above].

Regarding the amounts of the reactants, from 1 to 50 equivalents of the compound represented by the formula (13) may be used per 1 equivalent of the compound represented by the formula (14).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As an acid, if used, a mineral acid such as hydrochloric acid or sulfuric acid, a carboxylic acid such as formic acid, acetic acid, trifluoroacetic acid, mandelic acid or tartaric acid, a sulfonic acid such as methanesulfonic acid, p-toluenesulfonic acid, benzensulfonic acid, trifluoromethanesulfonic acid or camphor sulfonic acid, phosphorus oxychloride, Amberlite IR-120 (type H) or the like may be used in an amount of from 1 to 10 equivalents per 1 equivalent of a compound represented by the formula (14).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using from 1 to 10 equivalents of a compound represented by the formula (13) per 1 equivalent of a compound represented by the formula (14) in a solvent such as ethanol, toluene, tetrahydrofuran, 1,4-dioxane, acetonitrile, N,N-dimethylformamide, chloroform or methylene chloride, if necessary by using from 1 to 3 equivalents of an acid such as acetic acid, p-toluenesulfonic acid or hydrochloric acid at 0-100° C. for 10 minutes to 24 hours.

Some of the keto esters represented by the formula (15) used herein are known compounds, and some of them are commercially available. The rest of them can be readily synthesized from known compounds by known methods disclosed in the literature such as JP-A-2002-020366, J. Med. Chem., 2005, vol. 48, pages 3400.

Process C

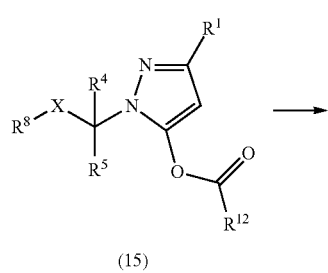

(15)

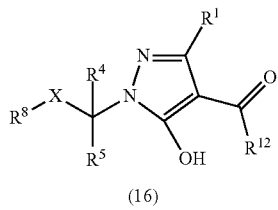

(16)

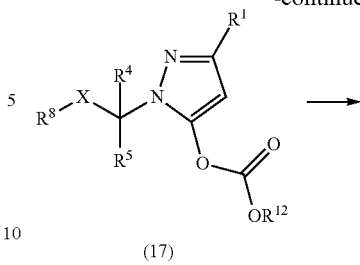

(17)

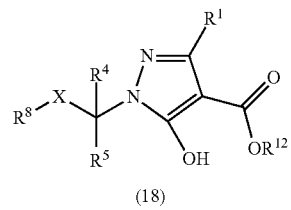

(18)

A compound represented by the formula (15) obtainable by Process A and a compound represented by the formula (17) [wherein $R^1$, $R^4$, $R^5$, $R^8$, $R^{12}$ and X are the same as defined above] are reacted, if necessary in the presence of a base, if necessary by using a solvent inert to the reaction, by a known method disclosed in the literature such as WO2007/142308 to obtain a compound of the present invention represented by the formula (16) [wherein $R^1$, $R^4$, $R^5$, $R^8$, $R^{12}$ and X are the same as defined above].

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (15) or (17).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using 1 equivalent of a compound represented by the formula (15) to (17) in a solvent such as ethanol, toluene, tetrahydrofuran, 1,4-dioxane, acetonitrile, N,N-dimethylformamide, chloroform or methylene chloride, if necessary by using from 1 to 3 equivalents of a base such as sodium hydride, potassium t-butoxide, potassium hydroxide, potassium carbonate, triethylamine or pyridine per 1 equivalent of the compound represented by the formula (15) or (17) at 0-100° C. for 10 minutes to 24 hours.

Process D

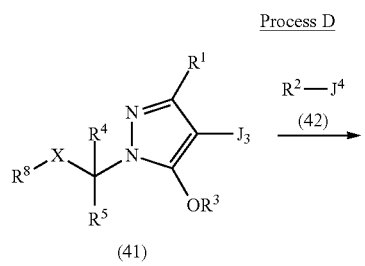

(41)

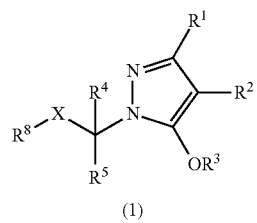

(1)

A compound represented by the formula (41) [wherein $R^1$, $R^3$, $R^4$, $R^5$, $R^8$ and X are the same as defined above, and $J^3$ is a chlorine atom, a bromine atom, an iodine atom or the like] and a compound represented by the formula (42) [wherein $R^2$ is the same as defined above, and $J^4$ is dihydroxyborane or the like] are reacted, if necessary in the presence of a metal catalyst, if necessary in the presence of a base, if necessary by using a solvent inert to the reaction, by a known method disclosed in the literature such as WO 2010/0794432 to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (42) may be used per 1 equivalent of the compound represented by the formula (41).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (41) or (42).

As the metal catalyst, if use, a palladium hydroxide catalyst such as $Pd(OH)_2$, a palladium oxide catalyst such as PdO, a palladium halide catalyst such as $PdBr_2$, $PdCl_2$ or $PdI_2$, a palladium acetate catalyst such as palladium acetate (Pd$(OAc)_2$) or palladium trifluoroacetate ($Pd(OCOCF_3)_2$), a palladium metal complex catalyst having a ligand such as $Pd(RNC)_2Cl_2$, $Pd(acac)_2$, diacetate bis(triphenylphosphine) palladium [$Pd(OAc)_2$ $(PPh_3)_2$], $Pd(PPh_3)_4$, $Pd_2$ $(dba)_3$, $Pd(NH_3)_2Cl_2$, $Pd(CH_3CN)_2Cl_2$, dichlorobis(benzonitrile) palladium [$Pd(PhCN)_2Cl_2$], $Pd(dppe)Cl_2$, $Pd(dppf)Cl_2$, $Pd[PCy_3]_2Cl_2$, $Pd(PPh_3)_2Cl_2$, $Pd[P(o-tolyl)_3]_2Cl_2$, $Pd(cod)_2Cl_2$, $Pd(PPh_3)(CH_3CN)_2Cl_2$, Bis(di-tert-butyl(4-dimethylaminophenyl)phosphine)dichloropalladium(II) or the like may, for example, be mentioned.

Such a metal catalyst may be used in an amount of from 1 to 10 equivalents per 1 equivalent of a compound represented by the formula (41) or (42).

Process E

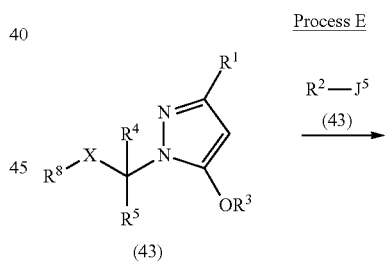

(43)

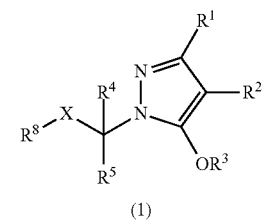

(1)

A compound represented by the formula (43) [wherein $R^1$, $R^3$, $R^4$, $R^5$, $R^8$ and X are the same as defined above] and a compound represented by the formula (44) [wherein $R^2$ is the same as defined above, and $J^5$ is a chlorine atom, a bromine atom, an iodine atom or the like] are reacted, if necessary in the presence of a base, if necessary by using a solvent inert to the reaction, by a known method disclosed in the literature such as Bioorganic & Medicinal Chemistry, 2006, vol. 14, p. 5061 to obtain a compound of the present invention represented by the formula (1) [wherein $R^1$, $R^2$, $R^3$, $R^4$, $R^5$, $R^8$ and X are the same as defined above].

Regarding the amounts of the reactants, from 1 to 50 equivalents of the compound represented by the formula (44) may be used per 1 equivalent of the compound represented by the formula (43).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide, potassium hydroxide or calcium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (43) or (44).

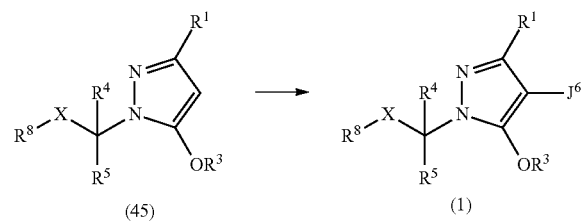

Process F

(45) → (1)

A compound represented by the formula (45) [wherein $R^1$, $R^3$, $R^4$, $R^5$, $R^8$ and X are は the same as defined above] is reacted, if necessary by using a solvent inert to the reaction, by a known method disclosed in the literature such as Bioorganic & Medicinal Chemistry, 2006, vol. 14, p. 5061 to obtain a compound of the present invention represented by the formula (1) [wherein $R^1$, $R^3$, $R^4$, $R^5$, $R^8$ and X are the same as defined above, and $J^6$ is a chlorine atom, a bromine atom, an iodine atom or the like].

As the halogenation reagent, N-bromosuccinimide, N-chlorosuccinimide, chlorine, bromine, potassium iodide, sodium iodide or the like may be used.

Regarding the amounts of the reactants, from 1 to 50 equivalents of a halogenations reagent may be used per 1 equivalent of a compound represented by the formula (45).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions.

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

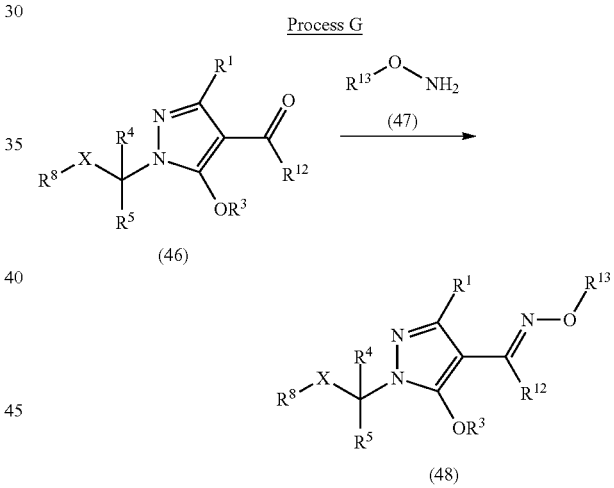

Process G

(46) → (48)

A compound represented by the formula (46) [wherein $R^1$, $R^3$, $R^4$, $R^5$, $R^8$, $R^{12}$ and X are the same as defined above] and a compound represented by the formula (47) are reacted, if necessary in the presence of a base, if necessary by using a solvent inert to the reaction, by a known method disclosed in the literature such as European Journal of Organic Chemistry, 2003, vol. 7, p. 1209 and Organic Letters, 2008, vol. 10, p. 1695 to obtain a compound of the present invention represented by the formula (48) [wherein $R^1$, $R^3$, $R^4$, $R^5$, $R^8$, $R^{12}$, $R^{13}$ and X are the same as defined above].

Regarding the amounts of the reactants, from 1 to 50 equivalents of the compound represented by the formula (47) may be used per 1 equivalent of the compound represented by the formula (46).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions.

As the base, if used, an alkali metal hydride such as sodium hydride or potassium hydride, an alkali metal hydroxide such as hydroxide, potassium hydroxide, calcium hydroxide or sodium acetate, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (46) or (47).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

In general, the reaction is preferably carried out by using 1 equivalent of a compound represented by the formula (46) and a compound represented by the formula (47) in a solvent such as ethanol, toluene, tetrahydrofuran, 1,4-dioxane, acetonitrile, N, N-dimethylformamide, chloroform or methylene chloride, if necessary by using from 1 to 3 equivalents of a base such as sodium hydride, potassium t-butoxide, potassium hydroxide, potassium carbonate, sodium acetate, triethylamine or pyrimidine per 1 equivalent of the compound represented by the formula (46) or (47) at 0~100° C. for 10 minutes to 24 hours.

Some of the amine compounds represented by the formula (47) used herein are known compounds, and some of them are commercially available. The rest of them can be readily synthesized from known compounds by known methods disclosed in the literature such as J. Am. Chem. Soc, 2011, vol. 133, p. 8704.

In Processes A, B, C, D, F and G, the reaction mixture obtained after the reaction is worked up by ordinary operations such as direct concentration, dissolution in an organic solvent followed by washing with water and concentration, or addition to ice-cold water followed by extraction with an organic solvent and concentration to obtain a compound of the present invention as intended. If purification is needed, it may be isolated or purified by a certain method such as recrystallization, column chromatography, thin layer chromatography and liquid chromatography.

The compound represented by the formula (13) used in Process B can be synthesized, for example, as follows.

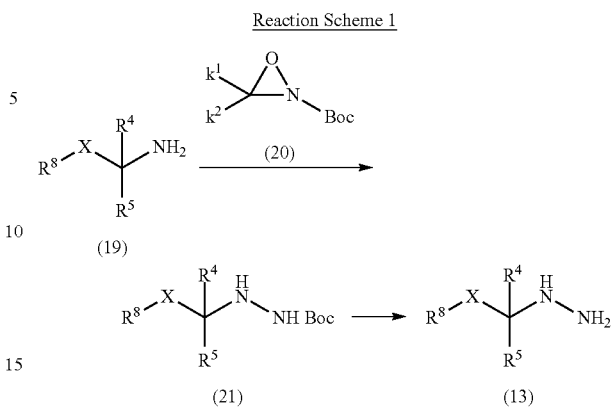

Reaction Scheme 1

A known substituted amine represented by the formula (19) [wherein $R^4$, $R^5$, $R^8$ and X are the same as defined above] and a compound represented by the formula (20) [wherein $k^1$ and $k^2$ are hydrogen atoms, trichloromethyl groups, cyclohexyl groups, phenyl groups, p-cyanophenyl groups, ethoxycarbonyl groups or the like, and Boc is a t-butoxycarbonyl group are reacted, if necessary by using a solvent inert to the reaction, by a known method disclosed in the literature such as Tetrahedron Lett., 1989, vol. 39, p. 6845 to obtain a compound represented by the formula (13) [wherein $R^4$, $R^5$, $R^8$ and X are the same as defined above].

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

Some of the compounds represented by the formula (19) used herein are known compounds, and some of them are commercially available. The rest of them can be readily synthesized from known compounds by known methods disclosed in the literature such as Journal of Medicinal Chemistry, 2009, vol. 52, p. 3982, Chem. Commun., 2001, p. 1792, and Synthesis 2000, vol. 12, p. 1709.

The compound represented by the formula (20) used herein can be synthesized readily from a known compound in accordance with Journal of Medicinal Chemistry, 2009, vol. 52, p. 1471 [52(5), 1471-1476; 2009] or WO2008/073987.

The compound represented by the formula (13) used in Process B can be synthesized in accordance with J. Chem. Soc., Chem. Commun., 1986, p. 176, or J. Chem. Soc., Chem. Commun., 1983, p. 1040, for example, as follows.

Reaction Scheme 2

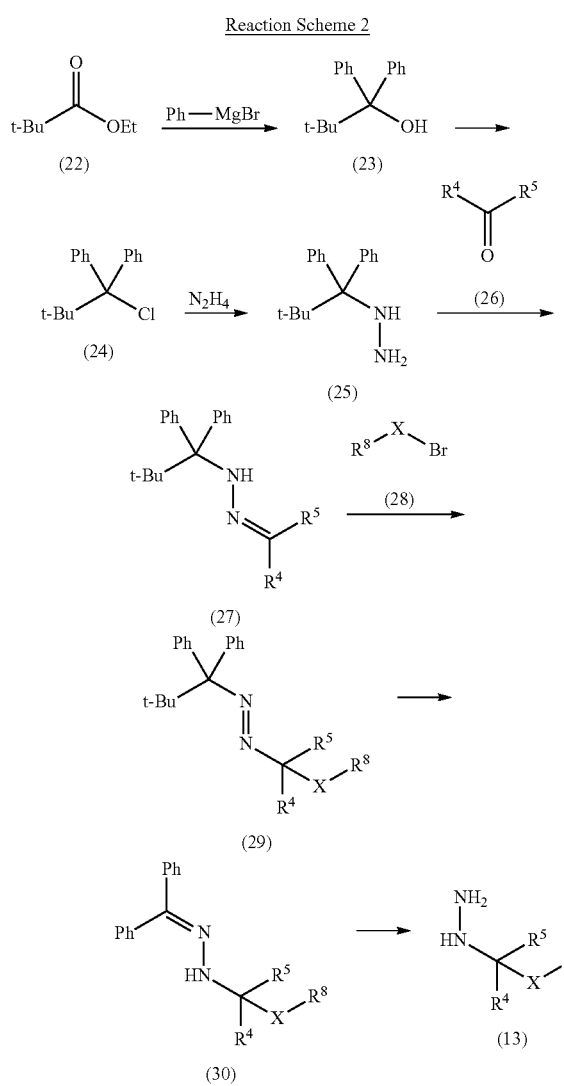

An ethyl pivalate represented by the formula (22) and a phenyl Grignard reagent by the formula are reacted, if necessary by using a solvent inert to the reaction, the resulting alcohol compound represented by the formula (23) is halogenated, and the resulting halide compound represented by the formula (24) is reacted with hydrazine to obtain a hydrazine compound represented by the formula (25).

The resulting hydrazine compound represented by the formula (25) is reacted with a carbonyl compound represented by the formula (26), if necessary by using a solvent inert to the reaction, the resulting hydrazine compound represented by the formula (27) is reacted with a halide compound represented by the formula (28), if necessary in the presence of a base, if necessary by using a solvent inert to the reaction, and the resulting hydrazine compound represented by the formula (29) is reacted in the presence of an acid, if necessary by using a solvent inert to the reaction to obtain a hydrazine compound represented by the formula (30).

The resulting hydrazine compound represented by the formula (30) is reacted in the presence of an acid, if necessary by using a solvent inert to the reaction to obtain a hydrazine compound represented by the formula (13).

As the solvent, if used, an aromatic hydrocarbon such as benzene, toluene or xylene, an aliphatic hydrocarbon such as hexane or heptane, an alicyclic hydrocarbon such as cyclohexane, an aromatic halohydrocarbon such as chlorobenzene or dichlorobenzene, an aliphatic halohydrocarbon such as dichloromethane, chloroform, carbon tetrachloride, 1,2-dichloroethane, 1,1,1-trichloroethane, trichloroethylene or tetrachloroethylene, an ether such as diethyl ether, 1,2-dimethoxyethane, tetrahydrofuran or 1,4-dioxane, an ester such as ethyl acetate or ethyl propionate, an amide such as dimethylformamide, dimethylacetamide or N-methyl-2-pyrrolidone, an amine such as triethylamine, tributylamine or N,N-dimethylaniline, a pyridine such as pyridine or picoline, an alcohol such as methanol, ethanol or ethylene glycol, acetonitrile, dimethyl sulfoxide, sulfolane, 1,3-dimethyl-1-imidazolidinone, water or the like may, for example, be mentioned, though it may be any solvent that does not hinder the progress of the reaction without any particular restrictions. These solvents may be used alone or in combinations of two or more.

As the base, if used, an alkali metal hydride such as sodium hydride or potassium hydride, an alkali metal hydroxide such as hydroxide or potassium hydroxide, an alkali metal alkoxide such as sodium ethoxide or potassium t-butoxide, an alkali metal amide such as lithium diidopropylamide, lithium diisopropylamide, lithium hexamethyldisilazane or sodium amide, an organic metal compound such as t-butyllithium, an alkali metal carbonate such as sodium carbonate, potassium carbonate or sodium hydrogen carbonate, an organic base such as triethylamine, tributylamine, N,N-dimethylaniline, pyridine, 4-(dimethylamino)pyridine or imidazole, 1,8-diazabicyclo[5,4,0]-7-undecene or the like may be used in an amount of from 1 to 10 equivalents per 1 equivalent of a compound represented by the formula (27).

As the acid, if used, a mineral acid such as hydrochloric acid or sulfuric acid, a carboxylic acid such as formic acid, acetic acid, trifluoroacetic acid, mandelic acid or tartaric acid, a sulfonic acid such as methanesulfonic acid, p-toluenesulfonic acid, benzensulfonic acid, trifluoromethanesulfonic acid or camphor sulfonic acid, phosphorus oxychloride, Amberlite IR-120 (type H) or the like may be used in an amount of from 1 to 10 equivalents per 1 equivalent of a compound represented by the formula (29) or (30).

The reaction temperature may be set arbitrarily within the range of from −60° C. to the refluxing temperature of the reaction mixture, and the reaction time may be set arbitrarily within the range of from 5 minutes to 100 hours, though it depends on the concentrations of the reactants and the reaction temperature.

Some of the compounds represented by the formula (22) used herein are known compounds, and some of them are commercially available. The rest of them can be readily synthesized by ordinary methods for synthesis of ester compounds disclosed in the literature.

Some of the compounds represented by the formula (26) used herein are known compounds, and some of them are commercially available. The rest of them can be readily synthesized by ordinary methods for synthesis of carbonyl compounds disclosed in the literature.

Some of the compounds represented by the formula (28) used herein are known compounds, and some of them are commercially available. The rest of them can be readily synthesized by ordinary methods for synthesis of halide compounds disclosed in the literature.

The compound represented by the formula (12) used in Process B can be synthesized in accordance with J. Am. Chem. Soc., 1958, vol. 80, p. 6562, for example, as follows.

Reaction Scheme 3

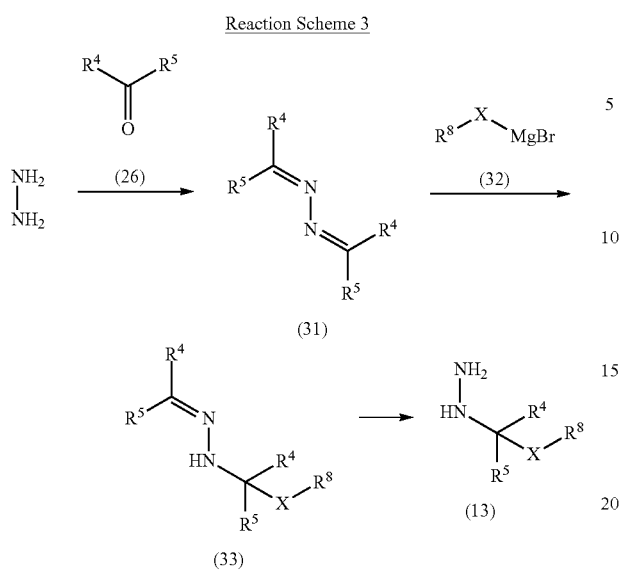

Hydrazine and a carbonyl compound represented by the formula (26) are reacted, if necessary by using a solvent inert to the reaction, and the resulting hydrazine compound represented by the formula (31) is reacted with a Grignard reagent represented by the formula (32) to obtain a hydrazine compound represented by the formula (33).

The resulting hydrazine compound represented by the formula (33) is reacted in the presence of an acid, if necessary by using a solvent inert to the reaction to obtain a hydrazine compound represented by the formula (13).

Some of the compounds represented by the formula (26) used herein are known compounds, and some of them are commercially available. The rest of them can be readily synthesized by ordinary methods for synthesis of carbonyl compounds disclosed in the literature.

Some of the compounds represented by the formula (32) used herein are known compounds, and some of them are commercially available. The rest of them can be readily synthesized by ordinary methods for synthesis of Grignard reagents disclosed in the literature.

In each of these reactions, the reaction mixture is worked up by ordinary operations to obtain each intermediate used as a starting compound.

Each intermediate produced in these processes can be used for the reaction in the next step without isolation or purification.

As specific compounds of the present invention, for example, those shown in Tables 2 to 15 may be mentioned. However, the compounds merely exemplify the present invention, and the present invention is by no means restricted thereto.

In the Tables, Et denotes ethyl group, and similarly, n-Pr and Pr-n denote normal propyl group, i-Pr and Pr-I denote isopropyl group, c-Pr and Pr-c denote cyclopropyl group, n-Bu and Bu-n denote normal butyl group, s-Bu and Bu-s denote secondary butyl group, i-Bu and Bu-I denote isobutyl group, t-Bu and Bu-t denote t-butyl group, c-Bu and Bu-c denote cyclobutyl group, n-Pen and Pen-n denote normal pentyl group, c-Pen and Pen-c denote cyclopentyl group, n-Hex and Hex-n denote normal hexyl group, c-Hex and Hex-c denote cyclohexyl group, and Ph denotes phenyl group.

The aromatic heterocyclic rings represented by A001 to A044 in the Tables have the following structures, respectively.

A001

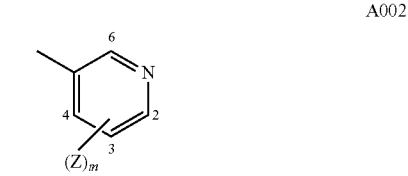

A002

A003

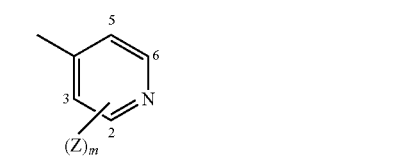

A004

A005

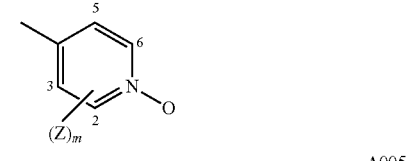

A006

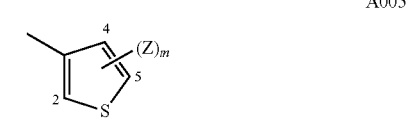

A007

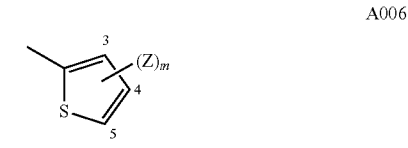

A008

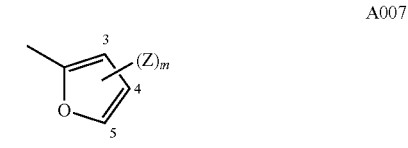

A009

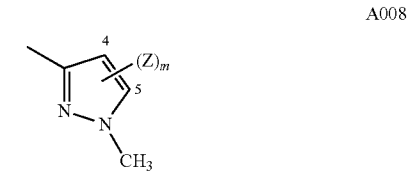

A010

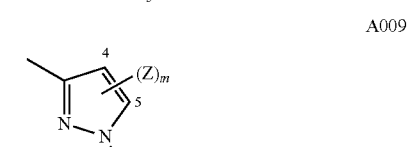

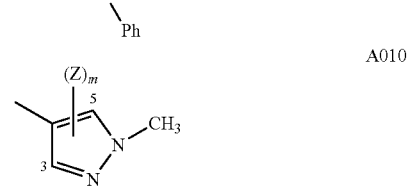

| | | |
|---|---|---|
| 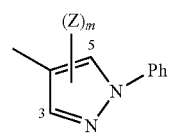 | A011 | 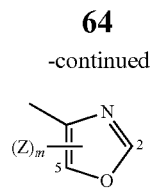 A022 |
| 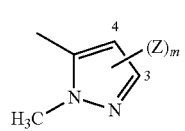 | A012 | 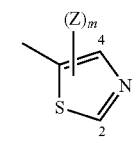 A023 |
| 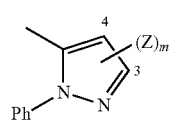 | A013 | 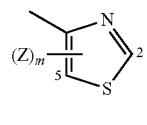 A024 |
| 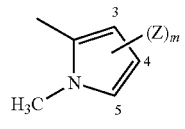 | A014 | A025 |
| 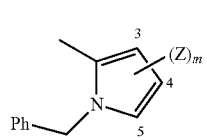 | A015 | 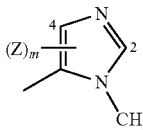 A026 |
| 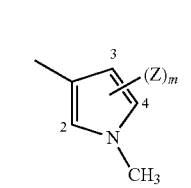 | A016 | 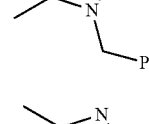 A027 |
| 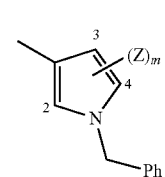 | A017 | A028 |
| 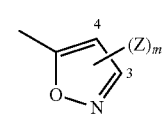 | A018 | 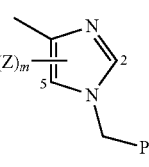 A029 |
| 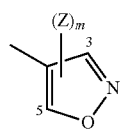 | A019 | 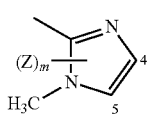 A030 |
| 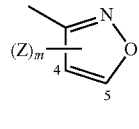 | A020 | 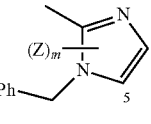 A031 |
| 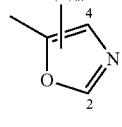 | A021 | 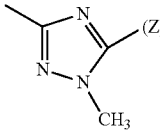 A032 |

The aliphatic heterocyclic rings represented by A051 to A068 in the Tables have the following structures, respectively.

-continued

| | |
|---|---|
| A060 | A101 |
| A061 | A102 |
| A062 | A103 |
| A063 | A104 |
| A064 | A105 |
| A065 | A106 |
| A066 | A107 |
| A067 | |
| A068 | |

The partially saturated heterocyclic rings represented by A101 to A107 in the Tables have the following structures, respectively.

TABLE 2
The locants for the substituents R²¹ and R⁸¹ in the Table correspond to the positions indicated in the following structural formulae.
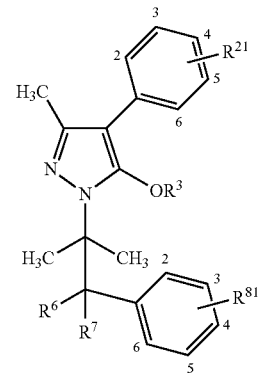
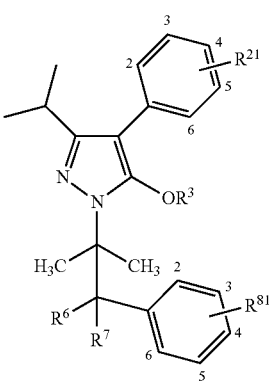
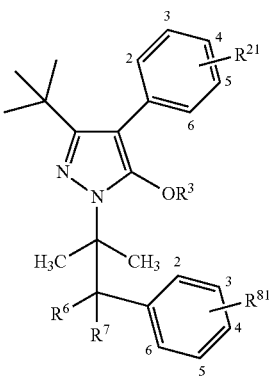
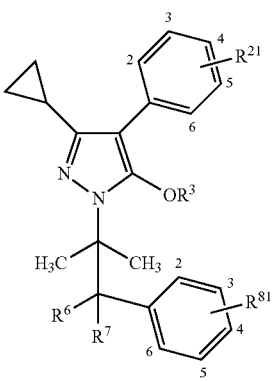
TABLE 2-continued
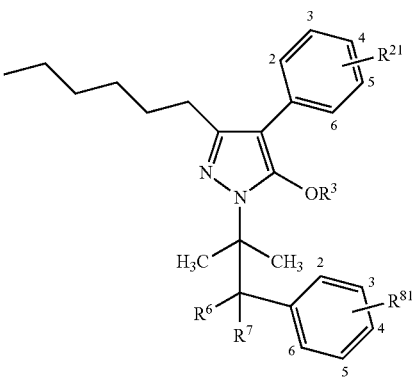
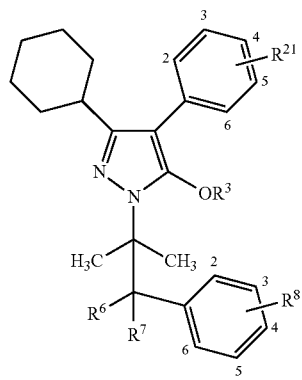
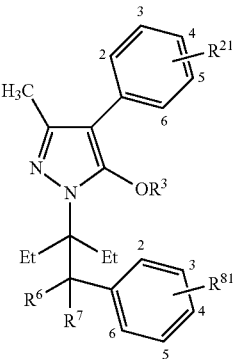
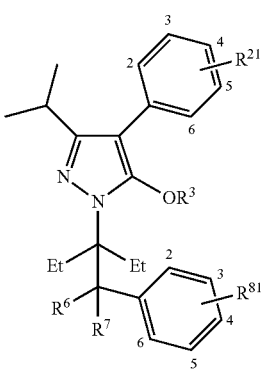

TABLE 2-continued
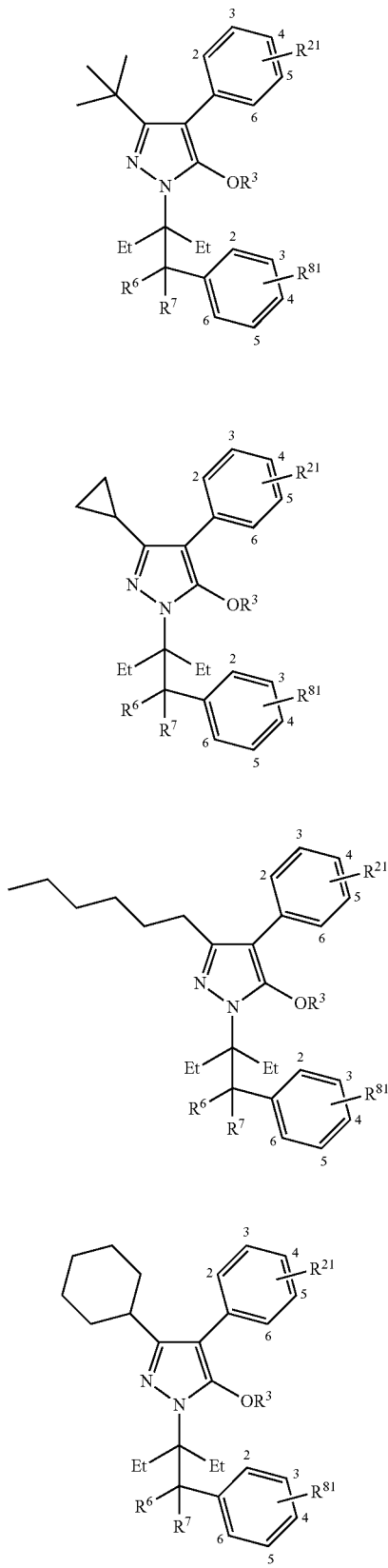
TABLE 2-continued
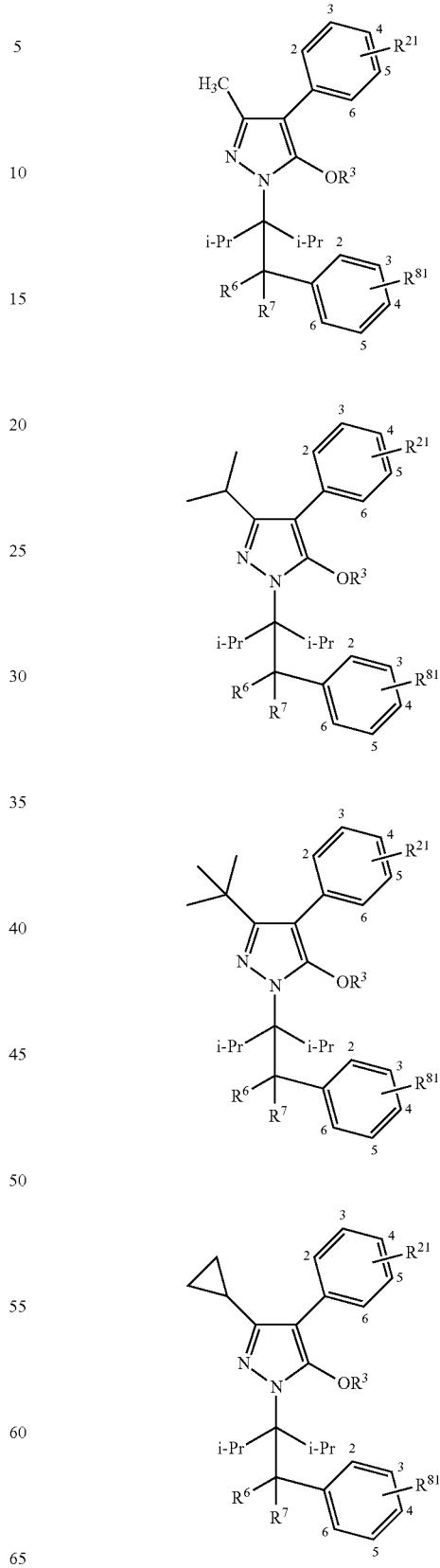

TABLE 2-continued
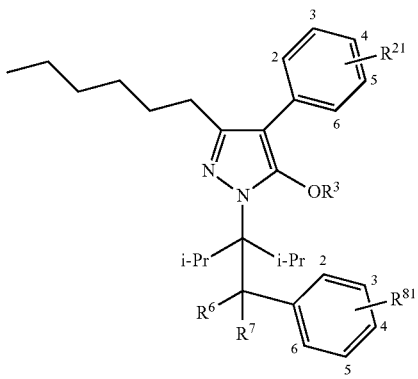
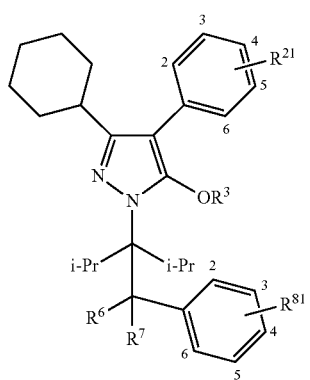
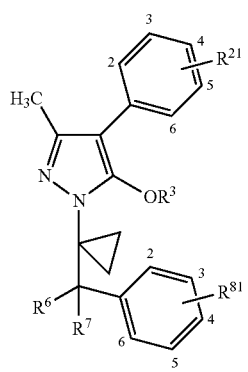
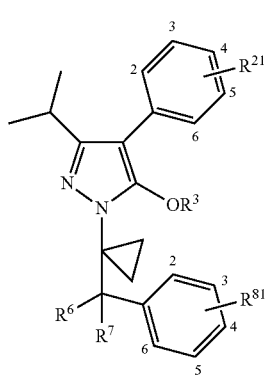
TABLE 2-continued
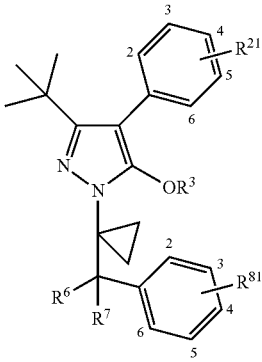
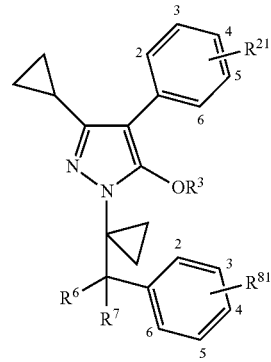
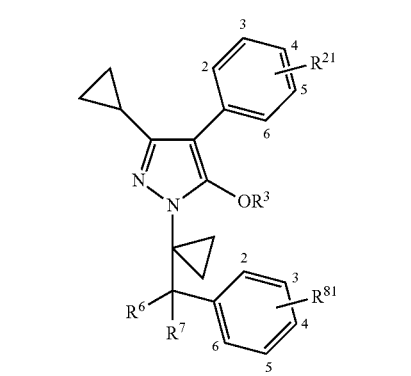
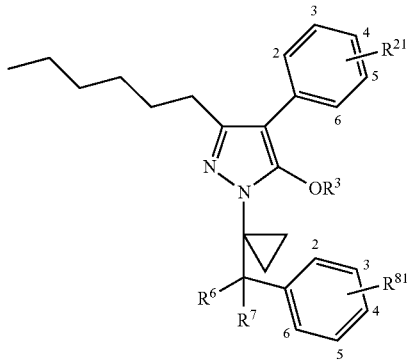
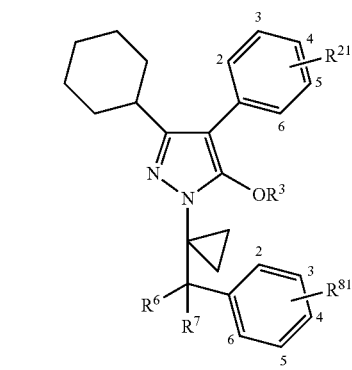
| $R^{21}$ | $R^{81}$ | $R^3$ | $R^6$ | $R^7$ |
|---|---|---|---|---|
| H | H | H | H | H |
| H | 4-F | H | H | H |
| H | 2-Cl | H | H | H |

TABLE 2-continued

| | | | | |
|---|---|---|---|---|
| H | 3-Cl | H | H | H |
| H | 4-Cl | H | H | H |
| H | 4-Cl | CH₃ | H | H |
| H | 4-Cl | CH₂Ph | H | H |
| H | 4-Cl | C(O)Ph | H | H |
| H | 4-Cl | C(O)OEt | H | H |
| H | 4-Cl | H | H | CH₃ |
| H | 4-Cl | CH₃ | H | CH₃ |
| H | 4-Cl | H | CH₃ | CH₃ |
| H | 4-Br | H | H | H |
| H | 4-I | H | H | H |
| H | 2,4-Cl₂ | H | H | H |
| H | 3,4-Cl₂ | H | H | H |
| H | 4-NO₂ | H | H | H |
| H | 4-CN | H | H | H |
| H | 2-CH₃ | H | H | H |
| H | 3-CH₃ | H | H | H |
| H | 4-CH₃ | H | H | H |
| H | 4-CH₃ | CH₃ | H | H |
| H | 4-CH₃ | CH₂Ph | H | H |
| H | 4-CH₃ | C(O)Ph | H | H |
| H | 4-CH₃ | C(O)OEt | H | H |
| H | 4-CH₃ | H | H | CH₃ |
| H | 4-CH₃ | CH₃ | H | CH₃ |
| H | 4-CH₃ | H | CH₃ | CH₃ |
| H | 4-Et | H | H | H |
| H | 4-n-Pr | H | H | H |
| H | 4-c-Pr | H | H | H |
| H | 4-i-Pr | H | H | H |
| H | 4-n-Bu | H | H | H |
| H | 4-c-Bu | H | H | H |
| H | 4-i-Bu | H | H | H |
| H | 4-t-Bu | H | H | H |
| H | 4-t-Bu | CH₃ | H | H |
| H | 4-t-Bu | CH₂Ph | H | H |
| H | 4-t-Bu | C(O)Ph | H | H |
| H | 4-t-Bu | C(O)OEt | H | H |
| H | 4-t-Bu | H | H | CH₃ |
| H | 4-t-Bu | CH₃ | H | CH₃ |
| H | 4-t-Bu | H | CH₃ | CH₃ |
| H | 4-n-Pen | H | H | H |
| H | 4-c-Pen | H | H | H |
| H | 4-n-Hex | H | H | H |
| H | 4-n-Hex | CH₃ | H | H |
| H | 4-n-Hex | CH₂Ph | H | H |
| H | 4-n-Hex | C(O)Ph | H | H |
| H | 4-n-Hex | C(O)OEt | H | H |
| H | 4-n-Hex | H | H | CH₃ |
| H | 4-n-Hex | CH₃ | H | CH₃ |
| H | 4-n-Hex | H | CH₃ | CH₃ |
| H | 4-c-Hex | H | H | H |
| H | 4-n-C₇H₁₅ | H | H | H |
| H | 4-n C₈H₁₇ | H | H | H |
| H | 4-n-C₉H₁₉ | H | H | H |
| H | 4-n-C₁₀H₂₁ | H | H | H |
| H | 2,4-(CH₃) | H | H | H |
| H | 3,4-(CH₃)₂ | H | H | H |
| H | 4-CF₃ | H | H | H |
| H | 4-OH | H | H | H |
| H | 2-OCH₃ | H | H | H |
| H | 3-OCH₃ | H | H | H |
| H | 4-OCH₃ | H | H | H |
| H | 4-O-n-Hex | H | H | H |
| H | 4-O-c-Hex | H | H | H |
| H | 2,4-(OCH₃)₂ | H | H | H |
| H | 3,4-(OCH₃)₂ | H | H | H |
| H | 4-OCH₂OCH₃ | H | H | H |
| H | 4-OC₂H₄OEt | H | H | H |
| H | 4-OCF₃ | H | H | H |
| H | 4-OPh | H | H | H |
| H | 4-OCH₂Ph | H | H | H |
| H | 4-C(CH₃)=NCH₃ | H | H | H |
| H | 4-C(CH₃)=NPh | H | H | H |
| H | 4-C(Ph)=NCH₃ | H | H | H |
| H | 4-C(Ph)=NPh | H | H | H |
| H | 4-C(CH₃)=NOCH₃ | H | H | H |
| H | 4-C(CH₃)=NOPh | H | H | H |
| H | 4-C(Ph)=NOCH₃ | H | H | H |
| H | 4-C(Ph)=NOPh | H | H | H |
| H | 4-C(O)CH₃ | H | H | H |
| H | 4-C(O)CF₃ | H | H | H |
| H | 4-C(O)Ph | H | H | H |
| H | 4-C(O)OCH₃ | H | H | H |
| H | 2-C(O)OEt | H | H | H |
| H | 3-C(O)OEt | H | H | H |
| H | 4-C(O)OEt | H | H | H |
| H | 4-C(O)OPh | H | H | H |
| H | 4-C(O)OCH₂Ph | H | H | H |
| H | 4-C(O)OCH(CH₃)Ph | H | H | H |
| H | 4-C(O)OC₂H₄Ph | H | H | H |
| H | 4-SCH₃ | H | H | H |
| H | 4-S(O)CH₃ | H | H | H |
| H | 4-S(O)₂CH₃ | H | H | H |
| H | 4-SPh | H | H | H |
| H | 4-S(O)Ph | H | H | H |
| H | 4-S(O)₂Ph | H | H | H |
| H | 4-OS(O)₂CH₃ | H | H | H |
| H | 4-OS(O)₂Ph | H | H | H |
| H | 4-N(CH₃)₂ | H | H | H |
| H | 4-N(CH₂Ph)₂ | H | H | H |
| H | 4-N(CH₃)(CH₂Ph) | H | H | H |
| H | 4-NHCH₃ | H | H | H |
| H | 4-NH(CH₂Ph) | H | H | H |
| H | 4-C(O)N(CH₃)₂ | H | H | H |
| H | 4-C(O)N(CH₂Ph)₂ | H | H | H |
| H | 4-C(O)N(CH₃)(CH₂Ph) | H | H | H |
| H | 4-C(O)NHCH₃ | H | H | H |
| H | 4-C(O)NH(CH₂Ph) | H | H | H |
| H | 4-C(O)NH(CH(CH₃)Ph) | H | H | H |
| H | 4-C(O)NH(C₂H₄Ph) | H | H | H |
| H | 4-C(S)NH₂ | H | H | H |
| H | 4-S(O)₂N(CH₃)₂ | H | H | H |
| H | 4-S(O)₂N(CH₂Ph)₂ | H | H | H |
| H | 4-S(O)₂N(CH₃)(CH₂Ph) | H | H | H |
| H | 4-S(O)₂NHCH₃ | H | H | H |
| H | 4-S(O)₂NHPh | H | H | H |
| H | 4-S(O)₂NH(CH₂Ph) | H | H | H |
| H | 4-S(O)₂NH{CH(CH₃)Ph} | H | H | H |
| H | 4-S(O)₂NH(C₂H₄Ph) | H | H | H |
| H | 4-Ph | H | H | H |
| H | 4-Ph | CH₃ | H | H |
| H | 4-Ph | CH₂Ph | H | H |
| H | 4-Ph | C(O)Ph | H | H |
| H | 4-Ph | C(O)OEt | H | H |
| H | 4-Ph | H | H | CH₃ |
| H | 4-Ph | CH₃ | H | CH₃ |
| H | 4-Ph | H | CH₃ | CH₃ |
| 4-F | H | H | H | H |
| 4-F | 4-Cl | H | H | H |
| 4-F | 4-Br | H | H | H |
| 4-F | 4-CH₃ | H | H | H |
| 4-F | 4-t-Bu | H | H | H |
| 4-F | 4-n-Hex | H | H | H |
| 4-F | 4-Ph | H | H | H |
| 2-Cl | H | H | H | H |
| 2-Cl | 4-Cl | H | H | H |
| 2-Cl | 4-Br | H | H | H |
| 2-Cl | 4-CH₃ | H | H | H |
| 2-Cl | 4-t-Bu | H | H | H |
| 2-Cl | 4-n-Hex | H | H | H |
| 2-Cl | 4-Ph | H | H | H |
| 3-Cl | H | H | H | H |
| 3-Cl | 4-Cl | H | H | H |
| 3-Cl | 4-Br | H | H | H |
| 3-Cl | 4-CH₃ | H | H | H |
| 3-Cl | 4-t-Bu | H | H | H |
| 3-Cl | 4-n-Hex | H | H | H |
| 3-Cl | 4-Ph | H | H | H |
| 4-Cl | H | H | H | H |
| 4-Cl | 4-Cl | H | H | H |
| 4-Cl | 4-Br | H | H | H |
| 4-Cl | 4-CH₃ | H | H | H |
| 4-Cl | 4-t-Bu | H | H | H |
| 4-Cl | 4-t-Bu | CH₃ | H | H |
| 4-Cl | 4-n-Hex | H | H | H |
| 4-Cl | 4-n-Hex | CH₃ | H | H |
| 4-Cl | 4-n-Hex | H | H | CH₃ |
| 4-Cl | 4-n-Hex | H | CH₃ | CH₃ |
| 4-Cl | 4-Ph | H | H | H |
| 4-Cl | 4-Ph | CH₃ | H | H |

TABLE 2-continued

| | | | | |
|---|---|---|---|---|
| 4-Br | H | H | H | H |
| 4-Br | 4-Cl | H | H | H |
| 4-Br | 4-Br | H | H | H |
| 4-Br | 4-CH$_3$ | H | H | H |
| 4-Br | 4-t-Bu | H | H | H |
| 4-Br | 4-n-Hex | H | H | H |
| 4-Br | 4-Ph | H | H | H |
| 3,4-Cl$_2$ | H | H | H | H |
| 3,4-Cl$_2$ | 4-Cl | H | H | H |
| 3,4-Cl$_2$ | 4-Br | H | H | H |
| 3,4-Cl$_2$ | 4-CH$_3$ | H | H | H |
| 3,4-Cl$_2$ | 4-t-Bu | H | H | H |
| 3,4-Cl$_2$ | 4-n-Hex | H | H | H |
| 3,4-Cl$_2$ | 4-Ph | H | H | H |
| 4-NO$_2$ | H | H | H | H |
| 4-NO$_2$ | 4-Cl | H | H | H |
| 4-NO$_2$ | 4-Br | H | H | H |
| 4-NO$_2$ | 4-CH$_3$ | H | H | H |
| 4-NO$_2$ | 4-t-Bu | H | H | H |
| 4-NO$_2$ | 4-n-Hex | H | H | H |
| 4-NO$_2$ | 4-Ph | H | H | H |
| 4-CN | H | H | H | H |
| 4-CN | 4-Cl | H | H | H |
| 4-CN | 4-Br | H | H | H |
| 4-CN | 4-CH$_3$ | H | H | H |
| 4-CN | 4-t-Bu | H | H | H |
| 4-CN | 4-n-Hex | H | H | H |
| 4-CN | 4-Ph | H | H | H |
| 2-CH$_3$ | H | H | H | H |
| 2-CH$_3$ | 4-Cl | H | H | H |
| 2-CH$_3$ | 4-Br | H | H | H |
| 2-CH$_3$ | 4-CH$_3$ | H | H | H |
| 2-CH$_3$ | 4-t-Bu | H | H | H |
| 2-CH$_3$ | 4-n-Hex | H | H | H |
| 2-CH$_3$ | 4-Ph | H | H | H |
| 3-CH$_3$ | H | H | H | H |
| 3-CH$_3$ | 4-Cl | H | H | H |
| 3-CH$_3$ | 4-Br | H | H | H |
| 3-CH$_3$ | 4-CH$_3$ | H | H | H |
| 3-CH$_3$ | 4-t-Bu | H | H | H |
| 3-CH$_3$ | 4-n-Hex | H | H | H |
| 3-CH$_3$ | 4-Ph | H | H | H |
| 4-CH$_3$ | H | H | H | H |
| 4-CH$_3$ | 4-Cl | H | H | H |
| 4-CH$_3$ | 4-Br | H | H | H |
| 4-CH$_3$ | 4-CH$_3$ | H | H | H |
| 4-CH$_3$ | 4-t-Bu | H | H | H |
| 4-CH$_3$ | 4-t-Bu | CH$_3$ | H | H |
| 4-CH$_3$ | 4-n-Hex | H | H | H |
| 4-CH$_3$ | 4-n-Hex | CH$_3$ | H | H |
| 4-CH$_3$ | 4-n-Hex | H | H | CH$_3$ |
| 4-CH$_3$ | 4-n-Hex | H | CH$_3$ | CH$_3$ |
| 4-CH$_3$ | 4-Ph | H | H | H |
| 4-CH$_3$ | 4-Ph | CH$_3$ | H | H |
| 4-c-Pr | H | H | H | H |
| 4-c-Pr | 4-Cl | H | H | H |
| 4-c-Pr | 4-Br | H | H | H |
| 4-c-Pr | 4-CH$_3$ | H | H | H |
| 4-c-Pr | 4-t-Bu | H | H | H |
| 4-c-Pr | 4-n-Hex | H | H | H |
| 4-c-Pr | 4-Ph | H | H | H |
| 4-i-Pr | H | H | H | H |
| 4-i-Pr | 4-Cl | H | H | H |
| 4-i-Pr | 4-Br | H | H | H |
| 4-i-Pr | 4-CH$_3$ | H | H | H |
| 4-i-Pr | 4-t-Bu | H | H | H |
| 4-i-Pr | 4-n-Hex | H | H | H |
| 4-i-Pr | 4-Ph | H | H | H |
| 4-t-Bu | H | H | H | H |
| 4-t-Bu | 4-Cl | H | H | H |
| 4-t-Bu | 4-Br | H | H | H |
| 4-t-Bu | 4-CH$_3$ | H | H | H |
| 4-t-Bu | 4-t-Bu | H | H | H |
| 4-t-Bu | 4-t-Bu | CH$_3$ | H | H |
| 4-t-Bu | 4-n-Hex | H | H | H |
| 4-t-Bu | 4-n-Hex | CH$_3$ | H | H |
| 4-t-Bu | 4-n-Hex | H | H | CH$_3$ |
| 4-t-Bu | 4-n-Hex | H | CH$_3$ | CH$_3$ |
| 4-t-Bu | 4-Ph | H | H | H |
| 4-t-Bu | 4-Ph | CH$_3$ | H | H |
| 4-n-Hex | H | H | H | H |
| 4-n-Hex | H | CH$_3$ | H | H |
| 4-n-Hex | H | CH$_2$Ph | H | H |
| 4-n-Hex | H | C(O)Ph | H | H |
| 4-n-Hex | H | C(O)OEt | H | H |
| 4-n-Hex | H | H | H | CH$_3$ |
| 4-n-Hex | H | CH$_3$ | H | CH$_3$ |
| 4-n-Hex | H | H | CH$_3$ | CH$_3$ |
| 4-n-Hex | 4-F | H | H | H |
| 4-n-Hex | 2-Cl | H | H | H |
| 4-n-Hex | 3-Cl | H | H | H |
| 4-n-Hex | 4-Cl | H | H | H |
| 4-n-Hex | 4-Cl | CH$_3$ | H | H |
| 4-n-Hex | 4-Cl | CH$_2$Ph | H | H |
| 4-n-Hex | 4-Cl | C(O)Ph | H | H |
| 4-n-Hex | 4-Cl | C(O)OEt | H | H |
| 4-n-Hex | 4-Cl | H | H | CH$_3$ |
| 4-n-Hex | 4-Cl | CH$_3$ | H | CH$_3$ |
| 4-n-Hex | 4-Cl | H | CH$_3$ | CH$_3$ |
| 4-n-Hex | 4-Br | H | H | H |
| 4-n-Hex | 4-I | H | H | H |
| 4-n-Hex | 2,4-Cl$_2$ | H | H | H |
| 4-n-Hex | 3,4-Cl$_2$ | H | H | H |
| 4-n-Hex | 4-NO$_2$ | H | H | H |
| 4-n-Hex | 4-CN | H | H | H |
| 4-n-Hex | 2-CH$_3$ | H | H | H |
| 4-n-Hex | 3-CH$_3$ | H | H | H |
| 4-n-Hex | 4-CH$_3$ | H | H | H |
| 4-n-Hex | 4-CH$_3$ | CH$_3$ | H | H |
| 4-n-Hex | 4-CH$_3$ | CH$_2$Ph | H | H |
| 4-n-Hex | 4-CH$_3$ | C(O)Ph | H | H |
| 4-n-Hex | 4-CH$_3$ | C(O)OEt | H | H |
| 4-n-Hex | 4-CH$_3$ | H | H | CH$_3$ |
| 4-n-Hex | 4-CH$_3$ | CH$_3$ | H | CH$_3$ |
| 4-n-Hex | 4-CH$_3$ | H | CH$_3$ | CH$_3$ |
| 4-n-Hex | 4-Et | H | H | H |
| 4-n-Hex | 4-n-Pr | H | H | H |
| 4-n-Hex | 4-c-Pr | H | H | H |
| 4-n-Hex | 4-i-Pr | H | H | H |
| 4-n-Hex | 4-n-Bu | H | H | H |
| 4-n-Hex | 4-c-Bu | H | H | H |
| 4-n-Hex | 4-i-Bu | H | H | H |
| 4-n-Hex | 4-t-Bu | H | H | H |
| 4-n-Hex | 4-t-Bu | CH$_3$ | H | H |
| 4-n-Hex | 4-t-Bu | CH$_2$Ph | H | H |
| 4-n-Hex | 4-t-Bu | C(O)Ph | H | H |
| 4-n-Hex | 4-t-Bu | C(O)OEt | H | H |
| 4-n-Hex | 4-t-Bu | H | H | CH$_3$ |
| 4-n-Hex | 4-t-Bu | CH$_3$ | H | CH$_3$ |
| 4-n-Hex | 4-t-Bu | H | CH$_3$ | CH$_3$ |
| 4-n-Hex | 4-n-Pen | H | H | H |
| 4-n-Hex | 4-c-Pen | H | H | H |
| 4-n-Hex | 4-n-Hex | H | H | H |
| 4-n-Hex | 4-n-Hex | CH$_3$ | H | H |
| 4-n-Hex | 4-n-Hex | CH$_2$Ph | H | H |
| 4-n-Hex | 4-n-Hex | C(O)Ph | H | H |
| 4-n-Hex | 4-n-Hex | C(O)OEt | H | H |
| 4-n-Hex | 4-n-Hex | H | H | CH$_3$ |
| 4-n-Hex | 4-n-Hex | CH$_3$ | H | CH$_3$ |
| 4-n-Hex | 4-n-Hex | H | CH$_3$ | CH$_3$ |
| 4-n-Hex | 4-c-Hex | H | H | H |
| 4-n-Hex | 4-n-C$_7$H$_{15}$ | H | H | H |
| 4-n-Hex | 4-n-C$_8$H$_{17}$ | H | H | H |
| 4-n-Hex | 4-n-C$_9$H$_{19}$ | H | H | H |
| 4-n-Hex | 4-n-C$_{10}$H$_{21}$ | H | H | H |
| 4-n-Hex | 2,4-(CH$_3$) | H | H | H |
| 4-n-Hex | 3,4-(CH$_3$)$_2$ | H | H | H |
| 4-n-Hex | 4-CF$_3$ | H | H | H |
| 4-n-Hex | 4-OH | H | H | H |
| 4-n-Hex | 2-OCH$_3$ | H | H | H |
| 4-n-Hex | 3-OCH$_3$ | H | H | H |
| 4-n-Hex | 4-OCH$_3$ | H | H | H |
| 4-n-Hex | 4-O-n-Hex | H | H | H |
| 4-n-Hex | 4-O-c-Hex | H | H | H |
| 4-n-Hex | 2,4-(OCH$_3$)$_2$ | H | H | H |
| 4-n-Hex | 3,4-(OCH$_3$)$_2$ | H | H | H |
| 4-n-Hex | 4-OCH$_2$OCH$_3$ | H | H | H |
| 4-n-Hex | 4-OC$_2$H$_4$OEt | H | H | H |
| 4-n-Hex | 4-OCF$_3$ | H | H | H |
| 4-n-Hex | 4-OPh | H | H | H |

TABLE 2-continued

| | | | | |
|---|---|---|---|---|
| 4-n-Hex | 4-OCH₂Ph | H | H | H |
| 4-n-Hex | 4-C(CH₃)=NCH₃ | H | H | H |
| 4-n-Hex | 4-C(CH₃)=NPh | H | H | H |
| 4-n-Hex | 4-C(Ph)=NCH₃ | H | H | H |
| 4-n-Hex | 4-C(Ph)=NPh | H | H | H |
| 4-n-Hex | 4-C(CH₃)=NOCH₃ | H | H | H |
| 4-n-Hex | 4-C(CH₃)=NOPh | H | H | H |
| 4-n-Hex | 4-C(Ph)=NOCH₃ | H | H | H |
| 4-n-Hex | 4-C(Ph)=NOPh | H | H | H |
| 4-n-Hex | 4-C(O)CH₃ | H | H | H |
| 4-n-Hex | 4-C(O)CF₃ | H | H | H |
| 4-n-Hex | 4-C(O)Ph | H | H | H |
| 4-n-Hex | 4-C(O)OCH₃ | H | H | H |
| 4-n-Hex | 2-C(O)OEt | H | H | H |
| 4-n-Hex | 3-C(O)OEt | H | H | H |
| 4-n-Hex | 4-C(O)OEt | H | H | H |
| 4-n-Hex | 4-C(O)OPh | H | H | H |
| 4-n-Hex | 4-C(O)OCH₂Ph | H | H | H |
| 4-n-Hex | 4-C(O)OCH(CH₃)Ph | H | H | H |
| 4-n-Hex | 4-C(O)OC₂H₄Ph | H | H | H |
| 4-n-Hex | 4-SCH₃ | H | H | H |
| 4-n-Hex | 4-S(O)CH₃ | H | H | H |
| 4-n-Hex | 4 S(O)₂CH₃ | H | H | H |
| 4-n-Hex | 4-SPh | H | H | H |
| 4-n-Hex | 4-S(O)Ph | H | H | H |
| 4-n-Hex | 4-S(O)₂Ph | H | H | H |
| 4-n-Hex | 4 OS(O)₂CH₃ | H | H | H |
| 4-n-Hex | 4-OS(O)₂Ph | H | H | H |
| 4-n-Hex | 4-N(CH₃)₂ | H | H | H |
| 4-n-Hex | 4-N(CH₂Ph)₂ | H | H | H |
| 4-n-Hex | 4-N(CH₃)(CH₂Ph) | H | H | H |
| 4-n-Hex | 4-NHCH₃ | H | H | H |
| 4-n-Hex | 4-NH(CH₂Ph) | H | H | H |
| 4-n-Hex | 4-C(O)N(CH₃)₂ | H | H | H |
| 4-n-Hex | 4-C(O)N(CH₂Ph)₂ | H | H | H |
| 4-n-Hex | 4-C(O)N(CH₃)(CH₂Ph) | H | H | H |
| 4-n-Hex | 4-C(O)NHCH₃ | H | H | H |
| 4-n-Hex | 4-C(O)NH(CH₂Ph) | H | H | H |
| 4-n-Hex | 4-C(O)NH{CH(CH₃)Ph} | H | H | H |
| 4-n-Hex | 4-C(O)NH(C₂H₄Ph) | H | H | H |
| 4-n-Hex | 4-C(S)NH₂ | H | H | H |
| 4-n-Hex | 4-S(O)₂N(CH₃)₂ | H | H | H |
| 4-n-Hex | 4-S(O)₂N(CH₂Ph)₂ | H | H | H |
| 4-n-Hex | 4-S(O)₂N(CH₃)(CH₂Ph) | H | H | H |
| 4-n-Hex | 4-S(O)₂NHCH₃ | H | H | H |
| 4-n-Hex | 4-S(O)₂NHPh | H | H | H |
| 4-n-Hex | 4-S(O)₂NH(CH₂Ph) | H | H | H |
| 4-n-Hex | 4-S(O)₂NH{CH(CH₃)Ph} | H | H | H |
| 4-n-Hex | 4-S(O)₂NH(C₂H₄Ph) | H | H | H |
| 4-n-Hex | 4-Ph | H | H | H |
| 4-n-Hex | 4-Ph | CH₃ | H | H |
| 4-n-Hex | 4-Ph | CH₂Ph | H | H |
| 4-n-Hex | 4-Ph | C(O)Ph | H | H |
| 4-n-Hex | 4-Ph | C(O)OEt | H | H |
| 4-n-Hex | 4-Ph | H | H | CH₃ |
| 4-n-Hex | 4-Ph | CH₃ | H | CH₃ |
| 4-n-Hex | 4-Ph | H | CH₃ | CH₃ |
| 4-c-Hex | H | H | H | H |
| 4-c-Hex | 4-Cl | H | H | H |
| 4-c-Hex | 4-Br | H | H | H |
| 4-c-Hex | 4-CH₃ | H | H | H |
| 4-c-Hex | 4-t-Bu | H | H | H |
| 4-c-Hex | 4-t-Bu | CH₃ | H | H |
| 4-c-Hex | 4-n-Hex | H | H | H |
| 4-c-Hex | 4-n-Hex | CH₃ | H | H |
| 4-c-Hex | 4-n-Hex | H | H | CH₃ |
| 4-c-Hex | 4-n-Hex | H | CH₃ | CH₃ |
| 4-c-Hex | 4-Ph | H | H | H |
| 4-c-Hex | 4-Ph | CH₃ | H | H |
| 3,4-(CH₃)₂ | H | H | H | H |
| 3,4-(CH₃)₂ | 4-Cl | H | H | H |
| 3,4-(CH₃)₂ | 4-Br | H | H | H |
| 3,4-(CH₃)₂ | 4-CH₃ | H | H | H |
| 3,4-(CH₃)₂ | 4-t-Bu | H | H | H |
| 3,4-(CH₃)₂ | 4-n-Hex | H | H | H |
| 3,4-(CH₃)₂ | 4-Ph | H | H | H |
| 2,4-(t-Bu)₂ | H | H | H | H |
| 2,4-(t-Bu)₂ | 4-Cl | H | H | H |
| 2,4-(t-Bu)₂ | 4-Br | H | H | H |
| 2,4-(t-Bu)₂ | 4-CH₃ | H | H | H |
| 2,4-(t-Bu)₂ | 4-t-Bu | H | H | H |
| 2,4-(t-Bu)₂ | 4-n-Hex | H | H | H |
| 2,4-(t-Bu)₂ | 4-Ph | H | H | H |
| 4-CF₃ | H | H | H | H |
| 4-CF₃ | 4-Cl | H | H | H |
| 4-CF₃ | 4-Br | H | H | H |
| 4-CF₃ | 4-CH₃ | H | H | H |
| 4-CF₃ | 4-t-Bu | H | H | H |
| 4-CF₃ | 4-n-Hex | H | H | H |
| 4-CF₃ | 4-Ph | H | H | H |
| 4-OH | H | H | H | H |
| 4-OH | 4-Cl | H | H | H |
| 4-OH | 4-Br | H | H | H |
| 4-OH | 4-CH₃ | H | H | H |
| 4-OH | 4-t-Bu | H | H | H |
| 4-OH | 4-n-Hex | H | H | H |
| 4-OH | 4-Ph | H | H | H |
| 4-OCH₃ | H | H | H | H |
| 4-OCH₃ | 4-Cl | H | H | H |
| 4-OCH₃ | 4-Br | H | H | H |
| 4-OCH₃ | 4-CH₃ | H | H | H |
| 4-OCH₃ | 4-t-Bu | H | H | H |
| 4-OCH₃ | 4-n-Hex | H | H | H |
| 4-OCH₃ | 4-Ph | H | H | H |
| 4-O—i-Pr | H | H | H | H |
| 4-O—i-Pr | 4-Cl | H | H | H |
| 4-O—i-Pr | 4-Br | H | H | H |
| 4-O—i-Pr | 4-CH₃ | H | H | H |
| 4-O—i-Pr | 4-t-Bu | H | H | H |
| 4-O—i-Pr | 4-n-Hex | H | H | H |
| 4-O—i-Pr | 4-Ph | H | H | H |
| 4-O—n-Hex | H | H | H | H |
| 4-O—n-Hex | 4-Cl | H | H | H |
| 4-O—n-Hex | 4-Br | H | H | H |
| 4-O—n-Hex | 4-CH₃ | H | H | H |
| 4-O—n-Hex | 4-t-Bu | H | H | H |
| 4-O—n-Hex | 4-n-Hex | H | H | H |
| 4-O—n-Hex | 4-Ph | H | H | H |
| 3,4-(OCH₃)₂ | H | H | H | H |
| 3,4-(OCH₃)₂ | 4-Cl | H | H | H |
| 3,4-(OCH₃)₂ | 4-Br | H | H | H |
| 3,4-(OCH₃)₂ | 4-CH₃ | H | H | H |
| 3,4-(OCH₃)₂ | 4-t-Bu | H | H | H |
| 3,4-(OCH₃)₂ | 4-n-Hex | H | H | H |
| 3,4-(OCH₃)₂ | 4-Ph | H | H | H |
| 4-OC₂H₄OEt | H | H | H | H |
| 4-OC₂H₄OEt | 4-Cl | H | H | H |
| 4-OC₂H₄OEt | 4-Br | H | H | H |
| 4-OC₂H₄OEt | 4-CH₃ | H | H | H |
| 4-OC₂H₄OEt | 4-t-Bu | H | H | H |
| 4-OC₂H₄OEt | 4-n-Hex | H | H | H |
| 4-OC₂H₄OEt | 4-Ph | H | H | H |
| 4-OPh | H | H | H | H |
| 4-OPh | 4-Cl | H | H | H |
| 4-OPh | 4-Br | H | H | H |
| 4-OPh | 4-CH₃ | H | H | H |
| 4-OPh | 4-t-Bu | H | H | H |
| 4-OPh | 4-n-Hex | H | H | H |
| 4-OPh | 4-Ph | H | H | H |
| 4-OCH₂Ph | H | H | H | H |
| 4-OCH₂Ph | 4-Cl | H | H | H |
| 4-OCH₂Ph | 4-Br | H | H | H |
| 4-OCH₂Ph | 4-CH₃ | H | H | H |
| 4-OCH₂Ph | 4-t-Bu | H | H | H |
| 4-OCH₂Ph | 4-n-Hex | H | H | H |
| 4-OCH₂Ph | 4-Ph | H | H | H |
| 4-Ph | H | H | H | H |
| 4-Ph | 4-Cl | H | H | H |
| 4-Ph | 4-Br | H | H | H |
| 4-Ph | 4-CH₃ | H | H | H |
| 4-Ph | 4-t-Bu | H | H | H |
| 4-Ph | 4-t-Bu | CH₃ | H | H |
| 4-Ph | 4-n-Hex | H | H | H |
| 4-Ph | 4-n-Hex | CH₃ | H | H |
| 4-Ph | 4-n-Hex | H | H | CH₃ |
| 4-Ph | 4-n-Hex | H | CH₃ | CH₃ |
| 4-Ph | 4-Ph | H | H | H |
| 4-Ph | 4-Ph | CH₃ | H | H |

TABLE 3
The locants for the substituent $R^{81}$ in the Table correspond to the positions indicated in the following structural formulae, and the expression — indicates unsubstituted.
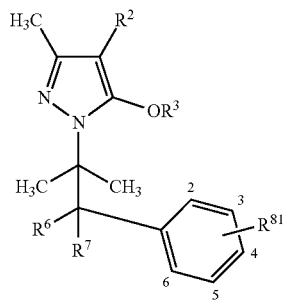
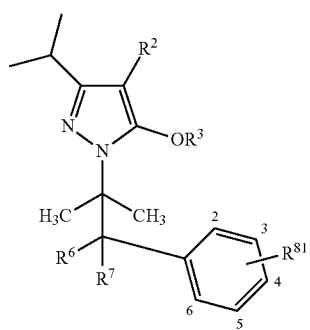
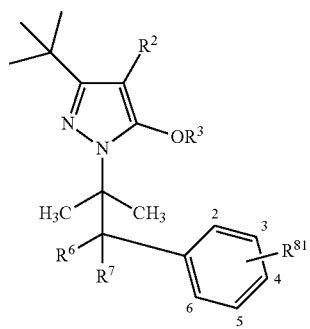
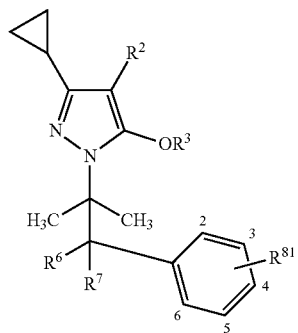

TABLE 3-continued
The locants for the substituent $R^{81}$ in the Table correspond to the positions indicated in the following structural formulae, and the expression — indicates unsubstituted.
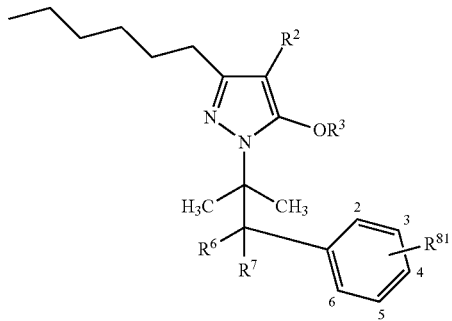
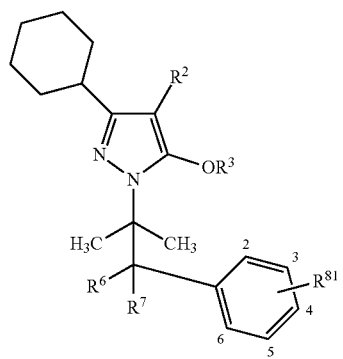
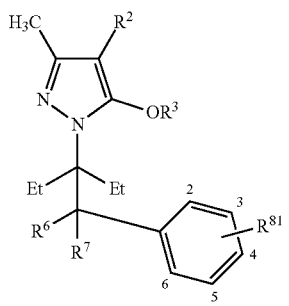
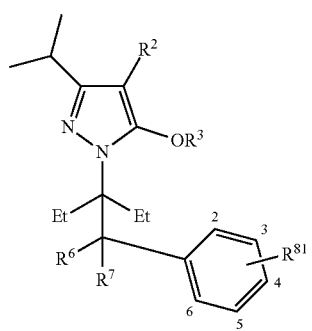

TABLE 3-continued
The locants for the substituent $R^{81}$ in the Table correspond to the positions indicated in the following structural formulae, and the expression — indicates unsubstituted.
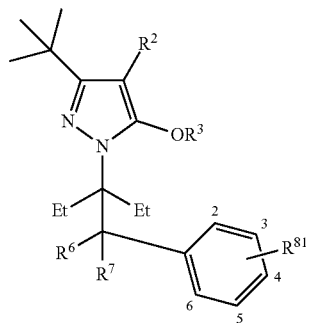
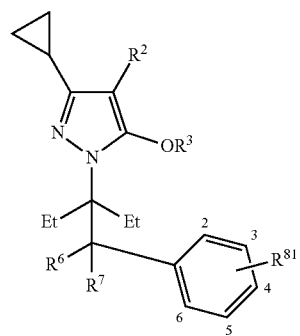
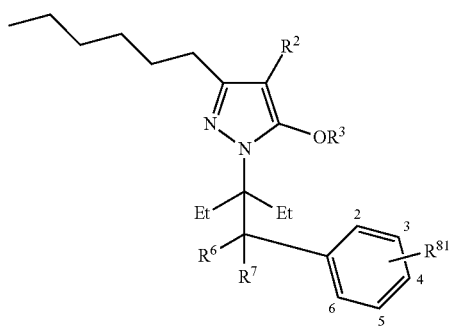
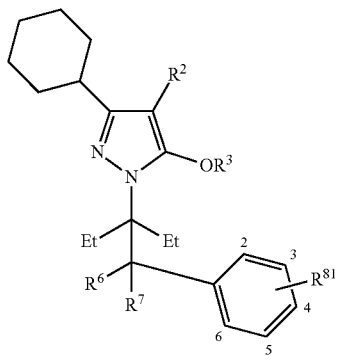

TABLE 3-continued
The locants for the substituent R⁸¹ in the Table correspond to the positions indicated in the following structural formulae, and the expression — indicates unsubstituted.
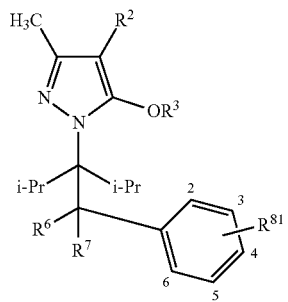
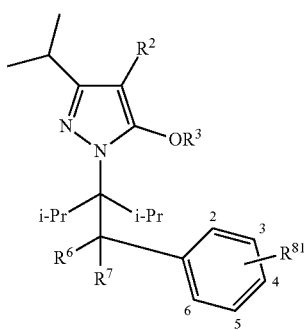
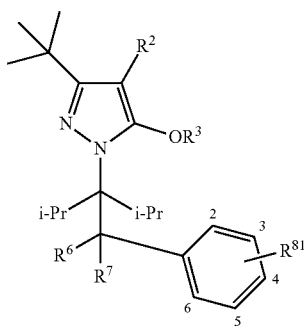
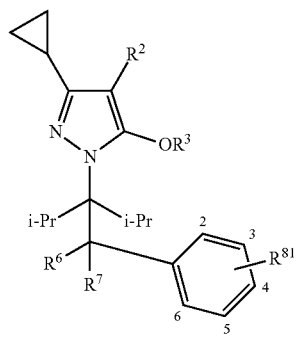

TABLE 3-continued
The locants for the substituent $R^{81}$ in the Table correspond to the positions indicated in the following structural formulae, and the expression — indicates unsubstituted.
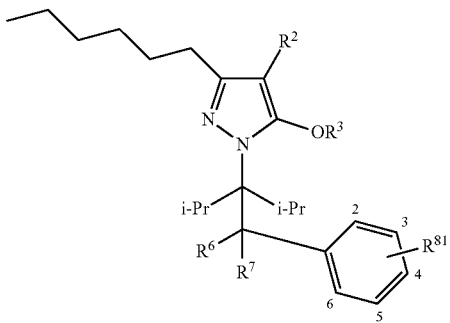
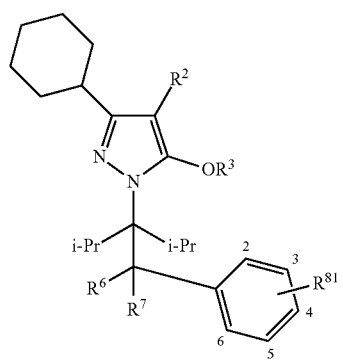
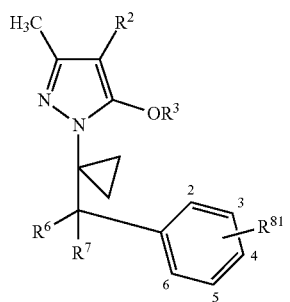
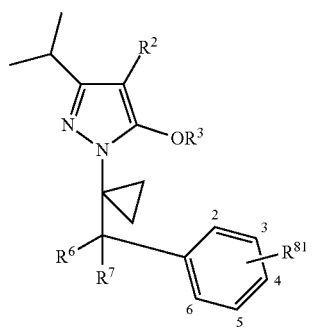

TABLE 3-continued
The locants for the substituent R[81] in the Table correspond to the positions indicated in the following structural formulae, and the expression — indicates unsubstituted.
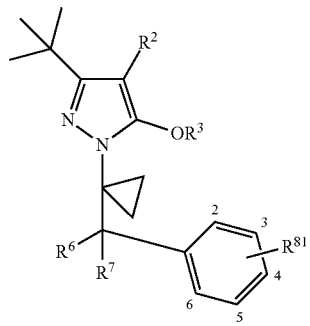
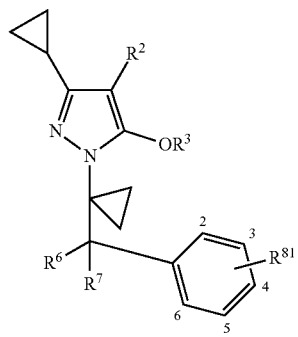
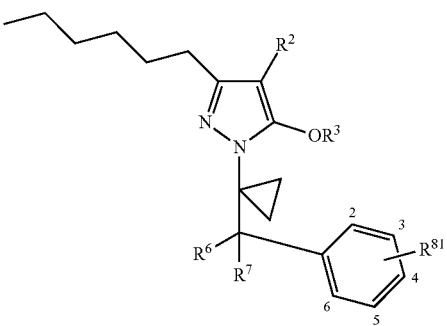
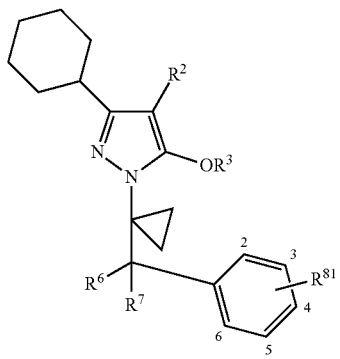
| R[2] | (Z) m | R[81] | R[3] | R[6] | R[7] |
|---|---|---|---|---|---|
| H | — | H | H | H | H |
| H | — | 4-CH$_3$ | H | H | H |
| F | — | H | H | H | H |
| CH$_3$ | — | H | H | H | H |
| Et | — | H | H | H | H |
| n-Pr | — | H | H | H | H |
| c-Pr | — | H | H | H | H |

TABLE 3-continued

The locants for the substituent R⁸¹ in the Table correspond to the positions indicated in the following structural formulae, and the expression — indicates unsubstituted.

| | | | | | |
|---|---|---|---|---|---|
| i-Pr | — | H | H | H | H |
| n-Bu | — | H | H | H | H |
| c-Bu | — | H | H | H | H |
| i-Bu | — | H | H | H | H |
| t-Bu | — | H | H | H | H |
| n-Pen | — | H | H | H | H |
| c-Pen | — | H | H | H | H |
| n-Hex | — | H | H | H | H |
| c-Hex | — | H | H | H | H |
| n-C₇H₁₅ | — | H | H | H | H |
| n-C₈H₁₇ | — | H | H | H | H |
| n-C₉H₁₉ | — | H | H | H | H |
| n-C₁₀H₂ | — | H | H | H | H |
| CF | — | H | H | H | H |
| C(Ph)=NCH₃ | — | H | H | H | H |
| C(CH₃)=NPh | — | H | H | H | H |
| C(Ph)=NOCH₃ | — | H | H | H | H |
| C(O)CH₃ | — | H | H | H | H |
| C(O)Et | — | H | H | H | H |
| C(O)CF₃ | — | H | H | H | H |
| C(O)Ph | — | H | H | H | H |
| C(O)Ph | — | 4-Cl | H | H | H |
| C(O)Ph | — | 4-Cl | H | H | CH₃ |
| C(O)Ph | — | 4-CH₃ | H | H | H |
| C(O)Ph | — | 4-CH₃ | CH₃ | H | H |
| C(O)Ph | — | 4-CH₃ | CH₂Ph | H | H |
| C(O)Ph | — | 4-CH₃ | C(O)Ph | H | H |
| C(O)Ph | — | 4-CH₃ | C(O)Et | H | H |
| C(O)Ph | — | 4-CH₃ | H | H | CH₃ |
| C(O)Ph | — | 4-CH₃ | H | CH₃ | CH₃ |
| C(O)Ph | — | 4-t-Bu | H | H | H |
| C(O)Ph | — | 4-t-Bu | H | H | CH₃ |
| C(O)Ph | — | 4-n-hex | H | H | H |
| C(O)Ph | — | 4-n-hex | H | H | CH₃ |
| C(O)Ph | — | 4-OCH₃ | H | H | H |
| C(O)Ph | — | 4-OCH₃ | H | H | CH₃ |
| C(O)Ph | — | 4-Ph | H | H | H |
| C(O)Ph | — | 4-Ph | H | H | CH₃ |
| C(O)CH₂Ph | — | H | H | H | H |
| C(O)CH(CH₃)Ph | — | H | H | H | H |
| C(O)C₂H₄Ph | — | H | H | H | H |
| C(O)OCH₃ | — | H | H | H | H |
| C(O)OEt | — | H | H | H | H |
| C(O)OEt | — | 4-Cl | H | H | H |
| C(O)OEt | — | 4-Cl | H | H | CH₃ |
| C(O)OEt | — | 4-CH₃ | H | H | H |
| C(O)OEt | — | 4-CH₃ | CH₃ | H | H |
| C(O)OEt | — | 4-CH₃ | CH₂Ph | H | H |
| C(O)OEt | — | 4-CH₃ | C(O)Ph | H | H |
| C(O)OEt | — | 4-CH₃ | C(O)OEt | H | H |
| C(O)OEt | — | 4-CH₃ | H | H | CH₃ |
| C(O)OEt | — | 4-CH₃ | H | CH₃ | CH₃ |
| C(O)OEt | — | 4-t-Bu | H | H | H |
| C(O)OEt | — | 4-t-Bu | H | H | CH₃ |
| C(O)OEt | — | 4-n-hex | H | H | H |
| C(O)OEt | — | 4-n-hex | H | H | CH₃ |
| C(O)OEt | — | 4-OCH₃ | H | H | H |
| C(O)OEt | — | 4-OCH₃ | H | H | CH₃ |
| C(O)OEt | — | 4-Ph | H | H | H |
| C(O)OEt | — | 4-Ph | H | H | CH₃ |
| C(O)OPh | — | H | H | H | H |
| C(O)OCH₂Ph | — | H | H | H | H |
| C(O)OCH(CH₃)Ph | — | H | H | H | H |
| C(O)OC₂H₄Ph | — | H | H | H | H |
| C(O)N(CHO₃)₂ | — | H | H | H | H |
| C(O)NHCH₃ | — | H | H | H | H |
| C(O)NH(CH₂Ph) | — | H | H | H | H |
| CH₂Ph | — | H | H | H | H |
| CH₂(4-Cl—Ph) | — | H | H | H | H |
| A001 | H | H | H | H | H |
| A001 | 3-n-Bu | H | H | H | H |
| A002 | H | H | H | H | H |
| A002 | 2-Cl | H | H | H | H |
| A003 | H | H | H | H | H |
| A004 | H | H | H | H | H |
| A005 | H | H | H | H | H |
| A005 | H | 4-Cl | H | H | H |

TABLE 3-continued

The locants for the substituent R[81] in the Table correspond to the positions indicated in the following structural formulae, and the expression — indicates unsubstituted.

| | | | | | |
|---|---|---|---|---|---|
| A005 | H | 4-Cl | H | H | CH$_3$ |
| A005 | H | 4-CH$_3$ | H | H | H |
| A005 | H | 4-CH$_3$ | CH$_3$ | H | H |
| A005 | H | 4-CH$_3$ | CH$_2$Ph | H | H |
| A005 | H | 4-CH$_3$ | C(O)Ph | H | H |
| A005 | H | 4-CH$_3$ | C(O)OEt | H | H |
| A005 | H | 4-CH$_3$ | H | H | CH$_3$ |
| A005 | H | 4-CH$_3$ | H | CH$_3$ | CH$_3$ |
| A005 | H | 4-t-Bu | H | H | H |
| A005 | H | 4-t-Bu | H | H | CH$_3$ |
| A005 | H | 4-n-hex | H | H | H |
| A005 | H | 4-n-hex | H | H | CH$_3$ |
| A005 | H | 4-OCH$_3$ | H | H | H |
| A005 | H | 4-OCH$_3$ | H | H | CH$_3$ |
| A005 | H | 4-Ph | H | H | H |
| A005 | H | 4-Ph | H | H | CH$_3$ |
| A005 | 2,5-(CH$_3$)$_2$ | H | H | H | H |
| A005 | 2,5-Cl$_2$ | H | H | H | H |
| A005 | 2-Br | H | H | H | H |
| A006 | H | H | H | H | H |
| A006 | H | 4-Cl | H | H | H |
| A006 | H | 4-Cl | H | H | CH$_3$ |
| A006 | H | 4-CH$_3$ | H | H | H |
| A006 | H | 4-CH$_3$ | CH$_3$ | H | H |
| A006 | H | 4-CH$_3$ | CH$_2$Ph | H | H |
| A006 | H | 4-CH$_3$ | C(O)Ph | H | H |
| A006 | H | 4-CH$_3$ | C(O)OEt | H | H |
| A006 | H | 4-CH$_3$ | H | H | CH$_3$ |
| A006 | H | 4-CH$_3$ | H | CH$_3$ | CH$_3$ |
| A006 | H | 4-t-Bu | H | H | H |
| A006 | H | 4-t-Bu | H | H | CH$_3$ |
| A006 | H | 4-n-hex | H | H | H |
| A006 | H | 4-n-hex | H | H | CH$_3$ |
| A006 | H | 4-OCH$_3$ | H | H | H |
| A006 | H | 4-OCH$_3$ | H | H | CH$_3$ |
| A006 | H | 4-Ph | H | H | H |
| A006 | H | 4-Ph | H | H | CH$_3$ |
| A006 | 3-CH$_3$ | H | H | H | H |
| A006 | 5-CH$_3$ | H | H | H | H |
| A006 | 3-Cl | H | H | H | H |
| A006 | 5-Et | H | H | H | H |
| A006 | 5-Cl | H | H | H | H |
| A006 | 5-Br | H | H | H | H |
| A006 | 3-Br | H | H | H | H |
| A006 | 4-Br | H | H | H | H |
| A006 | 5-NO$_2$ | H | H | H | H |
| A007 | H | H | H | H | H |
| A007 | 5-CH$_3$ | H | H | H | H |
| A007 | 3-CH$_3$ | H | H | H | H |
| A007 | 5-Br | H | H | H | H |
| A007 | 5-NO$_2$ | H | H | H | H |
| A007 | 5-Ph | H | H | H | H |
| A008 | 5-CH$_3$ | H | H | H | H |
| A009 | 5-CH$_3$ | H | H | H | H |
| A010 | 3,5-(CH$_3$)$_2$ | H | H | H | H |
| A010 | 3,5-Cl$_2$ | H | H | H | H |
| A011 | 3,5-(CH$_3$)$_2$ | H | H | H | H |
| A011 | 3,5-Cl$_2$ | H | H | H | H |
| A012 | 3-CH$_3$ | H | H | H | H |
| A012 | 3-CH$_3$ | H | H | H | H |
| A012 | 3-Cl | H | H | H | H |
| A013 | 3-CH$_3$ | H | H | H | H |
| A013 | 3-CH$_3$ | H | H | H | H |
| A013 | 3-Cl | H | H | H | H |
| A014 | H | H | H | H | H |
| A014 | H | 4-Cl | H | H | H |
| A014 | H | 4-Cl | H | H | CH$_3$ |
| A014 | H | 4-CH$_3$ | H | H | H |
| A014 | H | 4-CH$_3$ | CH$_3$ | H | H |
| A014 | H | 4-CH$_3$ | CH$_2$Ph | H | H |
| A014 | H | 4-CH$_3$ | C(O)Ph | H | H |
| A014 | H | 4-CH$_3$ | C(O)OEt | H | H |
| A014 | H | 4-CH$_3$ | H | H | CH$_3$ |
| A014 | H | 4-CH$_3$ | H | CH$_3$ | CH$_3$ |
| A014 | H | 4-t-Bu | H | H | H |
| A014 | H | 4-t-Bu | H | H | CH$_3$ |
| A014 | H | 4-n-hex | H | H | H |

TABLE 3-continued

The locants for the substituent $R^{81}$ in the Table correspond to the positions indicated in the following structural formulae, and the expression — indicates unsubstituted.

| | | | | | |
|---|---|---|---|---|---|
| A014 | H | 4-n-hex | H | H | $CH_3$ |
| A014 | H | 4-$OCH_3$ | H | H | H |
| A014 | H | 4-$OCH_3$ | H | H | $CH_3$ |
| A014 | H | 4-Ph | H | H | H |
| A014 | H | 4-Ph | H | H | $CH_3$ |
| A015 | H | H | H | H | H |
| A016 | 2,4-$(CH_3)_2$ | H | H | H | H |
| A016 | 2,4-$(CH_3)_2$ | 4-Cl | H | H | H |
| A016 | 2,4-$(CH_3)_2$ | 4-Cl | H | H | $CH_3$ |
| A016 | 2,4-$(CH_3)_2$ | 4-$CH_3$ | H | H | H |
| A016 | 2,4-$(CH_3)_2$ | 4-$CH_3$ | $CH_3$ | H | H |
| A016 | 2,4-$(CH_3)_2$ | 4-$CH_3$ | $CH_2Ph$ | H | H |
| A016 | 2,4-$(CH_3)_2$ | 4-$CH_3$ | C(O)Ph | H | H |
| A016 | 2,4-$(CH_3)_2$ | 4-$CH_3$ | C(O)OEt | H | H |
| A016 | 2,4-$(CH_3)_2$ | 4-$CH_3$ | H | H | $CH_3$ |
| A016 | 2,4-$(CH_3)_2$ | 4-$CH_3$ | H | $CH_3$ | $CH_3$ |
| A016 | 2,4-$(CH_3)_2$ | 4-t-Bu | H | H | H |
| A016 | 2,4-$(CH_3)_2$ | 4-t-Bu | H | H | $CH_3$ |
| A016 | 2,4-$(CH_3)_2$ | 4-n-hex | H | H | H |
| A016 | 2,4-$(CH_3)_2$ | 4-n-hex | H | H | $CH_3$ |
| A016 | 2,4-$(CH_3)_2$ | 4-$OCH_3$ | H | H | H |
| A016 | 2,4-$(CH_3)_2$ | 4-$OCH_3$ | H | H | $CH_3$ |
| A016 | 2,4-$(CH_3)_2$ | 4-Ph | H | H | H |
| A016 | 2,4-$(CH_3)_2$ | 4-Ph | H | H | $CH_3$ |
| A017 | 2,4-$(CH_3)_2$ | H | H | H | H |
| A018 | H | H | H | H | H |
| A018 | 3-$CH_3$ | H | H | H | H |
| A019 | 3-Ph, 5-$CH_3$ | H | H | H | H |
| A019 | 3,5-$(CH_3)_2$ | H | H | H | H |
| A020 | 5-$CH_3$ | H | H | H | H |
| A021 | 4-$CH_3$ | H | H | H | H |
| A022 | H | H | H | H | H |
| A023 | 2,4-$(CH_3)_2$ | H | H | H | H |
| A024 | 2-(4-pyridil) | H | H | H | H |
| A025 | H | H | H | H | H |
| A026 | H | H | H | H | H |
| A026 | 4-$CH_3$ | H | H | H | H |
| A027 | H | H | H | H | H |
| A027 | 4-$CH_3$ | H | H | H | H |
| A028 | H | H | H | H | H |
| A029 | H | H | H | H | H |
| A030 | H | H | H | H | H |
| A031 | H | H | H | H | H |
| A032 | H | H | H | H | H |
| A033 | H | H | H | H | H |
| A034 | H | H | H | H | H |
| A034 | 3,6-$Cl_2$ | H | H | H | H |
| A035 | H | H | H | H | H |
| A036 | H | H | H | H | H |
| A036 | H | 4-Cl | H | H | H |
| A036 | H | 4-Cl | H | H | $CH_3$ |
| A036 | H | 4-$CH_3$ | H | H | H |
| A036 | H | 4-$CH_3$ | $CH_3$ | H | H |
| A036 | H | 4-$CH_3$ | $CH_2Ph$ | H | H |
| A036 | H | 4-$CH_3$ | C(O)Ph | H | H |
| A036 | H | 4-$CH_3$ | C(O)OEt | H | H |
| A036 | H | 4-$CH_3$ | H | H | $CH_3$ |
| A036 | H | 4-$CH_3$ | H | $CH_3$ | $CH_3$ |
| A036 | H | 4-t-Bu | H | H | H |
| A036 | H | 4-t-Bu | H | H | $CH_3$ |
| A036 | H | 4-n-hex | H | H | H |
| A036 | H | 4-n-hex | H | H | $CH_3$ |
| A036 | H | 4-$OCH_3$ | H | H | H |
| A036 | H | 4-$OCH_3$ | H | H | $CH_3$ |
| A036 | H | 4-Ph | H | H | H |
| A036 | H | 4-Ph | H | H | $CH_3$ |
| A037 | H | H | H | H | H |
| A037 | H | 4-Cl | H | H | H |
| A037 | H | 4-Cl | H | H | $CH_3$ |
| A037 | H | 4-$CH_3$ | H | H | H |
| A037 | H | 4-$CH_3$ | $CH_3$ | H | H |
| A037 | H | 4-$CH_3$ | $CH_2Ph$ | H | H |
| A037 | H | 4-$CH_3$ | C(O)Ph | H | H |
| A037 | H | 4-$CH_3$ | C(O)OEt | H | H |
| A037 | H | 4-$CH_3$ | H | H | $CH_3$ |
| A037 | H | 4-$CH_3$ | H | $CH_3$ | $CH_3$ |
| A037 | H | 4-t-Bu | H | H | H |

TABLE 3-continued

The locants for the substituent $R^{81}$ in the Table correspond to the positions indicated in the following structural formulae, and the expression — indicates unsubstituted.

| | | | | | |
|---|---|---|---|---|---|
| A037 | H | 4-t-Bu | H | H | CH₃ |
| A037 | H | 4-n-hex | H | H | H |
| A037 | H | 4-n-hex | H | H | CH₃ |
| A037 | H | 4-OCH₃ | H | H | H |
| A037 | H | 4-OCH₃ | H | H | CH₃ |
| A037 | H | 4-Ph | H | H | H |
| A037 | H | 4-Ph | H | H | CH₃ |
| A037 | 6-OCH₃ | H | H | H | H |
| A037 | 6-Br | H | H | H | H |
| A038 | H | H | H | H | H |
| A038 | H | 4-Cl | H | H | H |
| A038 | H | 4-Cl | H | H | CH₃ |
| A038 | H | 4-CH₃ | H | H | H |
| A038 | H | 4-CH₃ | CH₃ | H | H |
| A038 | H | 4-CH₃ | CH₂Ph | H | H |
| A038 | H | 4-CH₃ | C(O)Ph | H | H |
| A038 | H | 4-CH₃ | C(O)OEt | H | H |
| A038 | H | 4-CH₃ | H | H | CH₃ |
| A038 | H | 4-CH₃ | H | CH₃ | CH₃ |
| A038 | H | 4-t-Bu | H | H | H |
| A038 | H | 4-t-Bu | H | H | CH₃ |
| A038 | H | 4-n-hex | H | H | H |
| A038 | H | 4-n-hex | H | H | CH₃ |
| A038 | H | 4-OCH₃ | H | H | H |
| A038 | H | 4-OCH₃ | H | H | CH₃ |
| A038 | H | 4-Ph | H | H | H |
| A038 | H | 4-Ph | H | H | CH₃ |
| A038 | 2-OCH₃ | H | H | H | H |
| A038 | 4-OCH₃ | H | H | H | H |
| A038 | 4-F | H | H | H | H |
| A039 | H | H | H | H | H |
| A039 | 3-CH₃ | H | H | H | H |
| A039 | 7-OCH₃ | H | H | H | H |
| A040 | H | H | H | H | H |
| A041 | H | H | H | H | H |
| A041 | H | 4-Cl | H | H | H |
| A041 | H | 4-Cl | H | H | CH₃ |
| A041 | H | 4-CH₃ | H | H | H |
| A041 | H | 4-CH₃ | CH₃ | H | H |
| A041 | H | 4-CH₃ | CH₂Ph | H | H |
| A041 | H | 4-CH₃ | C(O)Ph | H | H |
| A041 | H | 4-CH₃ | C(O)OEt | H | H |
| A041 | H | 4-CH₃ | H | H | CH₃ |
| A041 | H | 4-CH₃ | H | CH₃ | CH₃ |
| A041 | H | 4-t-Bu | H | H | H |
| A041 | H | 4-t-Bu | H | H | CH₃ |
| A041 | H | 4-n-hex | H | H | H |
| A041 | H | 4-n-hex | H | H | CH₃ |
| A041 | H | 4-OCH₃ | H | H | H |
| A041 | H | 4-OCH₃ | H | H | CH₃ |
| A041 | H | 4-Ph | H | H | H |
| A041 | H | 4-Ph | H | H | CH₃ |
| A041 | 6-NO₂ | H | H | H | H |
| A041 | 6-Br | H | H | H | H |
| A042 | H | H | H | H | H |
| A042 | H | 4-Cl | H | H | H |
| A042 | H | 4-Cl | H | H | CH₃ |
| A042 | H | 4-CH₃ | H | H | H |
| A042 | H | 4-CH₃ | CH₃ | H | H |
| A042 | H | 4-CH₃ | CH₂Ph | H | H |
| A042 | H | 4-CH₃ | C(O)Ph | H | H |
| A042 | H | 4-CH₃ | C(O)OEt | H | H |
| A042 | H | 4-CH₃ | H | H | CH₃ |
| A042 | H | 4-CH₃ | H | CH₃ | CH₃ |
| A042 | H | 4-t-Bu | H | H | H |
| A042 | H | 4-t-Bu | H | H | CH₃ |
| A042 | H | 4-n-hex | H | H | H |
| A042 | H | 4-n-hex | H | H | CH₃ |
| A042 | H | 4-OCH₃ | H | H | H |
| A042 | H | 4-OCH₃ | H | H | CH₃ |
| A042 | H | 4-Ph | H | H | H |
| A042 | H | 4-Ph | H | H | CH₃ |
| A042 | 5-Br | H | H | H | H |
| A043 | H | H | H | H | H |
| A044 | H | H | H | H | H |
| A051 | — | H | H | H | H |
| A052 | — | H | H | H | H |

TABLE 3-continued

The locants for the substituent $R^{81}$ in the Table correspond to the positions indicated in the following structural formulae, and the expression — indicates unsubstituted.

| | | | | | |
|---|---|---|---|---|---|
| A053 | — | H | H | H | H |
| A054 | — | H | H | H | H |
| A055 | — | H | H | H | H |
| A056 | — | H | H | H | H |
| A057 | — | H | H | H | H |
| A058 | — | H | H | H | H |
| A059 | — | H | H | H | H |
| A060 | — | H | H | H | H |
| A061 | — | H | H | H | H |
| A062 | — | H | H | H | H |
| A063 | — | H | H | H | H |
| A064 | — | H | H | H | H |
| A065 | — | H | H | H | H |
| A066 | — | H | H | H | H |
| A067 | — | H | H | H | H |
| A068 | — | H | H | H | H |
| A101 | — | H | H | H | H |
| A102 | — | H | H | H | H |
| A103 | — | H | H | H | H |
| A104 | — | H | H | H | H |
| A105 | — | H | H | H | H |
| A106 | — | H | H | H | H |
| A107 | — | H | H | H | H |

TABLE 4

The locants for the substituent $R^{21}$ herein correspond to the positions indicated in the following structural formulae, and the expression — indicates unsubstituted.

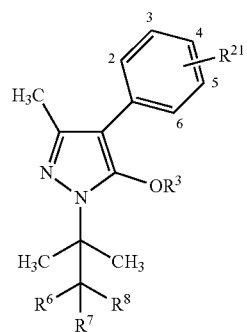

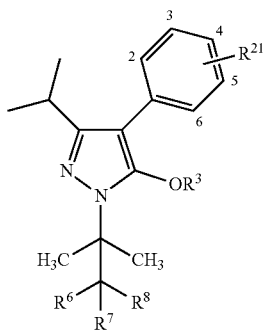

TABLE 4-continued
The locants for the substituent R²¹ herein correspond to the positions indicated in the following structural formulae, and the expression — indicates unsubstituted.
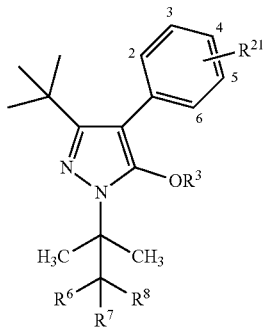
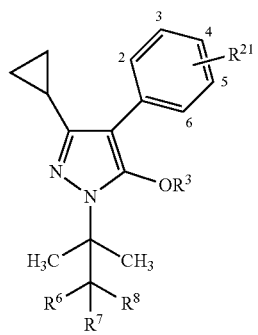
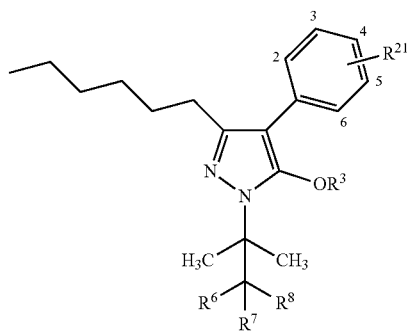
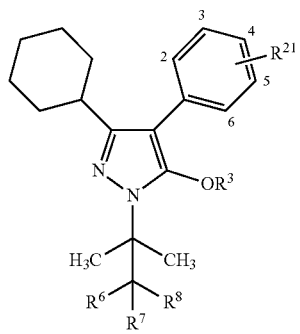

TABLE 4-continued
The locants for the substituent $R^{21}$ herein correspond to the positions indicated in the following structural formulae, and the expression — indicates unsubstituted.
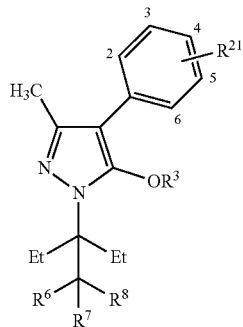
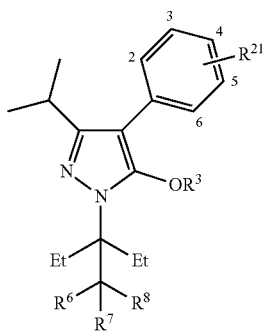
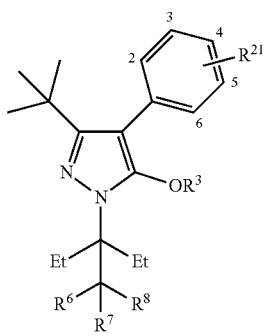
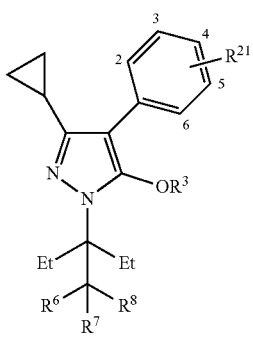

TABLE 4-continued
The locants for the substituent $R^{21}$ herein correspond to the positions indicated in the following structural formulae, and the expression — indicates unsubstituted.
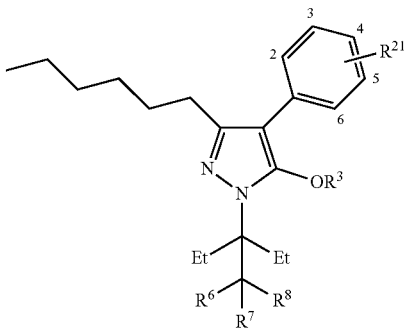
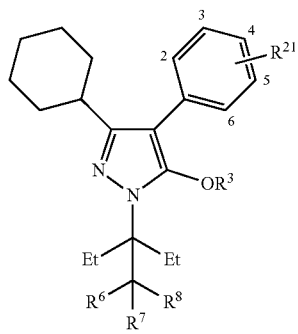
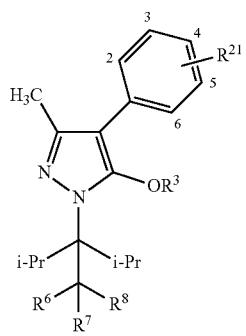
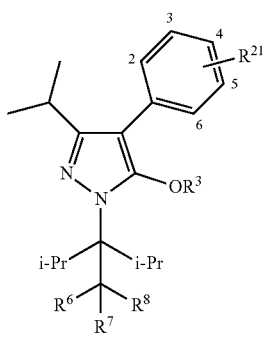

TABLE 4-continued
The locants for the substituent $R^{21}$ herein correspond to the positions indicated in the following structural formulae, and the expression — indicates unsubstituted.
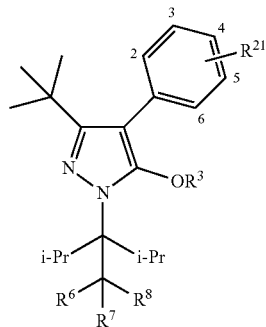
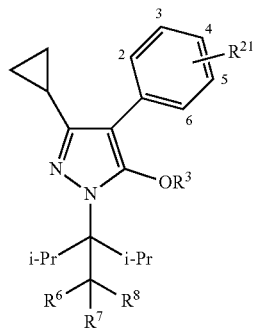
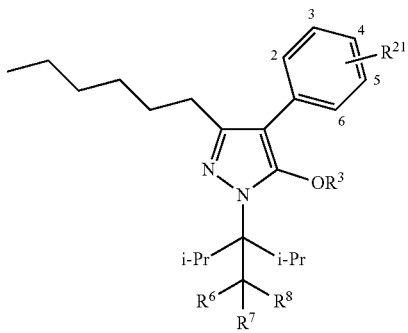
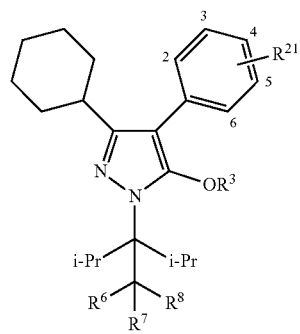

TABLE 4-continued
The locants for the substituent $R^{21}$ herein correspond to the positions indicated in the following structural formulae, and the expression — indicates unsubstituted.
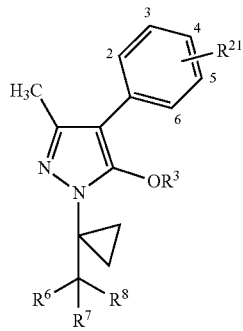
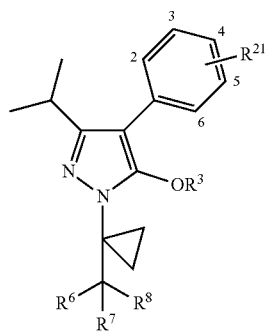
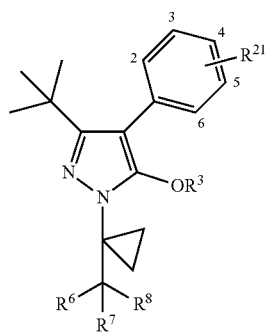
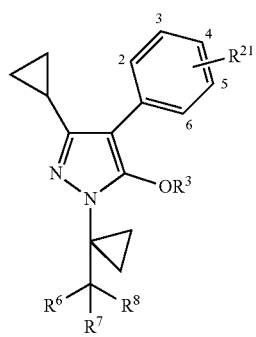

TABLE 4-continued

The locants for the substituent $R^{21}$ herein correspond to the positions indicated in the following structural formulae, and the expression — indicates unsubstituted.

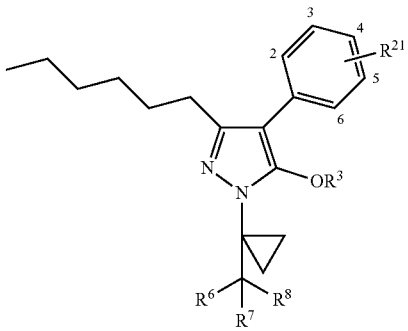

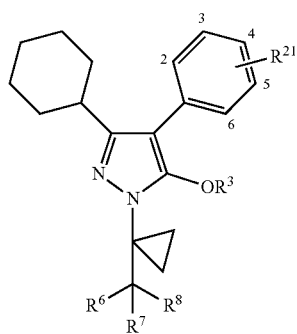

| $R^{21}$ | $R^8$ | (Z) m | $R^3$ | $R^6$ | $R^7$ |
|---|---|---|---|---|---|
| H | c-Pr | — | H | H | H |
| 4-Cl | c-Pr | — | H | H | H |
| 4-Cl | c-Pr | — | H | H | CH$_3$ |
| 4-CH$_3$ | c-Pr | — | H | H | H |
| 4-CH$_3$ | c-Pr | — | CH$_3$ | H | H |
| 4-CH$_3$ | c-Pr | — | CH$_2$Ph | H | H |
| 4-CH$_3$ | c-Pr | — | C(O)Ph | H | H |
| 4-CH$_3$ | c-Pr | — | C(O)OEt | H | H |
| 4-CH$_3$ | c-Pr | — | H | H | CH$_3$ |
| 4-CH$_3$ | c-Pr | — | H | CH$_3$ | CH$_3$ |
| 4-t-Bu | c-Pr | — | H | H | H |
| 4-t-Bu | c-Pr | — | H | H | CH$_3$ |
| 4-n-hex | c-Pr | — | H | H | H |
| 4-n-hex | c-Pr | — | CH$_3$ | H | H |
| 4-n-hex | c-Pr | — | CH$_2$Ph | H | H |
| 4-n-hex | c-Pr | — | C(O)Ph | H | H |
| 4-n-hex | c-Pr | — | C(O)OEt | H | H |
| 4-n-hex | c-Pr | — | H | H | CH$_3$ |
| 4-n-hex | c-Pr | — | H | CH$_3$ | CH$_3$ |
| 4-OCH$_3$ | c-Pr | — | H | H | H |
| 4-OCH$_3$ | c-Pr | — | H | H | CH$_3$ |
| 4-Ph | c-Pr | — | H | H | H |
| 4-Ph | c-Pr | — | H | H | CH$_3$ |
| H | c-Bu | — | H | H | H |
| H | c-Pen | — | H | H | H |
| H | c-Hex | — | H | H | H |
| 4-Cl | c-Hex | — | H | H | H |
| 4-Cl | c-Hex | — | H | H | CH$_3$ |
| 4-CH$_3$ | c-Hex | — | H | H | H |
| 4-CH$_3$ | c-Hex | — | CH$_3$ | H | H |
| 4-CH$_3$ | c-Hex | — | CH$_2$Ph | H | H |
| 4-CH$_3$ | c-Hex | — | C(O)Ph | H | H |
| 4-CH$_3$ | c-Hex | — | C(O)OEt | H | H |
| 4-CH$_3$ | c-Hex | — | H | H | CH$_3$ |
| 4-CH$_3$ | c-Hex | — | H | CH$_3$ | CH$_3$ |
| 4-t-Bu | c-Hex | — | H | H | H |
| 4-t-Bu | c-Hex | — | H | H | CH$_3$ |
| 4-n-hex | c-Hex | — | H | H | H |
| 4-n-hex | c-Hex | — | CH$_3$ | H | H |
| 4-n-hex | c-Hex | — | CH$_2$Ph | H | H |
| 4-n-hex | c-Hex | — | C(O)Ph | H | H |

TABLE 4-continued

The locants for the substituent $R^{21}$ herein correspond to the positions indicated in the following structural formulae, and the expression — indicates unsubstituted.

| | | | | | |
|---|---|---|---|---|---|
| 4-n-hex | c-Hex | — | C(O)OEt | H | H |
| 4-n-hex | c-Hex | — | H | H | CH$_3$ |
| 4-n-hex | c-Hex | — | H | CH$_3$ | CH$_3$ |
| 4-OCH$_3$ | c-Hex | — | H | H | H |
| 4-OCH$_3$ | c-Hex | — | H | H | CH$_3$ |
| 4-Ph | c-Hex | — | H | H | H |
| 4-Ph | c-Hex | — | H | H | CH$_3$ |
| H | c-C$_7$H$_{15}$ | — | H | H | H |
| H | c-C$_8$H$_{17}$ | — | H | H | H |
| H | bicyclo[2.2.1]heptan-2-yl | — | H | H | H |
| H | 1-adamantyl | — | H | H | H |
| H | 2-adamantyl | — | H | H | H |
| H | A001 | H | H | H | H |
| H | A001 | 3-n-Bu | H | H | H |
| H | A002 | H | H | H | H |
| H | A002 | 2-Cl | H | H | H |
| H | A003 | H | H | H | H |
| H | A004 | H | H | H | H |
| H | A005 | H | H | H | H |
| 4-Cl | A005 | H | H | H | H |
| 4-Cl | A005 | H | H | H | CH$_3$ |
| 4-CH$_3$ | A005 | H | H | H | H |
| 4-CH$_3$ | A005 | H | CH$_3$ | H | H |
| 4-CH$_3$ | A005 | H | CH$_2$Ph | H | H |
| 4-CH$_3$ | A005 | H | C(O)Ph | H | H |
| 4-CH$_3$ | A005 | H | C(O)OEt | H | H |
| 4-CH$_3$ | A005 | H | H | H | CH$_3$ |
| 4-CH$_3$ | A005 | H | H | CH$_3$ | CH$_3$ |
| 4-t-Bu | A005 | H | H | H | H |
| 4-t-Bu | A005 | H | H | H | CH$_3$ |
| 4-n-hex | A005 | H | H | H | H |
| 4-n-hex | A005 | H | CH$_3$ | H | H |
| 4-n-hex | A005 | H | CH$_2$Ph | H | H |
| 4-n-hex | A005 | H | C(O)Ph | H | H |
| 4-n-hex | A005 | H | C(O)OEt | H | H |
| 4-n-hex | A005 | H | H | H | CH$_3$ |
| 4-n-hex | A005 | H | H | CH$_3$ | CH$_3$ |
| 4-OCH$_3$ | A005 | H | H | H | H |
| 4-OCH$_3$ | A005 | H | H | H | CH$_3$ |
| 4-Ph | A005 | H | H | H | H |
| 4-Ph | A005 | H | H | H | CH$_3$ |
| H | A005 | 2,5-(CH$_3$)$_2$ | H | H | H |
| H | A005 | 2,5-Cl$_2$ | H | H | H |
| H | A005 | 2-Br | H | H | H |
| H | A006 | H | H | H | H |
| 4-Cl | A006 | H | H | H | H |
| 4-Cl | A006 | H | H | H | CH$_3$ |
| 4-CH$_3$ | A006 | H | H | H | H |
| 4-CH$_3$ | A006 | H | CH$_3$ | H | H |
| 4-CH$_3$ | A006 | H | CH$_2$Ph | H | H |
| 4-CH$_3$ | A006 | H | C(O)Ph | H | H |
| 4-CH$_3$ | A006 | H | C(O)OEt | H | H |
| 4-CH$_3$ | A006 | H | H | H | CH$_3$ |
| 4-CH$_3$ | A006 | H | H | CH$_3$ | CH$_3$ |
| 4-t-Bu | A006 | H | H | H | H |
| 4-t-Bu | A006 | H | H | H | CH$_3$ |
| 4-n-hex | A006 | H | H | H | H |
| 4-n-hex | A006 | H | CH$_3$ | H | H |
| 4-n-hex | A006 | H | CH$_2$Ph | H | H |
| 4-n-hex | A006 | H | C(O)Ph | H | H |
| 4-n-hex | A006 | H | C(O)OEt | H | H |
| 4-n-hex | A006 | H | H | H | CH$_3$ |
| 4-n-hex | A006 | H | H | CH$_3$ | CH$_3$ |
| 4-OCH$_3$ | A006 | H | H | H | H |
| 4-OCH$_3$ | A006 | H | H | H | CH$_3$ |
| 4-Ph | A006 | H | H | H | H |
| 4-Ph | A006 | H | H | H | CH$_3$ |
| H | A006 | 3-CH$_3$ | H | H | H |
| H | A006 | 5-CH$_3$ | H | H | H |
| H | A006 | 3-Cl | H | H | H |
| H | A006 | 5-Et | H | H | H |
| H | A006 | 5-Cl | H | H | H |
| H | A006 | 5-Br | H | H | H |
| H | A006 | 3-Br | H | H | H |
| H | A006 | 4-Br | H | H | H |
| H | A006 | 5-NO$_2$ | H | H | H |
| H | A007 | H | H | H | H |

TABLE 4-continued

The locants for the substituent $R^{21}$ herein correspond to the positions indicated in the following structural formulae, and the expression — indicates unsubstituted.

| | | | | | |
|---|---|---|---|---|---|
| H | A007 | 5-CH$_3$ | H | H | H |
| H | A007 | 3-CH$_3$ | H | H | H |
| H | A007 | 5-Br | H | H | H |
| H | A007 | 5-NO$_2$ | H | H | H |
| H | A007 | 5-Ph | H | H | H |
| H | A008 | 5-CH$_3$ | H | H | H |
| H | A009 | 5-CH$_3$ | H | H | H |
| H | A010 | 3,5-(CH$_3$)$_2$ | H | H | H |
| H | A010 | 3,5-Cl$_2$ | H | H | H |
| H | A011 | 3,5-(CH$_3$)$_2$ | H | H | H |
| H | A011 | 3,5-Cl$_2$ | H | H | H |
| H | A012 | 3-CH$_3$ | H | H | H |
| H | A012 | 3-Me | H | H | H |
| H | A012 | 3-Cl | H | H | H |
| H | A013 | 3-CH$_3$ | H | H | H |
| H | A013 | 3-Me | H | H | H |
| H | A013 | 3-Cl | H | H | H |
| H | A014 | H | H | H | H |
| 4-Cl | A014 | H | H | H | H |
| 4-Cl | A014 | H | H | H | CH$_3$ |
| 4-CH$_3$ | A014 | H | H | H | H |
| 4-CH$_3$ | A014 | H | CH$_3$ | H | H |
| 4-CH$_3$ | A014 | H | CH$_2$Ph | H | H |
| 4-CH$_3$ | A014 | H | C(O)Ph | H | H |
| 4-CH$_3$ | A014 | H | C(O)OEt | H | H |
| 4-CH$_3$ | A014 | H | H | H | CH$_3$ |
| 4-CH$_3$ | A014 | H | H | CH$_3$ | CH$_3$ |
| 4-t-Bu | A014 | H | H | H | H |
| 4-t-Bu | A014 | H | H | H | CH$_3$ |
| 4-n-hex | A014 | H | H | H | H |
| 4-n-hex | A014 | H | H | H | CH$_3$ |
| 4-OCH$_3$ | A014 | H | H | H | H |
| 4-OCH$_3$ | A014 | H | H | H | CH$_3$ |
| 4-Ph | A014 | H | H | H | H |
| 4-Ph | A014 | H | H | H | CH$_3$ |
| H | A015 | H | H | H | H |
| H | A016 | 2,4-(CH$_3$)$_2$ | H | H | H |
| 4-Cl | A016 | 2,4-(CH$_3$)$_2$ | H | H | H |
| 4-Cl | A016 | 2,4-(CH$_3$)$_2$ | H | H | CH$_3$ |
| 4-CH$_3$ | A016 | 2,4-(CH$_3$)$_2$ | H | H | H |
| 4-CH$_3$ | A016 | 2,4-(CH$_3$)$_2$ | CH$_3$ | H | H |
| 4-CH$_3$ | A016 | 2,4-(CH$_3$)$_2$ | CH$_2$Ph | H | H |
| 4-CH$_3$ | A016 | 2,4-(CH$_3$)$_2$ | C(O)Ph | H | H |
| 4-CH$_3$ | A016 | 2,4-(CH$_3$)$_2$ | C(O)OEt | H | H |
| 4-CH$_3$ | A016 | 2,4-(CH$_3$)$_2$ | H | H | CH$_3$ |
| 4-CH$_3$ | A016 | 2,4-(CH$_3$)$_2$ | H | CH$_3$ | CH$_3$ |
| 4-t-Bu | A016 | 2,4-(CH$_3$)$_2$ | H | H | H |
| 4-t-Bu | A016 | 2,4-(CH$_3$)$_2$ | H | H | CH$_3$ |
| 4-n-hex | A016 | 2,4-(CH$_3$)$_2$ | H | H | H |
| 4-n-hex | A016 | 2,4-(CH$_3$)$_2$ | H | H | CH$_3$ |
| 4-OCH$_3$ | A016 | 2,4-(CH$_3$)$_2$ | H | H | H |
| 4-OCH$_3$ | A016 | 2,4-(CH$_3$)$_2$ | H | H | CH$_3$ |
| 4-Ph | A016 | 2,4-(CH$_3$)$_2$ | H | H | H |
| 4-Ph | A016 | 2,4-(CH$_3$)$_2$ | H | H | CH$_3$ |
| H | A017 | 2,4-(CH$_3$)$_2$ | H | H | H |
| H | A018 | H | H | H | H |
| H | A018 | 3-CH$_3$ | H | H | H |
| H | A019 | 3-Ph, 5-CH$_3$ | H | H | H |
| H | A019 | 3,5-(CH$_3$)$_2$ | H | H | H |
| H | A020 | 5-CH$_3$ | H | H | H |
| H | A021 | 4-CH$_3$ | H | H | H |
| H | A022 | H | H | H | H |
| H | A023 | 2,4-(CH$_3$)$_2$ | H | H | H |
| H | A024 | 2-(4-pyridil) | H | H | H |
| H | A025 | H | H | H | H |
| H | A026 | H | H | H | H |
| H | A026 | 4-CH$_3$ | H | H | H |
| H | A027 | H | H | H | H |
| H | A027 | 4-CH$_3$ | H | H | H |
| H | A028 | H | H | H | H |
| H | A029 | H | H | H | H |
| H | A030 | H | H | H | H |
| H | A031 | H | H | H | H |
| H | A032 | H | H | H | H |
| H | A033 | H | H | H | H |
| H | A034 | H | H | H | H |
| H | A034 | 3,6-Cl$_2$ | H | H | H |

TABLE 4-continued

The locants for the substituent $R^{21}$ herein correspond to the positions indicated in the following structural formulae, and the expression — indicates unsubstituted.

| | | | | | |
|---|---|---|---|---|---|
| H | A035 | H | H | H | H |
| H | A036 | H | H | H | H |
| H | A037 | H | H | H | H |
| 4-Cl | A037 | H | H | H | H |
| 4-Cl | A037 | H | H | H | $CH_3$ |
| 4-$CH_3$ | A037 | H | H | H | H |
| 4-$CH_3$ | A037 | H | $CH_3$ | H | H |
| 4-$CH_3$ | A037 | H | $CH_2Ph$ | H | H |
| 4-$CH_3$ | A037 | H | C(O)Ph | H | H |
| 4-$CH_3$ | A037 | H | C(O)OEt | H | H |
| 4-$CH_3$ | A037 | H | H | H | $CH_3$ |
| 4-$CH_3$ | A037 | H | H | $CH_3$ | $CH_3$ |
| 4-t-Bu | A037 | H | H | H | H |
| 4-t-Bu | A037 | H | H | H | $CH_3$ |
| 4-n-hex | A037 | H | H | H | H |
| 4-n-hex | A037 | H | $CH_3$ | H | H |
| 4-n-hex | A037 | H | $CH_2Ph$ | H | H |
| 4-n-hex | A037 | H | C(O)Ph | H | H |
| 4-n-hex | A037 | H | C(O)OEt | H | H |
| 4-n-hex | A037 | H | H | H | $CH_3$ |
| 4-n-hex | A037 | H | H | $CH_3$ | $CH_3$ |
| 4-$OCH_3$ | A037 | H | H | H | H |
| 4-$OCH_3$ | A037 | H | H | H | $CH_3$ |
| 4-Ph | A037 | H | H | H | H |
| 4-Ph | A037 | H | H | H | $CH_3$ |
| H | A037 | 6-$OCH_3$ | H | H | H |
| H | A037 | 6-Br | H | H | H |
| H | A038 | H | H | H | H |
| 4-Cl | A038 | H | H | H | H |
| 4-Cl | A038 | H | H | H | $CH_3$ |
| 4-$CH_3$ | A038 | H | H | H | H |
| 4-$CH_3$ | A038 | H | $CH_3$ | H | H |
| 4-$CH_3$ | A038 | H | $CH_2Ph$ | H | H |
| 4-$CH_3$ | A038 | H | C(O)Ph | H | H |
| 4-$CH_3$ | A038 | H | C(O)OEt | H | H |
| 4-$CH_3$ | A038 | H | H | H | $CH_3$ |
| 4-$CH_3$ | A038 | H | H | $CH_3$ | $CH_3$ |
| 4-t-Bu | A038 | H | H | H | H |
| 4-t-Bu | A038 | H | H | H | $CH_3$ |
| 4-n-hex | A038 | H | H | H | H |
| 4-n-hex | A038 | H | $CH_3$ | H | H |
| 4-n-hex | A038 | H | $CH_2Ph$ | H | H |
| 4-n-hex | A038 | H | C(O)Ph | H | H |
| 4-n-hex | A038 | H | C(O)OEt | H | H |
| 4-n-hex | A038 | H | H | H | $CH_3$ |
| 4-n-hex | A038 | H | H | $CH_3$ | $CH_3$ |
| 4-$OCH_3$ | A038 | H | H | H | H |
| 4-$OCH_3$ | A038 | H | H | H | $CH_3$ |
| 4-Ph | A038 | H | H | H | H |
| 4-Ph | A038 | H | H | H | $CH_3$ |
| H | A038 | 2-$OCH_3$ | H | H | H |
| H | A038 | 4-$OCH_3$ | H | H | H |
| H | A038 | 4-F | H | H | H |
| H | A039 | H | H | H | H |
| H | A039 | 3-$CH_3$ | H | H | H |
| H | A039 | 7-$OCH_3$ | H | H | H |
| H | A040 | H | H | H | H |
| H | A041 | H | H | H | H |
| 4-Cl | A041 | H | H | H | H |
| 4-Cl | A041 | H | H | H | $CH_3$ |
| 4-$CH_3$ | A041 | H | H | H | H |
| 4-$CH_3$ | A041 | H | $CH_3$ | H | H |
| 4-$CH_3$ | A041 | H | $CH_2Ph$ | H | H |
| 4-$CH_3$ | A041 | H | C(O)Ph | H | H |
| 4-$CH_3$ | A041 | H | C(O)OEt | H | H |
| 4-$CH_3$ | A041 | H | H | H | $CH_3$ |
| 4-$CH_3$ | A041 | H | H | $CH_3$ | $CH_3$ |
| 4-t-Bu | A041 | H | H | H | H |
| 4-t-Bu | A041 | H | H | H | $CH_3$ |
| 4-n-hex | A041 | H | H | H | H |
| 4-n-hex | A041 | H | H | H | $CH_3$ |
| 4-$OCH_3$ | A041 | H | H | H | H |
| 4-$OCH_3$ | A041 | H | H | H | $CH_3$ |
| 4-Ph | A041 | H | H | H | H |
| 4-Ph | A041 | H | H | H | $CH_3$ |
| H | A041 | 6-$NO_2$ | H | H | H |
| H | A041 | 6-Br | H | H | H |

TABLE 4-continued

The locants for the substituent $R^{21}$ herein correspond to the positions indicated in the following structural formulae, and the expression — indicates unsubstituted.

| | | | | | |
|---|---|---|---|---|---|
| H | A042 | H | H | H | H |
| 4-Cl | A042 | H | H | H | H |
| 4-Cl | A042 | H | H | H | CH$_3$ |
| 4-CH$_3$ | A042 | H | H | H | H |
| 4-CH$_3$ | A042 | H | CH$_3$ | H | H |
| 4-CH$_3$ | A042 | H | CH$_2$Ph | H | H |
| 4-CH$_3$ | A042 | H | C(O)Ph | H | H |
| 4-CH$_3$ | A042 | H | C(O)OEt | H | H |
| 4-CH$_3$ | A042 | H | H | H | CH$_3$ |
| 4-CH$_3$ | A042 | H | H | CH$_3$ | CH$_3$ |
| 4-t-Bu | A042 | H | H | H | H |
| 4-t-Bu | A042 | H | H | H | CH$_3$ |
| 4-n-hex | A042 | H | H | H | H |
| 4-n-hex | A042 | H | H | H | CH$_3$ |
| 4-OCH$_3$ | A042 | H | H | H | H |
| 4-OCH$_3$ | A042 | H | H | H | CH$_3$ |
| 4-Ph | A042 | H | H | H | H |
| 4-Ph | A042 | H | H | H | CH$_3$ |
| H | A042 | 5-Br | H | H | H |
| H | A043 | H | H | H | H |
| 4-Cl | A043 | H | H | H | H |
| 4-Cl | A043 | H | H | H | CH$_3$ |
| 4-CH$_3$ | A043 | H | H | H | H |
| 4-CH$_3$ | A043 | H | CH$_3$ | H | H |
| 4-CH$_3$ | A043 | H | CH$_2$Ph | H | H |
| 4-CH$_3$ | A043 | H | C(O)Ph | H | H |
| 4-CH$_3$ | A043 | H | C(O)OEt | H | H |
| 4-CH$_3$ | A043 | H | H | H | CH$_3$ |
| 4-CH$_3$ | A043 | H | H | CH$_3$ | CH$_3$ |
| 4-t-Bu | A043 | H | H | H | H |
| 4-t-Bu | A043 | H | H | H | CH$_3$ |
| 4-n-hex | A043 | H | H | H | H |
| 4-n-hex | A043 | H | H | H | CH$_3$ |
| 4-OCH$_3$ | A043 | H | H | H | H |
| 4-OCH$_3$ | A043 | H | H | H | CH$_3$ |
| 4-Ph | A043 | H | H | H | H |
| 4-Ph | A043 | H | H | H | CH$_3$ |
| H | A044 | H | H | H | H |
| 4-Cl | A044 | H | H | H | H |
| 4-Cl | A044 | H | H | H | CH$_3$ |
| 4-CH$_3$ | A044 | H | H | H | H |
| 4-CH$_3$ | A044 | H | CH$_3$ | H | H |
| 4-CH$_3$ | A044 | H | CH$_2$Ph | H | H |
| 4-CH$_3$ | A044 | H | C(O)Ph | H | H |
| 4-CH$_3$ | A044 | H | C(O)OEt | H | H |
| 4-CH$_3$ | A044 | H | H | H | CH$_3$ |
| 4-CH$_3$ | A044 | H | H | CH$_3$ | CH$_3$ |
| 4-t-Bu | A044 | H | H | H | H |
| 4-t-Bu | A044 | H | H | H | CH$_3$ |
| 4-n-hex | A044 | H | H | H | H |
| 4-n-hex | A044 | H | H | H | CH$_3$ |
| 4-OCH$_3$ | A044 | H | H | H | H |
| 4-OCH$_3$ | A044 | H | H | H | CH$_3$ |
| 4-Ph | A044 | H | H | H | H |
| 4-Ph | A044 | H | H | H | CH$_3$ |
| H | A051 | — | H | H | H |
| H | A052 | — | H | H | H |
| H | A053 | — | H | H | H |
| H | A054 | — | H | H | H |
| H | A055 | — | H | H | H |
| H | A056 | — | H | H | H |
| H | A057 | — | H | H | H |
| H | A058 | — | H | H | H |
| H | A059 | — | H | H | H |
| H | A060 | — | H | H | H |
| H | A061 | — | H | H | H |
| H | A062 | — | H | H | H |
| H | A063 | — | H | H | H |
| H | A064 | — | H | H | H |
| H | A065 | — | H | H | H |
| H | A066 | — | H | H | H |
| H | A067 | — | H | H | H |
| H | A068 | — | H | H | H |
| H | A101 | — | H | H | H |
| H | A102 | — | H | H | H |
| H | A103 | — | H | H | H |
| H | A104 | — | H | H | H |

TABLE 4-continued
The locants for the substituent R²¹ herein correspond to the positions indicated in the following structural formulae, and the expression — indicates unsubstituted.
| H | A105 | — | H | H | H |
| H | A106 | — | H | H | H |
| H | A107 | — | H | H | H |
TABLE 5
The expression — indicates unsubstituted.
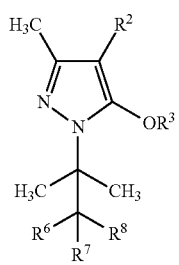
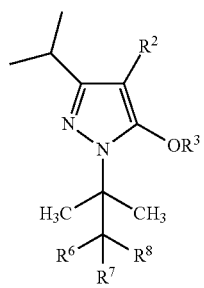
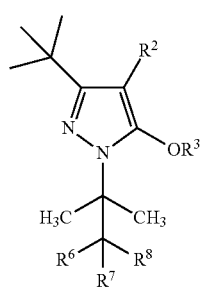
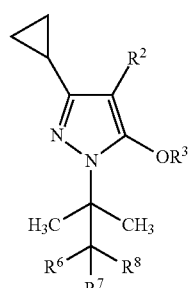
TABLE 5-continued
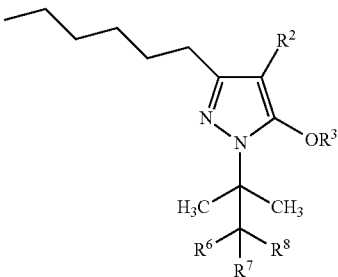
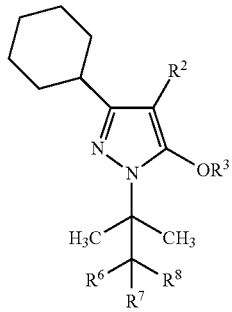
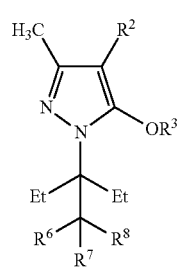
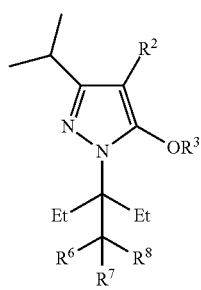

TABLE 5-continued
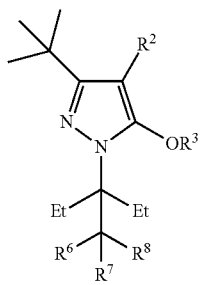
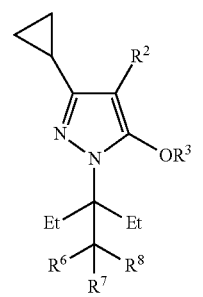
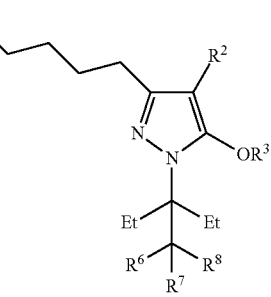
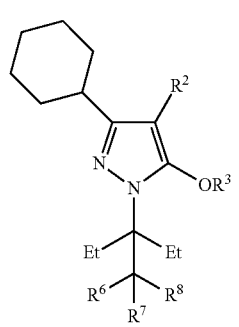
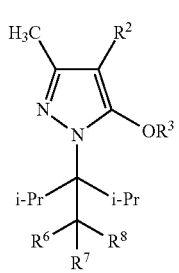
TABLE 5-continued
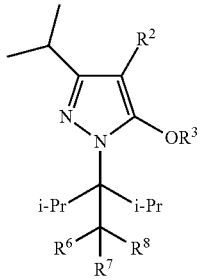
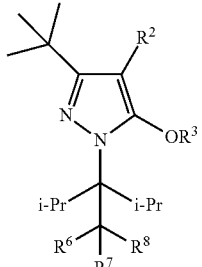
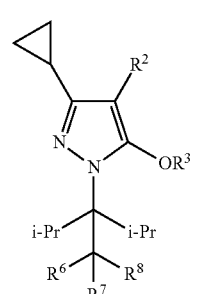
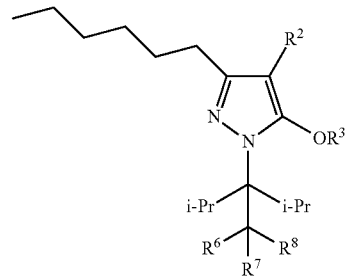
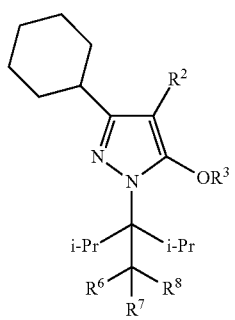

TABLE 5-continued

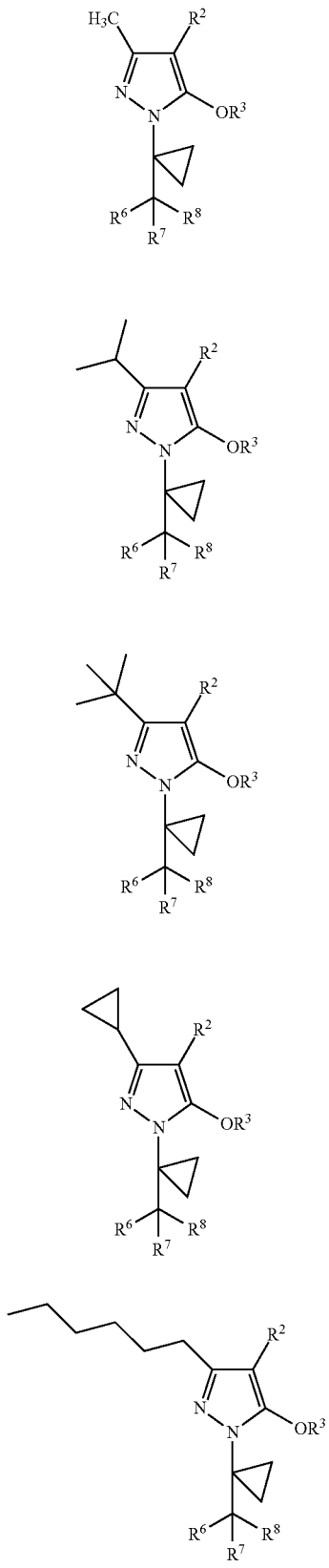

| R² | (Z)m on ring of R² | R⁸ | (Z)m on ring of R⁸ | R³ | R⁶ | R⁷ |
|---|---|---|---|---|---|---|
| H | — | c-Pr | — | H | H | H |
| CH₃ | — | c-Pr | — | H | H | H |
| H | — | c-Bu | — | H | H | H |
| CH₃ | — | c-Bu | — | H | H | H |
| H | — | c-Pen | — | H | H | H |
| CH₃ | — | c-Pen | — | H | H | H |
| H | — | c-Hex | — | H | H | H |
| CH₃ | — | c-Hex | — | H | H | H |
| CH₃ | — | c-Hex | — | CH₃ | H | H |
| CH₃ | — | c-Hex | — | CH₂Ph | H | H |
| CH₃ | — | c-Hex | — | C(O)Ph | H | H |
| CH₃ | — | c-Hex | — | C(O)OEt | H | H |
| CH₃ | — | c-Hex | — | H | H | CH₃ |
| CH₃ | — | c-Hex | — | H | CH₃ | CH₃ |
| C(O)CH₃ | — | c-Pr | — | H | H | H |
| C(O)CH₃ | — | c-Hex | — | H | H | H |
| C(O)CH₃ | — | c-Hex | — | CH₃ | H | H |
| C(O)CH₃ | — | c-Hex | — | CH₂Ph | H | H |
| C(O)CH₃ | — | c-Hex | — | C(O)Ph | H | H |
| C(O)CH₃ | — | c-Hex | — | C(O)OEt | H | H |
| C(O)CH₃ | — | c-Hex | — | H | H | CH₃ |
| C(O)CH₃ | — | c-Hex | — | H | CH₃ | CH₃ |
| C(O)Ph | — | c-Pr | — | H | H | H |
| C(O)Ph | — | c-Hex | — | H | H | H |
| C(O)Ph | — | c-Hex | — | CH₃ | H | H |
| C(O)Ph | — | c-Hex | — | CH₂Ph | H | H |
| C(O)Ph | — | c-Hex | — | C(O)Ph | H | H |
| C(O)Ph | — | c-Hex | — | C(O)OEt | H | H |
| C(O)Ph | — | c-Hex | — | H | H | CH₃ |
| C(O)Ph | — | c-Hex | — | H | CH₃ | CH₃ |
| A005 | H | A005 | H | H | H | H |
| A005 | H | A006 | H | H | H | H |
| A005 | H | A014 | H | H | H | H |
| A005 | H | A016 | 2,4-(CH₃)₂ | H | H | H |
| A005 | H | A037 | H | H | H | H |
| A005 | H | A038 | H | H | H | H |
| A005 | H | A041 | H | H | H | H |
| A005 | H | A042 | H | H | H | H |
| A005 | H | A043 | H | H | H | H |
| A005 | H | A044 | H | H | H | H |
| A006 | H | A005 | H | H | H | H |
| A006 | H | A006 | H | H | H | H |
| A006 | H | A006 | H | CH₃ | H | H |
| A006 | H | A006 | H | CH₂Ph | H | H |
| A006 | H | A006 | H | C(O)Ph | H | H |
| A006 | H | A006 | H | H | H | CH₃ |
| A006 | H | A006 | H | H | CH₃ | CH₃ |
| A006 | H | A014 | H | H | H | H |
| A006 | H | A016 | 2,4-(CH₃)₂ | CH | H | H |
| A006 | H | A037 | H | H | H | H |
| A006 | H | A037 | H | CH₃ | H | H |
| A006 | H | A037 | H | CH₂Ph | H | H |
| A006 | H | A037 | H | C(O)Ph | H | H |
| A006 | H | A037 | H | H | H | CH₃ |
| A006 | H | A037 | H | H | CH₃ | CH₃ |
| A006 | H | A038 | H | H | H | H |
| A006 | H | A038 | H | CH₃ | H | H |
| A006 | H | A038 | H | CH₂Ph | H | H |
| A006 | H | A038 | H | C(O)Ph | H | H |
| A006 | H | A038 | H | H | H | CH₃ |
| A006 | H | A038 | H | H | CH₃ | CH₃ |

TABLE 5-continued

| | | | | | |
|---|---|---|---|---|---|
| A006 | H | A041 | H | H | H |
| A006 | H | A041 | H | CH$_3$ | H | H |
| A006 | H | A041 | H | CH$_2$Ph | H | H |
| A006 | H | A041 | H | C(O)Ph | H | H |
| A006 | H | A041 | H | H | H | CH$_3$ |
| A006 | H | A041 | H | H | CH$_3$ | CH$_3$ |
| A006 | H | A042 | H | H | H | H |
| A006 | H | A042 | H | CH$_3$ | H | H |
| A006 | H | A042 | H | CH$_2$Ph | H | H |
| A006 | H | A042 | H | C(O)Ph | H | H |
| A006 | H | A042 | H | H | H | CH$_3$ |
| A006 | H | A042 | H | H | CH$_3$ | CH$_3$ |
| A006 | H | A043 | H | H | H | H |
| A006 | H | A044 | H | H | H | H |
| A014 | H | A005 | H | H | H | H |
| A014 | H | A006 | H | H | H | H |
| A014 | H | A014 | H | H | H | H |
| A014 | H | A016 | 2,4-(CH$_3$)$_2$ | H | H | H |
| A014 | H | A037 | H | H | H | H |
| A014 | H | A038 | H | H | H | H |
| A014 | H | A041 | H | H | H | H |
| A014 | H | A042 | H | H | H | H |
| A014 | H | A043 | H | H | H | H |
| A014 | H | A044 | H | H | H | H |
| A016 | 2,4-(CH$_3$)$_2$ | A005 | H | H | H | H |
| A016 | 2,4-(CH$_3$)$_2$ | A006 | H | H | H | H |
| A016 | 2,4-(CH$_3$)$_2$ | A014 | H | H | H | H |
| A016 | 2,4-(CH$_3$)$_2$ | A016 | 2,4-(CH$_3$)$_2$ | H | H | H |
| A016 | 2,4-(CH$_3$)$_2$ | A037 | H | H | H | H |
| A016 | 2,4-(CH$_3$)$_2$ | A038 | H | H | H | H |
| A016 | 2,4-(CH$_3$)$_2$ | A041 | H | H | H | H |
| A016 | 2,4-(CH$_3$)$_2$ | A042 | H | H | H | H |
| A016 | 2,4-(CH$_3$)$_2$ | A043 | H | H | H | H |
| A016 | 2,4-(CH$_3$)$_2$ | A044 | H | H | H | H |
| A036 | H | A005 | H | H | H | H |
| A036 | H | A006 | H | H | H | H |
| A036 | H | A014 | H | H | H | H |
| A036 | H | A016 | 2,4-(CH$_3$)$_2$ | H | H | H |
| A036 | H | A037 | H | H | H | H |
| A036 | H | A038 | H | H | H | H |
| A036 | H | A041 | H | H | H | H |
| A036 | H | A042 | H | H | H | H |
| A036 | H | A043 | H | H | H | H |
| A036 | H | A044 | H | H | H | H |
| A037 | H | A005 | H | H | H | H |
| A037 | H | A006 | H | H | H | H |
| A037 | H | A006 | H | CH$_3$ | H | H |
| A037 | H | A006 | H | CH$_2$Ph | H | H |
| A037 | H | A006 | H | C(O)Ph | H | H |
| A037 | H | A006 | H | H | H | CH$_3$ |
| A037 | H | A006 | H | H | CH$_3$ | CH$_3$ |
| A037 | H | A014 | H | H | H | H |
| A037 | H | A016 | 2,4-(CH$_3$)$_2$ | H | H | H |
| A037 | H | A037 | H | H | H | H |
| A037 | H | A037 | H | CH$_3$ | H | H |
| A037 | H | A037 | H | CH$_2$Ph | H | H |
| A037 | H | A037 | H | C(O)Ph | H | H |
| A037 | H | A037 | H | H | H | CH$_3$ |
| A037 | H | A037 | H | H | CH$_3$ | CH$_3$ |
| A037 | H | A038 | H | H | H | H |
| A037 | H | A038 | H | CH$_3$ | H | H |
| A037 | H | A038 | H | CH$_2$Ph | H | H |
| A037 | H | A038 | H | C(O)Ph | H | H |
| A037 | H | A038 | H | H | H | CH$_3$ |
| A037 | H | A038 | H | H | CH$_3$ | CH$_3$ |
| A037 | H | A041 | H | H | H | H |
| A037 | H | A041 | H | CH$_3$ | H | H |
| A037 | H | A041 | H | CH$_2$Ph | H | H |
| A037 | H | A041 | H | C(O)Ph | H | H |
| A037 | H | A041 | H | H | H | CH$_3$ |
| A037 | H | A041 | H | H | CH$_3$ | CH$_3$ |
| A037 | H | A042 | H | H | H | H |
| A037 | H | A042 | H | CH$_3$ | H | H |
| A037 | H | A042 | H | CH$_2$Ph | H | H |
| A037 | H | A042 | H | C(O)Ph | H | H |
| A037 | H | A042 | H | H | H | CH$_3$ |
| A037 | H | A042 | H | H | CH$_3$ | CH$_3$ |
| A037 | H | A043 | H | H | H | H |
| A037 | H | A044 | H | H | H | H |
| A038 | H | A005 | H | H | H | H |
| A038 | H | A006 | H | H | H | H |
| A038 | H | A006 | H | CH$_3$ | H | H |
| A038 | H | A006 | H | CH$_2$Ph | H | H |
| A038 | H | A006 | H | C(O)Ph | H | H |
| A038 | H | A006 | H | H | H | CH$_3$ |
| A038 | H | A006 | H | H | CH$_3$ | CH$_3$ |
| A038 | H | A014 | H | H | H | H |
| A038 | H | A016 | 2,4-(CH$_3$)$_2$ | H | H | H |
| A038 | H | A037 | H | H | H | H |
| A038 | H | A037 | H | CH$_3$ | H | H |
| A038 | H | A037 | H | CH$_2$Ph | H | H |
| A038 | H | A037 | H | C(O)Ph | H | H |
| A038 | H | A037 | H | H | H | CH$_3$ |
| A038 | H | A037 | H | H | CH$_3$ | CH$_3$ |
| A038 | H | A038 | H | H | H | H |
| A038 | H | A038 | H | CH$_3$ | H | H |
| A038 | H | A038 | H | CH$_2$Ph | H | H |
| A038 | H | A038 | H | C(O)Ph | H | H |
| A038 | H | A038 | H | H | H | CH$_3$ |
| A038 | H | A038 | H | H | CH$_3$ | CH$_3$ |
| A038 | H | A041 | H | H | H | H |
| A038 | H | A041 | H | CH$_3$ | H | H |
| A038 | H | A041 | H | CH$_2$Ph | H | H |
| A038 | H | A041 | H | C(O)Ph | H | H |
| A038 | H | A041 | H | H | H | CH$_3$ |
| A038 | H | A041 | H | H | CH$_3$ | CH$_3$ |
| A038 | H | A042 | H | H | H | H |
| A038 | H | A042 | H | CH$_3$ | H | H |
| A038 | H | A042 | H | CH$_2$Ph | H | H |
| A038 | H | A042 | H | C(O)Ph | H | H |
| A038 | H | A042 | H | H | H | CH$_3$ |
| A038 | H | A042 | H | H | CH$_3$ | CH$_3$ |
| A038 | H | A043 | H | H | H | H |
| A038 | H | A044 | H | H | H | H |
| A041 | H | A005 | H | H | H | H |
| A041 | H | A006 | H | H | H | H |
| A041 | H | A006 | H | CH$_3$ | H | H |
| A041 | H | A006 | H | CH$_2$Ph | H | H |
| A041 | H | A006 | H | C(O)Ph | H | H |
| A041 | H | A006 | H | H | H | CH$_3$ |
| A041 | H | A006 | H | H | CH$_3$ | CH$_3$ |
| A041 | H | A014 | H | H | H | H |
| A041 | H | A016 | 2,4-(CH$_3$)$_2$ | H | H | H |
| A041 | H | A037 | H | H | H | H |
| A041 | H | A037 | H | CH$_3$ | H | H |
| A041 | H | A037 | H | CH$_2$Ph | H | H |
| A041 | H | A037 | H | C(O)Ph | H | H |
| A041 | H | A037 | H | H | H | CH$_3$ |
| A041 | H | A037 | H | H | CH$_3$ | CH$_3$ |
| A041 | H | A038 | H | H | H | H |
| A041 | H | A038 | H | CH$_3$ | H | H |
| A041 | H | A038 | H | CH$_2$Ph | H | H |
| A041 | H | A038 | H | C(O)Ph | H | H |
| A041 | H | A038 | H | H | H | CH$_3$ |
| A041 | H | A038 | H | H | CH$_3$ | CH$_3$ |
| A041 | H | A041 | H | H | H | H |
| A041 | H | A041 | H | CH$_3$ | H | H |
| A041 | H | A041 | H | CH$_2$Ph | H | H |
| A041 | H | A041 | H | C(O)Ph | H | H |
| A041 | H | A041 | H | H | H | CH$_3$ |
| A041 | H | A041 | H | H | CH$_3$ | CH$_3$ |
| A041 | H | A042 | H | H | H | H |
| A041 | H | A042 | H | CH$_3$ | H | H |
| A041 | H | A042 | H | CH$_2$Ph | H | H |
| A041 | H | A042 | H | C(O)Ph | H | H |
| A041 | H | A042 | H | H | H | CH$_3$ |
| A041 | H | A042 | H | H | CH$_3$ | CH$_3$ |
| A041 | H | A043 | H | H | H | H |
| A041 | H | A044 | H | H | H | H |
| A042 | H | A005 | H | H | H | H |
| A042 | H | A006 | H | H | H | H |
| A042 | H | A006 | H | CH$_3$ | H | H |
| A042 | H | A006 | H | CH$_2$Ph | H | H |
| A042 | H | A006 | H | C(O)Ph | H | H |
| A042 | H | A006 | H | H | H | CH$_3$ |
| A042 | H | A006 | H | H | CH$_3$ | CH$_3$ |
| A042 | H | A014 | H | H | H | H |
| A042 | H | A016 | 2,4-(CH$_3$)$_2$ | H | H | H |
| A042 | H | A037 | H | H | H | H |
| A042 | H | A037 | H | CH$_3$ | H | H |

TABLE 5-continued

| | | | | | | |
|---|---|---|---|---|---|---|
| A042 | H | A037 | H | CH₂Ph | H | H |
| A042 | H | A037 | H | C(O)Ph | H | H |
| A042 | H | A037 | H | H | H | CH₃ |
| A042 | H | A037 | H | H | CH₃ | CH₃ |
| A042 | H | A038 | H | H | H | H |
| A042 | H | A038 | H | CH₃ | H | H |
| A042 | H | A038 | H | CH₂Ph | H | H |
| A042 | H | A038 | H | C(O)Ph | H | H |
| A042 | H | A038 | H | H | H | CH₃ |
| A042 | H | A038 | H | H | CH₃ | CH₃ |
| A042 | H | A041 | H | H | H | H |
| A042 | H | A041 | H | CH₃ | H | H |
| A042 | H | A041 | H | CH₂Ph | H | H |
| A042 | H | A041 | H | C(O)Ph | H | H |
| A042 | H | A041 | H | H | H | CH₃ |
| A042 | H | A041 | H | H | CH₃ | CH₃ |
| A042 | H | A042 | H | H | H | H |
| A042 | H | A042 | H | CH₃ | H | H |
| A042 | H | A042 | H | CH₂Ph | H | H |
| A042 | H | A042 | H | C(O)Ph | H | H |
| A042 | H | A042 | H | H | H | CH₃ |
| A042 | H | A042 | H | H | CH₃ | CH₃ |
| A042 | H | A043 | H | H | H | H |
| A042 | H | A044 | H | H | H | H |

TABLE 6

The locants for the substituents $R^{11}$, $R^{21}$ and $R^{81}$ in the Table correspond to the positions indicated in the following structural formulae.

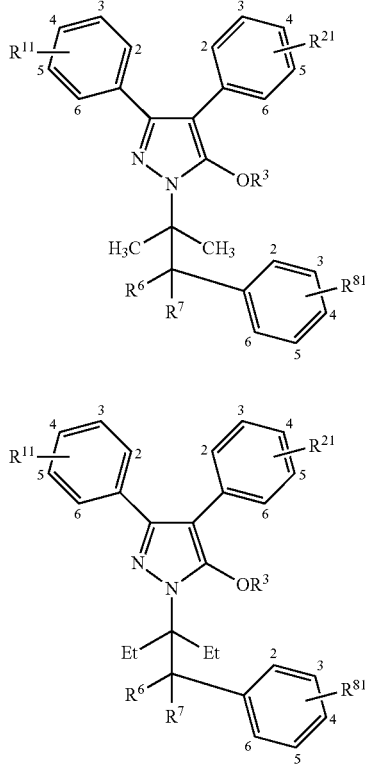

| $R^{11}$ | $R^{21}$ | $R^{81}$ | $R^3$ | $R^6$ | $R^7$ |
|---|---|---|---|---|---|
| H | H | H | H | H | H |
| H | 4-CH₃ | H | H | H | H |
| H | 4-t-Bu | H | H | H | H |
| H | 4-t-Bu | 4-CH₃ | H | H | H |
| H | 4-t-Bu | H | CH₃ | H | H |
| H | 4-t-Bu | 4-CH₃ | CH₃ | H | H |
| H | 4-n-Hex | H | H | H | H |
| H | 4-n-Hex | 4-Cl | H | H | H |
| H | 4-n-Hex | 4-Br | H | H | H |
| H | 4-n-Hex | 4-CH₃ | H | H | H |
| H | 4-n-Hex | H | CH₃ | H | H |
| H | 4-n-Hex | 4-CH₃ | CH₃ | H | H |
| H | 4-n-Hex | H | CH₂Ph | H | H |
| H | 4-n-Hex | H | C(O)OEt | H | H |
| H | 4-n-Hex | H | C(O)Ph | H | H |
| H | 4-n-Hex | H | H | H | CH₃ |
| H | 4-n-Hex | H | H | CH₃ | CH₃ |
| H | 4-Ph | H | H | H | H |
| H | 4-Ph | 4-CH₃ | H | H | H |
| H | 4-Ph | H | CH₃ | H | H |
| H | 4-Ph | 4-CH₃ | CH₃ | H | H |
| 4-F | H | H | H | H | H |
| 2-Cl | H | H | H | H | H |
| 3-Cl | H | H | H | H | H |
| 4-Cl | H | H | H | H | H |
| 4-Cl | 4-t-Bu | H | H | H | H |
| 4-Cl | 4-t-Bu | 4-CH₃ | H | H | H |
| 4-Cl | 4-n-Hex | H | H | H | H |
| 4-Cl | 4-n-Hex | 4-Cl | H | H | H |
| 4-Cl | 4-n-Hex | 4-Br | H | H | H |
| 4-Cl | 4-n-Hex | 4-CH₃ | H | H | H |
| 4-Cl | 4-Ph | H | H | H | H |
| 4-Cl | 4-Ph | 4-CH₃ | H | H | H |
| 4-Br | H | H | H | H | H |
| 3,4-Cl₂ | H | H | H | H | H |
| 4-NO₃ | H | H | H | H | H |
| 4-CN | H | H | H | H | H |
| 2-CH₃ | H | H | H | H | H |
| 3-CH₃ | H | H | H | H | H |
| 4-CH₃ | H | H | H | H | H |

TABLE 6-continued

| | | | | | |
|---|---|---|---|---|---|
| 4-CH₃ | 4-t-Bu | H | H | H | H |
| 4-CH₃ | 4-t-Bu | 4-CH₃ | H | H | H |
| 4-CH₃ | 4-n-Hex | H | H | H | H |
| 4-CH₃ | 4-n-Hex | 4-Cl | H | H | H |
| 4-CH₃ | 4-n-Hex | 4-Br | H | H | H |
| 4-CH₃ | 4-n-Hex | 4-CH₃ | H | H | H |
| 4-CH₃ | 4-Ph | H | H | H | H |
| 4-CH₃ | 4-Ph | 4-CH₃ | H | H | H |
| 3,4-(CH₃)₂ | H | H | H | H | H |
| 4-OCH₃ | H | H | H | H | H |
| 4-OCH₃ | 4-t-Bu | H | H | H | H |
| 4-OCH₃ | 4-n-Hex | H | H | H | H |
| 4-OCH₃ | 4-n-Hex | 4-Cl | H | H | H |
| 4-OCH₃ | 4-n-Hex | 4-Br | H | H | H |
| 4-OCH₃ | 4-n-Hex | 4-CH₃ | H | H | H |
| 4-OCH₃ | 4-Ph | H | H | H | H |
| 3,4-(OCH₃) | H | H | H | H | H |
| 4-Ph | H | H | H | H | H |

TABLE 7

The locants for the substituent $R^{81}$ in the Table correspond to the positions indicated in the following structural formulae.

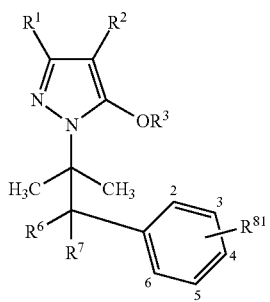

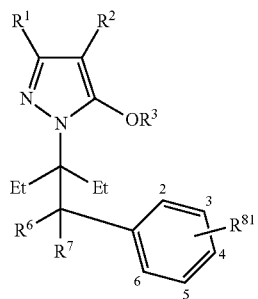

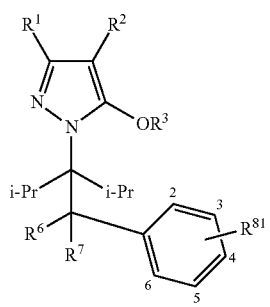

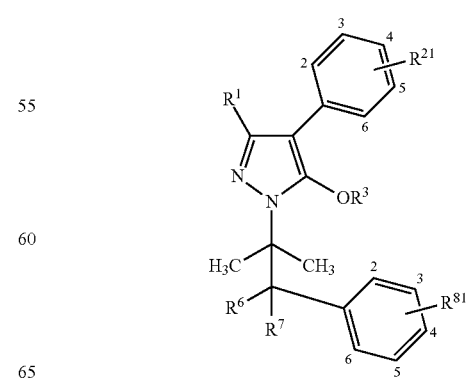

TABLE 7-continued

| $R^1$ | $R^2$ | (Z)m | $R^{81}$ | $R^3$ | $R^6$ | $R^7$ |
|---|---|---|---|---|---|---|
| H | H | — | H | H | H | H |
| Et | H | — | H | H | H | H |
| n-Pr | H | — | H | H | H | H |
| n-Bu | H | — | H | H | H | H |
| c-Bu | H | — | H | H | H | H |
| n-Pen | H | — | H | H | H | H |
| c-Pen | H | — | H | H | H | H |
| CF₃ | H | — | H | H | H | H |
| CF₃ | H | — | 4-CH₃ | H | H | H |
| CF₃ | H | — | 4-CH₃ | CH₃ | H | H |
| CF₃ | A005 | — | H | H | H | H |
| CF₃ | A006 | — | H | H | H | H |
| CF₃ | A014 | — | H | H | H | H |
| CF₃ | A016 | 2,4-(CH₃)₂ | H | H | H | H |
| CF₃ | A036 | H | H | H | H | H |
| CF₃ | A037 | — | H | H | H | H |
| CF₃ | A038 | — | H | H | H | H |
| CF₃ | A041 | — | H | H | H | H |
| CF₃ | A042 | — | H | H | H | H |
| CN | H | — | H | H | H | H |
| C(O)OEt | H | — | H | H | H | H |
| Ph | H | — | H | H | H | H |
| (4-CH₃)Ph | H | — | H | H | H | H |
| (4-i-Pr)Ph | H | — | H | H | H | H |
| (4-OCH₃)Ph | H | — | H | H | H | H |
| (4-OCH₃)Ph | H | — | 4-CH₃ | H | H | H |

TABLE 8

The locants for the substituents $R^{21}$ and $R^{81}$ in the Table correspond to the positions indicated in the following structural formulae, and the expression — indicates unsubstituted.

TABLE 8-continued

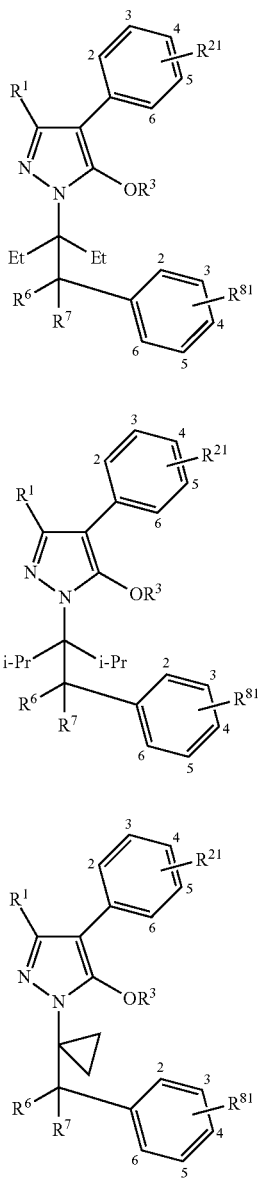

| R¹ | (Z)m | R²¹ | R⁸¹ | R³ | R⁶ | R⁷ |
|---|---|---|---|---|---|---|
| H | — | H | H | H | H | H |
| Et | — | H | H | H | H | H |
| n-Pr | — | H | H | H | H | H |
| n-Bu | — | H | H | H | H | H |
| CF₃ | — | H | H | H | H | H |
| CF₃ | — | 4-CH₃ | H | H | H | H |
| CF₃ | — | 4-CH₃ | 4-CH₃ | H | H | H |
| CF₃ | — | 4-CH₃ | 4-CH₃ | CH₃ | H | H |
| CF₃ | — | 4-CH₃ | 4-CH₃ | CH₃ | H | CH₃ |
| CF₃ | — | 4-t-Bu | H | H | H | H |
| CF₃ | — | 4-n-Hex | 4-CH₃ | H | H | H |
| CF₃ | — | 4-n-Hex | 4-CH₃ | CH₃ | H | H |
| CF₃ | — | 4-n-Hex | 4-CH₃ | CH₃ | H | CH₃ |
| CF₃ | — | 4-n-Hex | 4-CH₃ | CH₃ | CH₃ | CH₃ |
| CF₃ | — | 4-Ph | H | H | H | H |
| CO₂Et | — | H | H | H | H | H |
| A001 | H | H | H | H | H | H |
| A002 | H | H | H | H | H | H |
| A003 | H | H | H | H | H | H |
| A005 | H | H | H | H | H | H |
| A005 | 2,5-(CH₃)₂ | H | H | H | H | H |
| A005 | 2,5-Cl₂ | H | H | H | H | H |
| A005 | 2-Br | H | H | H | H | H |
| A006 | H | H | H | H | H | H |
| A006 | 3-CH₃ | H | H | H | H | H |
| A006 | 5-CH₃ | H | H | H | H | H |
| A006 | 3-Cl | H | H | H | H | H |
| A006 | 5-Et | H | H | H | H | H |
| A006 | 5-Cl | H | H | H | H | H |
| A006 | 5-Br | H | H | H | H | H |
| A006 | 3-Br | H | H | H | H | H |
| A006 | 4-Br | H | H | H | H | H |
| A006 | 5-NO₂ | H | H | H | H | H |
| A007 | H | H | H | H | H | H |
| A007 | 5-CH₃ | H | H | H | H | H |
| A007 | 3-CH₃ | H | H | H | H | H |
| A007 | 5-Br | H | H | H | H | H |
| A007 | 5-NO₂ | H | H | H | H | H |
| A007 | 5-Ph | H | H | H | H | H |
| A008 | 5-CH₃ | H | H | H | H | H |
| A009 | 5-CH₃ | H | H | H | H | H |
| A010 | 3,5-(CH₃)₂ | H | H | H | H | H |
| A010 | 3,5-Cl₂ | H | H | H | H | H |
| A011 | 3,5-(CH₃)₂ | H | H | H | H | H |
| A011 | 3,5-Cl₂ | H | H | H | H | H |
| A012 | 3-CH₃ | H | H | H | H | H |
| A012 | 3-CH₃ | H | H | H | H | H |
| A012 | 3-Cl | H | H | H | H | H |
| A013 | 3-CH₃ | H | H | H | H | H |
| A013 | 3-CH₃ | H | H | H | H | H |
| A013 | 3-Cl | H | H | H | H | H |
| A014 | H | H | H | H | H | H |
| A015 | H | H | H | H | H | H |
| A016 | 2,4-(CH₃)₂ | H | H | H | H | H |
| A017 | 2,4-(CH₃)₂ | H | H | H | H | H |
| A034 | H | H | H | H | H | H |
| A034 | 3,6-Cl₂ | H | H | H | H | II |
| A035 | H | H | H | H | H | H |
| A036 | H | H | H | H | H | H |
| A037 | H | H | H | H | H | H |
| A037 | 6-OCH₃ | H | H | H | H | H |
| A037 | 6-Br | H | H | H | H | H |
| A038 | H | H | H | H | H | H |
| A038 | 2-OCH₃ | H | H | H | H | H |
| A038 | 4-OCH₃ | H | H | H | H | H |
| A038 | 4-F | H | H | H | H | H |

TABLE 9

| R²¹ | R⁸¹ | R³ |
|---|---|---|
| H | H | H |
| H | 4-F | H |
| H | 2-Cl | H |
| H | 3-Cl | H |
| H | 4-Cl | H |
| H | 4-Cl | CH₃ |
| H | 4-Cl | CH₂Ph |
| H | 4-Cl | C(O)Ph |
| H | 4-Cl | C(O)OEt |
| H | 4-Br | H |
| H | 4-I | H |
| H | 2,4-Cl₂ | H |
| H | 3,4-Cl₂ | H |
| H | 4-NO₂ | H |
| H | 4-CN | H |
| H | 2-CH₃ | H |
| H | 3-CH₃ | H |
| H | 4-CH₃ | H |
| H | 4-CH₃ | CH₃ |
| H | 4-CH₃ | CH₂Ph |
| H | 4-CH₃ | C(O)Ph |
| H | 4-CH₃ | C(O)OEt |
| H | 4-Et | H |
| H | 4-n-Pr | H |
| H | 4-c-Pr | H |
| H | 4-i-Pr | H |
| H | 4-n-Bu | H |

TABLE 9-continued

| R²¹ | R⁸¹ | R³ |
|---|---|---|
| H | 4-c-Bu | H |
| H | 4-i-Bu | H |
| H | 4-t-Bu | H |
| H | 4-t-Bu | CH₃ |
| H | 4-t-Bu | CH₂Ph |
| H | 4-t-Bu | C(O)Ph |
| H | 4-t-Bu | C(O)OEt |
| H | 4-n-Pen | H |
| H | 4-c-Pen | H |
| H | 4-n-Hex | H |
| H | 4-n-Hex | CH₃ |
| H | 4-n-Hex | CH₂Ph |
| H | 4-n-Hex | C(O)Ph |
| H | 4-n-Hex | C(O)OEt |
| H | 4-c-Hex | H |
| H | 4-n-C₇H₁₅ | H |
| H | 4-n-C₈H₁₇ | H |
| H | 4-n-C₉H₁₉ | H |
| H | 4-n-C₁₀H₂₁ | H |
| H | 2, 4-(CH₃) | H |
| H | 3, 4-(CH₃)₂ | H |
| H | 4-CF₃ | H |
| H | 4-OH | H |
| H | 2-OCH₃ | H |
| H | 3-OCH₃ | H |
| H | 4-OCH₃ | H |
| H | 4-O—n-Hex | H |
| H | 4-O—c-Hex | H |
| H | 2, 4-(OCH₃)₂ | H |
| H | 3, 4-(OCH₃)₂ | H |
| H | 4-OCH₂OCH₃ | H |
| H | 4-OC₂H₄OEt | H |
| H | 4-OCF₃ | H |
| H | 4-OPh | H |
| H | 4-OCH₂Ph | H |
| H | 4-C(CH₃)=NCH₃ | H |
| H | 4-C(CH₃)=NPh | H |
| H | 4-C(Ph)=NCH₃ | H |
| H | 4-C(Ph)=NPh | H |
| H | 4-C(CH₃)=NOCH₃ | H |
| H | 4-C(CH₃)=NOPh | H |
| H | 4-C(Ph)=NOCH₃ | H |
| H | 4-C(Ph)=NOPh | H |
| H | 4-C(O)CH₃ | H |
| H | 4-C(O)CF₃ | H |
| H | 4-C(O)Ph | H |
| H | 4-C(O)OCH₃ | H |
| H | 2-C(O)OEt | H |
| H | 3-C(O)OEt | H |
| H | 4-C(O)OEt | H |
| H | 4-C(O)OPh | H |
| H | 4-C(O)OCH₂Ph | H |
| H | 4-C(O)OCH(CH₃)Ph | H |
| H | 4-C(O)OC₂H₄Ph | H |
| H | 4-SCH₃ | H |
| H | 4-S(O)CH₃ | H |
| H | 4-S(O)₂CH₃ | H |
| H | 4-SPh | H |
| H | 4-S(O)Ph | H |
| H | 4-S(O)₂Ph | H |
| H | 4-OS(O)₂CH₃ | H |
| H | 4-OS(O)₂Ph | H |
| H | 4-N(CH₃)₂ | H |
| H | 4-N(CH₂Ph)₂ | H |
| H | 4-N(CH₃)(CH₂Ph) | H |
| H | 4-NHCH₃ | H |
| H | 4-NH(CH₂Ph) | H |
| H | 4-C(O)N(CH₃)₂ | H |
| H | 4-C(O)N(CH₂Ph)₂ | H |
| H | 4-C(O)N(CH₃)(CH₂Ph) | H |
| H | 4-C(O)NHCH₃ | H |
| H | 4-C(O)NH(CH₂Ph) | H |
| H | 4-C(O)NH(CH(CH₃)Ph) | H |
| H | 4-C(O)NH(C₂H₄Ph) | H |
| H | 4-C(S)NH₂ | H |
| H | 4-S(O)₂N(CH₃)₂ | H |
| H | 4-S(O)₂N(CH₂Ph)₂ | H |
| H | 4-S(O)₂N(CH₃)(CH₂Ph) | H |
| H | 4-S(O)₂NHCH₃ | H |
| H | 4-S(O)₂NHPh | H |
| H | 4-S(O)₂NH(CH₂Ph) | H |
| H | 4-S(O)₂NH{CH(CH₃)Ph} | H |
| H | 4-S(O)₂NH(C₂H₄Ph) | H |
| H | 4-Ph | H |
| H | 4-Ph | CH₃ |
| H | 4-Ph | CH₂Ph |
| H | 4-Ph | C(O)Ph |
| H | 4-Ph | C(O)OEt |
| 4-F | H | H |
| 4-F | 4-Cl | H |
| 4-F | 4-Br | H |
| 4-F | 4-CH₃ | H |
| 4-F | 4-t-Bu | H |
| 4-F | 4-n-Hex | H |
| 4-F | 4-Ph | H |
| 2-Cl | H | H |
| 2-Cl | 4-Cl | H |
| 2-Cl | 4-Br | H |
| 2-Cl | 4-CH₃ | H |
| 2-Cl | 4-t-Bu | H |
| 2-Cl | 4-n-Hex | H |
| 2-Cl | 4-Ph | H |
| 3-Cl | H | H |
| 3-Cl | 4-Cl | H |
| 3-Cl | 4-Br | H |
| 3-Cl | 4-CH₃ | H |
| 3-Cl | 4-t-Bu | H |
| 3-Cl | 4-n-Hex | H |
| 3-Cl | 4-Ph | H |
| 4-Cl | H | H |
| 4-Cl | 4-Cl | H |
| 4-Cl | 4-Br | H |
| 4-Cl | 4-CH₃ | H |
| 4-Cl | 4-t-Bu | H |
| 4-Cl | 4-t-Bu | CH₃ |
| 4-Cl | 4-n-Hex | H |
| 4-Cl | 4-n-Hex | CH₃ |
| 4-Cl | 4-Ph | H |
| 4-Cl | 4-Ph | CH₃ |
| 4-Br | H | H |
| 4-Br | 4-Cl | H |
| 4-Br | 4-Br | H |
| 4-Br | 4-CH₃ | H |
| 4-Br | 4-t-Bu | H |
| 4-Br | 4-n-Hex | H |
| 4-Br | 4-Ph | H |
| 3, 4-Cl₂ | H | H |
| 3, 4-Cl₂ | 4-Cl | H |
| 3, 4-Cl₂ | 4-Br | H |
| 3, 4-Cl₂ | 4-CH₃ | H |
| 3, 4-Cl₂ | 4-t-Bu | H |
| 3, 4-Cl₂ | 4-n-Hex | H |
| 3, 4-Cl₂ | 4-Ph | H |
| 4-NO₂ | H | H |
| 4-NO₂ | 4-Cl | H |
| 4-NO₂ | 4-Br | H |
| 4-NO₂ | 4-CH₃ | H |
| 4-NO₂ | 4-t-Bu | H |
| 4-NO₂ | 4-n-Hex | H |
| 4-NO₂ | 4-Ph | H |
| 4-CN | H | H |
| 4-CN | 4-Cl | H |
| 4-CN | 4-Br | H |
| 4-CN | 4-CH₃ | H |
| 4-CN | 4-t-Bu | H |
| 4-CN | 4-n-Hex | H |
| 4-CN | 4-Ph | H |
| 2-CH₃ | H | H |
| 2-CH₃ | 4-Cl | H |
| 2-CH₃ | 4-Br | H |
| 2-CH₃ | 4-CH₃ | H |
| 2-CH₃ | 4-t-Bu | H |
| 2-CH₃ | 4-n-Hex | H |
| 2-CH₃ | 4-Ph | H |
| 3-CH₃ | H | H |
| 3-CH₃ | 4-Cl | H |

TABLE 9-continued

| $R^{21}$ | $R^{81}$ | $R^3$ |
|---|---|---|
| 3-CH$_3$ | 4-Br | H |
| 3-CH$_3$ | 4-CH$_3$ | H |
| 3-CH$_3$ | 4-t-Bu | H |
| 3-CH$_3$ | 4-n-Hex | H |
| 3-CH$_3$ | 4-Ph | H |
| 4-CH$_3$ | H | H |
| 4-CH$_3$ | 4-Cl | H |
| 4-CH$_3$ | 4-Br | H |
| 4-CH$_3$ | 4-CH$_3$ | H |
| 4-CH$_3$ | 4-t-Bu | H |
| 4-CH$_3$ | 4-t-Bu | CH$_3$ |
| 4-CH$_3$ | 4-n-Hex | H |
| 4-CH$_3$ | 4-n-Hex | CH$_3$ |
| 4-CH$_3$ | 4-Ph | H |
| 4-CH$_3$ | 4-Ph | CH$_3$ |
| 4-c-Pr | H | H |
| 4-c-Pr | 4-Cl | H |
| 4-c-Pr | 4-Br | H |
| 4-c-Pr | 4-CH$_3$ | H |
| 4-c-Pr | 4-t-Bu | H |
| 4-c-Pr | 4-n-Hex | H |
| 4-c-Pr | 4-Ph | H |
| 4-i-Pr | H | H |
| 4-i-Pr | 4-Cl | H |
| 4-i-Pr | 4-Br | H |
| 4-i-Pr | 4-CH$_3$ | H |
| 4-i-Pr | 4-t-Bu | H |
| 4-i-Pr | 4-n-Hex | H |
| 4-i-Pr | 4-Ph | H |
| 4-t-Bu | H | H |
| 4-t-Bu | 4-Cl | H |
| 4-t-Bu | 4-Br | H |
| 4-t-Bu | 4-CH$_3$ | H |
| 4-t-Bu | 4-t-Bu | H |
| 4-t-Bu | 4-t-Bu | CH$_3$ |
| 4-t-Bu | 4-n-Hex | H |
| 4-t-Bu | 4-n-Hex | CH$_3$ |
| 4-t-Bu | 4-Ph | H |
| 4-t-Bu | 4-Ph | CH$_3$ |
| 4-n-Hex | H | H |
| 4-n-Hex | H | CH$_3$ |
| 4-n-Hex | H | CH$_2$Ph |
| 4-n-Hex | H | C(O)Ph |
| 4-n-Hex | H | C(O)OEt |
| 4-n-Hex | 4-F | H |
| 4-n-Hex | 2-Cl | H |
| 4-n-Hex | 3-Cl | H |
| 4-n-Hex | 4-Cl | H |
| 4-n-Hex | 4-Cl | CH$_3$ |
| 4-n-Hex | 4-Cl | CH$_2$Ph |
| 4-n-Hex | 4-Cl | C(O)Ph |
| 4-n-Hex | 4-Cl | C(O)OEt |
| 4-n-Hex | 4-Br | H |
| 4-n-Hex | 4-I | H |
| 4-n-Hex | 2,4-Cl$_2$ | H |
| 4-n-Hex | 3,4-Cl$_2$ | H |
| 4-n-Hex | 4-NO$_2$ | H |
| 4-n-Hex | 4-CN | H |
| 4-n-Hex | 2-CH$_3$ | H |
| 4-n-Hex | 3-CH$_3$ | H |
| 4-n-Hex | 4-CH$_3$ | H |
| 4-n-Hex | 4-CH$_3$ | CH$_3$ |
| 4-n-Hex | 4-CH$_3$ | CH$_2$Ph |
| 4-n-Hex | 4-CH$_3$ | C(O)Ph |
| 4-n-Hex | 4-CH$_3$ | C(O)OEt |
| 4-n-Hex | 4-Et | H |
| 4-n-Hex | 4-n-Pr | H |
| 4-n-Hex | 4-c-Pr | H |
| 4-n-Hex | 4-i-Pr | H |
| 4-n-Hex | 4-n-Bu | H |
| 4-n-Hex | 4-c-Bu | H |
| 4-n-Hex | 4-i-Bu | H |
| 4-n-Hex | 4-t-Bu | H |
| 4-n-Hex | 4-t-Bu | CH$_3$ |
| 4-n-Hex | 4-t-Bu | CH$_2$Ph |
| 4-n-Hex | 4-t-Bu | C(O)Ph |
| 4-n-Hex | 4-t-Bu | C(O)OEt |
| 4-n-Hex | 4-n-Pen | H |
| 4-n-Hex | 4-c-Pen | H |
| 4-n-Hex | 4-n-Hex | H |
| 4-n-Hex | 4-n-Hex | CH$_3$ |
| 4-n-Hex | 4-n-Hex | CH$_2$Ph |
| 4-n-Hex | 4-n-Hex | C(O)Ph |
| 4-n-Hex | 4-n-Hex | C(O)OEt |
| 4-n-Hex | 4-c-Hex | H |
| 4-n-Hex | 4-n-C$_7$H$_{15}$ | H |
| 4-n-Hex | 4-n-C$_8$H$_{17}$ | H |
| 4-n-Hex | 4-n-C$_9$H$_{19}$ | H |
| 4-n-Hex | 4-n-C$_{10}$H$_{21}$ | H |
| 4-n-Hex | 2,4-(CH$_3$) | H |
| 4-n-Hex | 3,4-(CH$_3$)$_2$ | H |
| 4-n-Hex | 4-CF$_3$ | H |
| 4-n-Hex | 4-OH | H |
| 4-n-Hex | 2-OCH$_3$ | H |
| 4-n-Hex | 3-OCH$_3$ | H |
| 4-n-Hex | 4-OCH$_3$ | H |
| 4-n-Hex | 4-O—n-Hex | H |
| 4-n-Hex | 4-O—c-Hex | H |
| 4-n-Hex | 2,4-(OCH$_3$)$_2$ | H |
| 4-n-Hex | 3,4-(OCH$_3$)$_2$ | H |
| 4-n-Hex | 4-OCH$_2$OCH$_3$ | H |
| 4-n-Hex | 4-OC$_2$H$_4$OEt | H |
| 4-n-Hex | 4-OCF$_3$ | H |
| 4-n-Hex | 4-OPh | H |
| 4-n-Hex | 4-OCH$_2$Ph | H |
| 4-n-Hex | 4-C(CH$_3$)=NCH$_3$ | H |
| 4-n-Hex | 4-C(CH$_3$)=NPh | H |
| 4-n-Hex | 4-C(Ph)=NCH$_3$ | H |
| 4-n-Hex | 4-C(Ph)=NPh | H |
| 4-n-Hex | 4-C(CH$_3$)=NOCH$_3$ | H |
| 4-n-Hex | 4-C(CH$_3$)=NOPh | H |
| 4-n-Hex | 4-C(Ph)=NOCH$_3$ | H |
| 4-n-Hex | 4-C(Ph)=NOPh | H |
| 4-n-Hex | 4-C(O)CH$_3$ | H |
| 4-n-Hex | 4-C(O)CF$_3$ | H |
| 4-n-Hex | 4-C(O)Ph | H |
| 4-n-Hex | 4-C(O)OCH$_3$ | H |
| 4-n-Hex | 2-C(O)OEt | H |
| 4-n-Hex | 3-C(O)OEt | H |
| 4-n-Hex | 4-C(O)OEt | H |
| 4-n-Hex | 4-C(O)OPh | H |
| 4-n-Hex | 4-C(O)OCH$_2$Ph | H |
| 4-n-Hex | 4-C(O)OCH(CH$_3$)Ph | H |
| 4-n-Hex | 4-C(O)OC$_2$H$_4$Ph | H |
| 4-n-Hex | 4-SCH$_3$ | H |
| 4-n-Hex | 4-S(O)CH$_3$ | H |
| 4-n-Hex | 4-S(O)$_2$CH$_3$ | H |
| 4-n-Hex | 4-SPh | H |
| 4-n-Hex | 4-S(O)Ph | H |
| 4-n-Hex | 4-S(O)$_2$Ph | H |
| 4-n-Hex | 4-OS(O)$_2$CH$_3$ | H |
| 4-n-Hex | 4-OS(O)$_2$Ph | H |
| 4-n-Hex | 4-N(CH$_3$)$_2$ | H |
| 4-n-Hex | 4-N(CH$_2$Ph)$_2$ | H |
| 4-n-Hex | 4-N(CH$_3$)(CH$_2$Ph) | H |
| 4-n-Hex | 4-NHCH$_3$ | H |
| 4-n-Hex | 4-NH(CH$_2$Ph) | H |
| 4-n-Hex | 4-C(O)N(CH$_3$)$_2$ | H |
| 4-n-Hex | 4-C(O)N(CH$_2$Ph)$_2$ | H |
| 4-n-Hex | 4-C(O)N(CH$_3$)(CH$_2$Ph) | H |
| 4-n-Hex | 4-C(O)NHCH$_3$ | H |
| 4-n-Hex | 4-C(O)NH(CH$_2$Ph) | H |
| 4-n-Hex | 4-C(O)NH{CH(CH$_3$)Ph} | H |
| 4-n-Hex | 4-C(O)NH(C$_2$H$_4$Ph) | H |
| 4-n-Hex | 4-C(S)NH$_2$ | H |
| 4-n-Hex | 4-S(O)$_2$N(CH$_3$)$_2$ | H |
| 4-n-Hex | 4-S(O)$_2$N(CH$_2$Ph)$_2$ | H |
| 4-n-Hex | 4-S(O)$_2$N(CH$_3$)(CH$_2$Ph) | H |
| 4-n-Hex | 4-S(O)$_2$NHCH$_3$ | H |
| 4-n-Hex | 4-S(O)$_2$NHPh | H |
| 4-n-Hex | 4-S(O)$_2$NH(CH$_2$Ph) | H |
| 4-n-Hex | 4-S(O)$_2$NH{CH(CH$_3$)Ph} | H |
| 4-n-Hex | 4-S(O)$_2$NH(C$_2$H$_4$Ph) | H |
| 4-n-Hex | 4-Ph | H |
| 4-n-Hex | 4-Ph | CH$_3$ |
| 4-n-Hex | 4-Ph | CH$_2$Ph |

TABLE 9-continued

| R$^{21}$ | R$^{81}$ | R$^3$ |
|---|---|---|
| 4-n-Hex | 4-Ph | C(O)Ph |
| 4-n-Hex | 4-Ph | C(O)OEt |
| 4-c-Hex | H | H |
| 4-c-Hex | 4-Cl | H |
| 4-c-Hex | 4-Br | H |
| 4-c-Hex | 4-CH$_3$ | H |
| 4-c-Hex | 4-t-Bu | H |
| 4-c-Hex | 4-t-Bu | CH$_3$ |
| 4-c-Hex | 4-n-Hex | H |
| 4-c-Hex | 4-n-Hex | CH$_3$ |
| 4-c-Hex | 4-Ph | H |
| 4-c-Hex | 4-Ph | CH$_3$ |
| 3,4-(CH$_3$)$_2$ | H | H |
| 3,4-(CH$_3$)$_2$ | 4-Cl | H |
| 3,4-(CH$_3$)$_2$ | 4-Br | H |
| 3,4-(CH$_3$)$_2$ | 4-CH$_3$ | H |
| 3,4-(CH$_3$)$_2$ | 4-t-Bu | H |
| 3,4-(CH$_3$)$_2$ | 4-n-Hex | H |
| 3,4-(CH$_3$)$_2$ | 4-Ph | H |
| 2,4-(t-Bu)$_2$ | H | H |
| 2,4-(t-Bu)$_2$ | 4-Cl | H |
| 2,4-(t-Bu)$_2$ | 4-Br | H |
| 2,4-(t-Bu)$_2$ | 4-CH$_3$ | H |
| 2,4-(t-Bu)$_2$ | 4-t-Bu | H |
| 2,4-(t-Bu)$_2$ | 4-n-Hex | H |
| 2,4-(t-Bu)$_2$ | 4-Ph | H |
| 4-CF$_3$ | H | H |
| 4-CF$_3$ | 4-Cl | H |
| 4-CF$_3$ | 4-Br | H |
| 4-CF$_3$ | 4-CH$_3$ | H |
| 4-CF$_3$ | 4-t-Bu | H |
| 4-CF$_3$ | 4-n-Hex | H |
| 4-CF$_3$ | 4-Ph | H |
| 4-OH | H | H |
| 4-OH | 4-Cl | H |
| 4-OH | 4-Br | H |
| 4-OH | 4-CH$_3$ | H |
| 4-OH | 4-t-Bu | H |
| 4-OH | 4-n-Hex | H |
| 4-OH | 4-Ph | H |
| 4-OCH$_3$ | H | H |
| 4-OCH$_3$ | 4-Cl | H |
| 4-OCH$_3$ | 4-Br | H |
| 4-OCH$_3$ | 4-CH$_3$ | H |
| 4-OCH$_3$ | 4-t-Bu | H |
| 4-OCH$_3$ | 4-n-Hex | H |
| 4-OCH$_3$ | 4-Ph | H |
| 4-O—i-Pr | H | H |
| 4-O—i-Pr | 4-Cl | H |
| 4-O—i-Pr | 4-Br | H |
| 4-O—i-Pr | 4-CH$_3$ | H |
| 4-O—i-Pr | 4-t-Bu | H |
| 4-O—i-Pr | 4-n-Hex | H |
| 4-O—i-Pr | 4-Ph | H |
| 4-O—n-Hex | H | H |
| 4-O—n-Hex | 4-Cl | H |
| 4-O—n-Hex | 4-Br | H |
| 4-O—n-Hex | 4-CH$_3$ | H |
| 4-O—n-Hex | 4-t-Bu | H |
| 4-O—n-Hex | 4-n-Hex | H |
| 4-O—n-Hex | 4-Ph | H |
| 3,4-(OCH$_3$)$_2$ | H | H |
| 3,4-(OCH$_3$)$_2$ | 4-Cl | H |
| 3,4-(OCH$_3$)$_2$ | 4-Br | H |
| 3,4-(OCH$_3$)$_2$ | 4-CH$_3$ | H |
| 3,4-(OCH$_3$)$_2$ | 4-t-Bu | H |
| 3,4-(OCH$_3$)$_2$ | 4-n-Hex | H |
| 3,4-(OCH$_3$)$_2$ | 4-Ph | H |
| 4-OC$_2$H$_4$OEt | H | H |
| 4-OC$_2$H$_4$OEt | 4-Cl | H |
| 4-OC$_2$H$_4$OEt | 4-Br | H |
| 4-OC$_2$H$_4$OEt | 4-CH$_3$ | H |
| 4-OC$_2$H$_4$OEt | 4-t-Bu | H |
| 4-OC$_2$H$_4$OEt | 4-n-Hex | H |
| 4-OC$_2$H$_4$OEt | 4-Ph | H |
| 4-OPh | H | H |
| 4-OPh | 4-Cl | H |
| 4-OPh | 4-Br | H |
| 4-OPh | 4-CH$_3$ | H |
| 4-OPh | 4-t-Bu | H |
| 4-OPh | 4-n-Hex | H |
| 4-OPh | 4-Ph | H |
| 4-OCH$_2$Ph | H | H |
| 4-OCH$_2$Ph | 4-Cl | H |
| 4-OCH$_2$Ph | 4-Br | H |
| 4-OCH$_2$Ph | 4-CH$_3$ | H |
| 4-OCH$_2$Ph | 4-t-Bu | H |
| 4-OCH$_2$Ph | 4-n-Hex | H |
| 4-OCH$_2$Ph | 4-Ph | H |
| 4-Ph | H | H |
| 4-Ph | 4-Cl | H |
| 4-Ph | 4-Br | H |
| 4-Ph | 4-CH$_3$ | H |
| 4-Ph | 4-t-Bu | H |
| 4-Ph | 4-t-Bu | CH$_3$ |
| 4-Ph | 4-n-Hex | H |
| 4-Ph | 4-n-Hex | CH$_3$ |
| 4-Ph | 4-Ph | H |
| 4-Ph | 4-Ph | CH$_3$ |

The locants for the substituent R$^{21}$ and R$^{81}$ in the Table correspond to the positions indicated in the following structural formulae.

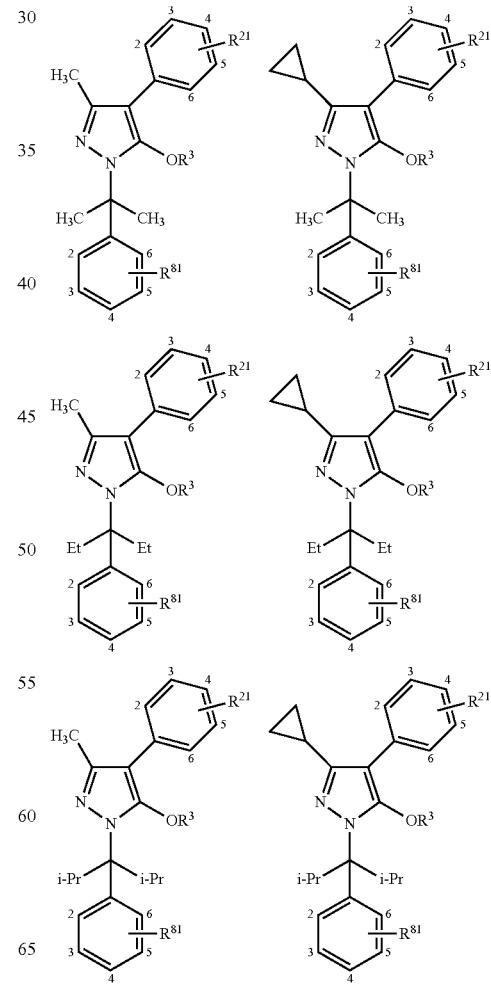

TABLE 9-continued

| R²¹ | R⁸¹ | R³ |
|---|---|---|

TABLE 9-continued

| R²¹ | R⁸¹ | R³ |
|---|---|---|

(structures shown with t-Bu/cyclohexyl substituted pyrazoles bearing CHEt₂, CH(i-Pr)₂, and cyclopropyl N-substituents with aryl groups)

TABLE 10

| R² | (Z)m | R⁸¹ | R³ |
|---|---|---|---|
| H | — | H | H |
| H | — | 4-CH₃ | H |
| F | — | H | H |
| CH₃ | — | H | H |
| Et | — | H | H |
| n-Pr | — | H | H |
| c-Pr | — | H | H |
| i-Pr | — | H | H |
| n-Bu | — | H | H |
| c-Bu | — | H | H |
| i-Bu | — | H | H |
| t-Bu | — | H | H |
| n-Pen | — | H | H |
| c-Pen | — | H | H |
| n-Hex | — | H | H |
| c-Hex | — | H | H |
| n-C₇H₁₅ | — | H | H |
| n-C₈H₁₇ | — | H | H |
| n-C₉H₁₉ | — | H | H |
| n-C₁₀H₂ | — | H | H |
| CF₃ | — | H | H |
| C(Ph)=NCH₃ | — | H | H |
| C(CH₃)=NPh | — | H | H |
| C(Ph)=NOCH₃ | — | H | H |
| C(O)CH₃ | — | H | H |

TABLE 10-continued

| R² | (Z)m | R⁸¹ | R³ |
|---|---|---|---|
| C(O)Et | — | H | H |
| C(O)CF₃ | — | H | H |
| C(O)Ph | — | H | H |
| C(O)Ph | — | 4-Cl | H |
| C(O)Ph | — | 4-CH₃ | H |
| C(O)Ph | — | 4-CH₃ | CH₃ |
| C(O)Ph | — | 4-CH₃ | CH₂Ph |
| C(O)Ph | — | 4-CH₃ | C(O)Ph |
| C(O)Ph | — | 4-CH₃ | C(O)OEt |
| C(O)Ph | — | 4-t-Bu | H |
| C(O)Ph | — | 4-n-hex | H |
| C(O)Ph | — | 4-OCH₃ | H |
| C(O)Ph | — | 4-Ph | H |
| C(O)CH₂Ph | — | H | H |
| C(O)CH(CH₃)Ph | — | H | H |
| C(O)C₂H₄Ph | — | H | H |
| C(O)OCH₃ | — | H | H |
| C(O)OEt | — | H | H |
| C(O)OEt | — | 4-Cl | H |
| C(O)OEt | — | 4-CH₃ | H |
| C(O)OEt | — | 4-CH₃ | CH₃ |
| C(O)OEt | — | 4-CH₃ | CH₂Ph |
| C(O)OEt | — | 4-CH₃ | C(O)Ph |
| C(O)OEt | — | 4-CH₃ | C(O)OEt |
| C(O)OEt | — | 4-t-Bu | H |
| C(O)OEt | — | 4-n-hex | H |
| C(O)OEt | — | 4-OCH₃ | H |
| C(O)OEt | — | 4-Ph | H |
| C(O)OPh | — | H | H |
| C(O)OCH₂Ph | — | H | H |
| C(O)OCH(CH₃)Ph | — | H | H |
| C(O)OC₂H₄Ph | — | H | H |
| C(O)N(CH₃)₂ | — | H | H |
| C(O)NHCH₃ | — | H | H |
| C(O)NH(CH₂Ph) | — | H | H |
| CH₂Ph | — | H | H |
| CH₂(4-Cl—Ph) | — | H | H |
| A001 | H | H | H |
| A001 | 3-n-Bu | H | H |
| A002 | H | H | H |
| A002 | 2-Cl | H | H |
| A003 | H | H | H |
| A004 | H | H | H |
| A005 | H | H | H |
| A005 | H | 4-Cl | H |
| A005 | H | 4-CH₃ | H |
| A005 | H | 4-CH₃ | CH₃ |
| A005 | H | 4-CH₃ | CH₂Ph |
| A005 | H | 4-CH₃ | C(O)Ph |
| A005 | H | 4-CH₃ | C(O)OEt |
| A005 | H | 4-t-Bu | H |
| A005 | H | 4-n-hex | H |
| A005 | H | 4-OCH₃ | H |
| A005 | H | 4-Ph | H |
| A005 | 2,5-(CH₃)₂ | H | H |
| A005 | 2,5-Cl₂ | H | H |
| A005 | 2-Br | H | H |
| A006 | H | H | H |
| A006 | H | 4-Cl | H |
| A006 | H | 4-CH₃ | H |
| A006 | H | 4-CH₃ | CH₃ |
| A006 | H | 4-CH₃ | CH₂Ph |
| A006 | H | 4-CH₃ | C(O)Ph |
| A006 | H | 4-CH₃ | C(O)OEt |
| A006 | H | 4-t-Bu | H |
| A006 | H | 4-n-hex | H |
| A006 | H | 4-OCH₃ | H |
| A006 | H | 4-Ph | H |
| A006 | 3-CH₃ | H | H |
| A006 | 5-CH₃ | H | H |
| A006 | 3-Cl | H | H |
| A006 | 5-Et | H | H |
| A006 | 5-Cl | H | H |
| A006 | 5-Br | H | H |
| A006 | 3-Br | H | H |
| A006 | 4-Br | H | H |
| A006 | 5-NO₂ | H | H |
| A007 | H | H | H |

TABLE 10-continued

| R² | (Z)m | R⁸¹ | R³ |
|---|---|---|---|
| A007 | 5-CH₃ | H | H |
| A007 | 3-CH₃ | H | H |
| A007 | 5-Br | H | H |
| A007 | 5-NO₂ | H | H |
| A007 | 5-Ph | H | H |
| A008 | 5-CH₃ | H | H |
| A009 | 5-CH₃ | H | H |
| A010 | 3, 5-(CH₃)₂ | H | H |
| A010 | 3, 5-Cl₂ | H | H |
| A011 | 3, 5-(CH₃)₂ | H | H |
| A011 | 3, 5-Cl₂ | H | H |
| A012 | 3-CH₃ | H | H |
| A012 | 3-CH₃ | H | H |
| A012 | 3-Cl | H | H |
| A013 | 3-CH₃ | H | H |
| A013 | 3-CH₃ | H | H |
| A013 | 3-Cl | H | H |
| A014 | H | H | H |
| A014 | H | 4-Cl | H |
| A014 | H | 4-CH₃ | H |
| A014 | H | 4-CH₃ | CH₃ |
| A014 | H | 4-CH₃ | CH₂Ph |
| A014 | H | 4-CH₃ | C(O)Ph |
| A014 | H | 4-CH₃ | C(O)OEt |
| A014 | H | 4-t-Bu | H |
| A014 | H | 4-n-hex | H |
| A014 | H | 4-OCH₃ | H |
| A014 | H | 4-Ph | H |
| A015 | H | H | H |
| A016 | 2, 4-(CH₃)₂ | H | H |
| A016 | 2, 4-(CH₃)₂ | 4-Cl | H |
| A016 | 2, 4-(CH₃)₂ | 4-CH₃ | H |
| A016 | 2, 4-(CH₃)₂ | 4-CH₃ | CH₃ |
| A016 | 2, 4-(CH₃)₂ | 4-CH₃ | CH₂Ph |
| A016 | 2, 4-(CH₃)₂ | 4-CH₃ | C(O)Ph |
| A016 | 2, 4-(CH₂)₃ | 4-CH₂ | C(O)OEt |
| A016 | 2, 4-(CH₃)₂ | 4-t-Bu | H |
| A016 | 2, 4-(CH₂)₂ | 4-n-hex | H |
| A016 | 2, 4-(CH₂)₂ | 4-OCH₃ | H |
| A016 | 2, 4-(CH₂)₂ | 4-Ph | H |
| A017 | 2, 4-(CH₃)₂ | H | H |
| A018 | H | H | H |
| A018 | 3-CH₂ | H | H |
| A019 | 3-Ph, 5-CH₂ | H | H |
| A019 | 3, 5-(CH₂)₂ | H | H |
| A020 | 5-CH₂ | H | H |
| A021 | 4-CH₂ | H | H |
| A022 | H | H | H |
| A023 | 2, 4-(CH₂)₂ | H | H |
| A024 | 2-(4-pyridil) | H | H |
| A025 | H | H | H |
| A026 | H | H | H |
| A026 | 4-CH₂ | H | H |
| A027 | H | H | H |
| A027 | 4-CH₃ | H | H |
| A028 | H | H | H |
| A029 | H | H | H |
| A030 | H | H | H |
| A031 | H | H | H |
| A032 | H | H | H |
| A033 | H | H | H |
| A034 | H | H | H |
| A034 | 3, 6-Cl₂ | H | H |
| A035 | H | H | H |
| A036 | H | H | H |
| A036 | H | 4-Cl | H |
| A036 | H | 4-CH₂ | H |
| A036 | H | 4-CH₂ | CH₂ |
| A036 | H | 4-CH₂ | CH₂Ph |
| A036 | H | 4-CH₃ | C(O)Ph |
| A036 | H | 4-CH₂ | C(O)OEt |
| A036 | H | 4-t-Bu | H |
| A036 | H | 4-n-hex | H |
| A036 | H | 4-OCH₂ | H |
| A036 | H | 4-Ph | H |
| A037 | H | H | H |
| A037 | H | 4-Cl | H |
| A037 | H | 4-CH₃ | H |
| A037 | H | 4-CH₃ | CH₃ |
| A037 | H | 4-CH₃ | CH₂Ph |
| A037 | H | 4-CH₃ | C(O)Ph |
| A037 | H | 4-CH₃ | C(O)OEt |
| A037 | H | 4-t-Bu | H |
| A037 | H | 4-n-hex | H |
| A037 | H | 4-OCH₃ | H |
| A037 | H | 4-Ph | H |
| A037 | 6-OCH₃ | H | H |
| A037 | 6-Br | H | H |
| A038 | H | H | H |
| A038 | H | 4-Cl | H |
| A038 | H | 4-CH₃ | H |
| A038 | H | 4-CH₃ | CH₃ |
| A038 | H | 4-CH₃ | CH₂Ph |
| A038 | H | 4-CH₃ | C(O)Ph |
| A038 | H | 4-CH₃ | C(O)OEt |
| A038 | H | 4-t-Bu | H |
| A038 | H | 4-n-hex | H |
| A038 | H | 4-OCH₃ | H |
| A038 | H | 4-Ph | H |
| A038 | 2-OCH₃ | H | H |
| A038 | 4-OCH₃ | H | H |
| A038 | 4-F | H | H |
| A039 | H | H | H |
| A039 | 3-CH₃ | H | H |
| A039 | 7-OCH₃ | H | H |
| A040 | H | H | H |
| A041 | H | H | H |
| A041 | H | 4-Cl | H |
| A041 | H | 4-CH₃ | H |
| A041 | H | 4-CH₃ | CH₃ |
| A041 | H | 4-CH₃ | CH₂Ph |
| A041 | H | 4-CH₃ | C(O)Ph |
| A041 | H | 4-CH₃ | C(O)OEt |
| A041 | H | 4-t-Bu | H |
| A041 | H | 4-n-hex | H |
| A041 | H | 4-OCH₃ | H |
| A041 | H | 4-Ph | H |
| A041 | 6-NO₂ | H | H |
| A041 | 6-Br | H | H |
| A042 | H | H | H |
| A042 | H | 4-Cl | H |
| A042 | H | 4-CH₃ | H |
| A042 | H | 4-CH₃ | CH₃ |
| A042 | H | 4-CH₃ | CH₂Ph |
| A042 | H | 4-CH₃ | C(O)Ph |
| A042 | H | 4-CH₃ | C(O)OEt |
| A042 | H | 4-t-Bu | H |
| A042 | H | 4-n-hex | H |
| A042 | H | 4-OCH₃ | H |
| A042 | H | 4-Ph | H |
| A042 | 5-Br | H | H |
| A043 | H | H | H |
| A044 | H | H | H |
| A051 | — | H | H |
| A052 | — | H | H |
| A053 | — | H | H |
| A054 | — | H | H |
| A055 | — | H | H |
| A056 | — | H | H |
| A057 | — | H | H |
| A058 | — | H | H |
| A059 | — | H | H |
| A060 | — | H | H |
| A061 | — | H | H |
| A062 | — | H | H |
| A063 | — | H | H |
| A064 | — | H | H |
| A065 | — | H | H |
| A066 | — | H | H |
| A067 | — | H | H |
| A068 | — | H | H |
| A101 | — | H | H |
| A102 | — | H | H |
| A103 | — | H | H |
| A104 | — | H | H |
| A105 | — | H | H |

TABLE 10-continued
| R² | (Z)m | R⁸¹ | R³ |
|---|---|---|---|
| A106 | — | H | H |
| A107 | — | H | H |
The locants for the substituent R⁸¹ in the Table correspond to the positions indicated in the following structural formulae, and the expression — indicates unsubstituted.
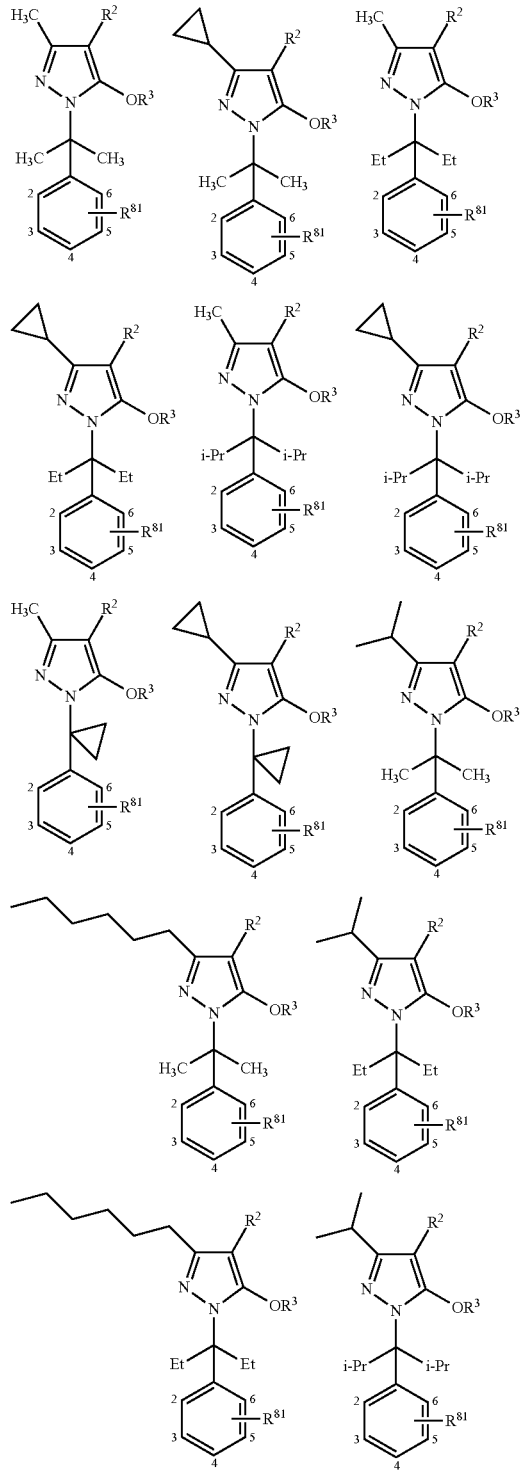

TABLE 10-continued

| R² | (Z)m | R⁸¹ | R³ |
|---|---|---|---|

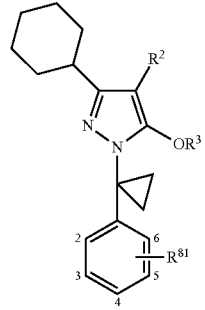

TABLE 11

| R²¹ | R⁸ | (Z)m | R³ |
|---|---|---|---|
| H | c-Pr | — | H |
| 4-Cl | c-Pr | — | H |
| 4-CH₃ | c-Pr | — | H |
| 4-CH₃ | c-Pr | — | CH₃ |
| 4-CH₃ | c-Pr | — | CH₂Ph |
| 4-CH₃ | c-Pr | — | C(O)Ph |
| 4-CH₃ | c-Pr | — | C(O)OEt |
| 4-t-Bu | c-Pr | — | H |
| 4-n-hex | c-Pr | — | H |
| 4-n-hex | c-Pr | — | CH₃ |
| 4-n-hex | c-Pr | — | CH₂Ph |
| 4-n-hex | c-Pr | — | C(O)Ph |
| 4-n-hex | c-Pr | — | C(O)OEt |
| 4-OCH₃ | c-Pr | — | H |
| 4-Ph | c-Pr | — | H |
| H | c-Bu | — | H |
| H | c-Pen | — | H |
| H | c-Hex | — | H |
| 4-Cl | c-Hex | — | H |
| 4-CH₃ | c-Hex | — | H |
| 4-CH₃ | c-Hex | — | CH₃ |
| 4-CH₃ | c-Hex | — | CH₂Ph |
| 4-CH₃ | c-Hex | — | C(O)Ph |
| 4-CH₃ | c-Hex | — | C(O)OEt |
| 4-t-Bu | c-Hex | — | H |
| 4-n-hex | c-Hex | — | H |
| 4-n-hex | c-Hex | — | CH₃ |
| 4-n-hex | c-Hex | — | CH₂Ph |
| 4-n-hex | c-Hex | — | C(O)Ph |
| 4-n-hex | c-Hex | — | C(O)OEt |
| 4-OCH₃ | c-Hex | — | H |
| 4-Ph | c-Hex | — | H |
| H | c-C₇H₁₅ | — | H |
| H | c-C₈H₁₇ | — | H |
| H | bicyclo[2.2.1]heptan-2-yl | — | H |
| H | 1-adamantyl | — | H |
| H | 2-adamantyl | — | H |
| H | A001 | H | H |
| H | A001 | 3-n-Bu | H |
| H | A002 | H | H |
| H | A002 | 2-Cl | H |
| H | A003 | H | H |
| H | A004 | H | H |
| H | A005 | H | H |
| 4-Cl | A005 | H | H |
| 4-CH₃ | A005 | H | H |
| 4-CH₃ | A005 | H | CH₃ |
| 4-CH₃ | A005 | H | CH₂Ph |
| 4-CH₃ | A005 | H | C(O)Ph |
| 4-CH₃ | A005 | H | C(O)OEt |
| 4-t-Bu | A005 | H | H |
| 4-n-hex | A005 | H | H |
| 4-n-hex | A005 | H | CH₃ |
| 4-n-hex | A005 | H | CH₂Ph |
| 4-n-hex | A005 | H | C(O)Ph |
| 4-n-hex | A005 | H | C(O)OEt |

TABLE 11-continued

| R²¹ | R⁸ | (Z)m | R³ |
|---|---|---|---|
| 4-OCH₃ | A005 | H | H |
| 4-Ph | A005 | H | H |
| H | A005 | 2, 5-(CH₃)₂ | H |
| H | A005 | 2, 5-Cl₂ | H |
| H | A005 | 2-Br | H |
| H | A006 | H | H |
| 4-Cl | A006 | H | H |
| 4-CH₃ | A006 | H | H |
| 4-CH₃ | A006 | H | CH₃ |
| 4-CH₃ | A006 | H | CH₂Ph |
| 4-CH₃ | A006 | H | C(O)Ph |
| 4-CH₃ | A006 | H | C(O)OEt |
| 4-t-Bu | A006 | H | H |
| 4-n-hex | A006 | H | H |
| 4-n-hex | A006 | H | CH₃ |
| 4-n-hex | A006 | H | CH₂Ph |
| 4-n-hex | A006 | H | C(O)Ph |
| 4-n-hex | A006 | H | C(O)OEt |
| 4-OCH₃ | A006 | H | H |
| 4-Ph | A006 | H | H |
| H | A006 | 3-CH₃ | H |
| H | A006 | 5-CH₃ | H |
| H | A006 | 3-Cl | H |
| H | A006 | 5-Et | H |
| H | A006 | 5-Cl | H |
| H | A006 | 5-Br | H |
| H | A006 | 3-Br | H |
| H | A006 | 4-Br | H |
| H | A006 | 5-NO₂ | H |
| H | A007 | H | H |
| H | A007 | 5-CH₃ | H |
| H | A007 | 3-CH₃ | H |
| H | A007 | 5-Br | H |
| H | A007 | 5-NO₂ | H |
| H | A007 | 5-Ph | H |
| H | A008 | 5-CH₃ | H |
| H | A009 | 5-CH₃ | H |
| H | A010 | 3, 5-(CH₂)₂ | H |
| H | A010 | 3, 5-Cl₂ | H |
| H | A011 | 3, 5-(CH₃)₂ | H |
| H | A011 | 3, 5-Cl₂ | H |
| H | A012 | 3-CH₃ | H |
| H | A012 | 3-Me | H |
| H | A012 | 3-Cl | H |
| H | A013 | 3-CH₃ | H |
| H | A013 | 3-Me | H |
| H | A013 | 3-Cl | H |
| H | A014 | H | H |
| 4-Cl | A014 | H | H |
| 4-CH₃ | A014 | H | H |
| 4-CH₃ | A014 | H | CH₃ |
| 4-CH₃ | A014 | H | CH₂Ph |
| 4-CH₃ | A014 | H | C(O)Ph |
| 4-CH₃ | A014 | H | C(O)OEt |
| 4-t-Bu | A014 | H | H |
| 4-n-hex | A014 | H | H |
| 4-OCH₃ | A014 | H | H |
| 4-Ph | A014 | H | H |
| H | A015 | H | H |
| H | A016 | 2, 4-(CH₂)₂ | H |
| 4-Cl | A016 | 2, 4-(CH₃)₂ | H |
| 4-CH₃ | A016 | 2, 4-(CH₃)₂ | H |
| 4-CH₃ | A016 | 2, 4-(CH₃)₂ | CH₃ |
| 4-CH₃ | A016 | 2, 4-(CH₃)₂ | CH₂Ph |
| 4-CH₃ | A016 | 2, 4-(CH₃)₂ | C(O)Ph |
| 4-CH₃ | A016 | 2, 4-(CH₃)₂ | C(O)OEt |
| 4-t-Bu | A016 | 2, 4-(CH₂)₂ | H |
| 4-n-hex | A016 | 2, 4-(CH₃)₂ | H |
| 4-OCH₃ | A016 | 2, 4-(CH₂)₂ | H |
| 4-Ph | A016 | 2, 4-(CH₃)₂ | H |
| H | A017 | H | H |
| H | A018 | 3-CH₃ | H |
| H | A019 | 3-Ph, 5-CH₃ | H |
| H | A019 | 3, 5-(CH₃)₂ | H |
| H | A020 | 5-CH₃ | H |
| H | A021 | 4-CH₃ | H |
| H | A022 | H | H |

TABLE 11-continued

| $R^{21}$ | $R^8$ | $(Z)m$ | $R^3$ |
|---|---|---|---|
| H | A023 | 2, 4-$(CH_3)_2$ | H |
| H | A024 | 2-(4-pyridil) | H |
| H | A025 | H | H |
| H | A026 | H | H |
| H | A026 | 4-$CH_3$ | H |
| H | A027 | H | H |
| H | A027 | 4-$CH_3$ | H |
| H | A028 | H | H |
| H | A029 | H | H |
| H | A030 | H | H |
| H | A031 | H | H |
| H | A032 | H | H |
| H | A033 | H | H |
| H | A034 | H | H |
| H | A034 | 3, 6-$Cl_2$ | H |
| H | A035 | H | H |
| H | A036 | H | H |
| H | A037 | H | H |
| 4-Cl | A037 | H | H |
| 4-$CH_3$ | A037 | H | H |
| 4-$CH_3$ | A037 | H | $CH_3$ |
| 4-$CH_3$ | A037 | H | $CH_2Ph$ |
| 4-$CH_3$ | A037 | H | C(O)Ph |
| 4-$CH_3$ | A037 | H | C(O)OEt |
| 4-t-Bu | A037 | H | H |
| 4-n-hex | A037 | H | H |
| 4-n-hex | A037 | H | $CH_3$ |
| 4-n-hex | A037 | H | $CH_2Ph$ |
| 4-n-hex | A037 | H | C(O)Ph |
| 4-n-hex | A037 | H | C(O)OEt |
| 4-$OCH_3$ | A037 | H | H |
| 4-Ph | A037 | H | H |
| H | A037 | 6-$OCH_3$ | H |
| H | A037 | 6-Br | H |
| H | A038 | H | H |
| 4-Cl | A038 | H | H |
| 4-$CH_3$ | A038 | H | H |
| 4-$CH_3$ | A038 | H | $CH_3$ |
| 4-$CH_3$ | A038 | H | $CH_2Ph$ |
| 4-$CH_3$ | A038 | H | C(O)Ph |
| 4-$CH_3$ | A038 | H | C(O)OEt |
| 4-t-Bu | A038 | H | H |
| 4-n-hex | A038 | H | H |
| 4-n-hex | A038 | H | $CH_3$ |
| 4-n-hex | A038 | H | $CH_2Ph$ |
| 4-n-hex | A038 | H | C(O)Ph |
| 4-n-hex | A038 | H | C(O)OEt |
| 4-$OCH_3$ | A038 | H | H |
| 4-Ph | A038 | H | H |
| H | A038 | 2-$OCH_3$ | H |
| H | A038 | 4-$OCH_3$ | H |
| H | A038 | 4-F | H |
| H | A039 | H | H |
| H | A039 | 3-$CH_3$ | H |
| H | A039 | 7-$OCH_3$ | H |
| H | A040 | H | H |
| H | A041 | H | H |
| 4-Cl | A041 | H | H |
| 4-$CH_3$ | A041 | H | H |
| 4-$CH_3$ | A041 | H | $CH_3$ |
| 4-$CH_3$ | A041 | H | $CH_2Ph$ |
| 4-$CH_3$ | A041 | H | C(O)Ph |
| 4-$CH_3$ | A041 | H | C(O)OEt |
| 4-t-Bu | A041 | H | H |
| 4-n-hex | A041 | H | H |
| 4-$OCH_3$ | A041 | H | H |
| 4-Ph | A041 | H | H |
| H | A041 | 6-$NO_2$ | H |
| H | A041 | 6-Br | H |
| H | A042 | H | H |
| 4-Cl | A042 | H | H |
| 4-$CH_3$ | A042 | H | H |
| 4-$CH_3$ | A042 | H | $CH_3$ |
| 4-$CH_3$ | A042 | H | $CH_2Ph$ |
| 4-$CH_3$ | A042 | H | C(O)Ph |
| 4-$CH_3$ | A042 | H | C(O)OEt |
| 4-t-Bu | A042 | H | H |
| 4-n-hex | A042 | H | H |
| 4-$OCH_3$ | A042 | H | H |
| 4-Ph | A042 | H | H |
| H | A042 | 5-Br | H |
| H | A043 | H | H |
| 4-Cl | A043 | H | H |
| 4-$CH_3$ | A043 | H | H |
| 4-$CH_3$ | A043 | H | $CH_3$ |
| 4-$CH_3$ | A043 | H | $CH_2Ph$ |
| 4-$CH_3$ | A043 | H | C(O)Ph |
| 4-$CH_3$ | A043 | H | C(O)OEt |
| 4-t-Bu | A043 | H | H |
| 4-n-hex | A043 | H | H |
| 4-$OCH_3$ | A043 | H | H |
| 4-Ph | A043 | H | H |
| H | A044 | H | H |
| 4-Cl | A044 | H | H |
| 4-$CH_3$ | A044 | H | H |
| 4-$CH_3$ | A044 | H | $CH_3$ |
| 4-$CH_3$ | A044 | H | $CH_2Ph$ |
| 4-$CH_3$ | A044 | H | C(O)Ph |
| 4-$CH_3$ | A044 | H | C(O)OEt |
| 4-t-Bu | A044 | H | H |
| 4-n-hex | A044 | H | H |
| 4-$OCH_3$ | A044 | H | H |
| 4-Ph | A044 | H | H |
| H | A051 | — | H |
| H | A052 | — | H |
| H | A053 | — | H |
| H | A054 | — | H |
| H | A055 | — | H |
| H | A056 | — | H |
| H | A057 | — | H |
| H | A058 | — | H |
| H | A059 | — | H |
| H | A060 | — | H |
| H | A061 | — | H |
| H | A062 | — | H |
| H | A063 | — | H |
| H | A064 | — | H |
| H | A065 | — | H |
| H | A066 | — | H |
| H | A067 | — | H |
| H | A068 | — | H |
| H | A101 | — | H |
| H | A102 | — | H |
| H | A103 | — | H |
| H | A104 | — | H |
| H | A105 | — | H |
| H | A106 | — | H |
| H | A107 | — | H |

The locants for the substituent $R^{21}$ in the Table correspond to the positions indicated in the following structural formulae, and the expression — indicates unsubstituted.

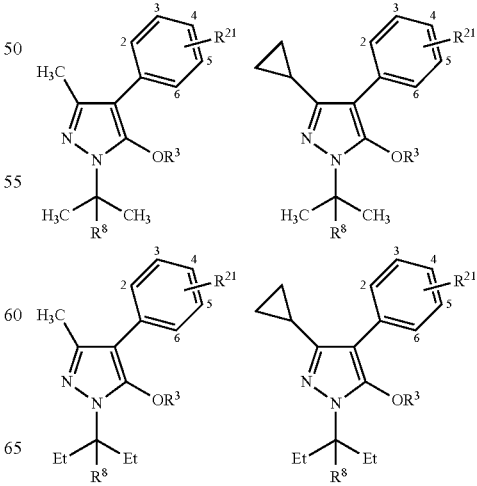

TABLE 11-continued

| R21 | R8 | (Z)m | R3 |
|---|---|---|---|

TABLE 11-continued
| R²¹ | R⁸ | (Z)m | R³ |
|---|---|---|---|
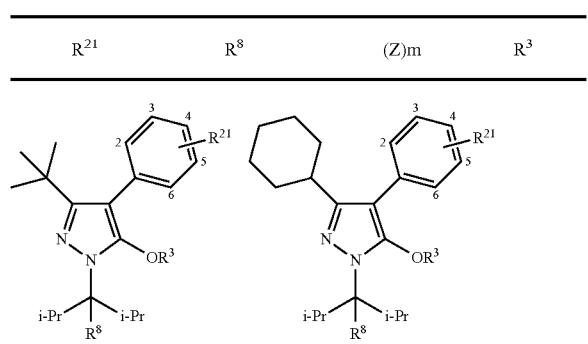
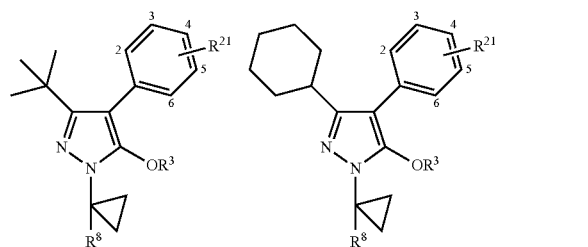
TABLE 12
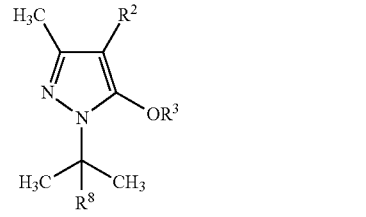
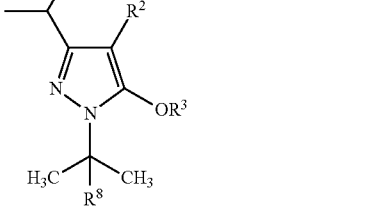
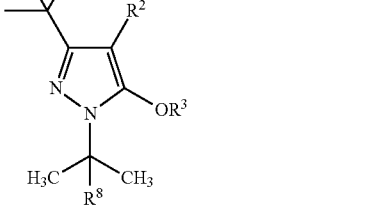
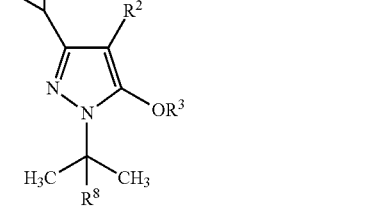
TABLE 12-continued
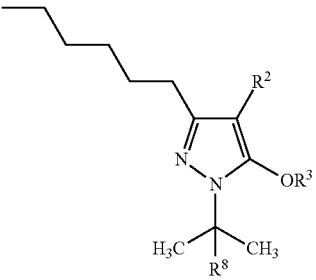
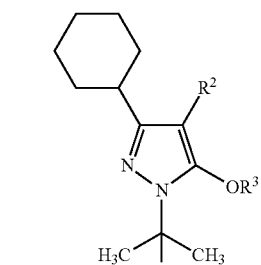
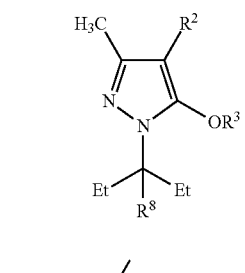
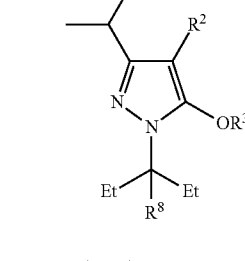
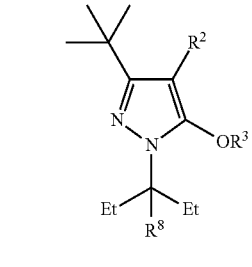
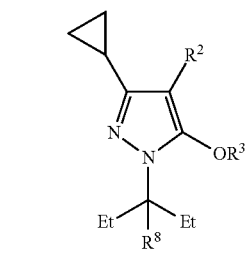

TABLE 12-continued
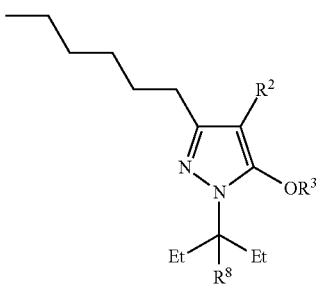
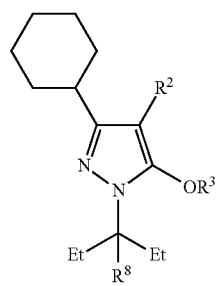
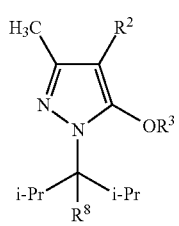
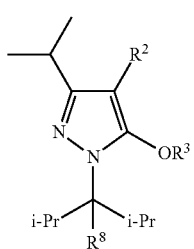
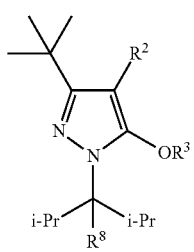
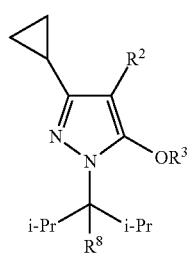
TABLE 12-continued
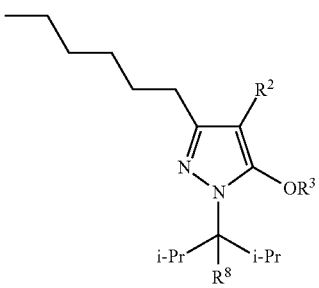
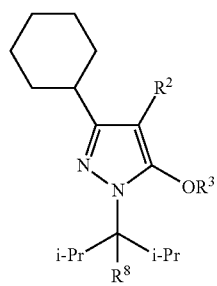
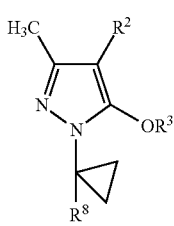
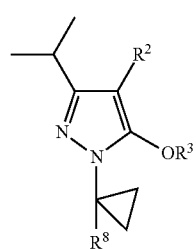
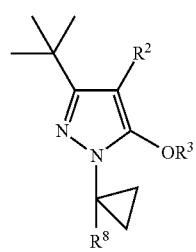
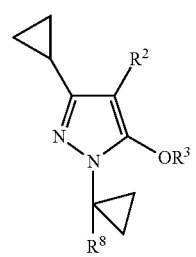

TABLE 12-continued

[Structures: Two pyrazole structures shown — top with pentyl chain at 3-position, R² at 4-position, OR³ at 5-position, and N-substituted cyclopropyl bearing R⁸; bottom with cyclohexyl at 3-position, R² at 4-position, OR³ at 5-position, and N-substituted cyclopropyl bearing R⁸.]

| R² | (Z)m on ring of R² | R⁸ | (Z)m on ring of R⁸ | R³ |
|---|---|---|---|---|
| H | — | c-Pr | — | H |
| CH₃ | — | c-Pr | — | H |
| H | — | c-Bu | — | H |
| CH₃ | — | c-Bu | — | H |
| H | — | c-Pen | — | H |
| CH₃ | — | c-Pen | — | H |
| H | — | c-Hex | — | H |
| CH₃ | — | c-Hex | — | H |
| CH₃ | — | c-Hex | — | CH₃ |
| CH₃ | — | c-Hex | — | CH₂Ph |
| CH₃ | — | c-Hex | — | C(O)Ph |
| CH₃ | — | c-Hex | — | C(O)OEt |
| C(O)CH₃ | — | c-Pr | — | H |
| C(O)CH₃ | — | c-Hex | — | H |
| C(O)CH₃ | — | c-Hex | — | CH₃ |
| C(O)CH₃ | — | c-Hex | — | CH₂Ph |
| C(O)CH₃ | — | c-Hex | — | C(O)Ph |
| C(O)CH₃ | — | c-Hex | — | C(O)OEt |
| C(O)Ph | — | c-Pr | — | H |
| C(O)Ph | — | c-Hex | — | H |
| C(O)Ph | — | c-Hex | — | CH₃ |
| C(O)Ph | — | c-Hex | — | CH₂Ph |
| C(O)Ph | — | c-Hex | — | C(O)Ph |
| C(O)Ph | — | c-Hex | — | C(O)OEt |
| A005 | H | A005 | H | H |
| A005 | H | A006 | H | H |
| A005 | H | A014 | H | H |
| A005 | H | A016 | 2,4-(CH₃)₂ | H |
| A005 | H | A037 | H | H |
| A005 | H | A038 | H | H |
| A005 | H | A041 | H | H |
| A005 | H | A042 | H | H |
| A005 | H | A043 | H | H |
| A005 | H | A044 | H | H |
| A006 | H | A005 | H | H |
| A006 | H | A006 | H | H |
| A006 | H | A006 | H | CH₃ |
| A006 | H | A006 | H | CH₂Ph |
| A006 | H | A006 | H | C(O)Ph |
| A006 | H | A014 | H | H |
| A006 | H | A016 | 2,4-(CH₃)₂ | CH |
| A006 | H | A037 | H | H |
| A006 | H | A037 | H | CH₃ |
| A006 | H | A037 | H | CH₂Ph |
| A006 | H | A037 | H | C(O)Ph |
| A006 | H | A038 | H | H |
| A006 | H | A038 | H | CH₃ |
| A006 | H | A038 | H | CH₂Ph |
| A006 | H | A038 | H | C(O)Ph |
| A006 | H | A041 | H | H |
| A006 | H | A041 | H | CH₃ |
| A006 | H | A041 | H | CH₂Ph |
| A006 | H | A041 | H | C(O)Ph |
| A006 | H | A042 | H | H |
| A006 | H | A042 | H | CH₃ |
| A006 | H | A042 | H | CH₂Ph |
| A006 | H | A042 | H | C(O)Ph |
| A006 | H | A043 | H | H |
| A006 | H | A044 | H | H |
| A014 | H | A005 | H | H |
| A014 | H | A006 | H | H |
| A014 | H | A014 | H | H |
| A014 | H | A016 | 2,4-(CH₃)₂ | H |
| A014 | H | A037 | H | H |
| A014 | H | A038 | H | H |
| A014 | H | A041 | H | H |
| A014 | H | A042 | H | H |
| A014 | H | A043 | H | H |
| A014 | H | A044 | H | H |
| A016 | 2,4-(CH₃)₂ | A005 | H | H |
| A016 | 2,4-(CH₃)₂ | A006 | H | H |
| A016 | 2,4-(CH₃)₂ | A014 | H | H |
| A016 | 2,4-(CH₃)₂ | A016 | 2,4-(CH₃)₂ | H |
| A016 | 2,4-(CH₃)₂ | A037 | H | H |
| A016 | 2,4-(CH₃)₂ | A038 | H | H |
| A016 | 2,4-(CH₃)₂ | A041 | H | H |
| A016 | 2,4-(CH₃)₂ | A042 | H | H |
| A016 | 2,4-(CH₃)₂ | A043 | H | H |
| A016 | 2,4-(CH₃)₂ | A044 | H | H |
| A036 | H | A005 | H | H |
| A036 | H | A006 | H | H |
| A036 | H | A014 | H | H |
| A036 | H | A016 | 2,4-(CH₃)₂ | H |
| A036 | H | A037 | H | H |
| A036 | H | A038 | H | H |
| A036 | H | A041 | H | H |
| A036 | H | A042 | H | H |
| A036 | H | A043 | H | H |
| A036 | H | A044 | H | H |
| A037 | H | A005 | H | H |
| A037 | H | A006 | H | H |
| A037 | H | A006 | H | CH₃ |
| A037 | H | A006 | H | CH₂Ph |
| A037 | H | A006 | H | C(O)Ph |
| A037 | H | A014 | H | H |
| A037 | H | A016 | 2,4-(CH₃)₂ | H |
| A037 | H | A037 | H | H |
| A037 | H | A037 | H | CH₃ |
| A037 | H | A037 | H | CH₂Ph |
| A037 | H | A037 | H | C(O)Ph |
| A037 | H | A038 | H | H |
| A037 | H | A038 | H | CH₃ |
| A037 | H | A038 | H | CH₂Ph |
| A037 | H | A038 | H | C(O)Ph |
| A037 | H | A041 | H | H |
| A037 | H | A041 | H | CH₃ |
| A037 | H | A041 | H | CH₂Ph |
| A037 | H | A041 | H | C(O)Ph |
| A037 | H | A042 | H | H |
| A037 | H | A042 | H | CH₃ |
| A037 | H | A042 | H | CH₂Ph |
| A037 | H | A042 | H | C(O)Ph |
| A037 | H | A043 | H | H |
| A037 | H | A044 | H | H |
| A038 | H | A005 | H | H |
| A038 | H | A006 | H | H |
| A038 | H | A006 | H | CH₃ |
| A038 | H | A006 | H | CH₂Ph |
| A038 | H | A006 | H | C(O)Ph |
| A038 | H | A014 | H | H |
| A038 | H | A016 | 2,4-(CH₃)₂ | H |
| A038 | H | A037 | H | H |
| A038 | H | A037 | H | CH₃ |
| A038 | H | A037 | H | CH₂Ph |
| A038 | H | A037 | H | C(O)Ph |
| A038 | H | A038 | H | H |
| A038 | H | A038 | H | CH₃ |
| A038 | H | A038 | H | CH₂Ph |
| A038 | H | A038 | H | C(O)Ph |

TABLE 12-continued

| | | | | |
|---|---|---|---|---|
| A038 | H | A041 | H | H |
| A038 | H | A041 | H | CH₃ |
| A038 | H | A041 | H | CH₂Ph |
| A038 | H | A041 | H | C(O)Ph |
| A038 | H | A042 | H | H |
| A038 | H | A042 | H | CH₃ |
| A038 | H | A042 | H | CH₂Ph |
| A038 | H | A042 | H | C(O)Ph |
| A038 | H | A043 | H | H |
| A038 | H | A044 | H | H |
| A041 | H | A005 | H | H |
| A041 | H | A006 | H | H |
| A041 | H | A006 | H | CH₃ |
| A041 | H | A006 | H | CH₂Ph |
| A041 | H | A006 | H | C(O)Ph |
| A041 | H | A014 | H | H |
| A041 | H | A016 | 2,4-(CH₃)₂ | H |
| A041 | H | A037 | H | H |
| A041 | H | A037 | H | CH₃ |
| A041 | H | A037 | H | CH₂Ph |
| A041 | H | A037 | H | C(O)Ph |
| A041 | H | A038 | H | H |
| A041 | H | A038 | H | CH₃ |
| A041 | H | A038 | H | CH₂Ph |
| A041 | H | A038 | H | C(O)Ph |
| A041 | H | A041 | H | H |
| A041 | H | A041 | H | CH₃ |
| A041 | H | A041 | H | CH₂Ph |
| A041 | H | A041 | H | C(O)Ph |
| A041 | H | A042 | H | H |
| A041 | H | A042 | H | CH₃ |
| A041 | H | A042 | H | CH₂Ph |
| A041 | H | A042 | H | C(O)Ph |
| A041 | H | A043 | H | H |
| A041 | H | A044 | H | H |
| A042 | H | A005 | H | H |
| A042 | H | A006 | H | H |
| A042 | H | A006 | H | CH₃ |
| A042 | H | A006 | H | CH₂Ph |
| A042 | H | A006 | H | C(O)Ph |
| A042 | H | A014 | H | H |
| A042 | H | A016 | 2,4-(CH₃)₂ | H |
| A042 | H | A037 | H | H |
| A042 | H | A037 | H | CH₃ |
| A042 | H | A037 | H | CH₂Ph |
| A042 | H | A037 | H | C(O)Ph |
| A042 | H | A038 | H | H |
| A042 | H | A038 | H | CH₃ |
| A042 | H | A038 | H | CH₂Ph |
| A042 | H | A038 | H | C(O)Ph |
| A042 | H | A041 | H | H |
| A042 | H | A041 | H | CH₃ |
| A042 | H | A041 | H | CH₂Ph |
| A042 | H | A041 | H | C(O)Ph |
| A042 | H | A042 | H | H |
| A042 | H | A042 | H | CH₃ |
| A042 | H | A042 | H | CH₂Ph |
| A042 | H | A042 | H | C(O)Ph |
| A042 | H | A043 | H | H |
| A042 | H | A044 | H | H |

The expression — indicates unsubstituted.

TABLE 13

The locants for the substituents $R^{11}$, $R^{21}$ and $R^{81}$ in the Table correspond to the positions indicated in the following structural formulae.

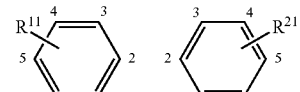

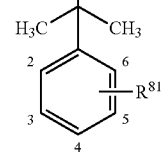

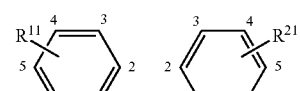

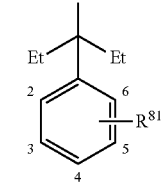

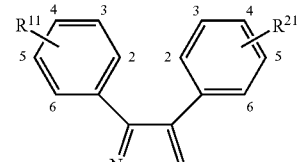

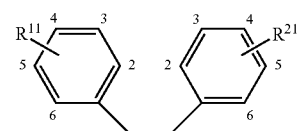

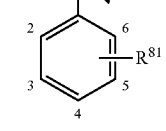

TABLE 13-continued

| R¹¹ | R²¹ | R⁸¹ | R³ |
|---|---|---|---|
| H | H | H | H |
| H | 4-CH₃ | H | H |
| H | 4-t-Bu | H | H |
| H | 4-t-Bu | 4-CH₃ | H |
| H | 4-t-Bu | H | CH₃ |
| H | 4-t-Bu | 4-CH₃ | CH₃ |
| H | 4-n-Hex | H | H |
| H | 4-n-Hex | 4-Cl | H |
| H | 4-n-Hex | 4-Br | H |
| H | 4-n-Hex | 4-CH₃ | H |
| H | 4-n-Hex | H | CH₃ |
| H | 4-n-Hex | 4-CH₃ | CH₃ |
| H | 4-n-Hex | H | CH₂Ph |
| H | 4-n-Hex | H | C(O)OEt |
| H | 4-n-Hex | H | C(O)Ph |
| H | 4-Ph | H | H |
| H | 4-Ph | 4-CH₃ | H |
| H | 4-Ph | H | CH₃ |
| H | 4-Ph | 4-CH₃ | CH₃ |
| 4-F | H | H | H |
| 2-Cl | H | H | H |
| 3-Cl | H | H | H |
| 4-Cl | H | H | H |
| 4-Cl | 4-t-Bu | H | H |
| 4-Cl | 4-t-Bu | 4-CH₃ | H |
| 4-Cl | 4-n-Hex | H | H |
| 4-Cl | 4-n-Hex | 4-Cl | H |
| 4-Cl | 4-n-Hex | 4-Br | H |
| 4-Cl | 4-n-Hex | 4-CH₃ | H |
| 4-Cl | 4-Ph | H | H |
| 4-Cl | 4-Ph | 4-CH₃ | H |
| 4-Br | H | H | H |
| 3,4-Cl₂ | H | H | H |
| 4-NO₂ | H | H | H |
| 4-CN | H | H | H |
| 2-CH₃ | H | H | H |
| 3-CH₃ | H | H | H |
| 4-CH₃ | H | H | H |
| 4-CH₃ | 4-t-Bu | H | H |
| 4-CH₃ | 4-t-Bu | 4-CH₃ | H |
| 4-CH₃ | 4-n-Hex | H | H |
| 4-CH₃ | 4-n-Hex | 4-Cl | H |
| 4-CH₃ | 4-n-Hex | 4-Br | H |
| 4-CH₃ | 4-n-Hex | 4-CH₃ | H |
| 4-CH₃ | 4-Ph | H | H |
| 4-CH₃ | 4-Ph | 4-CH₃ | H |
| 3,4-(CH₃)₂ | H | H | H |
| 4-OCH₃ | H | H | H |
| 4-OCH₃ | 4-t-Bu | H | H |
| 4-OCH₃ | 4-n-Hex | H | H |
| 4-OCH₃ | 4-n-Hex | 4-Cl | H |
| 4-OCH₃ | 4-n-Hex | 4-Br | H |
| 4-OCH₃ | 4-n-Hex | 4-CH₃ | H |
| 4-OCH₃ | 4-Ph | H | H |
| 3,4-(OCH₃) | H | H | H |
| 4-Ph | H | H | H |

TABLE 14

The locants for the substituent R⁸¹ herein correspond to the positions indicated in the following structural formulae, and the expression — indicates unsubstituted.

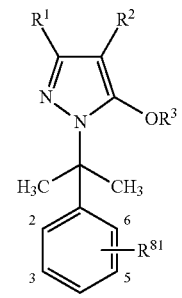

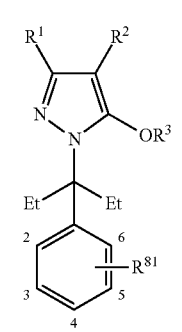

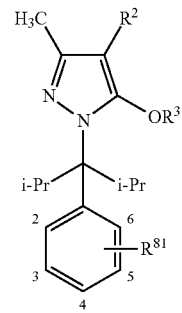

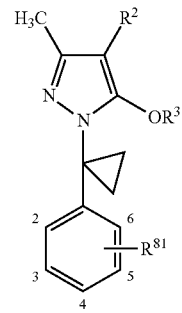

| R¹ | R² | (Z)m | R⁸¹ | R³ |
|---|---|---|---|---|
| H | H | — | H | H |
| Et | H | — | H | H |
| n-Pr | H | — | H | H |
| n-Bu | H | — | H | H |
| c-Bu | H | — | H | H |
| n-Pen | H | — | H | H |
| c-Pen | H | — | H | H |
| CF₃ | H | — | H | H |
| CF₃ | H | — | 4-CH₃ | H |
| CF₃ | H | — | 4-CH₃ | CH₃ |
| CF₃ | A005 | — | H | H |
| CF₃ | A006 | — | H | H |

TABLE 14-continued

| | | | | |
|---|---|---|---|---|
| CF₃ | A014 | — | H | H |
| CF₃ | A016 | 2,4-(CH₃)₂ | H | H |
| CF₃ | A036 | H | H | H |
| CF₃ | A037 | — | H | H |
| CF₃ | A038 | — | H | H |
| CF₃ | A041 | — | H | H |
| CF₃ | A042 | — | H | H |
| CN | H | — | H | H |
| C(O)OEt | H | — | H | H |
| Ph | H | — | H | H |
| (4-CH₃)Ph | H | — | H | H |
| (4-i-Pr)Ph | H | — | H | H |
| (4-OCH₃)Ph | H | — | H | H |
| (4-OCH₃)Ph | H | — | 4-CH₃ | H |

TABLE 15

The locants for the substituents $R^{21}$ and $R^{81}$ in the Table correspond to the positions indicated in the following structural formulae, and the expression — indicates unsubstituted.

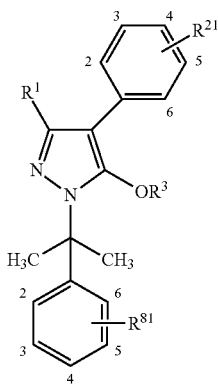

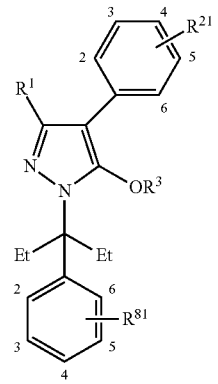

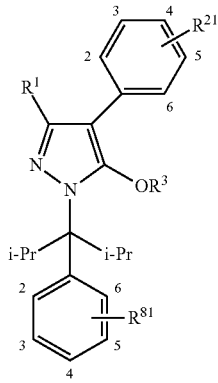

TABLE 15-continued

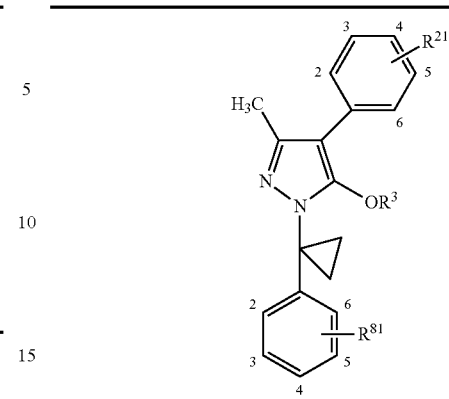

| R¹ | (Z)m | R²¹ | R⁸¹ | R³ |
|---|---|---|---|---|
| H | — | H | H | H |
| Et | — | H | H | H |
| n-Pr | — | H | H | H |
| n-Bu | — | H | H | H |
| CF₃ | — | H | H | H |
| CF₃ | — | 4-CH₃ | H | H |
| CF₃ | — | 4-CH₃ | 4-CH₃ | H |
| CF₃ | — | 4-CH₃ | 4-CH₃ | CH₃ |
| CF₃ | — | 4-t-Bu | H | H |
| CF₃ | — | 4-n-Hex | 4-CH₃ | H |
| CF₃ | — | 4-n-Hex | 4-CH₃ | CH₃ |
| CF₃ | — | 4-Ph | H | H |
| CO₂Et | — | H | H | H |
| A001 | H | H | H | H |
| A002 | H | H | H | H |
| A003 | H | H | H | H |
| A005 | H | H | H | H |
| A005 | 2,5-(CH₃)₂ | H | H | H |
| A005 | 2,5-Cl₂ | H | H | H |
| A005 | 2-Br | H | H | H |
| A006 | H | H | H | H |
| A006 | 3-CH₃ | H | H | H |
| A006 | 5-CH₃ | H | H | H |
| A006 | 3-Cl | H | H | H |
| A006 | 5-Et | H | H | H |
| A006 | 5-Cl | H | H | H |
| A006 | 5-Br | H | H | H |
| A006 | 3-Br | H | H | H |
| A006 | 4-Br | H | H | H |
| A006 | 5-NO₂ | H | H | H |
| A007 | H | H | H | H |
| A007 | 5-CH₃ | H | H | H |
| A007 | 3-CH₃ | H | H | H |
| A007 | 5-Br | H | H | H |
| A007 | 5-NO₂ | H | H | H |
| A007 | 5-Ph | H | H | H |
| A008 | 5-CH₃ | H | H | H |
| A009 | 5-CH₃ | H | H | H |
| A010 | 3,5-(CH₃)₂ | H | H | H |
| A010 | 3,5-Cl₂ | H | H | H |
| A011 | 3,5-(CH₃)₂ | H | H | H |
| A011 | 3,5-Cl₂ | H | H | H |
| A012 | 3-CH₃ | H | H | H |
| A012 | 3-CH₃ | H | H | H |
| A012 | 3-Cl | H | H | H |
| A013 | 3-CH₃ | H | H | H |
| A013 | 3-CH₃ | H | H | H |
| A013 | 3-Cl | H | H | H |
| A014 | H | H | H | H |
| A015 | H | H | H | H |
| A016 | 2,4-(CH₃)₂ | H | H | H |
| A017 | 2,4-(CH₃)₂ | H | H | H |
| A034 | H | H | H | H |
| A034 | 3,6-Cl₂ | H | H | H |
| A035 | H | H | H | H |
| A036 | H | H | H | H |
| A037 | H | H | H | H |
| A037 | 6-OCH₃ | H | H | H |
| A037 | 6-Br | H | H | H |

TABLE 15-continued

| A038 | H | H | H | H |
|------|------|---|---|---|
| A038 | 2-OCH₃ | H | H | H |
| A038 | 4-OCH₃ | H | H | H |
| A038 | 4-F | H | H | H |

EXAMPLES

Now, the present invention will be described in further detail with reference to Synthetic Examples and Assay Examples of the compounds of the present invention. However, it should be understood that the present invention is by no means restricted by these specific Examples.

The compounds obtained in the Synthetic Examples were identified by proton nuclear magnetic resonance ($^1$H NMR) by chemical shifts relative to tetramethylsilane (Me$_4$Si) as the standard.

Synthetic Examples

Synthetic Example 1

Synthesis of 4-(4-hexylphenyl)-3-isopropyl-1-(2-methyl-1-p-tolylpropan-2-yl)-1H-pyrazol-5-ol (Compound No. 3-07 of the Present Invention)

Step 1

Synthesis of Triphenyl(t-butoxycarbonylimino)phosphorane 25 g (0.19 mol) of t-butylcarbazate was dissolved in 80 mL of acetic acid and 160 mL of water, and 15 g (0.22 mol) of sodium nitrite was added in small portions under cooling with ice. The reaction solution was stirred for 30 minutes under cooling with ice and extracted with 250 ml of diisopropyl ether. The organic layer was washed with 200 mL of saturated aqueous sodium hydrogen carbonate twice and with 100 mL of saturated aqueous sodium chloride once successively, dried over anhydrous sodium sulfate and filtered to give a solution of t-butyl carbonazidate in diethyl ether.

To the solution of t-butyl carbonazidate in diethyl ether, 49.6 g (0.189 mol) of triphenylphosphine was added in small portions under cooling with ice, and the reaction solution was stirred at room temperature for 1 hour, and the precipitated solid was collected by filtration, washed with 200 mL of hexane and dried under reduced pressure to give 67 g of the desired product as white crystals.

Step 2

Synthesis of t-Butyl 3-(trichloromethyl)-1,2-oxaziridine-2-carboxylate 20.0 g (53.0 mol) of triphenyl(t-butoxycarbonylimino) phosphorane was suspended in 80 mL of toluene, mixed with 8.84 g (60.0 mmol) of anhydrous chloral and heated at 120° C. for 4 hours under reflux. After cooling to room temperature, 300 mL of hexane was added, and the resulting white solid was separated by filtration. The filtrate was concentrated under reduced pressure. The resulting brown liquid was dissolved in 200 mL of chloroform, and simultaneous addition of 3.74 g (50.0 mmol) of potassium carbonate in 20 mL of ice-cold water and 4.94 g (15 mmol) of OXONE (2KHSO$_5$.KHSO$_4$.K$_2$SO$_4$, supplied from Du Pont) in 40 mL of ice-cold water and 1 hour of stirring under cooling with ice were repeated three times. After removal of the aqueous layer, simultaneous addition of aqueous potassium carbonate and aqueous OXONE (2KHSO$_5$.KHSO$_4$.K$_2$SO$_4$, supplied from Du Pont) and 1 hour of stirring under cooling with ice were repeated three times, similarly. After removal of the aqueous layer, simultaneous addition of aqueous potassium carbonate and aqueous OXONE and 1 hour of stirring under cooling with ice were repeated three times, similarly. After removal of the aqueous layer, 11.2 g (150 mmol) of potassium carbonate in 60 mL of ice-cold water and 14.8 g (45 mmol) of OXONE in 120 mL of ice-cold water were added simultaneously, and the reaction solution was stirred for 1 hour of stirring under cooling with ice. After removal of the aqueous layer, aqueous potassium carbonate and aqueous OXONE were simultaneously added, the reaction solution was stirred for 1 hour of stirring under cooling with ice, similarly. After removal of the aqueous layer, aqueous potassium carbonate and aqueous OXONE were simultaneously added, the reaction solution was stirred for 1 hour of stirring under cooling with ice, similarly. After removal of the aqueous layer, the chloroform layer was dried over anhydrous sodium sulfate and filtered, and the filtrate was concentrated under reduced pressure. The resulting residue was purified by silica gel column chromatography using hexane-ethyl acetate {100:0 (volume ratio, hereinafter the same applies) to 80:20} as the eluent to give 10.3 g of the desired product as a pale yellow oil.

Step 3

Synthesis of 2-chloro-N-(2-methyl-1-p-tolylpropan-2-yl)acetamide 8.21 g, (50 mmol) of 2-methyl-1-p-tolylpropan-2-ol and 12.0 mL of acetic acid were dissolved in 11.3 g (0.15 mol) of chloroacetonitrile, mixed with 12.0 mL (0.15 mol) of sulfuric acid under cooling with ice and stirred at room temperature for 5 hours. The reaction solution was poured into 200 mL of ice-cold water and extracted with diisopropyl ether. The organic layer was washed with saturated aqueous sodium hydrogen carbonate and saturated aqueous sodium chloride successively, dried over anhydrous sodium sulfate and filtered, and the filtrate was concentrated under reduced pressure to give 10.8 g of the desired product as white crystals.

$^1$H NMR (CDCl$_3$, Me$_4$Si, 300 MHz) δ 7.11 (d, J=7.7 Hz, 2H), 7.03 (d, J=8.3 Hz, 2H), 6.24 (br, 1H), 3.94 (s, 2H), 2.98 (s, 2H). 2.33 (s, 3H), 1.37 (s, 6H) zz

Step 4

Synthesis of 2-methyl-1-p-tolylpropan-2-amine 6.24 g (26.0 mmol) of 2-chloro-N-(2-methyl-1-p-tolylpropan-2-yl)acetamide and 1.98 g (26.0 mmol) of thiourea were dissolved in 50 mL of ethanol, and 10.2 mL of acetic acid was added dropwise at room temperature. After 3 hours of stirring at 85° C., the resulting white suspension was allowed to cool and diluted with 300 mL of water. The reaction solution was basified with 20 wt % aqueous sodium hydroxide and extracted with hexane, and the extract was washed with saturated aqueous sodium chloride. The organic layer was concentrated under reduced pressure to give 4.04 g of the desired product as a yellow green liquid.

$^1$H NMR (CDCl$_3$, Me$_4$Si, 300 MHz) δ 7.02-7.13 (m, 4H), 2.61 (s, 2H), 2.33 (s, 3H). 1.18 (br, 2H), 1.16 (s, 6H)

Step 5

Synthesis of t-butyl 2-(2-methyl-1-p-tolylpropan-2-yl)hydrazinecarboxylate 2.40 g (14.7 mmol) of separately prepared 2-methyl-1-p-tolylpropan-2-amine was dissolved in 20 mL of methylene chloride, and 2.60 g (10.0 mmol) of separately prepared t-butyl 3-(trichloromethyl)-1,2-oxaziridine-2-carboxylate in 10 mL of methylene chloride was added under cooling with ice. The reaction solution was stirred under cooling with ice for 30 minutes and at room temperature for 1 hour, and the methylene chloride was removed under reduced pressure. The resulting residue was purified by silica gel column chromatography using hexane-ethyl acetate (100:0 to 0:100) as the eluent to give 1.61 g of the desired product as colorless crystals.

Step 6

Synthesis of 2-(4-hexylphenyl)-1-morpholinoethanethione 5.0 g (25 mmol) of 1-(4-hexylphenyl)ethanone was dissolved in 2.13 g (24.5 mmol) of morpholine and heated with 1.33 g (41.6 mmol) of sulfur at 115° C. for 5 hours under reflux. After completion of the reaction, the reaction solution was cooled to room temperature and mixed with methanol, and the reaction product precipitated as crystals were collected by filtration, washed and dried to give 4.50 g of the desired product as pale yellow crystals.

$^1$H NMR (CDCl$_3$, Me$_4$Si, 300 MHz) δ 7.11~7.26 (m, 4H), 4.3~4.5 (m, 4H), 3.6~3.9 (m, 4H) 3.35~3.48 (m, 2H), 2.55~2.60 (m, 2H), 1.51~1.70 (m, 2H), 1.23~1.42 (m, 6H), 0.82~1.01 (m, 3H)

Step 7

Synthesis of 2-(4-hexylphenyl)acetic acid 12.0 g (39.3 mmol) of 1-(4-hexylphenyl)ethanone was dissolved in 23.6 g (393 mmol) of glacial acetic acid mixed with 4.95 g (275 mmol) of water and 5.79 g (58.9 mmol) of sulfuric acid and heated at 150° C. for 6.5 hours under reflux. After completion of the reaction, the reaction solution was diluted with 400 mL of water and extracted with ethyl acetate. The resulting organic layer was dried over anhydrous magnesium sulfate and filtered, and the filtrate was concentrated under reduced pressure. The resulting residue was purified by silica gel column chromatography using ethyl acetate:hexane (1:20 to 1:4) as the eluent to give 5.74 g of the desired product as white crystals.

$^1$H NMR (CDCl$_3$, Me$_4$Si, 300 MHz) δ 7.08~7.21 (m, 4H), 3.61 (s, 2H), 2.55~2.61 (m, 2H), 1.51~1.67 (m, 2H), 1.20~1.41 (m, 6H), 0.86~0.90 (m, 3H)

Step 8

Synthesis of ethyl 2-(4-hexylphenyl)acetate 5.5 g (25 mmol) of 2-(4-hexylphenyl)acetic acid was dissolved in 11 mL of ethanol and mixed with 1.1 g (11.2 mmol) of sulfuric acid and stirred at 60° C. for 1 hour. The reaction was quenched with cold saturated aqueous sodium carbonate (100 ml), and the reaction solution was extracted with ethyl acetate. The organic layer was dried over anhydrous magnesium sulfate and filtered, and the filtrate was concentrated under reduced pressure to give 5.68 g of the desired product as a pale yellow oil.

$^1$H NMR (CDCl$_3$, Me$_4$Si, 300 MHz) δ 7.06~7.22 (m, 4H), 4.14 (q, J=7.2 Hz, 2H), 3.57 (s, 2H), 2.58 (t, J=7.8 Hz, 2H), 1.50~1.65 (m, 2H), 1.1~1.4 (m, 6H), 1.25 (t, J=7.2 Hz, 3H), 0.82~0.92 (m, 3H)

Step 9

Synthesis of ethyl 2-(4-hexylphenyl)-4-methyl-3-oxopentanoate 6.0 g (24 mmol) of ethyl 2-(4-hexylphenyl)acetate was dissolved in 130 mL of dry tetrahydrofuran under a nitrogen atmosphere and cooled to −60° C. After addition of 31.8 mL (36.2 mmol) of 1.14 M solution of lithiumdiisopropylamine in hexane/tetrahydrofuran, the solution was warmed to 0° C. and stirred for 1 hour. The reaction solution was cooled to −60° C. again and stirred with 3.6 g (34 mmol) of isobutyryl chloride at −60° C. to room temperature for 15 hours. The reaction was quenched with saturated aqueous sodium hydrogen carbonate (150 ml), and the reaction solution was extracted with ethyl acetate. The organic layer was dried over anhydrous magnesium sulfate and filtered, and the filtrate was concentrated under reduced pressure. The resulting residue was purified by silica gel column chromatography using ethyl acetate:hexane (0:100 to 1:9) as the eluent to give 5.39 g of the desired product as a pale yellow oil.

$^1$H NMR (CDCl$_3$, Me$_4$Si, 300 MHz) δ 7.11~7.33 (m, 4H), 4.84 (s, 1H), 4.19 (d, J=7.1 Hz, 2H), 2.67~2.81 (m, 1H), 2.59 (t, J=7.8 Hz, 2H), 1.50~1.71 (m, 2H), 1.22~1.42 (m, 6H), 1.27 (d, J=7.1 Hz, 3H), 1.12 (d, J=6.8 Hz, 3H), 1.01 (d, J=6.8 Hz, 3H), 0.81~0.95 (m, 3H)

Step 10

Synthesis of 4-(4-hexylphenyl)-3-isopropyl-1-(2-methyl-1-p-tolylpropan-2-yl)-1H-pyrazol-5-ol (Compound No. 3-07 of the Present Invention)

200 mg (0.72 mmol) of t-butyl 2-(2-phenylpropan-2-yl)hydrazinecarboxylate was dissolved in 3 mL of methylene chloride and stirred with 251 mg (1.3 mmol) of paratoluenesulfonic acid monohydrate at room temperature for 23 hours. The reaction solution was basified with saturated aqueous sodium hydrogen carbonate (50 ml) and separated, and the organic layer was dried over anhydrous sodium sulfate and filtered. The filtrate was concentrated under reduced pressure. The resulting residue was dissolved in 0.80 mL of toluene and 35 µL of acetic acid and stirred with 226 mg (0.71 mmol) of separately prepared ethyl 2-(4-hexylphenyl)-4-methyl-3-oxopentanoate at 90° C. for 8 hours. The reaction solution was cooled to room temperature, diluted with ethyl acetate, washed with saturated aqueous sodium hydrogen carbonate, dried over anhydrous sodium sulfate and filtered, and the filtrate was concentrated under reduced pressure. The resulting residue was purified by intermediate pressure silica gel column chromatography using hexane-ethyl acetate (1:20 to 1:3) as the eluent to give 130 mg of the desired product as a pale yellow solid.

$^1$H NMR (CDCl$_3$, Me$_4$Si, 300 MHz) δ 7.18~7.42 (m, 4H), 7.00 (s, 4H), 3.21 (s, 2H), 3.16 (sep, J=7.2 Hz, 1H), 2.61 (t, J=7.5 Hz, 2H), 2.29 (s, 3H), 1.62 (s, 6H), 1.54~1.58 (m, 2H), 1.26~1.36 (m, 6H), 1.07 (d, J=7.2 Hz, 6H), 0.87~0.92 (m, 3H)

Synthetic Example 2

Synthesis of 1-(2-methyl-1-phenylpropan-2-yl)-3-phenyl-1H-pyrazol-5(4H)-one (Compound No. 3-16 of the Present Invention)

Step 1

Synthesis of 1-(2-methyl-1-phenylpropan-2-yl)-2-(propan-2-ylidene)hydrazine Acetone azine (1.50 g, 13.4 mmol) was dissolved in 10 mL of diethyl ether mixed with 32 mL (19.2 mmol) of 0.6 M benzylmagnesium bromide in tetrahydrofuran and stirred at 45° C. for 24 hours. The reaction was quenched with saturated aqueous ammonium chloride (100 ml), and the reaction solution was extracted with ethyl acetate. The resulting organic layer was dried over anhydrous magnesium sulfate and filtered, and the filtrate was concentrated under reduced pressure. The resulting residue was purified by silica gel column chromatography using hexane-ethyl acetate (9:1 to 6:1) as the eluent to give 710 mg of the desired product as a pale yellow oil.

$^1$H NMR (CDCl$_3$, Me$_4$Si, 300 MHz) δ 7.03~7.28 (m, 5H), 4.2~4.4 (m, 1H), 2.78 (s, 2H), 1.99 (s, 3H), 1.62 (s, 3H), 1.18 (s, 6H)

Step 2

Synthesis of 1-(2-methyl-1-phenylpropan-2-yl)-3-phenyl-1H-pyrazol-5(4H)-one (Compound No. 3-16 of the Present Invention)

500 mg (2.45 mmol) of 1-(2-methyl-1-phenylpropan-2-yl)-2-(propan-2-ylidene)hydrazine was dissolved in 3.0 mL of glacial acetic acid and mixed with 429 mg (2.23 mmol) of ethyl 3-oxo-3-phenylpropanoate and stirred at 100° C. for 4 hours. The reaction solution was cooled to room temperature, diluted with ethyl acetate, neutralized with saturated aqueous sodium hydrogen carbonate (100 ml) and extracted with ethyl acetate. The resulting organic layer was dried over anhydrous sodium sulfate and filtered, and the filtrate was concentrated under reduced pressure. The resulting residue was purified by silica gel column chromatography using hexane-ethyl acetate (100:1 to 9:1) as the eluent to give 330 mg of the desired product as a pale orange solid.

$^1$H NMR (CDCl$_3$, Me$_4$Si, 300 MHz) δ 7.12~7.62 (m, 10H), 3.59 (s, 2H), 3.19 (s, 2H), 1.59 (s, 6H)

Synthetic Example 3

Synthesis of 3-(2-methyl-1-phenylpropan-2-yl)-1-(2-phenylpropan-2-yl)-1H-pyrazol-5(4H)-one (Compound No. 3-04 of the Present Invention)

Step 1

Synthesis of 2,2-dimethyl-3-phenylpropanoic acid

Hexamethyldisilazane (34 g, 0.21 mol) was dissolved in tetrahydrofuran (280 mL), and 1.67M n-butyllithium in hexane (127 mL, 0.21 mol) was added dropwise at −78° C. The reaction solution was warmed to 0° C. over 1 hour and then cooled to −78° C. again. Benzyl isobutyrate (25 g, 0.14 mol) in tetrahydrofuran (70 mL) was added dropwise, and the reaction solution was stirred at −78° C. for 1 hour. Chlorotrimethylsilane (36 mL, 0.12 mol) was further added dropwise at the same temperature, and the reaction solution was stirred for 1 hour, then warmed to room temperature and stirred for 19 hours. After completion of the reaction, the solvent was partially removed from the reaction solution under reduced pressure, and the resulting white suspension was diluted with hexane (200 mL) and filtered through Celite under a nitrogen atmosphere to remove the white solid from the reaction solution. The filtrate was distilled under reduced pressure, and the resulting pale yellow oil was heated at 100° C. for 2 hours to give a brown oil. The brown oil was mixed with 10 mL of 1 M hydrochloric acid and stirred at 60° C. for 4 hours, neutralized with saturated aqueous sodium hydrogen carbonate and extracted with ethyl acetate (100 mL×2) and chloroform (100 mL×2). The resulting organic layer was concentrated, and the resulting residue was purified by intermediate pressure silica gel column chromatography (silica gel 80 g, ethyl acetate 100%) to give 8.41 g of the desired product as white crystals.

$^1$H NMR (CDCl$_3$, Me$_4$Si, 300 MHz) δ 7.20-7.30 (m, 3H), 7.16 (d, J=7.1 Hz, 2H), 2.89 (s, 2H), 1.21 (s, 6H)

Step 2

Synthesis of 2,2-dimethyl-3-phenylpropanoyl chloride

To 2,2-dimethyl-3-phenylpropanoic acid (4.0 g, 0.023 mol) thionyl chloride (2.97 g, 0.025 mol) was added in small portions at room temperature, and the resulting solution was stirred at 70° C. for 3 hours, then at room temperature for another 15 hours. The reaction solution was fractionally distilled (113-115° C., 5 mmHg) to give 2.89 g of the desired product as a colorless liquid.

$^1$H NMR (CDCl$_3$, Me$_4$Si, 300 MHz) δ 7.20-7.30 (m, 3H), 7.18 (d, J=7.1 Hz, 2H), 2.97 (s, 2H), 1.28 (s, 6H)

Step 3

Synthesis of ethyl 4,4-dimethyl-3-oxo-5-phenylpentanoate

Ethyl 3-oxobutanoate (1.09 g, 8.3 mmol) in methylene chloride (16 mL) was mixed with anhydrous magnesium chloride (158 mg, 1.66 mmol), and the reaction solution was cooled to 0° C. and mixed with pyridine (1.34 mL, 16.6 mmol), stirred for 30 minutes, then mixed with 2,2-dimethyl-3-phenylpropanoyl chloride (1.64 g, 8.3 mmol) and stirred for another 30 minutes at the same temperature. The reaction solution was warmed to room temperature and stirred for 20 hours. The methylene chloride was distilled off under reduced pressure, and the residue was with ethanol (2 mL) and at room temperature for 2 days and with toluene (2 mL) at 60° C. for 5 hours. After completion of the reaction, the reaction solution was washed with saturated aqueous sodium hydrogen carbonate and extracted with ethyl acetate (50 mL×2). The solvent was removed from the resulting organic layer under reduced pressure, and the resulting brown oil was purified by intermediate pressure silica gel column chromatography (silica gel 12 g, ethyl acetate:hexane=1:19 to 1:9) to give 370 mg of the desired product as a light brown oil.

$^1$H NMR (CDCl$_3$, Me$_4$Si, 300 MHz) δ 7.18-7.32 (m, 3H), 7.10 (d, J=7.1 Hz, 2H), 4.18 (q, J=7.1 Hz, 3H), 3.46 (s, 2H), 2.83 (s, 2H), 1.29 (t, J=7.1 Hz, 3H), 1.15 (s, 6H)

Step 4

Synthesis of 3-(2-methyl-1-phenylpropan-2-yl)-1-(2-phenylpropan-2-yl)-1H-pyrazol-5(4H)-one (Compound No. 3-04 of the Present Invention)

tert-Butyl 2-(2-phenylpropan-2-yl)hydrazinecarboxylate (250 mg, 1.00 mmol) was dissolved in methylene chloride (2 mL), mixed with p-toluenesulfonic acid monohydrate (0.40 g, 2.1 mmol) and stirred at room temperature for 16 hours. After the stirring, the reaction solution was washed with saturated aqueous sodium hydrogen carbonate to terminate the reaction and then separated. The organic layer was washed with saturated aqueous sodium chloride, dried over anhydrous sodium sulfate and filtered, and the filtrate was concentrated under reduced pressure. The resulting residue was dissolved in toluene (3.0 mL) and acetic acid (70 µL), and mixed with ethyl 4,4-dimethyl-3-oxo-5-phenylpentanoate (248 mg, 1.00 mmol) and stirred at 90° C. for 3 hours. After completion of the reaction, the reaction solution was cooled to room temperature and mixed with ethyl acetate. The resulting organic layer was washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel 12 g, ethyl acetate:hexane=1:9 to 3:7) to give 42 mg of the desired product as a brown oil.

$^1$H NMR (CDCl$_3$, Me$_4$Si, 300 MHz) δ 7.15-7.34 (m, 8H), 6.98-7.10 (m, 2H), 3.08 (s, 2H), 2.79 (s, 2H)., 1.84 (s, 6H), 1.18 (s, 6H)

Synthetic Example 4

Synthesis of 5-methoxy-3-phenyl-1-(2-phenylpropan-2-yl)-1H-pyrazole (Compound No. 3-13 of the Present Invention) and 5-methoxy-4-methyl-3-phenyl-1-(2-phenylpropan-2-yl)-1H-pyrazole (Compound No. 3-14 of the Present Invention)

3-Phenyl-1-(2-phenylpropan-2-yl)-1H-pyrazol-5-ol (83 mg, 0.30 mmol) was dissolved in N,N-dimethylformamide (3.0 mL), and 55 wt % sodium hydride (suspended in mineral oil) (26 mg, 0.60 mmol) was added at room temperature. After 1 hour of stirring at room temperature, methyl iodide (18 µL, 0.30 mmol) was added dropwise, and the reaction solution was stirred at the same temperature for 18 hours. The reaction was quenched with water, and the reaction solution was extracted with ethyl acetate (10 mL×2). The organic layer was washed with saturated aqueous sodium chloride (10 mL) and dried over anhydrous sodium sulfate and concentrated under reduced pressure. The resulting residue was purified by intermediate pressure silica gel column chromatography (silica gel 12 g, hexane 100%) to give 35 mg of 5-methoxy-3-phenyl-1-(2-phenylpropan-2-yl)-1H-pyrazole as a colorless solid and 10 mg of 5-methoxy-4-methyl-3-phenyl-1-(2-phenylpropan-2-yl)-1H-pyrazole as a colorless oil, respectively.

5-methoxy-3-phenyl-1-(2-phenylpropan-2-yl)-1H-pyrazole $^1$H NMR (CDCl$_3$, Me$_4$Si, 300 MHz) δ 7.83 (d, J=7.4 Hz, 2H), 7.38 (t, J=7.4 Hz, 2H), 7.15-7.33 (m, 4H), 7.08 (d, J=7.1 Hz, 2H), 5.91 (s, 1H), 3.60 (s, 3H), 1.98 (s, 6H)

5-methoxy-4-methyl-3-phenyl-1-(2-phenylpropan-2-yl)-1H-pyrazole $^1$H NMR (CDCl$_3$, Me$_4$Si, 300 MHz) δ 7.73 (d, J=7.4 Hz, 2H), 7.41 (t, J=7.4 Hz, 2H), 7.16-7.36 (m, 4H), 3.16 (s, 3H), 2.10 (s, 3H), 1.98 (s, 6H)

Synthetic Example 5

Synthesis of 1-(1-(4-bromophenyl)-2-methylpropan-2-yl)-3-isopropyl-1H-pyrazol-5(4H)-one (Compound No. 3-12 of the Present Invention)

To 1-(2,2-dimethyl-1,1-diphenylpropyl)-2-(propan-2-ylidene)hydrazine (147 mg, 0.500 mmol) in tetrahydrofuran (5 mL), 1.61 M n-butylithium in hexane (0.37 mL, 0.60 mmol) was added dropwise at −78° C., and after 1 hour of stirring at the same temperature, p-bromobenzyl bromide (125 mg, 0.50 mmol) was added dropwise. The reaction solution was stirred at the same temperature for 1 hour, warmed to room temperature and stirred at room temperature for 18 hours. The reaction solution was quenched with saturated aqueous sodium hydrogen carbonate and extracted with ethyl acetate (10 mL×3). The resulting organic layer was concentrated under reduced pressure, and the resulting residue was dissolved in 2 mL of ethanol, mixed with trifluoroacetic acid (1 mL) and stirred at room temperature for 24 hours. After the stirring, the reaction solution was mixed with concentrated hydrochloric acid (3 mL) and stirred at 80° C. for 5 hours. After the stirring, the reaction solution was neutralized with saturated aqueous sodium hydrogen carbonate and extracted with methylene chloride. The resulting organic layer was washed with saturated aqueous sodium chloride, dried over anhydrous sodium sulfate and filtered, and the filtrate was concentrated under reduced pressure. The resulting residue was dissolved in toluene (3.0 mL) and acetic acid (70 µL), mixed with methyl isobutyrylacetic acid (72 mg, 0.50 mmol) and stirred at 90° C. for 3 hours. The reaction solution was allowed to cool to room temperature, diluted with ethyl acetate and washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel 12 g, ethyl acetate:hexane=1:9 to 3:7) to give 15 mg of the desired product as a brown oil.

$^1$H NMR (CDCl$_3$, Me$_4$Si, 300 MHz) δ 7.35 (d, J=8.6 Hz, 2H), 6.98 (d, J=8.6 Hz, 2H), 3.14 (s, 2H), 3.06 (s, 2H), 2.59 (sep, J=6.8 Hz, 1H), 1.50 (s, 6H), 1.10 (d, J=7.1 Hz, 6H)

Synthetic Example 6

Synthesis of ethyl 5-hydroxy-3-isopropyl-1-(2-phenylpropan-2-yl)-1H-pyrazole-4-carboxylate (Compound No. 4-27 of the Present Invention)

3-Isopropyl-1-(2-phenylpropan-2-yl)-1H-pyrazol-5(4H)-one (1.22 g, 5.00 mmol) and calcium hydroxide (435 mg, 7.50 mmol) were suspended in dioxane (20 mL), heated to 45° C. and stirred for 1 hour. After the stirring, the reaction solution was allowed to cool to room temperature, and after dropwise addition of ethyl chloroformate (597 mg, 5.50 mmol), stirred at 90° C. for 6 hours. After completion of the reaction, the resulting light brown suspension was poured into ice-cold 3 M hydrochloric acid and extracted with chloroform (20 mL×5). The resulting organic layer was washed with 0.06 M hydrochloric acid (50 mL×2), dried over anhydrous sodium sulfate and filtered, and the filtrate was concentrated under reduced pressure. The resulting residue was purified by intermediate pressure silica gel column chromatography (silica gel 40 g, ethyl acetate:hexane=1:19 to 1:9) to give 650 mg of the desired product as a yellow oil.

¹H NMR (CDCl₃, Me₄Si, 300 MHz) δ 9.71 (s, 1H), 7.13-7.33 (m, 3H)., 7.05-7.12 (m, 2H), 4.31 (q, J=7.1 Hz, 2H), 3.23 (sep, J=6.9 Hz, 1H), 1.94 (s, 6H), 1.36 (t, 7.3 Hz, 3H), 1.30 (d, J=6.8 Hz, 6H)

Synthetic Example 7

Synthesis of methyl 2-(5-oxo-1-(2-phenylpropan-2-yl)-4,5-dihydro-1H-pyrazol-3-yl)acetate (Compound No. 4-01 of the Present Invention)

tert-Butyl 2-(2-phenylpropan-2-yl)hydrazinecarboxylate (250 mg, 1.00 mmol) was dissolved in methylene chloride (2 mL), mixed with p-toluenesulfonic acid monohydrate (0.40 g, 2.1 mmol) and stirred at room temperature for 18 hours. The reaction solution was basified with saturated aqueous sodium hydrogen carbonate and separated. The organic layer was washed with saturated aqueous sodium chloride, dried over anhydrous sodium sulfate and filtered, and the filtrate was concentrated under reduced pressure. The resulting residue was dissolved in toluene (2.0 mL) and acetic acid (70 μL), mixed with dimethyl 1,3-acetonedicarboxylate (174 mg, 1.00 mmol) and stirred at 90° C. for 3 hours and at 105° C. for 3 hours. After completion of the reaction, the reaction solution was allowed to cool to room temperature and diluted with ethyl acetate. The organic layer was washed with saturated aqueous sodium hydrogen carbonate and then with saturated aqueous sodium chloride, dried over anhydrous sodium sulfate and filtered, and the filtrate was concentrated under reduced pressure. The resulting residue was purified by intermediate pressure silica gel column chromatography (silica gel 12 g, ethyl acetate:hexane=1:9 to 3:7) to give 96.3 mg of the desired product as a white solid.
¹H NMR (CDCl₃, Me₄Si, 300 MHz) δ 7.18-7.34 (m, 5H), 3.75 (s, 3H), 3.48 (s, 2H), 3.41 (s, 2H), 1.87 (s, 6H)

Synthetic Example 8

Synthesis of 4-bromo-3-isopropyl-1-(2-methyl-1-phenylpropan-2-yl)-1H-pyrazol-5(4H)-one (Compound No. 3-47 of the Present Invention)

3-Isopropyl-1-(2-methyl-1-phenylpropan-2-yl)-1H-pyrazol-5(4H)-one (1.2 g, 4.6 mmol) was dissolved in N,N-dimethylformamide (35 mL), mixed with N,N-bromosuccinimide (908 mg, 5.10 mmol) and stirred at room temperature for 30 minutes. The reaction solution was extracted with ethyl acetate. The organic layer was dried over anhydrous magnesium sulfate and filtered, and the filtrate wa concentrated under reduced pressure. The resulting residue was purified by suspending in hexane to give 1.26 g of the desired product as a pale blue solid.
¹H NMR (CDCl₃, Me₄Si, 300 MHz) δ 7.06-7.29 (m, 5H), 4.64 (s, 1H), 3.12 (d, J=13.4 Hz, 1H), 3.03 (d, J=13.4 Hz, 1H), 2.73-2.88 (m, 1H), 1.53 (s, 3H), 1.52 (s, 3H), 1.16 (d, J=6.9 Hz, 3H), 1.13 (d, J=7.2 Hz, 3H)

Synthetic Example 9

Synthesis of methyl 4-(5-hydroxy-3-isopropyl-1-(2-methyl-1-phenylpropan-2-yl)-1H-pyrazol-4-yl)benzoate (Compound No. 4-23 of the Present Invention)

4-Bromo-3-isopropyl-1-(2-methyl-1-phenylpropan-2-yl)-1H-pyrazol-5-yl benzoate (360 mg, 0.82 mmol) in 1,2-dimethoxyethane (4.8 ml) was mixed with 4-(methoxycarbonyl)phenylboronic acid (164 mg, 0.911 mmol), tetrakis(triphenylphosphine)palladium (80 mg, 0.07 mmol) and 2 M aqueous sodium carbonate (3.6 ml) and stirred at 86° C. for 16 hours under a nitrogen atmosphere. After completion of the reaction, the 1,2-dimethoxyethane was distilled off under reduced pressure, and the reaction solution was extracted with dichloromethane. The organic layer was dried over anhydrous magnesium sulfate and filtered, and the filtrate was purified by intermediate pressure silica gel column chromatography (silica gel 12 g, ethyl acetate:hexane=1:20 to 1:4) to give 100 mg of the desired product as a pale yellow solid mixture of tautomers.
¹H NMR (CDCl₃, Me₄Si, 300 MHz) δ 8.0-8.1 (m, 2H), 7.6-7.7 (m, 2H), 7.15-7.3 (m, 3H), 7.05-7.15 (m, 2H), 6.37 (br, 1H), 3.92 (s, 3H), 3.27 (s, 2H), 3.12-3.19 (m, 1H), 1.65 (s, 6H), 1.08 (d, J=7.2 Hz, 6H)
¹H NMR (CDCl₃, Me₄Si, 300 MHz) δ 8.0-8.1 (m, 2H), 7.6-7.7 (m, 2H), 7.15-7.3 (m, 3H), 7.05-7.15 (m, 2H), 4.2-4.3 (m, 1H), 3.92 (s, 3H), 3.1-3.2 (m, 2H), 2.35-2.5 (m, 1H), 1.65 (s, 6H), 0.95-1.05 (m, 6H)

Synthetic Example 10

Synthesis of (5-hydroxy-3-isopropyl-1-(2-methyl-1-phenylpropan-2-yl)-1H-pyrazol-4-yl)(phenyl)methanone (Compound No. 4-71 of the Present Invention)

Step 1

Synthesis of 4-bromo-3-isopropyl-1-(2-methyl-1-phenylpropan-2-yl)-1H-pyrazol-5-yl benzoate 4-Bromo-3-isopropyl-1-(2-methyl-1-phenylpropan-2-yl)-1H-pyrazol-5(4H)-one (3.00 g, 8.90 mmol) was dissolved in 39 mL of tetrahydrofuran and cooled with ice to 0° C., and after dropwise addition of 1.80 g (17.8 mmol) of triethylamine and 1.38 g (9.82 mmol) of benzoyl chloride, stirred at room temperature for 3 hours under a nitrogen atmosphere. The reaction was quenched with distilled water, and the reaction solution was extracted with ethyl acetate. The organic layer was dried over anhydrous sodium sulfate and filtered, and the filtrate was concentrated under reduced pressure. The resulting residue was purified by silica gel column chromatography (silica gel 12 g, ethyl acetate:hexane=1:20) to give 3.34 g of the desired product as a yellow oil.
¹H NMR (CDCl₃, Me₄Si, 300 MHz) δ 7.98-8.05 (m, 2H), 7.62-7.70 (m, 1H), 7.44-7.56 (m, 2H), 7.18-7.26 (m, 3H), 6.78-6.88 (m, 2H), 3.07 (s, 2H), 2.92-3.06 (m, 1H), 1.56 (s, 6H), 1.29 (d, J=6.9 Hz, 6H)

Step 2

Synthesis of (5-hydroxy-3-isopropyl-1-(2-methyl-1-phenylpropan-2-yl)-1H-pyrazol-4-yl)(phenyl)methanone (Compound No. 4-71 of the Present Invention)

1.60 g (3.63 mmol) of 4-bromo-3-isopropyl-1-(2-methyl-1-phenylpropan-2-yl)-1H-pyrazol-5-ylbenzoate was dissolved in 16 mL of tetrahydrofuran and cooled with a coolant (acetone/dry ice) to −60° C., and after dropwise addition of 2.60 ml (4.24 mmol) of 1.63 M n-butyllithium in n-hexane, stirred at 72° C. for 4 hours under a nitrogen atmosphere. The reaction was quenched with distilled water, and the reaction solution was extracted with ethyl acetate. The organic layer was dried over anhydrous magnesium sulfate and filtered, and the filtrate was concentrated under reduced pressure. The resulting residue was purified by silica gel column chromatography (silica gel 12 g, ethyl acetate:hexane=1:20) to give 520 mg of the desired product as a yellow oil.

$^1$H NMR (CDCl$_3$, Me$_4$Si, 300 MHz) δ 7.15-7.63 (m, 8H), 6.90-6.98 (m, 2H), 3.17 (s, 2H), 2.60-2.74 (m, 1H), 1.64 (s, 6H), 0.96 (d, J=6.9 Hz, 6H)

Synthetic Example 11

4-(4-Hexylphenyl)-5-hydroxy-1-(2-methyl-1-(p-tolyl)propan-2-yl)-1H-pyrazole-3-carbonitrile (Compound No. 4-86 of the Present Invention)

Step 1

Synthesis of ethyl 4-(4-hexylphenyl)-5-(methoxymethoxy)-1-(2-methyl-1-(p-tolyl)propan-2-yl)-1H-pyrazole-3-carboxylate 152 mg (0.329 mol) of ethyl 4-(4-hexylphenyl)-5-hydroxy-1-(2-methyl-1-(p-tolyl)propan-2-yl)-1H-pyrazole-3-carboxylate was dissolved in 1.6 mL of N,N-dimethylformamide, mixed with 26 mg (0.65 mmol) of 60 wt % sodium hydride (suspended in mineral oil) and 0.050 mL (0.66 mmol) of chloromethyl methyl ether under cooling with ice successively and stirred at room temperature for 3 hours. After completion of the reaction, the reaction mixture was diluted with diethyl ether and washed with 1 M hydrochloric acid, with saturated aqueous sodium hydrogen carbonate and with saturated aqueous sodium chloride successively. The organic layer was dried over anhydrous sodium sulfate and filtered, and the filtrate was concentrated under reduced pressure to give the desired product (crude yield 174 mg).

Step 2

Synthesis of 4-(4-hexylphenyl)-5-(methoxymethoxy)-1-(2-methyl-1-(p-tolyl)propan-2-yl)-1H-pyrazole-3-carboxylic acid Ethyl 4-(4-hexylphenyl)-5-(methoxymethoxy)-1-(2-methyl-1-(p-tolyl)propan-2-yl)-1H-pyrazole-3-carboxylate (138 mg) was dissolved in 2 mL of tetrahydrofuran and 0.7 mL of methanol, mixed with 0.27 mL (1.4 mmol) of 5 M aqueous sodium hydroxide and stirred at room temperature for 20 hours. After completion of the reaction, the reaction mixture was diluted with methylene chloride and washed with saturated aqueous ammonium chloride. The organic layer was dried over anhydrous sodium sulfate and filtered, and the filtrate was concentrated under reduced pressure to give the desired product (crude yield 142 mg).

Step 3

Synthesis of 4-(4-hexylphenyl)-5-(methoxymethoxy)-1-(2-methyl-1-(p-tolyl)propan-2-yl)-1H-pyrazole-3-carboxamide 4-(4-Hexylphenyl)-5-(methoxymethoxy)-1-(2-methyl-1-(p-tolyl)propan-2-yl)-1H-pyrazole-3-carboxylic acid (142 mg) was dissolved in 1.4 mL of ethanol and mixed with 125 mg (0.407 mmol) of (4.6-dimethoxy1,3,5-triazin-2-yl)-4-methylmorphlinium chloride with a 90% purity. The reaction solution was stirred at room temperature for 30 minutes and stirred with 0.54 mL (1.1 mmol) of 2 M ammonia in ethanol for 1.5 hours. After completion of the reaction, the solvent was distilled off under reduced pressure, and ethyl acetate was added. The organic layer was washed with saturated aqueous sodium hydrogen carbonate and with saturated aqueous sodium chloride successively, dried over anhydrous sodium sulfate and filtered, and the filtrate was concentrated under reduced pressure to give Compound 5 (crude yield 171 mg) as a white amorphous substance.

Step 4

Synthesis of 4-(4-hexylphenyl)-5-(methoxymethoxy)-1-(2-methyl-1-(p-tolyl)propan-2-yl)-1H-pyrazole-3-carbonitrile 171 mg of 4-(4-hexylphenyl)-5-(methoxymethoxy)-1-(2-methyl-1-(p-tolyl)propan-2-yl)-1H-pyrazole-3-carboxamide was dissolved in 2 mL of methylene chloride and mixed with 0.3 mL (2 mmol) of triethylamine. The reaction solution was cooled to 0° C. in an ice bath, and after dropwise addition of 0.080 mL (0.72 mmol) of trichloroacetyl chloride at room temperature for 1.5 hours. After completion of the reaction, the reaction mixture was mixed with methylene chloride and washed with saturated aqueous sodium hydrogen carbonate and with saturated aqueous sodium chloride successively. The organic layer was dried over anhydrous sodium sulfate and filtered, and the filtrate was concentrated under reduced pressure to give the desired product (crude yield 266 mg).

Step 5

Synthesis of 4-(4-hexylphenyl)-5-hydroxy-1-(2-methyl-1-(p-tolyl)propan-2-yl)-1H-pyrazole-3-carbonitrile (Compound No. 4-86 of the Present Invention)

266 mg of 4-(4-hexylphenyl)-5-(methoxymethoxy)-1-(2-methyl-1-(p-tolyl)propan-2-yl)-1H-pyrazole-3-carbonitrile was dissolved in 4 mL of tetrahydrofuran and 0.8 mL of methanol, mixed with 4 M hydrochloric acid in dioxane (0.70 mL, 2.8 mmol) and stirred at room temperature for 14 hours. After completion of the reaction, the solvent was partly distilled off under reduced pressure, and the crystals precipitated in the reaction mixture were separated by filtration and washed with isopropyl ether. The filtrate was combined with the isopropyl ether washing and concentrated under reduced pressure, and the resulting residue was purified by intermediate pressure silica gel column chromatography (silica gel 10 g, ethyl acetate:hexane=0:100 to 20:80) to give 88.1 mg of the desired product as a white solid.

m.p. 140-142° C.

Synthetic Example 12

1-(5-Hydroxy-3-isopropyl-1-(2-methyl-1-phenylpropan-2-yl)-1H-pyrazol-4-yl)ethanone O-methyl oxime (Compound No. 4-89 of the Present Invention)

150 mg (0.50 mmol) of 1-(5-hydroxy-3-isopropyl-1-(2-methyl-1-phenylpropan-2-yl)-1H-pyrazol-4-yl)ethanone, 209 mg (2.50 mmol) of methoxyamine hydrochloride and 286 mg (3.49 mmol) of sodium acetate were mixed with 1.3 ml of distilled water and 1.3 ml of ethanol and stirred at room temperature for 16 hours. After completion of the reaction, the reaction solution was extracted with ethyl acetate. The organic layer was dried over anhydrous magnesium sulfate and filtered, and the filtrate was concentrated under reduced pressure. The resulting residue was purified by silica gel column chromatography (silica gel 4 g, ethyl acetate:hexane=1:99) to give 70 mg of the desired product as an orange oil.

¹H NMR (CDCl₃, Me₄Si, 300 MHz) δ 7.12-7.22 (m, 3H), 6.84-6.95 (m, 2H), 3.87 (s, 3H), 3.16 (s, 2H), 2.98-3.12 (m, 1H), 2.25 (s, 3H), 1.57 (s, 6H), 1.21 (d, J=6.8 Hz, 6H)

Synthetic Example 13

4-(4-Hexylphenyl)-1-(2-methyl-1-(p-tolyl)propan-2-yl)-1H-pyrazol-5-ol (Compound No. 4-90 of the Present Invention)

Step 1

Synthesis of ethyl 3-(dimethylamino)-2-(4-hexylphenyl)acrylate 0.50 g (2.0 mmol) of ethyl 2-(4-hexylphenyl)acetate was dissolved in 7 mL of N,N-dimethylformamide, mixed with 0.31 mL (2.3 mmol) of N,N-dimethylformamide dimethyl acetal and stirred at 60° C. for 18 hours. After the stirring, the reaction mixture was further mixed with 0.65 mL (4.9 mmol) of N,N-dimethylformamide dimethyl acetal and stirred at 60° C. for 24 hours. After completion of the reaction, the reaction mixture was diluted with diethyl ether and washed with saturated aqueous sodium hydrogen carbonate and with saturated aqueous sodium chloride successively. The organic layer was dried over anhydrous sodium sulfate and filtered, and the filtrate was concentrated under reduced pressure to give the desired product as a brown liquid.

Step 2

Synthesis of 4-(4-hexylphenyl)-1-(2-methyl-1-(p-tolyl)propan-2-yl)-1H-pyrazol-5-ol (Compound No. 4-90 of the Present Invention)

Ethyl 3-(dimethylamino)-2-(4-hexylphenyl)acrylate and 0.50 g (1.8 mmol) of tert-butyl 2-(2-methyl-1-(p-tolyl)propan-2-yl)hydrazinecarboxylate were dissolved in 2 mL of acetic acid and stirred at 90° C. for 24 hours. After the stirring, the reaction mixture was mixed with 0.5 mL of acetic acid and stirred for 48 hours. After completion of the reaction, the reaction mixture was cooled to room temperature, diluted with diethyl ether and washed with distilled water, with saturated aqueous sodium hydrogen carbonate and with saturated aqueous sodium chloride successively. The organic layer was dried over anhydrous sodium sulfate and filtered, and the filtrate was concentrated under reduced pressure. The resulting residue was purified by intermediate pressure silica gel column chromatography (silica gel 30 g, ethyl acetate:hexane=0:100 to 35:65). The resulting solid was washed with isopropyl ether to give 164 mg of the desired product as a white solid.
m.p. 149-151° C.

Synthetic Example 14

Synthesis of tert-butyl 2-(2-methyl-1-(4-(trifluoromethyl)phenyl)propan-2-yl)hydrazinecarboxylate Step 1

Synthesis of 1-(2-azido-2-methylpropyl)-4-(trifluoromethyl)benzene 25 g (0.12 mol) of 4-trifluoromethylphenyl acetate was mixed with 300 mL of ethanol and concentrated sulfuric acid (95%, 5 mL) and stirred at 40° C. for 16 hours. After completion of the reaction, ethanol was distilled off under reduced pressure, and the reaction solution was diluted with ethyl acetate and washed with distilled water, with saturated aqueous sodium hydrogen carbonate and with saturated aqueous sodium chloride successively. The organic layer was dried over anhydrous sodium sulfate and filtered, and the filtrate was concentrated under reduced pressure to give 27.9 g of crude ethyl 2-(4-(trifluoromethyl)phenyl)acetate.

27.9 g of ethyl 2-(4-(trifluoromethyl)phenyl)acetate was dissolved in 150 mL of dry tetrahydrofuran, and 280 mL (0.28 mol) of 0.99 M methylmagnesium bromide in tetrahydrofuran was added dropwise under cooling with ice under a nitrogen atmosphere. The reaction mixture was stirred at room temperature for 2 hours, and after the stirring, the reaction was quenched with distilled water. The organic layer was washed with 1 M hydrochloric acid, with saturated aqueous sodium hydrogen carbonate and with saturated aqueous sodium chloride successively, dried over anhydrous sodium sulfate and filtered, and the filtrate was concentrated under reduced pressure to give 26.3 g of crude 2-methyl-1-(4-(trifluoromethyl)phenyl)propan-2-ol.

26.3 g of 2-methyl-1-(4-(trifluoromethyl)phenyl)propan-2-ol was dissolved in 400 mL of methylene chloride, and 25 mL (0.19 mol) of trimethylsilyl azide and 24 mL (0.19 mol) of boron trifluoride diethyl etherate complex were added dropwise under cooling with ice. The reaction mixture was stirred at room temperature for 20 hours. After completion of the reaction, the reaction mixture was washed with saturated aqueous sodium hydrogen carbonate and with saturated aqueous sodium chloride successively, dried over anhydrous sodium sulfate and filtered, and the filtrate was concentrated under reduced pressure to give 25.4 g of the desired product.

Step 2

Synthesis of 2-methyl-1-(4-(trifluoromethyl)phenyl)propan-2-amine 25.4 g of 1-(2-azido-2-methylpropyl)-4-(trifluoromethyl)benzene was dissolved in 210 mL of ethyl acetate and mixed with 0.84 g of 20 wt % palladium hydroxide carbon. The atmosphere in the reaction vessel was replaced with hydrogen gas, and the reaction solution was stirred at room temperature for 18 hours. After completion of the reaction, the palladium hydroxide carbon was filtered off, and the filtrate was mixed with 3 M hydrochloric acid and separated. The aqueous layer was basified with 5 M sodium hydroxide and extracted with methylene chloride. The organic layer was concentrated under reduced pressure to give 4.27 g of the desired product as a brown liquid.
¹H NMR (CDCl₃, Me₄Si, 300 MHz) δ 7.56 (d, J=8.3 Hz, 2H), 7.31 (d, J=8.1 Hz, 2H), 2.72 (s, 2H), 1.2-1.5 (m, 2H), 1.32 (s, 6H)

Step 3

Synthesis of tert-butyl 2-(2-methyl-1-(4-(trifluoromethyl)phenyl)propan-2-yl)hydrazinecarboxylate 4.2 g of 2-methyl-1-(4-(trifluoromethyl)phenyl)propan-2-amine was dissolved in 30 mL of methylene chloride and mixed with 5.6 g (21 mmol) of separately prepared t-butyl 3-(trichloromethyl)-1,2-oxaziridine-2-carboxylate under cooling with ice. The reaction solution was stirred at room temperature for 30 minutes, washed with 10% aqueous citric acid, with saturated aqueous sodium hydrogen carbonate and with saturated aqueous sodium chloride successively and dried over anhydrous sodium sulfate, and methylene chloride was removed under reduced pressure. The resulting residue was purified by intermediate pressure silica gel column chromatography (silica gel 100 g, ethyl acetate:hexane) to give 1.38 g of the desired product as a white solid.

$^1$H NMR (CDCl$_3$, Me$_4$Si, 300 MHz) δ 7.54 (d, J=8.3 Hz, 2H), 7.30 (d, J=8.2 Hz, 2H), 5.8-6.0 (m, 1H), 2.74 (s, 2H), 1.46 (s, 9H), 1.4-1.5 (m, 1H), 1.03 (s, 6H)

Synthetic Example 15

Synthesis of tert-butyl 2-(1-benzylcyclopropyl)hydrazinecarboxylate

Step 1

Synthesis of 1-benzylcyclopropanamine 4.5 g (38 mmol) of phenylacetonitrile was dissolved in 50 mL of tetrahydrofuran, mixed with 12.4 mL (41.9 mmol) of tetraisopropyl propylorthotitanate and 78 mL (76 mmol) of 0.98M ethylmagnesium bromide in tetrahydrofuran and stirred at room temperature for 1 hour. After the stirring, 9.6 mL (78 mmol) of boron trifluoride ethyl etherate complex was added, and the reaction solution was stirred at room temperature for another 1 hour. After completion of the reaction, 2 M aqueous sodium hydroxide was added, and the reaction solution was extracted with diethyl ether. After addition of 3 M hydrochloric acid, the organic layer was separated. The resulting aqueous layer was basified with 5 M aqueous sodium hydroxide and extracted with methylene chloride.

The solvent was removed from the organic layer under reduced pressure to give 3.28 g of the desired product.

$^1$H NMR (CDCl$_3$, Me$_4$Si, 300 MHz) δ 7.2-7.4 (m, 5H), 2.75 (s, 2H), 1.4-1.6 (m, 2H), 0.6-0.7 (m, 4H)

Step 2

Synthesis of tert-butyl 2-(1-benzylcyclopropyl)hydrazinecarboxylate 10.6 g (72.0 mmol) of 1-benzylcyclopropanamine was dissolved in 90 mL of methylene chloride, mixed with 14.3 g (54.5 mmol) of separately prepared-butyl 3-(trichloromethyl)-1,2-oxaziridine-2-carboxylate under cooling with ice, and stirred at room temperature for 30 minutes. After completion of the reaction, methylene chloride was distilled off under reduced pressure, and the resulting residue was purified by silica gel column chromatography (silica gel 350 g, ethyl acetate:hexane=1:20) to give 4.6 g of the desired product as a brown solid.

$^1$H NMR (CDCl$_3$, Me$_4$Si, 300 MHz) δ 7.2-7.4 (m, 5H), 5.8-6.0 (m, 1H), 3.9-4.2 (m, 1H), 2.87 (s, 2H), 1.45 (s, 9H), 0.75-0.85 (m, 2H), 0.5-0.55 (m, 2H)

Synthetic Example 16

Synthesis of tert-butyl 2-(3-benzylpentan-3-yl)hydrazinecarboxylate

Step 1

Synthesis of 3-benzylpentan-3-amine 3.0 g (26 mmol) of phenylacetonitrile was dissolved in 50 mL of tetrahydrofuran and mixed with 8.3 mL (28 mmol) fo titanium isopropoxide, and 115 mL (104 mmol) of 0.90 Methylmagnesium bromide in tetrahydrofuran was added dropwise under a nitrogen atmosphere. After 1 hour of stirring, the reaction was quenched by adding water dropwise under cooling with ice. The reaction mixture was diluted with ethyl acetate and separated. After addition of 1 M hydrochloric acid, the organic layer was separated. The aqueous layer was basified with 5 M aqueous sodium hydroxide and extracted with methylene chloride. The methylene chloride layer was concentrated under reduced pressure to give the desired product (crude yield 2.68 g).

$^1$H NMR (CDCl$_3$, Me$_4$Si, 300 MHz) δ 7.1-7.5 (m, 5H), 2.64 (s, 2H), 1.2-1.5 (m, 6H), 0.91 (t, J=7.5 Hz, 6H)

Step 2

Synthesis of tert-butyl 2-(3-benzylpentan-3-yl)hydrazinecarboxylate 2.68 g of 3-benzylpentan-3-amine was dissolved in 20 mL of methylene chloride, mixed with 4.8 g (18 mmol) of separately prepared t-butyl 3-(trichloromethyl)-1,2-oxaziridine-2-carboxylate under cooling with ice, and stirred at room temperature for 30 minutes, and the reaction solution was washed with 10% aqueous citric acid, with saturated aqueous sodium hydrogen carbonate and with saturated aqueous sodium chloride successively and dried over anhydrous sodium sulfate, and methylene chloride was removed under reduced pressure. The resulting residue was purified by intermediate pressure silica gel column chromatography (silica gel 30 g, ethyl acetate:hexane=0:100 to 20:80) to give 1.62 g of the desired product as a light brown solid.

$^1$H NMR (CDCl$_3$, Me$_4$Si, 300 MHz) δ 7.1-7.4 (m, 5H), 5.5-5.7 (br, 1H), 3.6-3.8 (Br, 1H), 2.66 (s, 2H), 1.55 (s, 9H), 1.3-1.5 (m, 4H), 0.93 (t, J=7.5 Hz, 6H)

Synthetic Example 17

Synthesis of ethyl 2-(furan-2-yl)-4-methyl-3-oxopentanoate

Step 1

Synthesis of 2-(furan-2-yl)acetic acid 25 g (0.25 mmol) of furfuryl alcohol was dissolved in 250 mL of tetrahydrofuran, mixed with 8.7 mL of phosphorus tribromide under cooling with ice and stirred at the same temperature for 90 minutes. After completion of the reaction, the reaction solution was diluted with diethyl ether and washed with distilled water, and the organic layer was washed with saturated aqueous sodium hydrogen carbonate and with saturated aqueous sodium chloride successively, dried over anhydrous magnesium sulfate and filtered. The filtrate was concentrated under reduced pressure to give crude 2-(bromomethyl)furan.

2-(Bromomethyl)furan was dissolved in 125 mL of N,N-dimethylformaide, mixed with 13.7 g (0.280 mmol) of sodium cyanide and stirred at room temperature for 11 hours. After the stirring, the reaction solution was mixed with 100 mL of N,N-dimethylformamide and 13.7 g (0.280 mmol) of sodium cyanide and stirred for another 8 hours. After completion of the reaction, the reaction solution was diluted with diethyl ether and washed with distilled water. The organic layer was washed with saturated aqueous sodium hydrogen carbonate and with saturated aqueous sodium chloride, dried over anhydrous sodium sulfate and filtered, and the filtrate was concentrated under reduced pressure to give crude 2-(furan-2-yl)acetonitrile.

2-(Furan-2-yl)acetonitrile was suspended in 300 mL of distilled water, mixed with 50 g (0.89 mmol) of potassium hydroxide and heated for 4 hours under reflux. After completion of the reaction, the reaction solution was diluted with diethyl ether and separated. The resulting aqueous layer was acidified with concentrated hydrochloric acid and extracted with ethyl acetate. The organic layer was washed with saturated aqueous sodium chloride, dried over anhydrous magnesium sulfate and filtered, and the filtrate was concentrated under reduced pressure to give 25.2 g of the desired product.

Step 2

Synthesis of ethyl 2-(furan-2-yl)acetate 24.8 g of 2-(furan-2-yl)acetic acid was dissolved in 590 mL of N,N-dimethylformamide and mixed with 32.6 g (0.236 mol) of potassium carbonate and 6.42 g (19.7 mmol) cesium carbonate successively. The reaction mixture was further mixed with 19 mL (0.24 mol) of iodoethane under cooling with ice and stirred at room temperature for 14 hours. After completion of the reaction, the reaction mixture was diluted with distilled water and extracted with ethyl acetate. The organic layer was washed with saturated aqueous sodium chloride, dried over anhydrous sodium sulfate and filtered, and the filtrate was concentrated under reduced pressure to give 17.0 g of the desired product as a brown liquid.

Step 3

Synthesis of ethyl 2-(furan-2-yl)-4-methyl-3-oxopentanoate

To 60 mL of tetrahydrofuran and 9.3 mL (66 mmol) of diisopropylamine, 38 mL (60 mmol) of 1.57 M n-butyllithium in n-hexane was added dropwise under a nitrogen atmosphere under cooling with ice, and the reaction mixture was warmed to room temperature and stirred for 30 minutes. After the stirring, the reaction mixture was cooled to −78° C., and after dropwise addition of 4.62 g (30.0 mmol) of ethyl 2-(furan-2-yl)acetate, stirred at the same temperature for 1 hour. After the stirring, 3.8 mL (36 mmol) of isobutyryl chloride was added at −78° C., and the reaction mixture was gradually warmed and then stirred at room temperature for 15 hours. After completion of the reaction, the reaction mixture was diluted with saturated aqueous ammonium chloride under cooling with ice and extracted with ethyl acetate. The organic layer was washed with saturated aqueous sodium hydrogen carbonate and with saturated aqueous sodium chloride successively, dried over anhydrous magnesium sulfate and filtered, and the filtrate was concentrated under reduced pressure. The resulting residue was purified by intermediate pressure silica gel column chromatography (silica gel 30 g, ethyl acetate:hexane=1:10) to give 22 g of the desired product as an orange liquid.

$^1$H NMR (CDCl$_3$, Me$_4$Si, 300 MHz) δ 13.5 (s, 1H), 7.4-7.5 (m, 1H), 6.35-6.45 (m, 1H), 6.1-6.2 (m, 1H), 4.19 (q, J=7.1 Hz, 2H), 2.4-2.6 (m, 1H), 1.22 (t, J=7.1 Hz, 3H), 1.11 (d, J=6.9 Hz, 6H)

Synthetic Example 18

Synthesis of O-hexylhydroxylamine

Step 1

Synthesis of 2-(hexyloxy)isoindoline-1,3-dione 3.0 g (18 mmol) of N-hydroxysuccinimide was dissolved in 30 mL of N,N-dimethylformamide, mixed with 0.81 g (20 mmol) of 60 wt % sodium hydride (dispersed in mineral oil) under cooling with ice and stirred at room temperature for 30 minutes. After the stirring, 2.8 mL (20 mmol) of bromohexane and 35 mg (0.23 mmol) of sodium iodide were added dropwise successively under cooling with ice, and the reaction mixture was stirred at 70° C. for 20 hours. After completion of the reaction, the reaction mixture was poured into ice-cold water, and the solid precipitated in the reaction mixture was collected by filtration and dried to give 5.82 g of the desired product as a white solid.

Step 2

Synthesis of O-hexylhydroxylamine 5.82 g of 2-(hexyloxy)isoindoline-1,3-dione was dissolved in 95 mL of methanol, mixed with 3.0 mL (62 mmol) of hydrazine monohydrate and stirred at 65° C. for 30 minutes. After completion of the reaction, the solid precipitated in the reaction mixture was collected by filtration and washed with methylene chloride. The filtrate was combined with the methylene chloride washings and concentrated under reduced pressure and distilled by simple distillation (column top 110° C.) to give a mixture of the desired product and hydrazine. The mixture was diluted with diethyl ether, washed with distilled water, dried over anhydrous sodium sulfate and filtered, and the filtrate was concentrated under reduced pressure to give 0.76 g of the desired product as a colorless liquid.

$^1$H NMR (CDCl$_3$, Me$_4$Si, 300 MHz) δ 5.84 (s, 2H), 3.49 (t, J=6.6 Hz, 3H), 1.4-1.6 (m, 2H), 1.2-1.4 (m, 6H), 0.86 (t, J=6.6 Hz, 3H)

The compounds of the present invention other than those mentioned above can be obtained in accordance with the previously mentioned processes and the Examples. Compounds obtained in the same manners as in Synthetic Examples 1 and 2 are listed in Tables 16 to 20 together with those obtained in the Examples. However, the present invention is not restricted thereto.

In the Tables, Et denotes ethyl group, and similarly, n-Pr and Pr-n denote normal propyl group, i-Pr and Pr-I denote isopropyl group, c-Pr and Pr-c denote cyclopropyl group, n-Bu and Bu-n denote normal butyl group, s-Bu and Bu-s denote secondary butyl group, i-Bu and Bu-I denote isobutyl group, t-Bu and Bu-t denote t-butyl group, c-Bu and Bu-c denote cyclobutyl group, n-Pen and Pen-n denote normal pentyl group, c-Pen and Pen-c denote cyclopentyl group, n-Hex and Hex-n denote normal hexyl group, c-Hex and Hex-c denote cyclohexyl group, and Ph denotes phenyl group.

In Table 16, Table 17, Table 18, Table 19 and Table 20, "No." means the numbers by which compounds of the present invention are designated.

TABLE 16

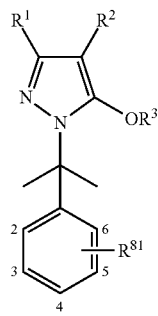

| No. | R¹ | R² | R³ | R⁸¹ |
|---|---|---|---|---|
| 1-01 | CH₃ | H | H | H |
| 1-02 | CH₃ | CH₃ | H | H |
| 1-03 | CH₃ | n-Hex | H | H |
| 1-04 | CH₃ | PhCH₂ | H | H |
| 1-06 | Ph | Ph | H | H |
| 1-07 | n-Pr | Ph | H | H |
| 1-11 | CH₃ | Ph | H | H |
| 3-01 | 4-(OCH₃)Ph | H | H | H |
| 3-02 | i-Pr | H | H | H |
| 3-03 | Ph | H | H | H |
| 3-04 | 1,1-(CH₃)₂-2-Ph—Et | H | H | H |
| 3-08 | i-Pr | (4-n-Hex)Ph | H | H |
| 3-13 | Ph | H | CH₃ | H |
| 3-14 | Ph | CH₃ | CH₃ | H |
| 3-27 | c-Pr | (4-n-Hex)Ph | H | H |
| 3-28 | i-Pr | (4-n-Hex)Ph | H | 4-Cl |
| 3-29 | c-Pr | (4-n-Hex)Ph | H | 4-Cl |
| 3-30 | (4-Ph)Ph | (4-n-Hex)Ph | H | 4-Cl |
| 3-31 | (4-Ph)Ph | n-Hex | H | 4-Cl |
| 3-32 | (4-t-Bu)Ph | (4-n-Hex)Ph | H | 4-Cl |
| 4-01 | CH₂C(O)OCH₃ | H | H | H |
| 4-12 | i-Pr | n-Pr | H | H |
| 4-13 | (4-Ph)Ph | (4-n-Hex)Ph | H | H |
| 4-14 | (4-Ph)Ph | n-Hex | H | H |
| 4-15 | (4-t-Bu)Ph | (4-n-Hex)Ph | H | H |
| 4-16 | (4-t-Bu)Ph | n-Hex | H | H |
| 4-17 | (4-t-Bu)Ph | n-Hex | H | 4-Cl |
| 4-27 | i-Pr | C(O)OEt | H | H |

TABLE 17

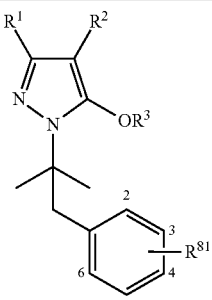

| No. | R¹ | R² | R³ | R⁸¹ |
|---|---|---|---|---|
| 1-12 | CH₃ | Ph | H | H |
| 2-01 | CH₃ | H | H | H |
| 2-02 | CH₃ | CH₃ | H | H |
| 2-03 | CH₃ | n-Hex | H | H |
| 2-04 | CH₃ | PhCH₂ | H | H |
| 2-05 | CF₃ | Ph | H | H |
| 2-06 | Ph | Ph | H | H |
| 2-07 | n-Pr | Ph | H | H |
| 2-09 | i-Pr | Ph | H | H |
| 2-10 | c-Pr | Ph | H | H |
| 2-12 | n-Bu | Ph | H | H |

TABLE 17-continued

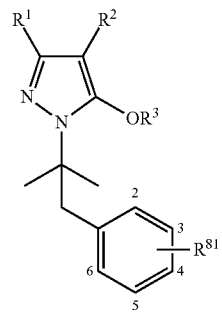

| No. | R¹ | R² | R³ | R⁸¹ |
|---|---|---|---|---|
| 2-14 | (4-CH₃)Ph | Ph | H | H |
| 2-15 | (4-Cl)Ph | Ph | H | H |
| 2-16 | (3,4-(OCH₃)₂)Ph | Ph | H | H |
| 2-18 | pyridin-2-yl | Ph | H | H |
| 2-19 | CH₃ | (4-CH₃)Ph | H | H |
| 2-20 | CH₃ | (2-CH₃)Ph | H | H |
| 2-21 | CH₃ | {3,4-(CH₃)₂}Ph | H | H |
| 2-22 | CH₃ | (4-Ph)Ph | H | H |
| 2-23 | CH₃ | (4-t-Bu)Ph | H | H |
| 2-24 | CH₃ | naphthalen-1-yl | H | H |
| 2-25 | CH₃ | (4-n-Hex)Ph | H | H |
| 2-28 | CH₃ | (4-OCH₃)Ph | H | H |
| 2-29 | CH₃ | benzo[d][1,3]dioxol-5-yl | H | H |
| 2-30 | CH₃ | {4-O(CH₂)₂OEt}Ph | H | H |
| 2-31 | CH₃ | (4-Cl)Ph | H | H |
| 2-32 | CH₃ | (3,4-Cl₂)Ph | H | H |
| 2-33 | CH₃ | thiophen-2-yl | H | H |
| 2-34 | i-Pr | (4-CH₃)Ph | H | H |
| 2-35 | i-Pr | (2-CH₃)Ph | H | H |
| 2-36 | i-Pr | {3,4-(CH₃)₂}Ph | H | H |
| 2-37 | i-Pr | (4-Ph)Ph | H | H |
| 2-38 | i-Pr | (4-t-Bu)Ph | H | H |
| 2-39 | i-Pr | naphthalen-1-yl | H | H |
| 2-40 | i-Pr | (4-n-Hex)Ph | H | H |
| 2-43 | i-Pr | (4-OCH₃)Ph | H | H |
| 2-44 | i-Pr | benzo[d][1,3]dioxol-5-yl | H | H |
| 2-45 | i-Pr | {4-O(CH₂)₂OEt}Ph | H | H |
| 2-46 | i-Pr | (4-Cl)Ph | H | H |
| 2-47 | i-Pr | (3,4-Cl₂)Ph | H | H |
| 2-48 | i-Pr | thiophen-2-yl | H | H |
| 2-49 | CH₃ | (4-CF₃)Ph | H | H |
| 2-50 | i-Pr | (4-CF₃)Ph | H | H |
| 3-05 | i-Pr | H | H | 4-CH₃ |
| 3-06 | (4-OCH₃)Ph | H | H | 4-CH₃ |
| 3-07 | i-Pr | (4-n-Hex)Ph | H | 4-CH₃ |
| 3-09 | CF₃ | H | H | 4-CH₃ |
| 3-10 | 1,1-(CH₃)₂-2-Ph—Et | H | H | 4-CH₃ |
| 3-11 | Ph | H | H | 4-CH₃ |
| 3-12 | i-Pr | H | H | 4-Br |
| 3-16 | Ph | H | H | H |
| 3-17 | i-Pr | H | H | H |
| 3-18 | i-Pr | (4-n-Hex)Ph | H | 2-CH₃ |
| 3-19 | i-Pr | H | H | 3-CH₃ |
| 3-20 | i-Pr | (4-n-Hex)Ph | H | 3-CH₃ |
| 3-21 | i-Pr | (4-n-Hex)Ph | PhC(O) | 3-CH₃ |
| 3-22 | i-Pr | H | H | 4-t-Bu |
| 3-23 | i-Pr | (4-n-Hex)Ph | PhC(O) | 4-t-Bu |
| 3-33 | i-Pr | (4-n-Hex)Ph | H | 4-Cl |
| 3-34 | c-Pr | (4-n-Hex)Ph | H | 4-Cl |
| 3-35 | (4-Ph)Ph | n-Pr | H | 4-Cl |
| 3-36 | (4-Ph)Ph | (4-n-Hex)Ph | H | 4-Cl |
| 3-37 | (4-t-Bu)Ph | (4-n-Hex)Ph | H | 4-Cl |
| 3-38 | i-Pr | (4-n-Hex)Ph | H | 4-OCH₃ |
| 3-39 | c-Pr | (4-n-Hex)Ph | H | 4-OCH₃ |
| 3-40 | (4-Ph)Ph | (4-n-Hex)Ph | H | 4-OCH₃ |
| 3-41 | (4-t-Bu)Ph | (4-n-Hex)Ph | H | 4-OCH₃ |
| 3-43 | i-Pr | H | PhC(O) | 4-t-Bu |
| 3-44 | i-Pr | n-Pr | H | H |
| 3-45 | (4-t-Bu)Ph | n-Hex | H | H |
| 3-46 | i-Pr | Br | H | 3-CH₃ |
| 3-47 | i-Pr | Br | H | H |

TABLE 17-continued

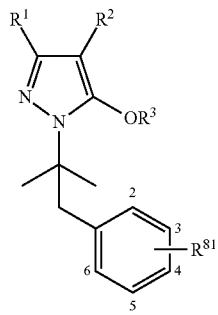

| No. | R¹ | R² | R³ | R⁸¹ |
|---|---|---|---|---|
| 3-48 | i-Pr | (4-n-Hex)Ph | H | 4-n-Hex |
| 3-49 | i-Pr | H | PhC(O) | H |
| 4-03 | i-Pr | (4-n-Hex)Ph | CH₃ | 4-n-Hex |
| 4-18 | (4-Ph)Ph | n-Hex | H | 4-Cl |
| 4-19 | (4-t-Bu)Ph | n-Hex | H | 4-Cl |
| 4-20 | (4-Ph)Ph | n-Hex | H | 4-OCH₃ |
| 4-21 | (4-t-Bu)Ph | n-Hex | H | 4-OCH₃ |
| 4-22 | i-Pr | n-Pr | H | 4-OCH₃ |
| 4-23 | i-Pr | (4-C(O)OMe)Ph | CH₃ | H |
| 4-56 | i-Pr | (4-n-C₈H₁₇)Ph | H | 4-CH₃ |
| 4-57 | i-Pr | (4-c-Hex)Ph | H | 4-CH₃ |
| 4-58 | i-Pr | furan-2-yl | H | 4-CH₃ |
| 4-59 | n-Hex | (4-n-Hex)Ph | H | 4-CH₃ |
| 4-60 | c-Hex | (4-n-Hex)Ph | H | 4-CH₃ |
| 4-61 | furan-2-yl | (4-n-Hex)Ph | H | 4-CH₃ |
| 4-62 | i-Pr | (4-n-Hex)Ph | H | C(O)OEt |
| 4-71 | i-Pr | C(O)Ph | H | H |
| 4-72 | (2,4-F₂)Ph | (4-n-Hex)Ph | H | 4-CH₃ |
| 4-73 | C(O)OEt | (4-n-Hex)Ph | H | 4-CH₃ |
| 4-74 | i-Pr | (4-n-Hex)Ph | H | 4-CF₃ |
| 4-75 | (2,4-F₂)Ph | (4-n-Hex)Ph | H | 4-CF₃ |
| 4-76 | C(O)OEt | (4-n-Hex)Ph | H | 4-CF₃ |
| 4-83 | i-Pr | (4-n-Hex)Ph | H | 2,4-F₂ |
| 4-84 | (2,4-F₂)Ph | (4-n-Hex)Ph | H | 2,4-F₂ |
| 4-85 | C(O)OEt | (4-n-Hex)Ph | H | 2,4-F₂ |
| 4-86 | CN | (4-n-Hex)Ph | H | 4-CH₃ |
| 4-88 | i-Pr | C(O)CH₃ | H | H |
| 4-89 | i-Pr | C(NOCH₃)CH₃ | H | H |
| 4-90 | H | (4-n-Hex)Ph | H | 4-CH₃ |
| 4-91 | i-Pr | C(NO-n-Hex)CH₃ | H | H |

TABLE 18

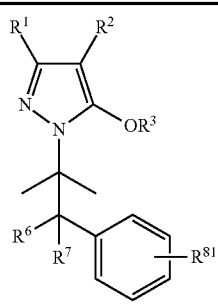

| No. | R¹ | R² | R³ | R⁶ | R⁷ | R⁸¹ |
|---|---|---|---|---|---|---|
| 3-24 | i-Pr | H | H | CH₃ | H | H |
| 3-25 | i-Pr | (4-n-Hex)Ph | H | CH₃ | H | H |

TABLE 19

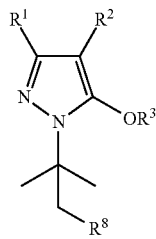

| No. | R¹ | R² | R³ | R⁸ |
|---|---|---|---|---|
| 4-28 | i-Pr | (4-n-Hex)Ph | H | naphthalen-1-yl |
| 4-29 | i-Pr | (4-n-C₈H₁₇)Ph | H | naphthalen-1-yl |
| 4-30 | i-Pr | (4-c-Hex)Ph | H | naphthalen-1-yl |
| 4-31 | i-Pr | furan-2-yl | H | naphthalen-1-yl |
| 4-32 | n-Hex | (4-n-Hex)Ph | H | naphthalen-1-yl |
| 4-33 | c-Hex | (4-n-Hex)Ph | H | naphthalen-1-yl |
| 4-34 | furan-2-yl | (4-n-Hex)Ph | H | naphthalen-1-yl |
| 4-35 | i-Pr | (4-n-Hex)Ph | H | thiophen-2-yl |
| 4-36 | i-Pr | (4-n-C₈H₁₇)Ph | H | thiophen-2-yl |
| 4-37 | i-Pr | (4-c-Hex)Ph | H | thiophen-2-yl |
| 4-38 | i-Pr | furan-2-yl | H | thiophen-2-yl |
| 4-39 | n-Hex | (4-n-Hex)Ph | H | thiophen-2-yl |
| 4-40 | c-Hex | (4-n-Hex)Ph | H | thiophen-2-yl |
| 4-41 | furan-2-yl | (4-n-Hex)Ph | H | thiophen-2-yl |
| 4-42 | i-Pr | (4-n-Hex)Ph | H | 1-adamantyl |
| 4-43 | i-Pr | (4-n-C₈H₁₇)Ph | H | 1-adamantyl |
| 4-44 | i-Pr | (4-c-Hex)Ph | H | 1-adamantyl |
| 4-45 | i-Pr | furan-2-yl | H | 1-adamantyl |
| 4-46 | n-Hex | (4-n-Hex)Ph | H | 1-adamantyl |
| 4-47 | c-Hex | (4-n-Hex)Ph | H | 1-adamantyl |
| 4-48 | furan-2-yl | (4-n-Hex)Ph | H | 1-adamantyl |
| 4-80 | i-Pr | (4-n-Hex)Ph | H | 2,3-dihydro-1H-inden-5-yl |
| 4-81 | (2,4-F₂)Ph | (4-n-Hex)Ph | H | 2,3-dihydro-1H-inden-5-yl |
| 4-82 | C(O)OEt | (4-n-Hex)Ph | H | 2,3-dihydro-1H-inden-5-yl |

TABLE 20

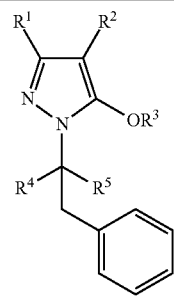

| No. | R¹ | R² | R³ | R⁴ | R⁵ |
|---|---|---|---|---|---|
| 4-49 | i-Pr | (4-n-Hex)Ph | H | —CH₂CH₂— | |
| 4-50 | i-Pr | (4-n-Oct)Ph | H | —CH₂CH₂— | |
| 4-51 | i-Pr | (4-c-Hex)Ph | H | —CH₂CH₂— | |
| 4-52 | i-Pr | furan-2-yl | H | —CH₂CH₂— | |
| 4-53 | n-Hex | (4-n-Hex)Ph | H | —CH₂CH₂— | |
| 4-54 | c-Hex | (4-n-Hex)Ph | H | —CH₂CH₂— | |
| 4-55 | furan-2-yl | (4-n-Hex)Ph | H | —CH₂CH₂— | |
| 4-87 | i-Pr | (4-n-Hex)Ph | H | C₂H₅ | C₂H₅ |

Next, the physical properties such as proton nuclear magnetic resonance (1H NMR) chemical shifts or melting points of the compounds listed in Tables 16 to 20 are shown in Table 21.

As compounds having a hydrogen atom as $R^3$ are known to have a tautomeric structure P-1, P-2 or P-3 depending on the $^1$H NMR measuring conditions, for these compounds, the $^1$H NMR measuring conditions, the structures of the tautomers and the mixing ratio of the tautomers, in the case of tautomeric mixtures, are shown in Table 21 as well as the physical properties.

$^1$H NMR was measured by using tetramethylsilane ($Me_4Si$) as the standard under the following conditions (i)~(iii).

(i); solvent $CDCl_3$, 300 MHz.
(ii); solvent DMSO-d6, 300 MHz.
(iii); solvent DMSO-d6, 400 MHz.

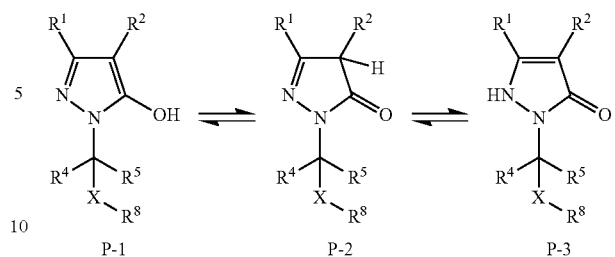

TABLE 21

| No. | measuring conditions | tautomers | mixing ratio | 1H NMR chemical shift or melting point |
|---|---|---|---|---|
| 1-01 | (i) | P-2 | | δ 7.2-7.4 (m, 5H), 3.22 (s, 2H), 2.07 (s, 3H), 1.87 (s, 6H) |
| 1-02 | (i) | P-2 | | δ 7.2-7.4 (m, 5H), 3.00 (q, J = 8.0 Hz, 1H), 2.03 (s, 3H), 1.91 (s, 6H), 1.30 (d, J = 7.7 Hz, 3H) |
| 1-03 | (ii) | | mixture of P-1 and P-3 6:4 | δ 9.33 (s, 1H), 6.8-7.5 (m, 5H), 2.1-2.3 (m, 2H), 2.03 (s, 3H), 1.80 (s, 6H), 1.1-1.4 (m, 8H), 0.8-0.9 (m, 3H)<br>δ 9.4-9.5 (br, 1H), 6.8-7.5 (m, 5H), 2.1-2.3 (m, 2H), 2.03 (s, 3H), 1.74 (s, 6H), 1.1-1.4 (m, 8H), 0.8-0.9 (m, 3H) |
| 1-04 | (i) | P-2 | | δ 6.8-7.4 (m, 10H), 2.9-3.7 (m, 3H), 1.4-2.2 (m, 9H) |
| 1-06 | (ii) | P-1 | | δ 9.89 (s, 1H), 7.0-7.5 (m, 15H), 1.96 (s, 6H) |
| 1-07 | (ii) | | mixture of P-1 and P-3 7:3 | δ 9.66 (s, 1H), 6.9-7.6 (m, 10H), 2.5-2.6 (m, 2H), 1.8-2.0 (m, 6H), 1.4-1.7 (m, 2H), 0.8-1.0 (m, 3H)<br>δ 10.27 (s, 1H), 6.9-7.6 (m, 10H), 2.6-2.7 (m, 2H), 1.8-2.0 (m, 6H), 1.4-1.7 (m, 2H), 0.8-1.0 (m, 3H) |
| 1-11 | | | | m.p. 224 to 225° C. |
| 1-12 | | | | m.p. 188 to 189° C. |
| 2-01 | (i) | P-2 | | δ 7.1-7.3 (m, 5H), 3.17 (s, 2H), 3.11 (s, 2H), 2.01 (s, 3H), 1.50 (s, 6H) |
| 2-02 | (i) | P-2 | | δ 7.0-7.3 (m, 5H), 2.8-3.3 (m, 3H), 1.2-2.1 (m, 12H) |
| 2-03 | (i) | P-2 | | δ 7.0-7.3 (m, 5H), 3.19 (d, J = 13.2 Hz, 1H), 3.06 (d, J = 13.2 Hz, 1H), 2.97 (t, J = 5.7 Hz, 1H), 1.98 (s, 3H), 1.49 (s, 6H), 0.8-1.4 (m, 13H) |
| 2-04 | (iii) | | mixture of P-1 and P-3 5:5 | δ 10.04 (s, 1H), 7.0-7.4 (m, 8H), 6.8-6.9 (m, 2H), 3.67 (s, 2H), 3.15 (s, 2H), 1.77 (s, 3H), 1.48 (s, 6H)<br>δ 9.43 (s, 1H), 7.0-7.4 (m, 8H), 6.8-6.9 (m, 2H), 3.46 (s, 2H), 3.21 (s, 2H), 1.90 (s, 3H), , 1.40 (s, 6H) |
| 2-05 | (ii) | P-1 | | δ 10.96 (s, 1H), 7.3-7.6 (m, 5H), 7.1-7.3 (m, 3H), 6.9-7.0 (m, 2H), 3.23 (s , 2H), 1.59 (s, 6H) |
| 2-06 | (ii) | P-1 | | δ 10.14 (s, 1H), 7.1-7.5 (m, 13H), 6.9-7.1 (m, 2H), 3.24 (s, 2H), 1.61 (s, 6H) |
| 2-07 | (ii) | | mixture of P-1 and P-3 5:5 | δ 9.89 (s, 1H), 6.8-7.6 (m, 10H), 3.26 (s, 2H), 2.3-2.5 (m, 2H), 1.52 (s, 6H), 1.3-1.5 (m, 2H), 0.7-0.9 (m, 3H)<br>δ 9.84 (s, 1H), 6.8-7.6 (m, 10H), 3.17 (s, 2H), 2.3-2.5 (m, 2H), 1.49 (s, 6H), 1.3-1.5 (m, 2H), 0.7-0.9 (m, 3H) |
| 2-09 | (ii) | | mixture of P-1 and P-3 7:3 | δ 9.79 (s, 1H), 7.3-7.5 (m, 4H), 7.1-7.3 (m, 4H), 6.8-6.9 (m, 2H), 3.14 (s, 2H), 2.87 (sep, J = 6.9 Hz, 1H), 1.53 (s, 6H), 1.02 (d, J = 6.8 Hz, 6H)<br>δ 9.39 (s, 1H), 7.3-7.5 (m, 4H), 7.1-7.3 (m, 4H), 7.0-7.1 (m, 2H), 3.20 (s, 2H), 2.8-3.1 (m, 1H), 1.53 (s, 6H), 1.06 (d, J = 7.1 Hz, 6H) |
| 2-10 | (ii) | | mixture of P-1 and P-3 7:3 | δ 9.95 (s, 1H), 7.51 (d, J = 6.9 Hz, 2H), 7.3-7.5 (m, 3H), 7.1-7.3 (m, 3H), 6.8-6.9 (m, 2H), 3.14 (s, 2H), 1.6-1.8 (m, 1H), 1.49 (s, 6H), 0.6-0.7 (m, 4H)<br>δ 9.19 (s, 1H), 7.75 (d, J = 7.4 Hz, 2H), 7.3-7.5 (m, 3H), 7.1-7.3 (m, 3H), 7.0-7.1 (m, 2H), 3.21 (s, 2H), 1.8-2.0 (m, 1H), 1.46 (s, 6H) 0.8-0.9 (m, 4H) |
| 2-12 | (ii) | | mixture of P-1 and P-3 5:5 | δ 9.90 (s, 1H), 6.8-7.6 (m, 10H), 3.25 (s, 2H), 2.42 (t, J = 7.6 Hz, 2H), 1.52 (s, 6H),, 1.1-1.5 (m, 4H), 0.7-0.9 (m, 3H)<br>δ 9.84 (s, 1H), 6.8-7.6 (m, 10H), 3.17 (s, 2H), 2.42 (t, J = 7.6 Hz, 2H), 1.49 (s, 6H), 1.1-1.5 (m, 4H), 0.7-0.9 (m, 3H) |
| 2-14 | (ii) | P-1 | | δ 9.9-10.2 (br, 1H), 6.9-7.4 (m, 14H), 3.24 (s, 2H), 2.24 (s, 3H), 1.59 (s, 6H) |
| 2-15 | (ii) | P-1 | | δ 10.25 (s, 1H), 7.1-7.5 (m, 12H), 6.9-7.1 (m, 2H), 3.24 (s, 2H), 1.60 (s, 6H) |
| 2-16 | (ii) | P-1 | | δ 10.11 (s, 1H), 6.6-7.4 (m, 13H), 3.71 (s, 3H), 3.48 (s, 3H), 3.24 (s, 2H), 1.59 (s, 6H) |
| 2-18 | (ii) | P-1 | | δ 10.22 (s, 1H), 8.36 (d, J = 4.7 Hz, 1H), 7.69 (t, J = 7.8 Hz, 1H), 7.42 (d, J = 8.0 Hz, 1H), 7.1-7.4 (m, 9H), 6.99 (d, J = Hz, 2H) 3.27 (s, 2H), 1.61 (s, 6H) |
| 2-19 | (ii) | | mixture of P-1 and P-3 5:5 | δ 9.97 (s, 1H), 6.9-7.6 (m, 9H), 3.19 (s, 2H), 2.31 (s, 3H), 2.04 (s, 3H), 1.46 (s, 6H)<br>δ 9.89 (s, 1H), 6.9-7.6 (m, 9H), 3.28 (s, 2H), 2.31 (s, 3H), 2.15 (s, 3H), 1.46. (s, 6H) |
| 2-20 | (ii) | | mixture of P-1 and P-3 6:4 | δ 9.97 (s, 1H), 7.1-7.3 (m, 7H), 6.9-7.0 (m, 2H), 3.0-3.4 (m, 2H), 2.19 (s, 3H), 1.79 (s, 3H), 1.51 (s, 6H)<br>δ 9.83 (s, 1H), 7.1-7.3 (m, 7H), 6.9-7.0 (m, 2H), 3.0-3.4 (m, 2H), 2.26 (s, 3H), 1.89 (s, 3H), 1.45 (s, 6H) |
| 2-21 | (ii) | | mixture of P-1 and P-3 5:5 | δ 9.84 (s, 1H), 7.41 (s, 1H), 7.0-7.3 (m, 6H), 6.95 (d, J = 7.1 Hz, 2H), 3.28 (s, 2H), 2.24 (s, 3H), 2.22 (s, 3H), 2.15 (s, 3H), 1.44 (s, 6H)<br>δ 9.94 (s, 1H), 7.41 (s, 1H), 7.0-7.3 (m, 6H), 6.95 (d, J = 7.1 Hz, 2H), 3.18(s, 2H), 2.24 (s, 3H), 2.22 (s, 3H), 2.03 (s, 3H), 1.50 (s, 6H), |

TABLE 21-continued

| No. | measuring conditions | tautomers | mixing ratio | 1H NMR chemical shift or melting point |
|---|---|---|---|---|
| 2-22 | (ii) | | mixture of P-1 and P-3 6:4 | δ 10.08 (s, 1H), 6.9-7.8 (m, 14H), 3.31 (s, 2H), 2.24 (s, 3H), 1.48 (s, 6H)<br>δ 10.15 (s, 1H), 6.9-7.8 (m, 14H), 3.21 (s, 2H), 2.11 (s, 3H), 1.53 (s, 6H) |
| 2-23 | (ii) | | mixture of P-1 and P-3 6:4 | δ 9.88 (s, 1H), 6.9-7.6 (m, 9H), 3.28 (s, 2H), 2.16 (s, 3H), 1.45 (s, 6H), 1.30 (s, 18H)<br>δ 9.97 (s, 1H), 6.9-7.6 (m, 9H), 3.18 (s, 2H), 2.05 (s, 3H), 1.50 (s, 6H), 1.30 (s, 18H) |
| 2-24 | (ii) | | mixture of P-1 and P-3 7:3 | δ 10.00 (s, 1H), 6.9-8.0 (m, 12H), 3.29 (d, J = 14.0 Hz, 1H), 3.13(d, J = 12.7 Hz, 1H), 1.77 (s, 3H), 1.58 (s, 6H)<br>δ 10.06 (s, 1H), 6.9-8.0 (m, 12H), 3.1-3.4 (m, 2H), 1.90 (s, 3H), 1.52 (s, 6H) |
| 2-25 | (ii) | | mixture of P-1 and P-3 6:4 | δ 9.88 (s, 1H), 6.9-7.7 (m, 9H), 3.29 (s, 2H), 3.57 (t, J = 7.5 Hz, 2H), 2.16 (s, 3H), 1.4-1.7 (m, 8H), 1.30 (s, 6H), 0.8-1.0 (m, 3H)<br>δ 9.96 (s, 1H), 6.9-7.7 (m, 9H), 3.18 (s, 2H), 3.57 (t, J = 7.5 Hz, 2H), 2.04 (s, 3H), 1.4-1.7 (m, 8H), 1.30 (s, 6H), 0.8-1.0 (m, 3H) |
| 2-28 | (ii) | | mixture of P-1 and P-3 5:5 | δ 9.90 (s, 1H), 6.9-7.6 (m, 9H), 3.76 (s, 3H), 3.19 (s, 2H), 2.03 (s, 3H), 1.45 (s, 6H)<br>δ 9.80 (s, 1H), 6.9-7.6 (m, 9H), 3.76 (s, 3H), 3.28 (s, 2H), 2.13 (s, 3H), 1.45 (s, 6H) |
| 2-29 | (ii) | | mixture of P-1 and P-3 5:5 | δ 9.94 (s, 1H), 6.8-7.4 (m, 8H), 6.00 (s, 2H), 3.27 (s, 2H), 2.15 (s, 3H), 2.04 (s, 3H), 1.44 (s, 6H)<br>δ 9.89 (s, 1H), 6.8-7.4 (m, 8H), 6.01 (s, 2H), 3.17 (s, 2H), 2.02 (s, 3H), 2.04 (s, 3H), 1.49 (s, 6H) |
| 2-30 | (ii) | | mixture of P-1 and P-3 6:4 | δ 9.80 (s, 1H), 7.52 (d, J = 8.5 Hz, 2H) 7.1-7.4 (m, 5H), 6.9-7.1 (m, 2H), 4.0-4.2 (m, 2H), 3.6-3.8 (m, 2H), 3.51 (q, J = 7.0 Hz, 2H), 3.29 (s, 2H), 2.14 (s, 3H), 1.44 (s, 6H), 1.14 (t, J = 7.0 Hz, 6H)<br>δ 9.90 (s, 1H), 7.52 (d, J = 8.5 Hz, 2H) 7.1-7.4 (m, 5H), 6.9-7.1 (m, 2H), 4.0-4.2 (m, 2H), 3.6-3.8 (m, 2H), 3.51 (q, J = 7.0 Hz, 2H), 3.19 (s, 2H), 2.02 (s, 3H), 1.50 (s, 6H), 1.14 (t, J = 7.0 Hz, 6H) |
| 2-31 | (ii) | | mixture of P-1 and P-3 7:3 | δ 10.16 (s, 1H), 6.9-7.8 (m, 9H), 3.29 (s, 2H), 2.19 (s, 3H), 1.46 (s, 6H)<br>δ 10.16 (s, 1H), 6.9-7.8 (m, 9H), 3.18 (s, 2H), 2.06 (s, 31), 1.51 (s, 6H) |
| 2-32 | (ii) | | mixture of P-1 and P-3 7:3 | δ 10.4-10.5 (m, 1H), 6.8-8.2 (m, 8H), 3.1-3.4 (m, 2H), 2.1-2.4 (m, 3H), 1.48 (s, 6H)<br>δ 10.3-10.4 (m, 1H), 6.8-8.2 (m, 8H), 3.1-3.4 (m, 2H), 2.0-2.2 (m, 3H), 1.48 (s, 6H) |
| 2-33 | (ii) | | mixture of P-1 and P-3 8:2 | δ 10.3 (s, 1H), 6.9-7.5 (m, 8H), 3.28 (s, 2H), 2.26 (s, 3H), 1.45 (s, 6H)<br>δ 10.2 (s, 1H), 6.9-7.5 (m, 8H), 3.18 (s, 2H), 2.12 (s, 3H), 1.50 (s, 6H) |
| 2-34 | (ii) | | mixture of P-1 and P-3 8:2 | δ 9.73 (s, 1H), 7.1-7.4 (m, 7H), 6.8-6.9 (m, 2H), 3.13 (s, 2H), 2.84 (sep, J = 7.1 Hz, 1H), 2.31 (s, 3H), 1.52 (s, 6H), 1.01 (d, J = 6.9 Hz, 6H)<br>δ 9.31 (s, 1H), 7.1-7.4 (m, 7H), 7.0-7.1 (m, 2H), 3.20 (s, 2H), 2.9-3.1 (m, 1H), 2.31 (s, 3H), 1.52 (s, 6H), 1.05 (d, J = 6.9 Hz, 6H) |
| 2-35 | (ii) | | mixture of P-1 and P-3 8:2 | δ 9.76 (s, 1H), 7.1-7.3 (m, 7H), 6.8-6.9 (m, 2H), 3.21 (d, J = 12.7 Hz, 1H), 3.0 δ (d, J = 13.2 Hz, 1H), 2.4-2.6 (m, 1H), 2.18 (s, 3H), 1.51 (s, 6H), 0.95 (d, J = 6.9 Hz, 3H)<br>δ 9.41 (s, 1H), 7.1-7.3 (m, 7H), 7.0-7.1 (m, 2H), 3.1-3.4 (m, 2H), 2.4-2.6 (m, 1H), 2.22 (s, 3H), 1.55 (s, 6H), 0.86 (d, J = 6.9 Hz, 3H) |
| 2-36 | (ii) | | mixture of P-1 and P-3 7:3 | δ 9.70 (s, 1H), 6.8-7.3 (m, 8H), 3.14 (s, 2H), 2.85 (sep, J = 7.7 Hz, 1H), 2.23 (s, 3H), 2.22 (s, 3H), 1.52 (s, 6H), 1.01 (d, J = 6.9 Hz, 6H)<br>δ 9.28 (s, 1H), 6.8-7.3 (m, 8H), 3.20 (s, 2H), 2.9-3.1 (m, 1H), 2.24 (s, 3H), 2.22 (s, 3H), 1.51 (s, 6H), 1.05 (d, J = 7.1 Hz, 6H) |
| 2-37 | (ii) | | mixture of P-1 and P-3 7:3 | δ 9.91 (s, 1H), 6.8-7.8 (m, 14H), 3.16 (s, 2H), 2.93 (sep, J = 6.9 Hz, 1H), 1.54 (s, 6H), 1.06 (d, J = 6.9 Hz, 6H)<br>δ 9.48 (s, 1H), 6.8-7.8 (m, 14H), 3.22 (s, 2H), 3.0-3.1 (m, 1H), 1.54 (s, 6H), 1.10 (d, J = 7.1 Hz, 6H) |
| 2-38 | (ii) | | mixture of P-1 and P-3 8:2 | δ 9.7-9.8 (m, 1H), 7.1-7.5 (m, 7H), 6.8-6.9 (m, 2H), 3.13 (s, 2H), 2.8-2.9 (m, 1H), 1.52 (s, 6H), 1.31 (s, 9H), 1.03 (d, J = 6.6 Hz, 6H)<br>δ 9.3-9.4 (m, 1H), 7.1-7.5 (m, 7H), 7.0-7.1 (m, 2H), 3.2-3.3 (m, 2H), 2.9-3.1 (m, 1H), 1.52 (s, 6H), 1.31 (s, 9H), 1.03 (d, J = 6.6 Hz, 6H) |
| 2-39 | (ii) | | mixture of P-1 and P-3 8:2 | δ 9.76 (s, 1H), 7.2-8.1 (m, 10H), 6.9-7.0 (m, 2H), 3.1-3.3 (m, 2H), 2.4-2.8 (m, 1H), 1.60 (s, 6H), 0.87 (d, J = 6.9 Hz, 6H)<br>δ 9.6-9.7 (m, 1H), 7.2-8.1 (m, 10H), 7.14 (d, J = 8.0 Hz, 2H), 3.1-3.3 (m, 2H), 2.4-2.8 (m, 1H), 1.55 (s, 6H), 0.96 (d, J = 6.6 Hz, 6H) |
| 2-40 | (ii) | | mixture of P-1 and P-3 6:4 | δ 9.72 (s, 1H), 7.1-7.4 (m, 7H), 6.8-6.9 (m, 2H), 3.14 (s, 2H), 2.85 (sep, J = 5.5 Hz, 1H), 2.57 (t, J = 6.7 Hz, 2H), 1.52 (s, 6H), 1.5-1.7 (m, 2H), 1.2-1.4 (m, 6H), 1.0-1.2 (m, 6H), 0.8-1.0 (m, 3H)<br>δ 9.3-9.4 (m, 1H), 7.1-7.4 (m, 7H), 7.0-7.1 (m, 2H), 3.19 (s, 2H), 2.9-3.1 (m, 1H), 2.57 (t, J = 6.7 Hz, 1H), 1.52 (s, 6H), 1.5-1.7 (m, 2H), 1.2-1.4 (m, 6H), 1.0-1.2 (m, 6H), 0.8-1.0 (m, 3H) |
| 2-43 | (ii) | | mixture of P-1 and P-3 7:3 | δ 9.68 (s, 1H), 6.8-7.4 (m, 9H), 3.77 (s, 3H), 3.13 (s, 2H), 2.82 (sep, J = 6.6 Hz, 1H), 1.52 (s, 6H), 1.01 (d, J = 6.8 Hz, 6H)<br>δ 9.27 (s, 1H), 6.8-7.4 (m, 9H), 3.77 (s, 3H), 3.20 (s, 2H), 2.9-3.1 (m, 1H), 1.52 (s, 6H), 1.05 (d, J = 7.0 Hz, 6H) |
| 2-44 | (ii) | | mixture of P-1 and P-3 7:3 | δ 9.73 (s, 1H), 6.7-7.5 (m, 8H), 6.02 (s 2H), 3.12 (s, 2H), 2.83 (sep, J = 6.8 Hz, 1H), 1.51 (s, 6H), 1.01 (d, J = 6.8 Hz, 6H)<br>δ 9.33 (s, 1H), (5.7-7.5 (m, 8H), 6.02 (s 2H), 3.19 (s, 2H), 2.9-3.1 (m, 1H), 1.51 (s, 6H), 1.0-1.2 (m, 6H) |
| 2-45 | (ii) | | mixture of P-1 and P-3 7:3 | δ 9.68 (s, 1H), 6.8-7.4 (m, 9H), 4.0-4.2 (m, 2H), 3.6-3.8 (m, 2H), 3.51 (q, J = 6.9 Hz, 2H), 3.13 (s, 2H), 2.82 (sep, J = 6.9 Hz, 1H), 1.52 (s, 6H), 1.14 (t, J = 6.9 Hz, 3H), 1.00 (d, J = 6.9 Hz, 6H)<br>δ 9.27 (s, 1H), 6.8-7.4 (m, 9H), 4.0-4.2 (m, 2H), 3.6-3.8 (m, 2H), 3.51 (q, J = 6.9 Hz, 2H), 3.20 (s, 2H), 2.94 (sep, J = 8.8 Hz, 1H), 1.52 (s, 6H), 1.14 (t, J = 6.9 Hz, 3H), 1.05 (d, J = 6.9 Hz, 6H) |

TABLE 21-continued

| No. | measuring conditions | tautomers | mixing ratio | 1H NMR chemical shift or melting point |
|---|---|---|---|---|
| 2-46 | (ii) | | mixture of P-1 and P-3 7:3 | δ 9.91 (s, 1H), 7.1-7.5 (m, 7H), 6.8-6.9 (m, 2H), 3.36 (s, 3H), 3.13 (s, 2H), 2.8-2.95 (m, 1H), 1.52 (s, 6H), 1.02 (d, J = 6.9 Hz, 6H)<br>δ 9.55 (s, 1H), 7.1-7.5 (m, 7H), 7.0-7.1 (m, 2H), 3.31 (s, 3H), 3.20 (s, 2H), 2.95-3.1 (m, 1H), 1.52 (s, 6H), 1.06 (d, J = 6.9 Hz, 6H) |
| 2-47 | (ii) | P-1 | | δ 10.0-10.2 (br, 1H), 7.4-7.8 (m, 2H), 7.1-7.4 (m, 4H), 6.8-7.1 (m, 2H), 3.15 (s, 2H), 2.8-3.1 (m, 1H), 1.53 (s, 6H), 1.05 (d, J = 6.6 Hz, 6H) |
| 2-48 | (ii) | | mixture of P-1 and P-3 6:4 | δ 10.05 (s, 1H), 6.8-7.5 (m, 8H), 3.14 (s, 2H), 2.8-3.1 (m, 1H), 1.51 (s, 6H), 1.08 (d, J = 6.6 Hz, 6H)<br>δ 9.61 (s, 1H), 6.8-7.5 (m, 8H), 3.22 (s, 2H), 2.8-3.1 (m, 1H), 1.51 (s, 6H), 1.13 (d, J = 6.8 Hz, 6H) |
| 2-49 | (ii) | | mixture of P-1 and P-3 7:3 | δ 10.41 (s, 1H), 6.9-8.1 (m, 9H), 3.29 (s, 2H), 2.24 (s, 3H), 1.49 (s, 6H)<br>δ 10.3-10.4 (br, 1H), 6.9-8.1 (m, 9H), 3.1-3.4 (m, 2H), 2.12 (s, 3H), 1.49 (s, 6H) |
| 2-50 | (ii) | | mixture of P-1 and P-3 8:2 | δ 10.09 (s, 1H), 6.8-7.9 (m, 9H), 3.15 (s, 2H), 2.8-3.0 (m, 1H), 1.54 (s, 6H), 1.05 (s, 6H)<br>δ 9.7-9.8 (br, 1H), 6.8-7.9 (m, 9H), 3.1-3.3 (m, 2H), 3.0-3.1 (m, 1H), 1.54 (s, 6H), 1.03 (s, 6H) |
| 3-01 | (i) | P-2 | | δ 7.60 (dd, J = 6.8, 2,1 Hz, 2H), 7.20-7.30 (m, 5H), 6.91 (dd, J = 6.8, 2, 4 Hz, 2H), 3.8 (s, 3H), 3.60 (s, 2H), 1.94 (s, 6H) |
| 3-02 | (i) | P-2 | | δ 7.15-7.35 (m. 5H), 3.20 (s, 2H), 2.68 (sep, J = 6.8Hz, 1H), 1.86 (s, 6H), 1.17 (d, J = 6.8Hz, 6H) |
| 3-03 | (i) | P-2 | | δ 7.62-7.70 (m, 2H), 7.20-7.45 (m, 8H), 3.63 (s, 2H), 1.95 (s, 6H) |
| 3-04 | (i) | P-2 | | δ 7.15-7.34 (m, 8H), 6.98-7.10 (m, 2H), 3.08 (s, 2H), 2.79 (s, 2H)., 1.84 (s, 6H), 1.18 (s, 6H) |
| 3-05 | (i) | P-2 | | δ 7.04 (d, J = 8.0 Hz, 2H), 6.98 (d, J = 8.0 Hz, 2H), 3.13 (s, 2H), 3.05 (s, 2H), 2.59 (sep, J = 6.8 Hz, 1H), 2.30 (s, 3H), 1.50 (s, 6H), 1.09 (d, 6.8 Hz, 6H) |
| 3-06 | (i) | P-2 | | δ 7.55 (dd, J = 6.8, 2.1 Hz, 2H), 7.03 (s, 4H), 6.91 (d, J = 8.6 Hz, 2H), 3.84 (s, 3H), 3.14 (s, 2H), 3.56 (s, 2H), 2.28 (s, 3H), 1.56 (s, 6H) |
| 3-07 | (i) | P-2 | | δ 7.18~7.42 (m, 4H), 7.00 (s, 4H), 3.21 (s, 2H), 3.16 (sep, J = 7.2 Hz, 1H), 2.61 (t, J = 7.5 Hz, 2H), 2.29 (s, 3H), 1.62 (s, 6H), 1.54~1.58 (m, 2H), 1.26-1.36 (m, 6H), 1.07 (d, J = 7.2 Hz, 6H), 0.87~0.92 (m, 3H) |
| 3-08 | (i) | P-2 | | δ 6.91~7.42 (m, 9H), 3.22 (sep, J = 7.2 Hz, 1H), 2.4~2.7 (m, 2H), 1.55 (s, 6H), 1.53~1.57 (m, 2H), 1.23~1.35 (m, 6H), 1.12 (d, J = 7.2 Hz, 6H), 0.8~0.9 (m, 3H) |
| 3-09 | | | | m.p. 144.6 to 145.5° C. |
| 3-10 | (i) | P-2 | | δ 6.91-7.33 (m, 9H), 3.06 (s, 2H), 3.05 (s, 2H), 2.73 (s, 2H), 2.31 (s, 3H), 1.49 (s, 6H), 1.10 (s, 6H) |
| 3-11 | (i) | P-2 | | δ 7.55-7.66 (m, 2H), 7.25-7.42 (m, 3H), 7.03 (s, 4H), 3.58 (s, 2H), 3.14 (s, 2H), 2.28 (s, 3H), 1.58 (s, 6H) |
| 3-12 | (i) | P-2 | | δ 7.35 (d, J = 8.6 Hz, 2H), 6.98 (d, J = 8.6 Hz, 2H), 3.14 (s, 2H), 3.06 (s, 2H), 2.59 (sep, J = 6.8 Hz, 1H), 1.50 (s, 6H), 1.10 (d, J = 7.1 Hz, 6H) |
| 3-13 | (i) | P-1 | | δ 7.83 (d, J = 7.4 Hz, 2H), 7.38 (t, J = 7.4 Hz, 2H), 7.15-7.33 (m, 4H), 7.08 (d, J = 7.1 Hz, 2H), 5.91 (s, 1H), 3.60 (s, 3H), 1.98 (s, 6H) |
| 3-14 | (i) | P-1 | | δ 7.73 (d, J = 7.4 Hz, 2H), 7.41 (t, J = 7.4 Hz, 2H), 7.16-7.36 (m, 4H), 3.16 (s, 3H), 2.10 (s, 3H), 1.98 (s, 6H) |
| 3-16 | (i) | P-2 | | δ 7.12~7.62 (m, 10H), 3.59 (s, 2H), 3.19 (s, 2H), 1.59 (s, 6H) |
| 3-17 | (i) | P-2 | | δ 7.09-7.25 (m, 5H), 3.13 (s, 2H), 3.09 (s, 2H), 2.58 (sep, J = 7.2 Hz, 1H), 1.52 (s, 6H), 1.09 (d, J = 6.9 Hz, 6H) |
| 3-18 | (i) | | mixture of P-1 and P-2 4:6 | δ 6.94-7.46 (m, 8H), 6.17 (br, 1H), 3.18 (s, 2H), 3.13-3.17 (m, 1H), 2.55-2.66 (m, 2H), 2.35 (s, 3H), 1.64 (s, 6H), 1.50-1.64 (m, 2H), 1.11 (d, J = 6.9 Hz, 6H), 0.95-1.20 (m, 6H), 0.75-0.95 (m, 3H)<br>δ 6.94-7.46 (m, 8H), 4.17 (s, 1H), 3.30 (s, 2H), 2.55-2.66 (m, 2H), 2.40-2.60 (m, 1H), 2.36 (s, 3H), 1.55 (s, 6H), 1.50-1.64 (m, 2H), 1.11 (d, J = 7.2 Hz, 6H), 0.95-1.20 (m, 6H), 0.75-0.95 (m, 3H) |
| 3-19 | (i) | P-2 | | δ 7.25-7.15 (m, 1H), 6.95-7.05 (m, 1H), 6.85-7.05 (m, 2H), 3.13 (s, 2H), 3.05 (s, 2H), 2.59 (sep, J = 7.2 Hz, 1H), 2.29 (s, 3H), 1.51 (s, 6H), 1.09 (d, J = 6.9 Hz, 6H) |
| 3-20 | (i) | | mixture of P-1 and P-2 5:5 | δ 6.88-7.47 (m, 8H), 6.14 (br, 1H), 3.21 (s, 2H), 3.13-3.20 (m, 1H), 2.52- 2.65 (m, 2H), 2.26 (s, 3H), 1.64 (s, 6H), 1.49-1.63 (m, 2H), 1.21-1.39 (m, 6H), 0.95-1.05 (m, 6H), 0.82-0.93 (m, 3H)<br>δ 6.88-7.47 (m, 8H), 4.12 (s, 1H), 2.52-2.65 (m, 2H), 2.40-2.55 (m, 1H), 2.30 (s, 3H), 1.55 (s, 6H), 1.49-1.63 (m, 2H), 1.21-1.39 (m, 6H), 1.05-1.15 (m, 6H), 0.82-0.93 (m, 3H) |
| 3-21 | (i) | P-1 | | $^1$H NMR (CDCl$_3$, Me$_4$Si, 300 MHz) δ 7.95-8.0 (m, 2H), 7.6-7.7 (m, 1H), 7.45-7.55 (m, 2H), 7.0-7.1 (m, 1H), 6.9-7.0 (m, 1H), 6.6-6.7 (m, 1H), 6.56 (s, 1H), 6 6.03 (s, 1H), 3.09 (s, 2H), 2.92 (sep, J = 6.9 Hz, 1H), 2.22 (s, 3H), 1.64 (s, 6H), 1.25 (d, J 6.9 Hz, 6H) |
| 3-22 | (i) | P-2 | | δ 7.2-7.3 (m, 2H), 7.0-7.1 (m, 2H), 3.14 (s, 2H), 3.06 (s, 2H), 2.50-2.65 (m, 1H), 1.52 (s, 6H), 1.29 (s, 9H), 1.08 (d, J 6.9 Hz, 6H) |
| 3-23 | (i) | | mixture of P-1 and P-2 5:5 | δ 6.90-7.47 (m, 8H), 6.13 (br, 1H), 3.20 (s, 2H), 3.05-3.19 (m, 1H), 2.52-2.67 (m, 2H), 1.65 (s, 6H), 1.52-1.63 (m, 2H), 1.22-1 41 (m, 6H), 1.27 (s, 9H), 0.94-1.09 (m, 6H), 0.83-0.93 (m, 3H)<br>δ 6.90-7.47 (m, 8H), 4.13 (s, 1H), 3.05-3.19 (m, 2H), 2.52-2.67 (m, 2H), 2.39-2.51 (m, 1H), 1.65 (s, 6H), 1.52-1.63 (m, 2H), 1.22-1.41 (m, 6H), 1.31 (s, 9H), 0.94-1.09 (m, 6H), 0.83-0.93 (m, 3H) |
| 3-24 | (i) | P-2 | | δ 7.12-7.30 (m, 5H), 3.63 (d, J = 7.2 Hz, 1H), 3.10 (s, 2H), 2.50-2.65 (m, 1H), 1.56 (s, 6H), 1.40 (s, 3H), 1.26 (d, J = 7.2 Hz, 3H), 1.08 (d, J = 7.2 Hz, 3H), 1.56 (d, J = 6.9 Hz, 3H) |

TABLE 21-continued

| No. | measuring conditions | tautomers | mixing ratio | 1H NMR chemical shift or melting point |
|---|---|---|---|---|
| 3-25 | (i) | | mixture of P-1 and P-2 5:5 | δ 6.88-7.45 (m, 9H), 6.07 (br, 1H), 3.93-4.06 (m, 1H), 3.11 (sep, J = 7.2 Hz, 1H), 2.52-2.65 (m, 2H), 1.81-1.20 (m, 8H), 1.59 (s, 6H), 0.83-1.20 (m, 12H) |
| | | | | δ 6.88-7.45 (m, 9H), 4.11 (s, 1H), 3.68-3.77 (m, 1H), 2.52-2.65 (m, 2H), 2.35-2.52 (m, 1H), 1.81-1.20 (m, 8H), 1.59 (s, 6H), 0.83-1.20 (m, 12H) |
| 3-27 | (ii) | | mixture of P-1 and P-3 9:1 | δ 9.63 (s, 1H), 7.36 (d, J = 7.7 Hz, 2H), 7.05-7.3 (m, 5H), 6.98 (d, J = 7.4 Hz, 2H), 2.45-2.6 (m, 2H), 1.84 (s, 6H), 1.7-1.9 (m, 1H), 1.45-1.65 (m, 2H), 1.2-1.35 (m, 6H), 0.7-1.05 (m, 7H) |
| | | | | δ 9.45-9.55 (br, 1H), 7.5-7.6 (m, 2H), 7.05-7.3 (m, 5H), 6.98 (d, J = 7.4 Hz, 2H), 2.45-2.6 (m, 2H), 1.84 (s, 6H), 1.7-1.9 (m, 1H), 1.45-1.65 (m, 2H), 1.2-1.35 (m, 6H), 0.7-1.05 (m, 7H) |
| 3-28 | (ii) | | mixture of P-1 and P-3 1:9 | δ 9.7-9.8 (br, 1H), 7.34 (d, J = 8.6 Hz, 2H), 7.1-7.3 (m, 4H), 7.00 (d, J = 8.5 Hz, 2H), 3.05-3.2 (m, 1H), 2.4-2.6 (m, 2H), 1.82 (s, 6H), 1.5-1.6 (m, 2H), 1.2-1.35 (m, 6H), 1.14 (d, J = 6.8 Hz, 6H), 0.75-0.9 (m, 3H) |
| | | | | δ 9.56 (s, 1H), 7.34 (d, J = 8.6 Hz, 2H), 7.1-7.3 (m, 4H), 7.00 (d, J = 8.5 Hz, 2H), 2.95-3.05 (m, 1H), 2.4-2.6 (m, 2H), 1.87 (s, 6H), 1.5-1.6 (m, 2H), 1.2-1.35 (m, 6H), 1.14 (d, J = 6.8 Hz, 6H), 0.75-0.9 (m, 3H) |
| 3-29 | (ii) | | mixture of P-1 and P-3 9:1 | δ 9.67 (s, 1H), 7.3-7.4 (m, 4H), 7.17 (d, J = 7.5 Hz 2H), 7.00 (d, J = 8.5 Hz, 2H), 2.4-2.6 (m, 2H), 1.7-1.9 (m, 1H) 1.83 (s, 6H), 1.45-1.65 (m, 2H), 1.2-1.35 (m, 6H), 0.7-1.1 (m, 7H) |
| | | | | δ 9.45-9.55 (br, 1H), 7.5-7.6 (m, 2H), 7.3-7.4 (m, 2H), 7.17 (d, J = 7.5 Hz 2H), 7.00 (d, J = 8.5 Hz, 2H), 2.4-2.6 (m, 2H), 1.7-1.9 (m, 1H) 1.83 (s, 6H), 1.45-1.65 (m, 2H), 1.2-1.35 (m, 6H), 0.7-1.1 (m, 7H) |
| 3-30 | (ii) | P-1 | | δ 9.88 (br, 1H), 7.66 (d, J = 7.4 Hz, 2H), 7.59 (d, J = 7.7 Hz, 2H), 7.3-7.55 (m, 7H), 7.1-7.2 (m, 6H), 2.4-2.6 (m, 2H), 1.96 (s, 6H), 1.5-1.65 (m, 2H), 1.2-1.4 (m, 6H), 0.85 (t, J = 6.9 Hz, 3H) |
| 3-31 | (ii) | P-1 | | δ 9.70 (s, 1H), 7.65-8.05 (m, 6H), 7.0-7.6 (m, 7H), 2.4-2.55 (m, 2H), 1.91 (s, 6H), 1.3-1.55 (m, 2H), 1.1-1.3 (m, 6H), 0.7-0.9 (m, 3H) |
| 3-32 | (ii) | P-1 | | δ 9.80 (s, 1H), 7.25-7.4 (m, 6H), 7.05-7.15 (m, 6H), 2.45-2.6 (m, 2H), 1.93 (s, 6H), 1.45-1.65 (m, 2H), 1.2-1.35 (m, 6H), 1.26 (s, 9H), 0.8-0.9 (m, 3H) |
| 3-33 | (ii) | | mixture of P-1 and P-3 7:3 | δ 9.75 (s, 1H), 7.15-7.4 (m, 6H) 6.83 (d, J = 8.4 Hz, 2H), 3.12 (s, 2H), 2.84 (sep, J = 6.8 Hz, 1H), 2.57 (t, J = 7.5 Hz 2H), 1.53 (s, 6H), 1.4-1.65 (m, 2H), 1.2-1.4 (m, 6H), 1.00 (d, J = 6.8 Hz, 6H), 0.8-0.9 (m, 3H) |
| | | | | δ 9.31 (s, 1H), 7.15-7.4 (m, 6H) 7.05 (d, J = 8.3 Hz, 2H), 3.20 (s, 2H), 2.9-3.05 (m, 1H), 2.57 (t, J = 7.5 Hz 2H), 1.51 (s, 6H), 1.4-1.65 (m, 2H), 1.2-1.4 (m, 6H), 1.05 (d, J = 7.1 Hz, 6H), 0.8-0.9 (m, 3H) |
| 3-34 | (ii) | | mixture of P-1 and P-3 7:3 | δ 9.88 (s, 1H), 7.40 (d, J = 8.0 Hz, 2H), 7.15-7.3 (m, 4H), 6.85 (d, J = 8.3 Hz, 2H), 3.12 (s, 2H), 2.57 (t, J = 7.4 Hz, 2H), 1.65-1.75 (m, 1H), 1.55-1.65 (m, 2H), 1.49 (s, 6H), 1.2-1.4 (m, 6H), 0.87 (t, J = 6.8 Hz, 3H), 0.55-0.75 (m, 4H) |
| | | | | δ 9.06 (s, 1H), 7.63 (d, J = 8.0 Hz, 2H), 7.15-7.3 (m, 4H), 7.07 (d, J = 8.0 Hz, 2H), 3.22 (s, 2H), 2.57 (t, J = 7.4 Hz, 2H), 1.65-1.75 (m, 1H), 1.55-1.65 (m, 2H), 1.43 (s, 6H), 1.2-1.4 (m, 6H), 0.87 (t, J = 6.8 Hz, 3H), 0.55-0.75 (m, 4H) |
| 3-35 | (ii) | | mixture of P-1 and P-3 6:4 | δ 9.51 (s, 1H), 7.14 (d, J = 8.3 Hz, 2H), 6.72 (d, J = 8.2 Hz, 2H), 3.06 (s, 2H), 2.69 (sep, J = 6.9 Hz, 1H), 2.15-2.3 (m, 2H), 1.46 (s, 6H), 1.4-1.6 (m, 2H), 1.05 (d, J = 6.9 Hz, 6H), 0.88 (t, J = 7.1 Hz, 3H) |
| | | | | δ 8.78 (s, 1H), 7.22 (d, J = 8.5 Hz, 2H), 7.00 (d, J = 8.5 Hz, 2H), 3.16 (s, 2H), 2.69 (sep, J = 6.9 Hz, 1H),, 2.05-2.15 (m, 2H), 1.42 (s, 6H), 1.4-1.6 (m, 2H), 1.05 (d, J = 6.9 Hz, 6H), 0.88 (t, J = 7.1 Hz, 3H) |
| 3-36 | (ii) | P-1 | | δ 10.14 (s, 1H), 7.63 (d, J = 7.7 Hz, 2H), 7.52 (d, J = 8.5 Hz, 2H), 7.1-7.5 (m, 11H), 6.97 (d, J = 8.2 Hz, 2H), 3.24 (s, 2H), 2.45-2.65 (m, 2H), 1.61 (s, 6H), 1.5-1.65 (m, 2H), 1.2-1.4 (m, 6H), 0.8-0.9 (m, 3H) |
| 3-37 | (ii) | | mixture of P-1 and P-3 9:1 | δ 10.04 (s, 1H), 7.0-7.65 (m, 10H), 6.94 (d, J = 8.5 Hz, 2H), 3.21 (s, 2H), 2.45-2.65 (m, 2H), 1.59 (s, 6H), 1.45-1.6 (m, 2H), 1.2-1.35 (m, 6H), 1.22 (s, 9H), 0.8-0.95 (m, 3H) |
| | | | | δ 9.85-9.95 (m, 1H), 6.9-7.65 (m, 10H), 3.21 (s, 2H), 2.45-2.65 (m, 2H), 1.59 (s, 6H), 1.45-1.6 (m, 2H), 1.2-1.35 (m, 6H), 1.23 (s, 9H), 0.8-0.95 (m, 3H) |
| 3-38 | (ii) | | mixture of P-1 and P-3 8:2 | δ 9.66 (s, 1H), 7.1-7.25 (m, 4H) 6.76 (d, J = 8.5 Hz, 2H), 6.70 (d, J = 8.2 Hz, 2H), 3.68 (s, 3H), 3.06 (s, 2H), 2.75-2.9 (m, 1H), 2.57 (t, J = 7.4 Hz, 2H), 1.5-1.65 (m, 2H), 1.50 (s, 6H), 1.2-1.4 (m, 6H), 1.02 (d, J = 6.9 Hz, 6H), 0.87 (t J = 6.9 Hz, 3H) |
| | | | | δ 9.25-9.35 (br, 1H), 7.25-7.35 (m, 4H), 6.85-6.95 (m, 4H), 3.68 (s, 3H), 3.12 (s, 2H), 2.9-3.05 (m, 1H), 2.57 (t, J = 7.4 Hz 2H), 1.5-1.65 (m, 2H), 1.50 (s, 6H), 1.2-1.4 (m, 6H), 1.07 (d, J = 7.1 Hz, 6H), 0.87 (t J = 6.9 Hz, 3H) |
| 3-39 | (ii) | P-2 | | δ 7.4-7.55 (m, 2H) 7.20 (d, J = 8.1 Hz, 2H), 6.84 (d, J = 8.3 Hz, 2H), 6.73 (d, J = 8.6 Hz, 2H), 3.69 (s, 3H), 3.08 (s, 2H), 2.5-2.6 (m, 2H), 1.65-1.8 (m, 1H), 1.55-1.65 (m, 2H), 1.45 (s, 6H), 1.2-1.4 (m, 6H), 0.8-1.0 (m, 3H), 0.7-0.8 (m, 2H), 0.6-0.7 (m, 2H) |
| 3-40 | (ii) | P-1 | | δ 10.0-10.1 (m, 1H), 7.75 (d, J = 8.5 Hz, 2H), 6.85-7.7 (m, 13H), 6.76 (d, J = 8.8 Hz, 2H), 3.71 (s, 3H), 3.05-3.25 (m, 2H), 2.45-2.65 (m, 2H), 1.45-1.65 (m, 8H), 1.15-1.35 (m, 6H), 0.8-0.9 (m, 3H) |
| 3-41 | (ii) | | mixture of P-1 and P-3 7:3 | δ 10.85 (s, 1H), 6.75-7.3 (m, 12H), 3.73 (s, 3H), 3.05-3.25 (m, 2H), 2.45-2.65 (m, 2H), 1.56 (s, 6H), 1.4-1.65 (m, 2H), 1.2-1.4 (m, 6H), 1.24 (s, 9H), 0.8-0.9 (m, 3H) |
| | | | | δ 9.9-10.0 (m, 1H), 6.75-7.65 (m, 12H), 3.67 (s, 3H), 3.05-3.25 (m, 2H), 2.45-2.65 (m, 2H), 1.56 (s, 6H), 1.4-1.65 (m, 2H), 1.2-1.4 (m, 6H), 1.24 (s, 9H), 0.8-0.9 (m, 3H) |
| 3-43 | (i) | P-1 | | δ 7.9-8.0 (m, 2H), 7.6-7.7 (m, 1H), 7.45-7.55 (m, 2H), 7.20 (d, J = 8.3 Hz, 2H), 6.74 (d, J = 8.2 Hz, 1H), 6.04 (s, 1H), 3.10 (s, 2H), 2.83-3.00 (m, 1H), 1.64 (s, 6H), 1.25 (s, 9H), 1.24 (d, J = 7.2 Hz, 6H) |

TABLE 21-continued

| No. | measuring conditions | tautomers | mixing ratio | 1H NMR chemical shift or melting point |
|---|---|---|---|---|
| 3-44 | (i) | | mixture of P-1 and P-2 1:9 | δ 7.01-7.40 (m, 5H), 5.84 (br, 1H), 3.0-3.25 (m, 2H), 2.75-2.91 (m, 1H), 2.2-2.3 (m, 2H), 1.52 (s, 6H), 1.45-1.91 (m, 2H), 1.01-1.44 (m, 6H), 0.83-1.01 (m, 3H) |
| | | | | δ 7.01-7.40 (m, 5H), 3.00-3.28 (m, 3H), 2.45-2.65 (m, 1H), 1.52 (s, 6H), 1.45-1.91 (m, 2H), 1.01-1.44 (m, 6H), 0.83-1.01 (m, 3H) |
| 3-45 | (i) | P-1 | | δ 7.85-7.95 (m, 2H), 7.35-7.45 (m, 2H), 7.1-7.3 (m, 5H), 3.94 (br, 1H), 3.2-3.3 (m, 1H), 3.05-3.15 (m, 1H), 1.85-2.0 (m, 1H), 1.57 (s, 3H), 1.55 (s, 3H), 1.33 (s, 9H), 0.95-1.19 (m, 8h), 0.74-0.82 (m, 3H) |
| 3-46 | (i) | P-2 | | δ 7.05-7.2 (m, 1H), 6.95-7.05 (m, 1H), 6.85-6.95 (m, 2H), 4.64 (s, 1H), 2.92-3.13 (m, 2H), 2.73-2.89 (m, 1H), 2.30 (s, 3H), 1.46-1.61 (m, 6H), 1.06-1.19 (m, 6H) |
| 3-47 | (i) | P-2 | | $^1$H NMR (CDCl$_3$, Me$_4$Si, 300 MHz) δ 7.06-7.29 (m, 5H), 4.64 (s, 1H), 3.12 (d, J = 13.4 Hz, 1H), 3.03 (d, J = 13.4 Hz, 1H), 2.73-2.88 (m, 1H), 1.53 (s, 3H), 152 (s, 3H), 1.16 (d, J = 6.9 Hz, 3H), 1.13 (d, J = 7.2 Hz, 3H) |
| 3-48 | (i) | | mixture of P-1 and P-2 5:5 | δ 6.89-7.47 (m, 8H), 6.13 (br, 1H), 3.20 (s, 2H), 3.12-3.19 (m, 1H), 2.49-2.65 (m, 4H), 1.63 (s, 6H), 1.45-1.62 (m, 4H), 1.20-1.43 (m, 12H), 0.96-1.19 (m, 6H), 0.81-0.93 (m, 6H) |
| | | | | δ 6.89-7.47 (m, 8H), 4.11 (s, 1H), 3.11 (s, 2H), 2.49-2.65 (m, 4H), 2.35-2.50 (m, 1H), 1.54 (s, 6H), 1.45-1.62 (m, 4H), 1.20-1.43 (m, 12H), 0.96-1.19 (m, 6H), 0.18-0.93 (m, 6H) |
| 3-49 | (i) | P-1 | | δ 7.13-7.19 (m, 3H), 6.73-6.82 (m, 2H), 5.95 (s, 1H), 3.07 (s, 2H), 2.87 (sep, J = 6.9 Hz, 1H), 2.15 (s, 3H), 1.58 (s, 6H), 1.21 (d, J = 7.2 Hz, 6H) |
| 4-01 | (i) | P-2 | | δ 7.18-7.34 (m, 5H), 3.75 (s, 3H), 3.48 (s, 2H), 3.41 (s, 2H), 1.87 (s, 6H) |
| 4-03 | (i) | P-1 | | δ 7.08-7.30 (m, 7H), 6.87-6.76 (m, 2H), 3.25 (s, 3H), 3.11 (s, 2H), 2.95 (sep, J = 6.9 Hz, 1H), 2.62 (t, J = 7.6 Hz, 2H), 1.63 (s, 6H), 1.51-1.70 (m, 2H), 1.21-1.42 (m, 6H), 1.15 (d, J = 6.8 Hz, 6H), 0.89 (t, J = 6.8 Hz, 3H) |
| 4-12 | (ii) | | mixture of P-1 and P-3 8:2 | δ 9.26 (s, 1H), 7.1-7.3 (m, 3H), 6.89 (d, J = 6.9 Hz, 2H), 2.82 (sep, J = 6.9 Hz, 1H), 2.20 (t, J = 7.8 Hz, 2H), 1.82 (s, 6H), 1.37 (m, 2H), 1.19 (d, J = 7.3 Hz, 6H), 0.8-0.9 (m, 3H) |
| | | | | δ 9.23 (s, 1H), 7.1-7.3 (m, 3H), 7.04 (d, J = 7.0 Hz, 2H), 2.8-3.0 (m, 1H), 2.0-2.15 (m, 2H), 1.79 (s, 6H), 1.37 (m, 2H), 1.21 (d, J = 6.9 Hz, 6H), 0.8-0.9 (m, 3H) |
| 4-13 | (ii) | P-1 | | δ 9.87 (s, 1H), 7.66 (d, J = 7.7 Hz, 2H), 7.59 (d, J = 8.3 Hz, 2H), 7.1-7.5 (m, 10H), 2.5-2.6 (m, 2H), 1.97 (s, 6H), 1.5-1.6 (m, 2H), 1.2-1.4 (m, 6H), 0.7-0.9 (m, 3H) |
| 4-14 | (ii) | | mixture of P-1 and P-2 6:4 | δ 9.68 (s, 1H), 7.0-8.0 (m, 14H), 2.4-2.6 (m, 2H), 1.92 (s, 6H), 1.0-1.5 (m, 8H), 0.7-0.9 (m, 3H) |
| | | | | δ 7.0-8.0 (m, 14H), 3.31 (s, 1H), 2.4-2.6 (m, 2H), 1.87 (s, 6H), 1.0-1.5 (m, 8H), 0.7-0.9 (m, 3H) |
| 4-15 | (ii) | P-1 | | δ 9.78 (s, 1H), 7.05-7.35 (m, 13H), 2.5-2.6 (m, 2H), 1.95 (s, 6H), 1.5-1.6 (m, 2H), 1.28 (s, 9H), 1.2-1.4 (m, 6H), 0.7-0.9 (m, 3H) |
| 4-16 | (ii) | P-1 | | δ 9.59 (s, 1H), 7.55 (d, J = 8.6 Hz, 2H), 7.41 (d, J = 8.6 Hz, 2H), 7.1-7.35 (m, 3H), 7.00 (d, J = 7.0 Hz, 2H), 2.4-2.5 (m, 2H), 1.90 (s, 6H), 1.8-1.9 (m, 2H), 1.05-1.45 (m, 6H), 1.31 (s, 9H), 0.7-0.9 (m, 3H) |
| 4-17 | (ii) | | mixture of P-1 and P-3 1:6 | δ 9.63 (s, 1H), 7.54 (d, J = 8.0 Hz, 2H), 7.35-7.45 (m, 4H), 7.41 (d, J = 8.6 Hz, 2H), 2.4-2.5 (m, 2H), 1.88 (s, 6H), 1.8-1.9 (m, 2H), 1.0-1.4 (m, 6H), 1.30 (s, 9H), 0.7-0.8 (m, 3H) |
| | | | | δ 9.7-9.8 (m, 1H), 7.83 (d, J = 8.5 Hz, 2H), 7.1-7.6 (m, 6H), 2.4-2.5 (m, 2H), 1.88 (s, 6H), 1.8-1.9 (m, 2H), 1.0-1.4 (m, 6H), 1.30 (s, 9H), 0.7-0.8 (m, 3H) |
| 4-18 | (ii) | | mixture of P-1 and P-3 8:2 | δ 9.96 (s, 1H), 7.3-7.7 (m, 9H), 7.19 (d, J = 8.4 Hz, 2H), 6.87 (d, J = 8.4 Hz, 2H), 3.20 (s, 2H), 2.45-2.6 (m, 2H), 1.56 (s, 6H), 1.35-1.55 (m, 2H), 1.2-1.35 (m, 6H), 0.8-0.9 (m, 3H) |
| | | | | δ 9.45 (br, 1H), 7.78 (d, J = 8.6 Hz, 2H), 7.1-7.7 (m, 11H), 3.26 (s, 2H), 2.45-2.6 (m, 2H), 1.50 (s, 6H), 1.35-1.55 (m, 2H), 1.2-1.35 (m, 6H), 0.8-0.9 (m, 3H) |
| 4-19 | (ii) | | mixture of P-1 and P-3 8:2 | δ 9.87 (s, 1H), 6.8-7.9 (m, 8H), 3.17 (s, 2H), 2.4-2.55 (m, 2H), 1.53 (s, 6H), 1.28 (s, 9H), 1.0-1.5 (m, 8H), 0.7-0.9 (m, 3H) |
| | | | | δ 9.3-9.4 (m, 1H), 6.8-7.9 (m, 8H), 3.23 (s, 2H), 2.2-2.4 (m, 2H), 1.47 (s, 6H), 1.25 (s, 9H), 1.0-1.5 (m, 8H), 0.7-0.9 (m, 3H) |
| 4-20 | (ii) | | mixture of P-1 and P-3 6:4 | δ 9.90 (s, 1H), 7.3-7.7 (m, 9H), 6.80 (d, J = 8.4 Hz, 2H), 6.70 (d, J = 8.3 Hz, 2H), 3.67 (s, 3H), 3.13 (s, 2H), 2.4-2.6 (m, 2H), 1.54 (s, 6H), 1.4-1.6 (m, 2H), 1.0-1.2 (m, 6H), 0.7-0.9 (m, 3H) |
| | | | | δ 9.4-9.5 (m, 1H), 6.6-7.8 (m, 13H), 3.68 (s, 3H), 3.17 (s, 2H), 2.4-2.6 (m, 2H), 1.48 (s, 6H), 1.28 (s, 9H), 1.4-1.6 (m, 2H), 1.0-1.2 (m, 6H), 0.7-0.9 (m, 3H) |
| 4-21 | (ii) | | mixture of P-1 and P-3 7:3 | δ 9.80 (s, 1H), 6.6-7.9 (m, 8H), 3.67 (s, 3H), 3.11 (s, 2H), 2.4-2.6 (m, 2H), 1.51 (s, 6H), 1.28 (s, 9H), 1.0-1.6 (m, 8H), 0.7-0.9 (m, 3H) |
| | | | | δ 9.35 (m, 1H), 6.6-7.9 (m, 8H), 3.68 (s, 3H), 3.15 (s, 2H), 2.2-2.4 (m, 2H), 1.45 (s, 6H), 1.0-1.6 (m, 8H), 1.25 (s, 9H), 0.7-0.9 (m, 3H) |
| 4-22 | (ii) | | mixture of P-1 and P-3 6:4 | δ 9.43 (s, 1H), 6.66 (s, 4H), 3.67 (s, 3H), 3.01 (s, 2H), 2.6-2.8 (m, 2H), 2.2-2.3 (m, 2H), 1.44 (s, 6H), 1.3-1.5 (m, 2H), 1.07 (d, J = 6.8 Hz, 6H), 0.89 (t, J = 7.3 Hz, 3H) |
| | | | | δ 8.78 (s, 1H), 6.91 (d, J = 8.3 Hz, 2H), 6.73 (d, J = 8.3 Hz, 2H), 3.68 (s, 3H), 3.08 (s, 2H), 2.7-2.9 (m, 2H), 2.0-2.2 (m, 2H), 1.39 (s, 6H), 1.3-1.5 (m, 2H), 1.07 (d, J = 6.8 Hz, 6H), 0.89 (t, J = 7.3 Hz, 3H) |
| 4-23 | (i) | | mixture of P-1 and P-2 9:1 | δ 8.0-8.1 (m, 2H), 7.6-7.7 (m, 2H), 7.15-7.3 (m, 3H), 7.05-7.15 (m, 2H), 6.37 (br, 1H), 3.92 (s, 3H), 3.27 (s, 2H), 3.12-3.19 (m, 1H), 1.65 (s, 6H), 1.08 (d, J = 7.2 Hz, 6H) |
| | | | | δ 8.0-8.1 (m, 2H), 7.6-7.7 (m, 2H), 7.15-7.3 (m, 3H), 7.05-7.15 (m, 2H), 4.2-4.3 (m, 1H), 3.92 (s, 3H), 3.1-3.2 (m, 2H), 2.35-2.5 (m, 1H), 1.65 (s, 6H), 0.95-1.05 (m, 6H) |

TABLE 21-continued

| No. | measuring conditions | tautomers | mixing ratio | 1H NMR chemical shift or melting point |
|---|---|---|---|---|
| 4-27 | (i) | P-1 | | δ 9.71 (s, 1H), 7.13-7.33 (m, 3H)., 7.05-7.12 (m, 2H), 4.31 (q, J = 7.1 Hz, 2H), 3.23 (sep, J = 6.9 Hz, 1H), 1.94 (s, 6H), 1.36 (t, 7.3 Hz, 3H), 1.30 (d, J = 6.8 Hz, 6H) |
| 4-28 | (ii) | | mixture of P-1 and P-3 6:4 | δ 9.66 (s, 1H), 6.9-8.3 (m, 11H), 3.60 (s, 2H), 2.82 (sep, J = 6.7 Hz, 1H), 2.58 (t, J = 8.0 Hz, 2H), 1.60 (s, 6H), 1.5-1.7 (m, 2H), 1.2-1.4 (m, 6H), 0.97 (d, J = 5.9 Hz, 6H), 0.87 (t, J = 7.0 Hz, 3H)<br>δ 9.29 (s, 1H), 6.9-8.3 (m, 11H), 3.69 (s, 2H), 2.95 (sep, J = 6.6 Hz, 1H), 2.58 (t, J = 8.0 Hz, 2H), 1.57 (s, 6H), 1.5-1.7 (m, 2H), 1.2-1.4 (m, 6H), 0.99 (d, J = 6.3 Hz, 6H), 0.87 (t, J = 7.0 Hz, 3H) |
| 4-29 | (ii) | | mixture of P-1 and P-3 7:3 | δ 9.66 (s, 1H), 6.9-8.3 (m, 11H), 3.60 (s, 2H), 2.82 (sep, J = 6.5 Hz, 1H), 2.58 (t, J = 7.7 Hz, 2H), 1.59 (s, 6H), 1.5-1.7 (m, 2H), 1.2-1.4 (m, 10H), 0.97 (d, J = 6.6 Hz, 6H), 0.86 (t, J = 6.4 Hz, 3H)<br>δ 9.29 (s, 1H), 6.9-8.3 (m, 11H), 3.69 (s, 2H), 2.85-3.0 (m, 1H), 2.58 (t, J = 7.7 Hz, 2H), 1.59 (s, 6H), 1.5-1.7 (m, 2H), 1.2-1.4 (m, 10H), 0.97 (d, J = 6.6 Hz, 6H), 0.86 (t, J = 6.4 Hz, 3H) |
| 4-30 | (ii) | | mixture of P-1 and P-3 7:3 | δ 9.68 (s, 1H), 6.8-8.3 (m, 11H), 3.59 (s, 2H), 2.82 (sep, J = 6.7 Hz, 1H), 1.65-1.8 (m, 5H), 1.59 (s, 6H), 1.1-1.5 (m, 6H), 0.98 (d, J = 6.6 Hz, 6H)<br>δ 9.29 (s, 1H), 6.8-8.3 (m, 11H), 3.69 (s, 2H), 2.85-3.0 (m, 1H), 1.65-1.8 (m, 5H), 1.59 (s, 6H), 1.1-1.5 (m, 6H), 1.04 (d, J = 6.6 Hz, 6H) |
| 4-31 | (ii) | | mixture of P-1 and P-3 7:3 | δ 10.17 (s, 1H), 6.3-8.3 (m, 10H), 3.62 (s, 2H), 2.95 (sep, J = 5.2 Hz, 1H), 1.57 (s, 6H), 1.03 (d, J = 5.3 Hz, 6H)<br>δ 9.69 (s, 1H), 6.3-8.3 (m, 10H), 3.71 (s, 2H), 3.24 (sep, J = 5.2 Hz, 1H), 1.54 (s, 6H), 1.09 (d, J = 5.3 Hz, 6H) |
| 4-32 | (ii) | | mixture of P-1 and P-3 5:5 | δ 9.81 (s, 1H), 8.0-8.15 (m, 1H), 7.7-7.85 (m, 2H), 6.9-7.6 (m, 8H), 3.62 (s, 2H), 2.58 (t, J = 7.9 Hz, 2H), 2,3-2.45 (m, 2H), 1.57 (s, 6H), 1.0-1.4 (m, 16H), 0.85-1.0 (m, 3H), 0.7-0.85 (m, 3H)<br>δ 9.72 (s, 1H), 8.25-8.35 (m, 1H), 7.85-7.95 (m, 2H), 6.9-7.6 (m, 8H), 3.72 (s, 2H), 2.58 (t, J = 7.9 Hz, 2H), 2,3-2.45 (m, 2H), 1.54 (s, 6H), 1.0-1.4 (m, 16H), 0.85-1.0 (m, 3H), 0.7-0.85 (m, 3H) |
| 4-33 | (ii) | | mixture of P-1 and P-3 8:2 | δ 9.61 (s, 1H), 6.8-8.3 (m, 11H), 3.59 (s, 2H), 2.58 (t, J = 7.5 Hz, 2H), 2.4-2.55 (m, 1H), 1.59 (s, 6H), 1.0-1.7 (m, 18H), 0.8-0.9 (m, 3H)<br>δ 9.28 (s, 1H), 6.8-8.3 (m, 11H), 3.69 (s, 2H), 2.58 (t, J = 7.5 Hz, 2H), 2.4-2.55 (m, 1H), 1.59 (s, 6H), 1.0-1.7 (m, 18H), 0.8-0.9 (m, 3H) |
| 4-34 | (ii) | P-1 | | δ 10.25 (s, 1H), 8.1-8.2 (m, 1H), 7.8-7.9 (m, 1H), 7.77 (d, J = 7.9 Hz, 1H), 7.45-7.55 (m, 3H), 7.35 (t J = 8.1 Hz, 1H), 7.15-7.25 (m, 4H), 7.07 (d, J = 7.1 Hz, 1H), 6.3-6.4 (m, 1H), 5.95-6.05 (m, 1H), 3.71 (s, 2H), 2.59 (t, J = 7.8 Hz, 2H), 1.63 (s, 6H), 1.45-1.7 (m, 2H), 1.2-1.45 (m, 6H), 0.8-0.9 (m, 3H) |
| 4-35 | (ii) | | mixture of P-1 and P-3 8:2 | δ 9.74 (s, 1H), 7.1-7.35 (m, 5H), 6.8-6.95 (m, 1H), 6.6-6.7 (m, 1H), 3.42 (s, 2H), 2.89 (sep, J = 6.5 Hz, 1H), 2.57 (t, J = 7.7 Hz, 2H), 1.57 (s, 6H), 1.45-1.65 (m, 2H), 1.2-1.4 (m, 6H), 1.06 (d, J = 6.5 Hz, 6H), 0.8-0.9 (m, 3H)<br>δ 9.41 (s, 1H), 7.1-7.35 (m, 5H), 6.8-6.95 (m, 1H), 6.7-6.8 (m, 1H), 3.48 (s, 2H), 2.95-3.1 (m, 1H), 2.57 (t, J = 7.7 Hz, 2H), 1.57 (s, 6H), 1.45-1.65 (m, 2H), 1.2-1.4 (m, 6H), 1.06 (d, J = 6.5 Hz, 6H), 0.8-0.9 (m, 3H) |
| 4-36 | (ii) | | mixture of P-1 and P-3 8:2 | δ 9.74 (s, 1H), 7.1-7.35 (m, 5H), 6.8-6.95 (m, 1H), 6.6-6.7 (m, 1H), 3.43 (s, 2H), 2.8-2.95 (m, 1H), 2.57 (t, J = 7.7 Hz, 2H), 1.52 (s, 6H), 1.5-1.65 (m, 2H), 1.2-1.4 (m, 10H), 1.06 (d, J = 6.2 Hz, 6H), 0.85 (t, J = 6.9 Hz, 3H)<br>δ 9.45-9.55 (m, 1H), 7.1-7.35 (m, 5H), 6.8-6.95 (m, 1H), 6.7-6.8 (m, 1H), 3.47 (s, 2H), 2.95-3.1 (m, 1H), 2.57 (t, J = 7.7 Hz, 2H), 1.52 (s, 6H), 1.5-1.65 (m, 2H), 1.2-1.4 (m, 10H), 1.06 (d, J = 6.2 Hz, 6H), 0.85 (t, J = 6.9 Hz, 3H) |
| 4-37 | (ii) | | mixture of P-1 and P-3 7:3 | δ 9.76 (s, 1H), 7.1-7.35 (m, 5H), 6.8-6.95 (m, 1H), 6.6-6.8 (m, 1H), 3.42 (s, 2H), 2.89 (sep, J = 6.5 Hz, 1H), 2.4-2.55 (m, 1H), 1.65-1.9 (m, 5H), 1.52 (s, 6H), 1.1-1.5 (m, 5H), 1.07 (d, J = 6.6 Hz, 6H)<br>δ 9.41 (s, 1H), 7.1-7.35 (m, 5H), 6.8-6.95 (m, 1H), 6.6-6.8 (m, 1H), 3.4-3.5 (m, 2H), 2.95-3.1 (m, 1H), 2.4-2.55 (m, 1H), 1.65-1.9 (m, 5H), 1.52 (s, 6H), 1.1-1.5 (m, 5H), 1.07 (d, J = 6.6 Hz, 6H) |
| 4-38 | (ii) | | mixture of P-1 and P-3 7:3 | δ 10.15 (s, 1H), 7.61 (s, 1H), 7.26 (d, J = 3.8 Hz, 1H), 6.6-6.95 (m, 2H), 6.50 (s, 1H), 6.32 (d, J = 5.4 Hz, 1H), 3.42 (s, 2H), 3.02 (sep, J = 5.2 Hz, 1H), 1.52 (s, 6H), 1.12 (d, J = 5.2 Hz, 6H)<br>δ 9.82 (s, 1H), 7.59 (s, 1H), 7.29 (d, J = 3.7 Hz, 1H), 6.6-6.95 (m, 2H), 6.50 (s, 1H), 6.32 (d, J = 5.4 Hz, 1H), 3.50 (s, 2H), 3.02 (sep, J = 5.2 Hz, 1H), 1.50 (s, 6H), 1.19 (d, J = 5.3 Hz, 6H) |
| 4-39 | (ii) | P-1 | | δ 9.84 (s, 1H), 7.1-7.5 (m, 5H), 6.8-6.95 (m, 1H), 6.6-6.8 (m, 1H), 3.4-3.6 (m, 2H), 2.56 (t, J = 7.7 Hz, 2H), 2.3-2.45 (m, 2H), 1.50 (s, 6H), 1.05-1.65 (m, 16H), 0.75-0.9 (m, 6H) |
| 4-40 | (ii) | | mixture of P-1 and P-3 7:3 | δ 9.70 (s, 1H), 7.1-7.35 (m, 5H), 6.8-6.95 (m, 1H), 6.6-6.8 (m, 1H), 3.42 (s, 2H), 2.57 (t, J = 7.6 Hz, 2H), 2.4-2.55 (m, 1H), 1.52 (s, 6H), 1.05-1.75 (m, 18H), 0.8-0.9 (m, 3H)<br>δ 9.34 (s, 1H), 7.1-7.35 (m, 5H), 6.8-6.95 (m, 1H), 6.6-6.8 (m, 1H), 3.48 (s, 2H), 2.57 (t, J = 7.6 Hz, 2H), 2.4-2.55 (m, 1H), 1.52 (s, 6H), 1.05-1.75 (m, 18H), 0.8-0.9 (m, 3H) |
| 4-41 | (ii) | P-1 | | δ 10.30 (s, 1H), 7.53 (s, 1H), 7.28 (d, J = 5.2 Hz, 1H), 7.20 (s, 4H), 6.90 (t, J = 3.5 Hz, 1H), 6.73 (s, 1H), 6.38 (s, 1H), 6.07 (s, 1H), 3.50 (s, 2H), 2.59 (t, J = 7.5 Hz, 2H), 1.58 (s, 6H), 1.5-1.65 (m, 2H), 1.2-1.4 (m, 6H), 0.8-0.9 (m, 3H) |

TABLE 21-continued

| No. | measuring conditions | tautomers | mixing ratio | 1H NMR chemical shift or melting point |
|---|---|---|---|---|
| 4-42 | (ii) | | mixture of P-1 and P-3 9:1 | δ 9.57 (s, 1H), 7.1-7.25 (m, 4H), 2.87 (sep, J = 7.1 Hz, 1H), 2.56 (t, J = 8.0 Hz, 2H), 1.62 (s, 6H), 1.45-1.85 (m, 13H), 1.25-1.4 (m, 12H), 1.10 (d, J = 6.8 Hz, 6H), 0.8-0.9 (m, 3H)<br>δ 9.60 (s, 1H), 7.1-7.25 (m, 4H), 3.0-3.15 (m, 1H), 2.56 (t, J = 8.0 Hz, 2H), 1.62 (s, 6H), 1.45-1.85 (m, 13H), 1.25-1.4 (m, 12H), 1.21 (d, J = 7.1 Hz, 6H), 0.8-0.9 (m, 3H) |
| 4-43 | (ii) | P-1 | | δ 9.57 (s, 1H), 7.17 (s, 4H), 2.8-2.95 (m, 1H), 2.56 (t, J = 7.8 Hz, 2H), 1.62 (s, 6H), 1.2-1.9 (m, 29H), 1.10 (d, J = 6.7 Hz, 6H), 0.86 (t, J = 7.2 Hz, 3H) |
| 4-44 | (ii) | P-1 | | δ 9.58 (s, 1H), 7.19 (dd, J = 8.2 Hz, 13.4 Hz, 4H), 2.8-2.95 (m, 1H), 2.4-2.55 (m, 1H), 1.61 (s, 6H), 1.15-1.9 (m, 27H), 1.11 (d, J = 6.8 Hz, 6H) |
| 4-45 | (ii) | | mixture of P-1 and P-3 8:2 | δ 9.94 (s, 1H), 7.58 (s, 1H), 6.4-6.5 (m, 1H), 6.27 (d, J = 2.4 Hz, 1H), 3.02 (sep, J = 5.2 Hz, 1H), 1.64 (s, 6H), 1.3-1.85 (m, 17H), 1.13 (d, J = 5.1 Hz, 6H)<br>δ 9.94 (s, 1H), 7.56 (s, 1H), 6.67 (d, J = 2.2 Hz, 1H), 6.4-6.5 (m, 1H), 3.35-3.45 (m, 1H), 1.64 (s, 6H), 1.3-1.85 (m, 17H), 1.26 (d, J = 5.3 Hz, 6H) |
| 4-46 | (ii) | P-1 | | δ 9.64 (s, 1H), 7.36 (d, J = 7.8 Hz, 2H), 7.13 (d, J = 8.7 Hz, 2H), 2.45-2.65 (m, 4H), 1.59 (s, 6H), 1.05-1.85 (m, 33H), 0.7-0.9 (m, 6H) |
| 4-47 | (ii) | P-1 | | δ 9.53 (s, 1H), 7.1-7.2 (m, 4H), 2.56 (t, J = 8.0 Hz, 2H), 2.45-2.55 (m, 1H), 1.61 (s, 6H), 1.1-1.8 (m, 35H), 0.86 (t, J = 6.8 Hz, 3H) |
| 4-48 | (ii) | P-1 | | δ 10.04 (s, 1H), 7.56 (s, 1H), 7.17 (s, 4H), 6.40 (s, 1H), 6.09 (d, J = 2.9 Hz, 1H), 2.58 (t, J = 7.7 Hz, 2H), 1.75-1.9 (m, 6H), 1.65 (s, 6H), 1.2-1.7 (m, 19H), 0.8-0.95 (m, 3H) |
| 4-49 | (ii) | | mixture of P-1 and P-3 6:4 | δ 10.21 (s, 1H), 7.2-7.4 (m, 7H), 7.05 (d, J = 4.9 Hz, 2H), 2.93 (s, 2H), 2.8-2.9 (m, H), 2.5-2.6 (m, 2H), 1.5-1.65 (m, 2H), 0.9-1.35 (m, 16H), 0.86 (t, J = 5.3 Hz, 3H)<br>δ 9.73 (s, 1H), 7.2-7.4 (m, 7H), 6.96 (d, J = 4.6 Hz, 2H), 2.99 (s, 2H), 2.9-3.05 (m, 1H), 2.5-2.6 (m, 2H), 1.5-1.65 (m, 2H), 0.9-1.35 (m, 16H), 0.86 (t, J = 5.3 Hz, 3H) |
| 4-50 | (ii) | | mixture of P-1 and P-3 6:4 | δ 10.21 (s, 1H), 7.1-7.3 (m, 7H), 7.05 (d, J = 4.8 Hz, 2H), 2.93 (s, 2H), 2.8-2.9 (m, 1H), 2.5-2.6 (m, 2H), 1.5-1.6 (m, 2H), 0.9-1.35 (m, 20H), 0.86 (t, J = 5.4 Hz, 3H)<br>δ 9.72 (s, 1H), 7.1-7.3 (m, 7H), 6.95 (d, J = 4.3 Hz, 2H), 2.99 (s, 2H), 2.9-3.0 (m, 1H), 2.5-2.6 (m, 2H), 1.5-1.6 (m, 2H), 0.9-1.35 (m, 20H), 0.86 (t, J = 5.4 Hz, 3H) |
| 4-51 | (ii) | | mixture of P-1 and P-3 6:4 | δ 10.21 (s, 1H), 7.1-7.3 (m, 7H), 7.05 (d, J = 4.6 Hz, 2H), 2.93 (s, 2H), 2.8-2.9 (m, 1H), 2.4-2.6 (m, 1H), 1.75-1.85 (m, 4H), 0.95-1.5 (m, 16H)<br>δ 9.74 (s, 1H), 7.1-7.3 (m, 7H), 6.9-7.0 (m, 2H), 2.98 (s, 2H), 2.9-3.0 (m, 1H), 2.4-2.6 (m, 1H), 1.65-1.75 (m, 4H), 0.95-1.5 (m, 16H) |
| 4-52 | (ii) | | mixture of P-1 and P-3 6:4 | δ 10.57 (s, 1H), 7.53 (s, 1H), 7.1-7.25 (m, 5H), 7.04 (d, J = 4.6 Hz, 1H), 6.62 (d, J = 2.4 Hz, 1H), 6.45-6.5 (m, 1H), 2.92 (s, 2H), 2.9-3.05 (m, 1H), 1.0-1.25 (m, 8H), 0.85-1.0 (m, 2H)<br>δ 10.21 (s, 1H), 7.59 (s, 1H), 7.1-7.25 (m, 5H), 6.97 (d, J = 4.5 Hz, 1H), 6.4-6.5 (m, 1H), 6.28 (d, J = 2.4 Hz, 1H), 2.98 (s, 2H), 2.75-2.85 (m, 1H), 1.0-1.25 (m, 8H), 0.85-1.0 (m, 2H) |
| 4-53 | (ii) | | mixture of P-1 and P-3 7:3 | δ 10.41 (s, 1H), 6.95-7.45 (m, 9H), 2.95-3.1 (m, 2H), 2.55 (t, J = 5.8 Hz, 2H), 2.40 (d, J = 5.8 Hz, 2H), 1.5-1.65 (m, 2H), 1.0-1.4 (m, 16H), 0.75-0.95 (m, 8H)<br>δ 9.80 (s, 1H), 6.95-7.45 (m, 9H), 2.95-3.1 (m, 2H), 2.55 (t, J = 5.8 Hz, 2H), 2.40 (d, J = 5.8 Hz, 2H), 1.5-1.65 (m, 2H), 1.0-1.4 (m, 16H), 0.75-0.95 (m, 8H) |
| 4-54 | (ii) | | mixture of P-1 and P-3 6:4 | δ 10.22 (s, 1H), 7.1-7.3 (m, 7H), 7.0-7.1 (m, 2H), 2.92 (s, 2H), 2.56 (t, J = 5.8 Hz, 2H), 2.45-2.7 (m, 1H), 1.5-1.65 (m, 8H), 1.25-1.5 (m, 8H), 1.0-1.25 (m, 4H), 0.8-0.95 (m, 5H))<br>δ 9.69 (s, 1H), 7.1-7.3 (m, 7H), 6.9-7.0 (m, 2H), 2.98 (s, 2H), 2.56 (t, J = 5.8 Hz, 2H), 2.45-2.7 (m, 1H), 1.5-1.65 (m, 8H), 1.25-1.5 (m, 8H), 1.0-1.25 (m, 4H), 0.8-0.95 (m, 5H)) |
| 4-55 | (ii) | P-1 | | δ 10.21 (s, 1H), 7.53 (s, 1H), 7.05-7.35 (m, 9H), 6.40 (s, 1H), 6.08 (s, 1H), 3.10 (s, 2H), 2.57 (t, J = 5.8 Hz, 2H), 1.5-1.65 (m, 2H), 1.2-1.4 (m, 6H), 0.9-1.0 (m, 2H), 0.8-0.9 (m, 5H) |
| 4-56 | (ii) | | mixture of P-1 and P-3 7:3 | δ 9.68 (s, 1H), 7.1-7.35 (m, 4H), 6.85-7.1 (m, 2H), 6.65-6.85 (m, 2H), 3.09 (s, 2H), 2.86 (sep, J = 6.8 Hz, 1H), 2.57 (t, J = 7.4 Hz, 2H), 2.22 (s, 3H), 1.50 (s, 6H), 1.4-1.65 (m, 2H), 1.15-1.4 (m, 10H), 1.02 (d, J = 6.2 Hz, 6H), 0.8-0.95 (m, 3H)<br>δ 9.29 (s, 1H), 7.1-7.35 (m, 4H), 6.85-7.1 (m, 4H), 3.14 (s, 2H), 2.95-3.05 (m, 1H), 2.57 (t, J = 7.4 Hz, 2H), 2.22 (s, 3H), 1.50 (s, 6H), 1.4-1.65 (m, 2H), 1.15-1.4 (m, 10H), 1.0-1.1 (m, 6H), 0.8-0.95 (m, 3H) |
| 4-57 | (ii) | | mixture of P-1 and P-3 7:3 | δ 9.69 (s, 1H), 7.15-7.2 (m, 4H), 6.85-7.0 (m, 2H), 6.73 (d, J = 7.9 Hz, 2H), 3.09 (s, 2H), 2.85 (sep, J = 6.7 Hz, 1H), 2.45-2.55 (m, 1H), 2.22 (s, 3H), 1.65-1.9 (m, 5H), 1.50 (s, 6H), 1.15-1.5 (m, 5H), 1.02 (d, J = 6.8 Hz, 6H)<br>δ 9.29 (s, 1H), 7.30 (d, J = 7.9 Hz, 2H), 7.15-7.2 (m, 2H), 6.85-7.0 (m, 4H), 3.14 (s, 2H), 2.95-3.05 (m, 1H), 2.45-2.55 (m, 1H), 2.22 (s, 3H), 1.65-1.9 (m, 5H), 1.50 (s, 6H), 1.15-1.5 (m, 5H), 1.06 (d, J = 7.1 Hz, 6H) |
| 4-58 | (ii) | | mixture of P-1 and P-3 7:3 | δ 10.11 (s, 1H), 7.61 (s, 1H), 6.96 (d, J = 5.6 Hz, 2H), 6.74 (d, J = 5.7 Hz, 2H), 6.50 (s, 1H), 6.32 (s, 1H), 3.10 (s, 2H), 2.98 (sep, J = 5.3 Hz, 1H), 2.22 (s, 3H), 1.49 (s, 6H), 1.07 (d, J = 5.2 Hz, 6H)<br>δ 9.70 (s, 1H), 7.59 (s, 1H), 6.85-7.05 (m, 4H), 6.50 (s, 1H), 6.32 (s, 1H), 3.17 (s, 2H), 2.98 (sep, J = 5.3 Hz, 1H), 2.22 (s, 3H), 1.46 (s, 6H), 1.15 (d, J = 4.6 Hz, 6H) |

TABLE 21-continued

| No. | measuring conditions | tautomers | mixing ratio | 1H NMR chemical shift or melting point |
|---|---|---|---|---|
| 4-59 | (ii) | | mixture of P-1 and P-3 5:5 | δ 9.79 (s, 1H), 7.1-7.3 (m, 4H), 6.9-7.05 (m, 2H), 6.77 (d, J = 7.7 Hz, 2H), 3.18 (s, 2H), 2.57 (t, J = 7.5 Hz, 2H), 2.35-2.5 (m, 2H), 2.22 (s, 3H), 1.49 (s, 6H), 1.55-1.65 (m, 2H), 1.2-1.45 (m, 8H), 1.05-1.2 (m, 6H), 0.85-0.9 (m, 3H), 0.7-0.85 (m, 3H) <br> δ 9.71 (s, 1H), 7.42 (d, J = 7.9 Hz, 2H), 7.1-7.3 (m, 4H), 6.9-7.05 (m, 2H), 3.11 (s, 2H), 2.57 (t, J = 7.5 Hz, 2H), 2.35-2.5 (m, 2H), 2.22 (s, 3H), 1.46 (s, 6H), 1.55-1.65 (m, 2H), 1.2-1.45 (m, 8H), 1.05-1.2 (m, 6H), 0.85-0.9 (m, 3H), 0.7-0.85 (m, 3H) |
| 4-60 | (ii) | | mixture of P-1 and P-3 7:3 | δ 9.64 (s, 1H), 7.15-7.25 (m, 4H), 6.85-7.05 (m, 2H), 6.65-6.8 (m, 2H), 3.09 (s, 2H), 2.58 (t, J = 7.8 Hz, 2H), 2.4-2.65 (m, 1H), 2.22 (s, 3H), 1.45-1.75 (m, 8H), 1.50 (s, 6H), 1.25-1.4 (m, 8H), 1.05-1.25 (m, 2H), 0.8-0.95 (m, 3H) <br> δ 9.2-9.3 (m, 1H), 7.15-7.35 (m, 4H), 6.85-7.05 (m, 4H), 3.1-3.2 (m, 2H), 2.58 (t, J = 7.8 Hz, 2H), 2.4-2.65 (m, 1H), 2.22 (s, 3H), 1.45-1.75 (m, 8H), 1.50 (s, 6H), 1.25-1.4 (m, 8H), 1.05-1.25 (m, 2H), 0.8-0.95 (m, 3H) |
| 4-61 | (ii) | P-1 | | δ 10.23 (s, 1H), 7.52 (s, 1H), 7.20 (s, 4H), 7.00 (d, J = 7.4 Hz, 2H), 6.86 (d, J = 7.8 Hz, 2H), 6.37 (d, J = 1.6 Hz, 1H), 6.03 (d, J = 2.82 Hz, 1H), 3.19 (s, 2H), 2.59 (t, J = 7.8 Hz, 2H), 2.22 (s, 3H), 1.54 (s, 6H), 1.45-1.7 (m, 2H), 1.2-1.45 (m, 6H), 0.8-0.9 (m, 3H) |
| 4-62 | (ii) | P-1 | | δ 7.22 (d, J = 8.1 Hz, 2H), 7.11 (d, J = 8.2 Hz, 2H), 6.99 (d, J = 7.7 Hz, 2H), 6.69 (d, J = 7.9 Hz, 2H), 4.11 (q, J = 7.1 Hz, 2H), 3.01 (s, 2H), 2.9-3.0 (m, 1H), 2.58 (t, J = 7.8 Hz, 2H), 2.23 (s, 3H), 1.45-1.65 (m, 2H), 1.51 (s, 6H), 1.2-1.4 (m, 6H), 1.09 (d, J = 6.9 Hz, 6H), 1.07 (t, J = 7.1 Hz, 3H), 0.8-0.9 (m, 3H) |
| 4-71 | (i) | P-1 | | δ 7.15-7.63 (m, 8H), 6.90-6.98 (m, 2H), 3.17 (s, 2H), 2.60-2.74 (m, 1H), 1.64 (s, 6H), 0.96 (d, j = 6.9 Hz, 6H) |
| 4-72 | | | | m.p. 117 to 119° C. |
| 4-73 | | | | m.p. 69 to 71° C. |
| 4-74 | | | | m.p. 113 to 115° C. |
| 4-75 | | | | m.p. 102 to 104° C. |
| 4-76 | | | | m.p. 101 to 103° C. |
| 4-80 | | | | m.p. 88 to 90° C. |
| 4-81 | | | | m.p. 58 to 60° C. |
| 4-82 | | | | m.p. 133 to 135° C. |
| 4-83 | | | | m.p. 109 to 111° C. |
| 4-84 | | | | m.p. 108 to 110° C. |
| 4-85 | | | | m.p. 88 to 90° C. |
| 4-86 | | | | m.p. 140 to 142° C. |
| 4-87 | | | | m.p. 108 to 110° C. |
| 4-88 | (i) | P-1 | | δ 12.7-13.1 (br, 1H), 7.12-7.21 (m, 3H), 6.84-6.94 (m, 2H), 3.11 (s, 2H), 3.04-3.15 (m, 1H), 2.42 (s, 3H), 1.58 (s, 6H), 1.27 (d, J = 6.9 Hz, 6H) |
| 4-89 | (i) | P-1 | | δ 10.7-11.4 (br, 1H), 7.12-7.22 (m, 3H), 6.84-6.95 (m, 2H), 3.87 (s, 3H), 3.16 (s, 2H), 2.98-3.12 (m, 1H), 2.25 (s, 3H), 1.57 (s, 6H),. 1.21 (d, J = 6.8 Hz, 6H) |
| 4-90 | | | | m.p. 149 to 151° C. |
| 4-91 | (ii) | P-1 | | δ 9.6-9.9 (br, 1H), 7.1-7.25 (m, 3H), 6.8-6.9 (m, 2H), 4.02 (t, J = 6.6 Hz, 2H), 3.11 (s, 2H), 3.07 (sep, J = 7.5 Hz, 1H), 2.11 (s, 3H), 1.5-1.7 (m, 2H), 1.49 (s, 6H), 1.2-1.4 (m, 6H), 1.09 (d, J = 6.8 Hz, 6H), 0.87 (t, J = 6.8 Hz, 3H) |

Now, the present invention will be described in further detail with reference to Assay Examples. The $CO_2$ concentration (%) in a $CO_2$ incubator is expressed by the ratio of $CO_2$ in the atmosphere in vol %. PBS denotes phosphate-buffered saline (Sigma-Aldrich Japan), and FBS denotes fetal bovine serum (Hana-Nesco Bio).

Assay Example 1

Expansion of $CD34^+$ Cells and $CD34^+CD38^-$ Cells Using Human Cord Blood-Derived $CD34^+$ Cells Human cord blood-derived $CD34^+$ cells were purchased from Lonza and plated on a 24-well plate (Corning) (10000 cells/1 mL/well). As the culture medium, StemSpan SFEM (StemCell Technologies) containing 100 ng/mL SCF (Wako Pure Chemical Industries) and 20 ng/mL TPO (PeproTech) in terms of final concentration was used, and Compound No. 2-40 dissolved in dimethyl sulfoxide was added to the medium in an amount of 0.1% (v/v) to a final concentration of 0.1 to 1 μg/mL. As a negative control, the medium containing 0.1% (v/v) dimethyl sulfoxide was used.

After the cells were incubated in liquid culture at 37° C. for 7 days in a $CO_2$ incubator (5% $CO_2$), the number of viable cells was counted by trypan blue assay. The number of $CD34^+$ cells and $CD34^+CD38^-$ cells was calculated as follows. After the incubation, the cells in the liquid culture was stained with a CD34 antibody (APC, Becton, Dickinson and Company) and a CD38 antibody (PE, Becton, Dickinson and Company), then washed with PBS(−) containing 2% (v/v) FBS and stained with propidium iodide (Sigma-Aldrich Japan) added to a final concentration of 5 μg/mL. The stained cells were analyzed with a BD FACSCANTO™ II flow cytometer (Becton, Dickinson and Company) to determined the proportions of $CD34^+$ cells and $CD34^+CD38^-$ cells, which was multiplied by the number of viable cells to calculate the numbers of $CD34^+$ cells and $CD34^+CD38^-$ cells.

The results demonstrate that the compounds of the present invention showed excellent expansion activity on $CD34^+$ cells and $CD34^+CD38^-$ cells and have expansion activity on hematopoietic stem cells and hematopoietic progenitor cells. The expansion efficiencies in the presence of 0.1 to 1 μg/mL of Compound No. 2-40 based on the number of $CD34^+$ cells in the absence of the compound are shown in FIG. 1. The expansion efficiencies in the presence of 0.1 to 1 μg/mL of Compound No. 2-40 based on the number of $CD34^+CD38^-$ cells in the absence of the compound are shown in FIG. 2.

Assay Example 2

Expansion of CD34+CD38− Cells Using Human Cord Blood-Derived CD34+ Cells

Human cord blood-derived CD34+ cells purchased from the same supplier as in Assay Example 1 were plated on a 24-well plate (Corning) (10000 cells/1 mL/well). As the culture medium, StemSpan SFEM (StemCell Technologies) containing 100 ng/mL SCF (Wako Pure Chemical Industries) was used, and the combination of 20 ng/mL TPO (PeproTech) in terms of final concentration with 100 ng/mL Flt3-ligand (FL, Wako Pure Chemical Industries) in terms of final concentration or 1 μg/mL Compound No. 2-40 in terms of final concentration was added.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Assay Example 1.

The results demonstrate that the compound of the present invention showed excellent expansion activity on CD34+CD38− cells in the presence of SCF alone, in the presence of SCF and TPO and in the presence of SCF, TPO and FL, as compared with when the compound of the present invention was not added.

The expansion efficiencies in the presence of Compound No. 2-40 and various cyclokines based on the number of CD34+CD38− cells in the presence of 100 ng/mL SCF in terms of final concentration in the absence of the compound are shown in FIG. 3.

Assay Example 3

Expansion of CD34+CD38− Cells Using Human Cord Blood-Derived CD34+ Cells

Human cord blood-derived CD34+ cells purchased from the same supplier as in Assay Example 1 were plated on a 24-well plate (Corning) (10000 cells/1 mL/well). As the culture medium, StemSpan SFEM (StemCell Technologies) containing 100 ng/mL SCF (Wako Pure Chemical Industries) in terms of final concentration and 20 ng/mL TPO (PeproTech) in terms of final concentration was used, and Compounds Nos. 1-01 to 4-91 dissolved in dimethyl sulfoxide were added in an amount of 0.1% (v/v) to a final concentration of 0.01 to 10 μg/mL. As a negative control, the medium containing 0.1% (v/v) dimethyl sulfoxide was used.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Assay Example 1.

The results demonstrate that the compounds of the present invention showed excellent expansion activities on CD34+ cells and CD34+CD38− cells and have expansion activity on hematopoietic stem cells and hematopoietic progenitor cells. The expansion efficiencies in the presence of 0.01 to 10 μg/mL of the compounds based on the number of CD34+CD38− cells in the absence of the compounds are shown in Table 22 on a scale of A for expansion efficiencies of 4 or greater, B for expansion efficiencies of at least 3 and less than 4, and C for expansion efficiencies of at least 1.5 and less than 3.

TABLE 22

| Compound No. | Expansion efficiency |
| --- | --- |
| 1-01 | C |
| 1-02 | A |
| 1-03 | C |
| 1-04 | A |
| 1-07 | A |
| 2-01 | B |
| 2-02 | B |
| 2-03 | C |
| 2-04 | B |
| 2-06 | A |
| 2-07 | A |
| 2-09 | B |
| 2-10 | A |
| 2-12 | A |
| 2-14 | A |
| 2-15 | A |
| 2-16 | A |
| 2-18 | C |
| 2-19 | B |
| 2-20 | A |
| 2-21 | A |
| 2-22 | A |
| 2-23 | B |
| 2-24 | B |
| 2-25 | A |
| 2-28 | A |
| 2-29 | A |
| 2-30 | B |
| 2-31 | A |
| 2-32 | B |
| 2-33 | B |
| 2-49 | B |
| 2-34 | A |
| 2-35 | A |
| 2-36 | A |
| 2-37 | A |
| 2-38 | B |
| 2-39 | B |
| 2-40 | A |
| 2-43 | A |
| 2-44 | B |
| 2-45 | B |
| 2-46 | B |
| 2-47 | A |
| 2-48 | A |
| 2-50 | B |
| 3-01 | A |
| 3-02 | A |
| 3-03 | A |
| 3-05 | B |
| 3-06 | A |
| 3-07 | A |
| 3-08 | A |
| 3-09 | C |
| 3-10 | A |
| 3-11 | A |
| 3-12 | B |
| 3-16 | A |
| 3-17 | C |
| 3-18 | A |
| 3-19 | C |
| 3-20 | A |
| 3-21 | C |
| 3-22 | A |
| 3-23 | A |
| 3-24 | C |
| 3-25 | A |
| 3-27 | A |
| 3-28 | A |
| 3-29 | A |
| 3-30 | A |
| 3-32 | A |
| 3-33 | A |
| 3-34 | A |

TABLE 22-continued

| Compound No. | Expansion efficiency |
| --- | --- |
| 3-35 | C |
| 3-36 | A |
| 3-37 | A |
| 3-38 | A |
| 3-39 | A |
| 3-40 | B |
| 3-41 | A |
| 3-43 | B |
| 3-46 | C |
| 3-47 | C |
| 3-48 | B |
| 3-49 | C |
| 4-01 | C |
| 4-12 | C |
| 4-13 | B |
| 4-14 | C |
| 4-15 | B |
| 4-16 | B |
| 4-23 | A |
| 4-28 | A |
| 4-29 | A |
| 4-30 | A |
| 4-32 | B |
| 4-33 | A |
| 4-34 | C |
| 4-35 | B |
| 4-36 | A |
| 4-37 | C |
| 4-39 | C |
| 4-40 | C |
| 4-41 | A |
| 4-42 | A |
| 4-43 | A |
| 4-44 | A |
| 4-45 | C |
| 4-46 | B |
| 4-47 | B |
| 4-48 | A |
| 4-49 | B |
| 4-50 | C |
| 4-51 | C |
| 4-53 | A |
| 4-54 | A |
| 4-55 | C |
| 4-56 | A |
| 4-57 | B |
| 4-59 | B |
| 4-60 | B |
| 4-61 | C |
| 4-62 | A |
| 4-72 | B |
| 4-73 | B |
| 4-74 | A |
| 4-75 | B |
| 4-76 | C |
| 4-80 | B |
| 4-81 | B |
| 4-82 | C |
| 4-83 | B |
| 4-84 | B |
| 4-85 | C |
| 4-86 | C |
| 4-87 | A |
| 4-88 | C |
| 4-89 | C |
| 4-91 | B |

Assay Example 4

Expansion of CD34+CD38− Cells Using Human Cord Blood-Derived CD34+CD38− Cells

Human cord blood-derived CD34+ cells purchased from the same supplier as in Assay Example 1 were stained with an anti CD34 antibody (APC, Becton Dickinson) and an anti CD38 antibody (PE, Becton Dickinson) and sorted by a flow-cytometer JSAN (Bay Bioscience) to collect CD34+CD38− cells. The collected cells were plated on a 24-well plate (Corning) (10000 cells/1 mL/well). As the culture medium, StemSpan SFEM (StemCell Technologies) containing 100 ng/mL SCF (Wako Pure Chemical Industries) in terms of final concentration and 20 ng/mL TPO in terms of final concentration was used, and Compound No. 2-40 dissolved in dimethyl sulfoxide was added in an amount of 0.1% (v/v) to the medium to a final concentration of 1 μg/mL. As a negative control, the medium containing 0.1% (v/v) dimethyl sulfoxide was used.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Assay Example 1.

The results demonstrate that the compound of the present invention showed excellent expansion activity on CD34+CD38− cells and have expansion activity on hematopoietic stem cells and hematopoietic progenitor cells. The expansion efficiencies in the presence of 1 μg/mL of Compound No. 2-40 based on the number of CD34+CD38− cells in the absence of the compound are shown in FIG. 4.

Assay Example 5

Expansion of HPP-CFU and CFU-GEMM Using Human Cord Blood-Derived CD34+ Cells

The effects of Compound No. 2-40 of the present invention on hematopoietic progenitor cells were measured by blood cell colony forming assay. The liquid cell cultures obtained in Assay Example 1 were poured into 3.5-cm Petri dishes with MethoCult GF H4435 culture medium (StemCell Technologies) at 500 cells/dish and incubated in a $CO_2$ incubator (5% $CO_2$, 37° C.) for 12 days. The numbers of HPP-CFC colonies and CFU-GEMM colonies in each plate were counted under a microscope according to the routine method. The assay was carried out at least in duplicate, and the numbers of HPP-CFC colonies and CFU-GEMM colonies were averaged and evaluated.

The results demonstrate that the compounds of the present invention remarkably stimulated formation of HPP-CFU colonies and CFU-GEMM colonies and have expansion activity on hematopoietic progenitor cells.

The results are shown in Table 23.

TABLE 23

| Specific Compound | Number of HPP-CFC colonies | Number of CFU-GEMM colonies |
| --- | --- | --- |
| None | 30 | 3 |
| Compound No. 2-40 | 37 | 7 |

Assay Example 6

Transplantation of Cell Culture into Immunodeficient (NOD/SCID) Mice

Human cord blood-derived CD34+ cells cultured in the presence of 1 μg/mL Compound No. 2-9, 2-37 or 2-40 in terms of final concentration or in the presence of 0.1% (v/v) dimethyl sulfoxide instead of them in the same manner as in Assay Example 1 were transplanted into at least five 7- to 8-week-old NOD/SCID mice by tail vein injection at $3 \times 10^4$ cells/mouse in terms of the initial number of CD34+ cells after a sublethal dose of irradiation (2.75 to 3 Gy). Eight weeks after the transplantation, the mice were killed, and the bone marrow cells were collected from both thighbones. Subsequently, the bone marrow cells were stained with a human CD45 antibody (APC, Becton, Dickinson and Company), then washed with PBS(−) containing 2% (v/v) FBS and stained with propidium iodide (Sigma-Aldrich Japan) added to a final concentration of 5 μg/mL. The stained cells were analyzed by flow cytometry to determine the proportion of human CD45+ cells in the bone marrow cells. The results demonstrate that the specific compounds of the present invention have excellent SRC expanding effects and have expansion activities on hematopoietic stem cells.

The engrafted proportion of human CD45+ cells in the mice transplanted with the CD34+ cells cultured in the presence of 1 μg/mL of Compound No. 2-9, 2-37 or 2-40 based on the proportion of human CD45+ cells in the mice transplanted with those in the absence of them are shown in FIG. 5.

INDUSTRIAL APPLICABILITY

The specific compounds of the present invention can expand human hematopoietic stem cells and/or hematopoietic progenitor cells in culture ex vivo in a less differentiated state when used as an active ingredient, as compared with in their absence. Cells expanded or transfected by using the compounds of the present invention are useful as a hematopoietic cell transplant for diseases accompanied by hematopoietic dysfunction, ischemia or immune dysfunction and hence application of the cells to cell therapy and gene therapy is expected.

The entire disclosures of Japanese Patent Application No. 2010-268775 filed on Dec. 1, 2010 and Japanese Patent Application No. 2011-217827 filed on Sep. 30, 2011 including specifications, claims, drawings and summaries are incorporated herein by reference in their entireties.

The invention claimed is:

1. A method of producing hematopoietic stem cells and/or hematopoietic progenitor cells, the method comprising expanding CD 34+ hematopoietic stem cells and/or hematopoietic progenitor cells by contacting the hematopoietic stem cells in an ex vivo culture with stem cell factor (SCF) and a pyrazole compound represented by the formula (1):

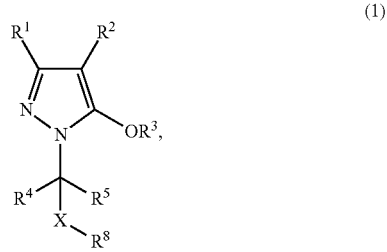

wherein:
$R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, and when a is an integer of at least 2, each $R^{11}$ may be identical with or different from one another;
$R^2$ is a hydrogen atom, a halogen atom, $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another, when there are two neighboring $R^{21}$'s, the two neighboring $R^{21}$'s may form —OCH$_2$O—, —OCH$_2$CH$_2$O— or —CH═CHCH═CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present;
$R^3$ is a hydrogen atom;
X is —(CR$^6$R$^7$)$_n$—;
each of $R^4$ and $R^5$ is independently $C_1$-$C_4$ alkyl;
each of $R^6$ and $R^7$ is a hydrogen atom;
$R^8$ is D2, F1, F2, phenyl or phenyl optionally substituted with k $R^{81}$'s, and when k is an integer of at least 2, each $R^{81}$ may be identical with or different from one another;
when there are two neighboring $R^{81}$'s, the two neighboring $R^{81}$'s may form —OCH$_2$O—, —CH$_2$CH$_2$CH$_2$— or —CH═CHCH═CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present;
D2 is an aromatic heterocyclic rings represented by the following structural formula,

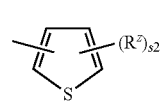

F1 to F2 are rings represented by the following formulae, respectively,

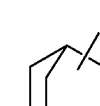

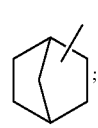

$R^z$ is a halogen atom, $C_1$-$C_6$ alkyl, phenoxy, or phenyl and when s2 is an integer of at least 2, each $R^z$ may be identical with or different from one another, and
$R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro;
$R^{12}$ is $C_1$-$C_6$ alkyl;
$R^{17}$ is —C(O)OR$^{12}$, or phenyl;
$R^{21}$ is a halogen atom, nitro, cyano, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, or phenyl;
$R^{81}$ is a halogen atom, $C_1$-$C_6$ alkyl, $C_1$-$C_6$ haloalkyl, $C_1$-$C_6$ alkoxy, phenyl or phenoxy;
Z is a halogen atom, or $C_1$-$C_6$ alkyl;
a, e, k are integers of from 1 to 5;
s2 is an integer of from 0 to 3;
n is an integer of 1;

a tautomer of the compound or a pharmaceutically acceptable salt or solvate thereof.

2. The method according to claim 1, wherein the hematopoietic stem cells and/or hematopoietic progenitor cells to be expanded ex vivo are CD34$^+$CD38$^-$ cells.

3. The method according to claim 1, wherein the cells to be expanded are HPP-CFU colony forming cells.

4. The method according to claim 1, wherein the cells to be expanded are SCID-repopulating cells (SRC).

5. The method according to claim 1, wherein the hematopoietic stem cells are obtained from the bone marrow, the liver, the spleen, peripheral blood or cord blood.

6. The method according to claim 5, wherein the hematopoietic stem cells are obtained from cord blood.

7. The method according to claim 6, comprising culturing hematopoietic stem cells and/or hematopoietic progenitor cells in the presence of at least one species selected from the group consisting of stem cell factor (SCF), thrombopoietin (TPO) and flk2/flt3 ligand (FL).

8. A method for producing transformed hematopoietic stem cells, the method comprising transferring a gene into hematopoietic stem cells and/or hematopoietic progenitor cells while culturing the hematopoietic stem cells and/or hematopoietic progenitor cells ex vivo in the presence of a compound represented by the following formula (I)

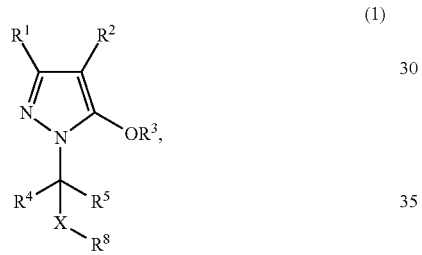

a tautomer or pharmaceutically acceptable salt of the compound or a solvate thereof, or expanding hematopoietic stem cells carrying a gene transferred into them by culturing the hematopoietic stem cells ex vivo in the presence of the compound represented by the formula (I), a tautomer or pharmaceutically acceptable salt of the compound or a solvate thereof,
wherein:
R$^1$ is C$_1$-C$_6$ alkyl, C$_1$-C$_6$ alkyl substituted with R$^{17}$, C$_1$-C$_6$ haloalkyl, C$_3$-C$_6$ cycloalkyl, phenyl or phenyl substituted with a R$^{11}$'s, and when a is an integer of at least 2, each R$^{11}$ may be identical with or different from one another;
R$^2$ is a hydrogen atom, a halogen atom, C$_1$-C$_6$ alkyl, D2, benzyl, benzyl having a benzene ring optionally substituted with e R$^{21}$'s, phenyl or phenyl optionally substituted with e R$^{21}$'s, when e is an integer of at least 2, each R$^{21}$ may be identical with or different from one another,
when there are two neighboring R$^{21}$'s, the two neighboring R$^{21}$'s may form —OCH$_2$O—, —OCH$_2$CH$_2$O— or —CH=CHCH=CH— to form, together with the carbon atoms attached to the two R$^{21}$'s, a 5-membered or 6-membered ring which may have one or more hydrogen atoms on the ring-constituting carbon atoms replaced by one or more Z's which may be identical with or different from one another, if two or more Z's are present;
R$^3$ is a hydrogen atom;
X is —(CR$^6$R$^7$)$_n$—;
each of R4 and R5 is independently C$_1$-C$_4$ alkyl;

each of R$^6$ and R$^7$ is a hydrogen atom;
R$^8$ is D2, F1, F2, phenyl or phenyl optionally substituted with k R$^{81}$'s, and when k is an integer of at least 2, each R$^{81}$ may be identical with or different from one another;
when there are two neighboring R$^{81}$'s, the two neighboring R$^{81}$'s may form —OCH$_2$O—, —CH$_2$CH$_2$CH$_2$— or —CH=CHCH=CH— to form, together with the carbon atoms attached to the two R$^{81}$'s, a 5-membered or 6-membered ring which may have one or more hydrogen atoms on the ring-constituting carbon atoms replaced by one or more Z's which may be identical with or different from one another, if two or more Z's are present;
D2 is an aromatic heterocyclic rings represented by the following structural formula,

F1 to F2 are rings represented by the following formulae, respectively,

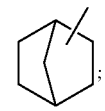

R$^z$ is a halogen atom, and when s2 is an integer of at least 2, each R$^z$ may be identical with or different from one another, and
R$^{11}$ is a halogen atom, C$_1$-C$_6$ alkyl, C$_1$-C$_6$ alkoxy, C$_1$-C$_6$ haloalkyl, C$_1$-C$_6$ haloalkoxy or nitro;
R$^{12}$ is C$_1$-C$_6$ alkyl;
R$^{14}$ is a halogen atom, nitro, cyano, C$_1$-C$_6$ alkyl, C$_1$-C$_6$ haloalkyl, C$_1$-C$_6$ alkoxy, C$_1$-C$_6$ haloalkoxy, phenoxy or phenyl;
R$^{17}$ is —C(O)OR$^{12}$, or phenyl;
R$^{21}$ is a halogen atom, nitro, cyano, C$_1$-C$_{10}$ alkyl, C$_1$-C$_6$ alkoxy, C$_1$-C$_2$ alkoxy(C$_1$-C$_2$) alkoxy, C$_1$-C$_6$ haloalkyl,
R$^{81}$ is a halogen atom, C$_1$-C$_6$ alkyl, C$_1$-C$_6$ haloalkyl, C$_1$-C$_6$ alkoxy, phenyl or phenoxy;
Z is a halogen atom, or C$_1$-C$_6$ alkyl;
a, e, k are integers of from 1 to 5;
s2 is an integer of from 0 to 3; and
n is 1.

9. The method according to claim 8, wherein the culturing occurs in the presence of a culture medium comprising at least one blood cell stimulating factor.

10. The method according to claim 9, wherein the blood cell stimulating factor is at least one species selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

11. The method according to claim 8, wherein the hematopoietic stem cells and/or hematopoietic progenitor cells are obtained from the bone marrow, the liver, the spleen, peripheral blood or cord blood.

12. A method of producing hematopoietic stem cells and/or hematopoietic progenitor cells, the method comprising expanding CD34+ hematopoietic stem cells and/or hematopoietic progenitor cells by contacting the hematopoietic stem cells in an ex vivo culture with stem cell factor and a pyrazole compound represented by the formula (1):

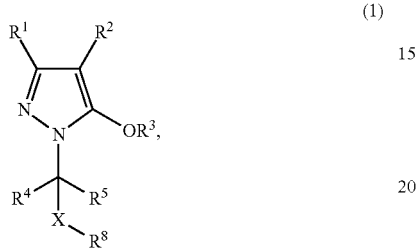

(1)

wherein:
$R^1$ is $C_1$-$C_6$ alkyl, $C_1$-$C_6$ alkyl substituted with $R^{17}$, $C_1$-$C_6$ haloalkyl, $C_3$-$C_6$ cycloalkyl, phenyl or phenyl substituted with a $R^{11}$'s, when a is an integer of at least 2, each $R^{11}$ may be identical with or different from one another;
$R^2$ is $C_1$-$C_6$ alkyl, D2, benzyl, benzyl having a benzene ring optionally substituted with e $R^{21}$'s, phenyl or phenyl optionally substituted with e $R^{21}$'s, when e is an integer of at least 2, each $R^{21}$ may be identical with or different from one another;
when there are two neighboring $R^{21}$'s, the two neighboring $R^{21}$'s may form —OCH$_2$O—, —OCH$_2$CH$_2$O— or —CH=CHCH=CH— to form, together with the carbon atoms attached to the two $R^{21}$'s, a 5-membered or 6-membered ring which may have one or more hydrogen atoms on the ring-constituting carbon atoms replaced by one or more Z's which may be identical with or different from one another, if two or more Z's are present;
$R^3$ is a hydrogen atom;
X is a single bond;
each of $R^4$ and $R^5$ is independently $C_1$-$C_4$ alkyl;
$R^8$ is D2, F1, F2, phenyl or phenyl optionally substituted with k $R^{81}$'s, and when k is an integer of at least 2, each $R^{81}$ may be identical with or different from one another, and
when there are two neighboring $R^{81}$'s, the two neighboring $R^{81}$'s may form —OCH$_2$O—, —CH$_2$CH$_2$CH$_2$— or —CH=CHCH=CH— to form, together with the carbon atoms attached to the two $R^{81}$'s, a 5-membered or 6-membered ring which may have one or more hydrogen atoms on the ring-constituting carbon atoms replaced by one or more Z's which may be identical with or different from one another, if two or more Z's are present,
D2 is an aromatic heterocyclic ring represented by the following structural formula,

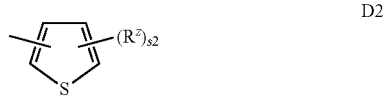

D2

F1 to F2 are rings represented by the following formulae, respectively,

F1

F2

$R^z$ is a halogen atom, $C_1$-$C_6$ alkyl, phenoxy or phenyl, and when s2 is an integer of at least 2, each $R^z$ may be identical with or different from one another, and
$R^{11}$ is a halogen atom, $C_1$-$C_6$ alkyl, $C_1$-$C_6$ alkoxy, $C_1$-$C_6$ haloalkyl, $C_1$-$C_6$ haloalkoxy or nitro,
$R^{12}$ is $C_1$-$C_6$ alkyl;
$R^{17}$ is —C(O)O$R^{12}$ or phenyl;
$R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, nitro, cyano or phenyl;
$R^{81}$ is a halogen atom, $C_1$-$C_6$ alkyl, $C_1$-$C_6$ haloalkyl, $C_1$-$C_6$ alkoxy or phenoxy;
Z is a halogen atom or $C_1$-$C_6$ alkyl;
a, e, and k are integers of from 1 to 5;
s2 s an integer of from 0 to 3;
a tautomer of the compound or a pharmaceutically acceptable salt or solvate thereof.

13. The method according to claim 1, wherein
$R^2$ is a hydrogen atom, a halogen atom, $C_1$-$C_6$ alkyl, D2, benzyl, phenyl or phenyl optionally substituted with e $R^{21}$'s, when e is an integer of at least 2, each $R^{21}$ may be identical with or different from one another;
when there are two neighboring $R^{21}$'s, the two neighboring $R^{21}$'s may form —OCH$_2$O—, or —CH=CHCH=CH— to form, together with the carbon atoms attached to the two $R^{21}$'s, a 5-membered or 6-membered ring;
$R^8$ is D2, F1, phenyl or phenyl optionally substituted with k $R^{81}$'s, and when k is an integer of at least 2, each $R^{81}$ may be identical with or different from one another, when there are two neighboring $R^{81}$'s, the two neighboring $R^{81}$'s may form —CH$_2$CH$_2$CH$_2$— or —CH=CHCH=CH— to form, together with the carbon atoms attached to the two $R^{81}$'s, a 5-membered ring or a 6-membered ring;
$R^{11}$ is a halogen atom, $C_1$-$C_6$ alkyl or $C_1$-$C_6$ alkoxy;
$R^{17}$ is phenyl;
$R^{21}$ is a halogen atom, $C_1$-$C_{10}$ alkyl, $C_1$-$C_6$ alkoxy, $C_1$-$C_2$ alkoxy($C_1$-$C_2$) alkoxy, $C_1$-$C_6$ haloalkyl, or phenyl;
$R^{81}$ is a halogen atom, $C_1$-$C_6$ alkyl, $C_1$-$C_6$ haloalkyl or $C_1$-$C_6$ alkoxy;
a tautomer of the compound, or a pharmaceutically acceptable salt or solvate thereof.

14. The method according to claim 12, wherein
$R^1$ is $C_1$-$C_6$ alkyl, $C_3$-$C_6$ cycloalkyl, or phenyl substituted with a $R^{11}$'s, and when a is an integer of at least 2, each $R^{11}$ may be identical with or different from one another;
$R^2$ is a $C_1$-$C_6$ alkyl, benzyl, phenyl or phenyl optionally substituted with e $R^{21}$'s, when e is an integer of at least 2, each $R^{21}$ may be identical with or different from one another;

$R^8$ is phenyl or phenyl optionally substituted with k $R^{81}$'s, and when k is an integer of at least 2, each $R^{81}$ may be identical with or different from one another,
$R^{11}$ is a $C_1$-$C_6$ alkyl;
$R^{21}$ is a $C_1$-$C_{10}$ alkyl;
$R^{81}$ is a halogen atom;
a tautomer of the compound, or a pharmaceutically acceptable salt or solvate thereof.

15. The method according to claim 12, wherein the pyrozole compound is a compound of the following formula:

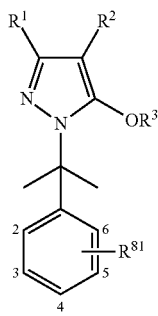

wherein
$R^1$ is $CH_3$; $R^2$ is $CH_3$; and $R^3$ and $R^{81}$ are H;
$R^1$ is $CH_3$; $R^2$ is n-hexyl; and $R^3$ and $R^{81}$ are H;
$R^1$ is $CH_3$; $R^2$ is phenyl-$CH_2$; and $R^3$ and $R^{81}$ are H;
$R^1$ is n-propyl; $R^2$ is phenyl; and $R^3$ and $R^{81}$ are H;
$R^1$ is i-propyl; $R^2$ is (4-n-hexyl)phenyl; and $R^3$ and $R^{81}$ are H;
$R^1$ is c-propyl; $R^2$ is (4-n-hexyl)phenyl; and $R^3$ and $R^{81}$ are H;
$R^1$ is i-propyl; $R^2$ is (4-n-hexyl)phenyl; $R^3$ is H; and $R^{81}$ is 4-Cl;
$R^1$ is c-propyl; $R^2$ is (4-n-hexyl)phenyl; $R^3$ is H; and $R^{81}$ is 4-Cl;
$R^1$ is (4-t-butyl)phenyl; $R^2$ is (4-n-hexyl)phenyl; $R^3$ is H; and $R^{81}$ is 4-Cl;
$R^1$ is i-propyl; $R^2$ is n-propyl; and $R^3$ and $R^{81}$ are H;
$R^1$ is (4-t-butyl)phenyl; $R^2$ is (4-n-hexyl)phenyl; and $R^3$ and $R^{81}$ are H; or
$R^1$ is (4-t-butyl)phenyl; $R^2$ is n-hexyl; and $R^3$ and $R^{81}$ are H.

16. The method according to claim 1, wherein the pyrozole compound is a compound of the following formula:

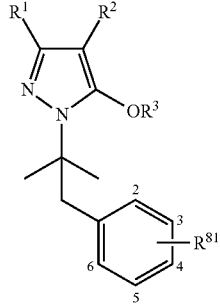

wherein
$R^1$ is $CH_3$; $R^2$ is H; and $R^3$ and $R^{81}$ are H;
$R^1$ is $CH_3$; $R^2$ is $CH_3$; and $R^3$ and $R^{81}$ are H;
$R^1$ is $CH_3$; $R^2$ is n-hexyl; and $R^3$ and $R^{81}$ are H;
$R^1$ is $CH_3$; $R^2$ is phenyl-$CH_2$; and $R^3$ and $R^{81}$ are H;
$R^1$ is phenyl; $R^2$ is phenyl; and $R^3$ and $R^{81}$ are H;
$R^1$ is n-propyl; $R^2$ is phenyl; and $R^3$ and $R^{81}$ are H;
$R^1$ is i-propyl; $R^2$ is phenyl; and $R^3$ and $R^{81}$ are H;
$R^1$ is c-propyl; $R^2$ is phenyl; and $R^3$ and $R^{81}$ are H;
$R^1$ is n-butyl; $R^2$ is phenyl; and $R^3$ and $R^{81}$ are H;
$R^1$ is (4-$CH_3$)phenyl; $R^2$ is phenyl; and $R^3$ and $R^{81}$ are H;
$R^1$ is (4-Cl)phenyl; $R^2$ is phenyl; and $R^3$ and $R^{81}$ are H;
$R^1$ is ((3,4-$(OCH_3)_2$)phenyl; $R^2$ is phenyl; and $R^3$ and $R^{8'}$ are H;
$R^1$ is $CH_3$; $R^2$ is (4-$CH_3$)phenyl; and $R^3$ and $R^{81}$ are H;
$R^1$ is $CH_3$; $R^2$ is (2-$CH_3$)phenyl; and $R^3$ and $R^{81}$ are H;
$R^1$ is $CH_3$; $R^2$ is {3,4-$(CH_3)_2$} phenyl; and $R^3$ and $R^{81}$ are H;
$R^1$ is $CH_3$; $R^2$ is (4-phenyl)phenyl; and $R^3$ and $R^{81}$ are H;
$R^1$ is $CH_3$; $R^2$ is (4-t-butyl)phenyl; and $R^3$ and $R^{81}$ are H;
$R^1$ is $CH_3$; $R^2$ is napthalen-1-yl; and $R^3$ and $R^{81}$ are H;
$R^1$ is $CH_3$; $R^2$ is (4-n-hexyl)phenyl; and $R^3$ and $R^{81}$ are H;
$R^1$ is $CH_3$; $R^2$ is (4-$OCH_3$)phenyl; and $R^3$ and $R^{81}$ are H;
$R^1$ is $CH_3$; $R^2$ is benzo[d][1,3]dioxol-5-yl; and $R^3$ and $R^{81}$ are H;
$R^1$ is $CH_3$; $R^2$ is ({4-$O(CH_2)_2$O-ethyl}phenyl; and $R^3$ and $R^{81}$ are H;
$R^1$ is $CH_3$; $R^2$ is (4-Cl)phenyl; and $R^3$ and $R^{81}$ are H;
$R^1$ is $CH_3$; $R^2$ is (3,4-$Cl_2$)phenyl; and $R^3$ and $R^{81}$ are H;
$R^1$ is $CH_3$; $R^2$ is thiophen-2-yl; and $R^3$ and $R^{81}$ are H;
$R^1$ is i-propyl; $R^2$ is (4-$CH_3$)phenyl; and $R^3$ and $R^{81}$ are H;
$R^1$ is i-propyl; $R^2$ is (2-$CH_3$)phenyl; and $R^3$ and $R^{81}$ are H;
$R^1$ is i-propyl; $R^2$ is {3,4-$(CH_3)_2$}phenyl; and $R^3$ and $R^{81}$ are H;
$R^1$ is i-propyl; $R^2$ is (4-phenyl)phenyl; and $R^3$ and $R^{8'}$ are H;
$R^1$ is i-propyl; $R^2$ is (4-t-butyl)phenyl; and $R^3$ and $R^{81}$ are H;
$R^1$ is i-propyl; $R^2$ is napathalen-1-yl; and $R^3$ and $R^{81}$ are H;
$R^1$ is i-propyl; $R^2$ is (4-n-hexyl)phenyl; and $R^3$ and $R^{8'}$ are H;
$R^1$ is i-propyl; $R^2$ is (4-$OCH_3$)phenyl; and $R^3$ and $R^{81}$ are H;
$R^1$ is i-propyl; $R^2$ is benzo[d][1,3]dioxol-5-yl; and $R^3$ and $R^{81}$ are H;
$R^1$ is i-propyl; $R^2$ is {4-$O(CH_2)_2$O-ethyl}phenyl; and $R^3$ and $R^{81}$ are H;
$R^1$ is i-propyl; $R^2$ is (4-Cl)phenyl; and $R^3$ and $R^{81}$ are H;
$R^1$ is i-propyl; $R^2$ is (3,4-$Cl_2$)phenyl; and $R^3$ and $R^{81}$ are H;
$R^1$ is i-propyl; $R^2$ is thiophen-2-yl; and $R^3$ and $R^{81}$ are H;
$R^1$ is $CH_3$; $R^2$ is (4-$CF_3$)phenyl; and $R^3$ and $R^{81}$ are H;
$R^1$ is i-propyl; $R^2$ is (4-$CF_3$)phenyl; and $R^3$ and $R^{81}$ are H;
$R^1$ is i-propyl; $R^2$ is H; $R^3$ is H; and $R^{81}$ is 4-$CH_3$;
$R^1$ is (4-$OCH_3$)phenyl; $R^2$ is H; $R^3$ is H; and $R^{81}$ is 4-$CH_3$;
$R^1$ is i-propyl; $R^2$ is (4-n-hexyl)phenyl; $R^3$ is H; and $R^{81}$ is 4-$CH_3$;
$R^1$ is $CF_3$; $R^2$ is H; $R^3$ is H; and $R^{81}$ is 4-$CH_3$;
$R^1$ is 1,1-$(CH_3)_2$-2-phenyl-ethyl; $R^2$ is H; $R^3$ is H; and $R^{81}$ is 4-$CH_3$;
$R^1$ is phenyl; $R^2$ is H; $R^3$ is H; and $R^{81}$ is 4-$CH_3$;
$R^1$ is i-propyl; $R^2$ is H; $R^3$ is H; and $R^{81}$ is 4-Br;
$R^1$ is phenyl; and $R^2$, $R^3$ and $R^{81}$ are H;
$R^1$ is i-propyl; and $R^2$, $R^3$ and $R^{81}$ are H;
$R^1$ is i-propyl; $R^2$ is (4-n-hexyl)phenyl; $R^3$ is H; and $R^{81}$ is 2-$CH_3$;
$R^1$ is i-propyl; $R^2$ is H; $R^3$ is H; and $R^{81}$ is 3-$CH_3$;
$R^1$ is i-propyl; $R^2$ is (4-n-hexyl)phenyl; $R^3$ is H; and $R^{81}$ is 3-$CH_3$;
$R^1$ is i-propyl; $R^2$ is H; $R^3$ is H; and $R^{81}$ is 4-t-butyl;
$R^1$ is i-propyl; $R^2$ is (4-n-hexyl)phenyl; $R^3$ is H; and $R^{81}$ is 4-Cl;

R¹ is c-propyl; R² is (4-n-hexyl)phenyl; R³ is H; and R⁸¹ is 4-Cl;

R¹ is i-propyl; R² is n-propyl; R³ is H; and R⁸¹ is 4-Cl;

R¹ is (4-t-butyl)phenyl; R² is (4-n-hexyl)phenyl; R³ is H; and R⁸¹ is 4-Cl;

R¹ is i-propyl; R² is (4-n-hexyl)phenyl; R³ is H; and R⁸¹ is 4-OCH₃;

R¹ is c-propyl; R² is (4-n-hexyl)phenyl; R³ is H; and R⁸¹ is 4-OCH₃;

R¹ is (4-t-butyl)phenyl; R² is (4-n-hexyl)phenyl; R³ is H; and R⁸¹ is 4-OCH₃;

R¹ is i-propyl; R² is Br; R³ is H; and R⁸¹ is 3-CH₃;

R¹ is i-propyl; R² is Br; R³ is H; and R⁸¹ is H;

R¹ is i-propyl; R² is (4-n-hexyl)phenyl; R³ is H; and R⁸¹ is 4-n-hexyl;

R¹ is i-propyl; R² is (4-n-C₈H₁₇)phenyl; R³ is H; and R⁸¹ is 4-CH₃;

R¹ is n-hexyl; R² is (4-n-hexyl)phenyl; R³ is H; and R⁸¹ is 4-CH₃;

R¹ is c-hexyl; R² is (4-n-hexyl)phenyl; R³ is H; and R⁸¹ is 4-CH₃;

R¹ is (2,4-F₂)phenyl; R² is (4-n-hexyl)phenyl; R³ is H; and R⁸¹ is 4-CH₃;

R¹ is i-propyl; R² is (4-n-hexyl)phenyl; R³ is H; and R⁸¹ is 4-CF₃;

R¹ is (2,4-F₂)phenyl; R² is (4-n-hexyl)phenyl; R³ is H; and R⁸¹ is 4-CF₃;

R¹ is i-propyl; R² is (4-n-hexyl)phenyl; R³ is H; and R⁸¹ is 2,4-F₂; or

R¹ is (2,4-F₂)phenyl; R² is (4-n-hexyl)phenyl; R³ is H; and R⁸¹ is 2,4-F₂.

17. The method according to claim 1, wherein the pyrozole compound is a compound of the following formula:

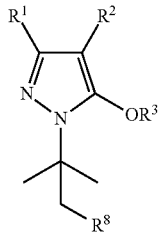

wherein

R¹ is i-propyl; R² is (4-n-hexyl)phenyl; R³ is H; and R⁸ is naphthalene-1-yl;

R¹ is i-propyl; R² is (4-n-C₈H₁₇)phenyl; R³ is H; and R⁸ is naphthalene-1-yl;

R¹ is n-hexyl; R² is (4-n-hexyl)phenyl; R³ is H; and R⁸ is naphthalene-1-yl;

R¹ is c-hexyl; R² is (4-n-hexyl)phenyl; R³ is H; and R⁸ is naphthalene-1-yl;

R¹ is i-propyl; R² is (4-n-hexyl)phenyl; R³ is H; and R⁸ is thiophen-2-yl;

R¹ is i-propyl; R² is (4-n-C₈H₁₇)phenyl; R³ is H; and R⁸ is thiophen-2-yl;

R¹ is n-hexyl; R² is (4-n-hexyl)phenyl; R³ is H; and R⁸ is thiophen-2-yl;

R¹ is c-hexyl; R² is (4-n-hexyl)phenyl; R³ is H; and R⁸ is thiophen-2-yl;

R¹ is i-propyl; R² is (4-n-hexyl)phenyl; R³ is H; and R⁸ is 1-adamantyl;

R¹ is i-propyl; R² is (4-n-C₈H₁₇)phenyl; R³ is H; and R⁸ is 1-adamantyl;

R¹ is n-hexyl; R² is (4-n-hexyl)phenyl; R³ is H; and R⁸ is 1-adamantyl;

R¹ is c-hexyl; R² is (4-n-hexyl)phenyl; R³ is H; and R⁸ is 1-adamantyl;

R¹ is i-propyl; R² is (4-n-hexyl)phenyl; R³ is H; and R⁸ is 2,3-dihydro-1H-inden-5-yl; or R¹ is (2,4-F₂); R² is (4-n-hexyl)phenyl; R³ is H; and R⁸ is 2,3-dihydro-1H-inden-5-yl.

18. The method according to claim 1, wherein the pyrozole compound is a compound of the following formula:

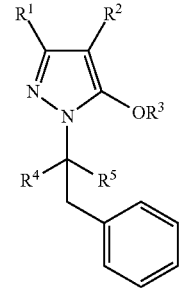

wherein R¹ is i-propyl; R² is (4-n-hexyl)phenyl; R³ is H; and R⁴ and R⁵ are C₂H₅.

* * * * *